US011833214B2

(12) United States Patent
Hilderbrand et al.

(10) Patent No.: US 11,833,214 B2
(45) Date of Patent: Dec. 5, 2023

(54) METHODS OF PREPARING CELL-BINDING AGENT-DRUG CONJUGATES

(71) Applicant: IMMUNOGEN, INC., Waltham, MA (US)

(72) Inventors: Scott A Hilderbrand, Swampscott, MA (US); Daniel F. Milano, Reading, MA (US)

(73) Assignee: IMMUNOGEN, INC., Waltham, MA (US)

( * ) Notice: Subject to any disclaimer, the term of this patent is extended or adjusted under 35 U.S.C. 154(b) by 587 days.

(21) Appl. No.: 16/825,127

(22) Filed: Mar. 20, 2020

(65) Prior Publication Data

US 2020/0405874 A1 Dec. 31, 2020

Related U.S. Application Data

(60) Provisional application No. 62/856,942, filed on Jun. 4, 2019, provisional application No. 62/821,707, filed on Mar. 21, 2019.

(51) Int. Cl.

| | |
|---|---|
| *C07K 16/40* | (2006.01) |
| *A61P 35/00* | (2006.01) |
| *A61K 47/68* | (2017.01) |
| *A61K 31/5365* | (2006.01) |
| *A61K 31/537* | (2006.01) |
| *A61K 31/5513* | (2006.01) |
| *A61K 31/5517* | (2006.01) |
| *C07K 16/28* | (2006.01) |

(52) U.S. Cl.
CPC ........ *A61K 47/6803* (2017.08); *A61K 31/537* (2013.01); *A61K 31/5365* (2013.01); *A61K 31/5513* (2013.01); *A61K 31/5517* (2013.01); *A61K 47/6849* (2017.08); *A61K 47/6871* (2017.08); *C07K 16/2866* (2013.01); *C07K 16/2896* (2013.01); *C07K 16/40* (2013.01)

(58) Field of Classification Search
CPC ................ C07K 16/40; C07K 16/2866; C07K 16/2896; A61K 47/68; A61K 47/6803; A61K 47/6871; A61K 47/6849; A61K 47/6889; A61K 31/5365; A61K 31/537; A61K 31/5513; A61K 31/5517; A61P 35/00

See application file for complete search history.

(56) References Cited

FOREIGN PATENT DOCUMENTS

| | | |
|---|---|---|
| WO | 2011/130613 A1 | 10/2011 |
| WO | 2017/004026 A1 | 1/2017 |
| WO | 2018/098258 A2 | 5/2018 |
| WO | 2018/160539 A1 | 9/2018 |
| WO | 2019/140141 A1 | 7/2019 |
| WO | 2020/005945 A1 | 1/2020 |

OTHER PUBLICATIONS

International Search Report and Written Opinion for Application No. PCT/US2020/023897, dated Jul. 31, 2020, 19 pages.

*Primary Examiner* — Brenda L Coleman
(74) *Attorney, Agent, or Firm* — McCarter & English, LLP; Xin Zhang

(57) ABSTRACT

The present invention provides methods of preparing a cell-binding agent-cytotoxic agent conjugate comprising a cell-binding agent (CysCBA) having one or more unpaired cysteine residues covalently linked to a cytotoxic agent. Also provided are conjugates prepared by the methods described herein and pharmaceutical composition and methods of use thereof.

9 Claims, 8 Drawing Sheets

Specification includes a Sequence Listing.

METHODS OF PREPARING CELL-BINDING AGENT-DRUG CONJUGATES

RELATED APPLICATIONS

This application claims priority to U.S. Provisional Application No. 62/821,707, filed on Mar. 21, 2019, and U.S. Provisional Application No. 62/856,942, filed on Jun. 4, 2019, the contents of each of which are hereby incorporated by reference in their entireties.

FIELD OF THE INVENTION

The present invention generally relates to methods of preparing cell-binding agent-drug conjugates comprising a cell-binding agent having one or more unpaired cysteine residues covalently linked to a cytotoxic agent.

BACKGROUND OF THE INVENTION

Cell binding agent-drug conjugates (such as antibody-drug conjugates (ADC)) are emerging as a powerful class of anti-tumor agents with efficacy across a range of cancers. Cell binding agent-drug conjugates (such as ADCs) are commonly composed of three distinct elements: a cell-binding agent (e.g., an antibody); a linker; and a cytotoxic moiety. The cytotoxic drug moiety can be covalently linked to cysteine thiol groups on the antibody through a thiol-reactive group, such as a maleimide group, to form site-specific ADCs. Cysteine-engineered antibodies can be employed for making site-specific ADCs. However, during antibody production, the engineered cysteines are often capped by other thiol-containing moieties, such as cysteine or glutathione, to form disulfides. Prior to conjugation with the cytotoxic agent, the disulfides need to be treated with a reducing agent to remove the capping moiety and to form a free thiol for reacting with the cytotoxic agent. Such treatment also reduces the antibody interchain disulfide bonds, which need to be re-formed by a selective oxidation step without re-oxidizing the free thiol group on the engineered cysteines. The selective oxidation is achieved by the use of a mild oxidizing agent and the removal of reducing agent and capping agents, such as cysteine and/or glutathione. The reduction and selective oxidation steps introduce complexity into the process of making ADCs with cysteine engineered antibodies and often require multiple purification steps, which renders the process cumbersome and less efficient for large scale manufacture of ADCs.

Therefore, there is a need to develop new efficient methods for preparing ADCs of engineered cysteine antibodies that are suitable for large scale manufacturing process.

SUMMARY OF THE INVENTION

The present invention is based on the surprising findings that ADCs comprising a cysteine-engineered antibody covalently linked to a cytotoxic agent can be prepared with high purity and reaction yield by a one-pot process that does not require purification in between reaction steps. Moreover, comparative data show that the one-pot process unexpectedly increases monomer percentage of the final ADC product when compared with the ADC prepared by a multi-step process that requires purification in between reactions steps (see Example 5).

In certain embodiments, the present invention provides a method of preparing a cell-binding agent-cytotoxic agent conjugate comprising a cell-binding agent (CysCBA) having one or more unpaired cysteine residues covalently linked to a cytotoxic agent, wherein the method comprises the steps of:
  (a) reacting a reducing agent with a capped cell-binding agent (cCysCBA) having one or more unpaired cysteine residues capped with a capping agent to form a reduced cell-binding agent, wherein the capping agent is removed to form a free thiol (—SH) group in the reduced cell-binding agent;
  (b) reacting the reduced cell-binding agent with a selective oxidizing agent to form the CysCBA, wherein the free thiol group in the unpaired cysteine residue is not oxidized; and
  (c) reacting the CysCBA with a compound of formula (I):

or a pharmaceutically acceptable salt thereof, thereby forming the conjugate, wherein the reduced cell-binding agent in step (a) is used in step (b) without purification; and the CysCBA in step (b) is used in step (c) without purification, wherein:
  D is a cytotoxic agent; and
  L is a linker.

In certain embodiments, the present invention provides a continuous method of preparing a cell-binding agent-cytotoxic agent conjugate (ADC) comprising a cell-binding agent (CysCBA) having one or more unpaired cysteine residues covalently linked to a cytotoxic agent, wherein the method comprises the steps of:
  (a) reacting a reducing agent with a capped cell-binding agent (cCysCBA) having one or more unpaired cysteine residues capped with a capping agent to form a reduced cell-binding agent, wherein the capping agent is removed to form a free thiol (—SH) group in the reduced cell-binding agent;
  (b) reacting the reduced cell-binding agent with a selective oxidizing agent to form the CysCBA, wherein the free thiol group in the unpaired cysteine residue is not oxidized; and
  (c) reacting the CysCBA with a compound of formula (I):

or a pharmaceutically acceptable salt thereof, thereby forming the conjugate,
  wherein the reduced cell-binding agent in step (a) is used in step (b) without purification; the CysCBA step (b) is used in step (c) without purification, and any one or more steps selected from steps (a) to (c) are performed continuously, and wherein:

D is a cytotoxic agent; and

L is a linker

In certain embodiments, the present invention provides a continuous method of preparing a cell-binding agent-cytotoxic agent conjugate (ADC) comprising a cell-binding agent (CysCBA) having one or more unpaired cysteine residues covalently linked to a cytotoxic agent, wherein the method comprises the steps of:

(a) reacting a reducing agent with a capped cell-binding agent (cCysCBA) having one or more unpaired cysteine residues capped with a capping agent to form a reduced cell-binding agent, wherein the capping agent is removed to form a free thiol (—SH) group in the reduced cell-binding agent;

(b) reacting the reduced cell-binding agent with a selective oxidizing agent to form the CysCBA, wherein the free thiol group in the unpaired cysteine residue is not oxidized; and (c) reacting the CysCBA with a compound of formula (I):

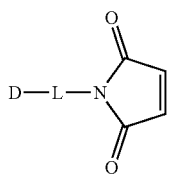

(I)

or a pharmaceutically acceptable salt thereof, thereby forming the conjugate; and (d) removing unconjugated compound of formula (I);

wherein the reduced cell-binding agent in step (a) is used in step (b) without purification; the CysCBA step (b) is used in step (c) without purification, and any one or more steps selected from steps (a) to (d) are performed continuously; and wherein:

D is a cytotoxic agent; and

L is a linker

In certain embodiments, the present invention provides a method of preparing an antibody-cytotoxic agent conjugate (ADC) represented by the following formula:

comprising the steps of:

(a) reacting a reducing agent with a capped cysteine-engineered antibody (cCysAb) represented by the following formula:

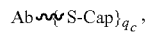

to form a reduced antibody or antigen-binding fragment thereof, wherein the capping agent (Cap) is removed to form a free thiol (—SH) group in the reduced antibody or antigen-binding fragment thereof;

(b) reacting the reduced antibody or antigen-binding fragment thereof with a selective oxidizing agent to form the CysAb, wherein the free thiol group in the engineered cysteine residue is not oxidized; and (c) reacting the CysAb with a compound represented by the following formula:

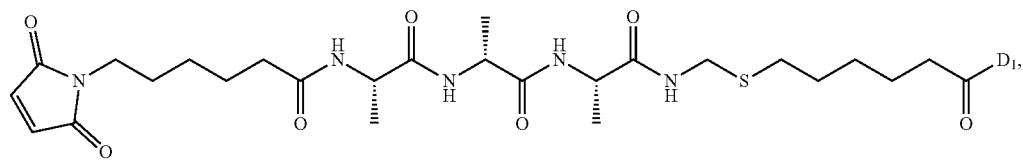

(I1)

or a pharmaceutically acceptable salt thereof, thereby forming the ADC, wherein the reduced antibody or antigen-binding fragment thereof in step (a) is used in step (b) without purification, and the CysAb or antigen-binding fragment thereof in step (b) is used in step (c) without purification, wherein:

Ab⁓S— is a cysteine-engineered antibody (CysAb) or antigen-binding fragment thereof covalently linked to the cytotoxic agent through the thiol group located on the engineered cysteine residue; and wherein the CysAb or antigen-binding fragment thereof is a humanized anti-ADAM9 antibody or ADAM9-binding fragment thereof comprising a $CDR_H1$ domain, a $CDR_H2$ domain, and a $CDR_H3$ domain and a $CDR_L1$ domain, a $CDR_L2$ domain, and a $CDR_L3$ domain having the sequences of SEQ ID NOs: 24, 25, and 26 and SEQ ID NOs: 21, 22, 23, respectively;

$q_c$ is 1 or 2;

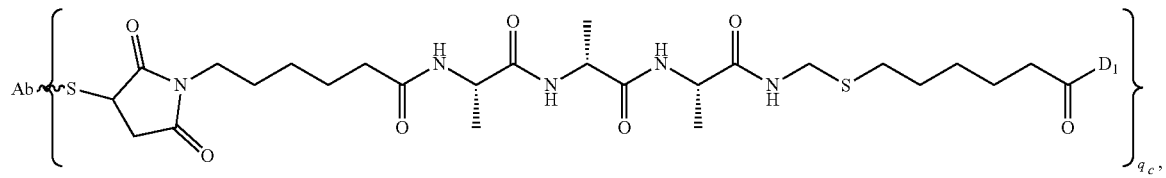

$D_1$ is represented by the following formula:

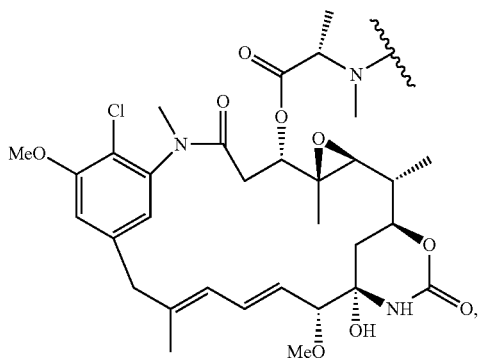

and

Cap is a capping agent.

In certain embodiments, the present invention provides a continuous method of preparing an antibody-cytotoxic agent conjugate (ADC) represented by the following formula:

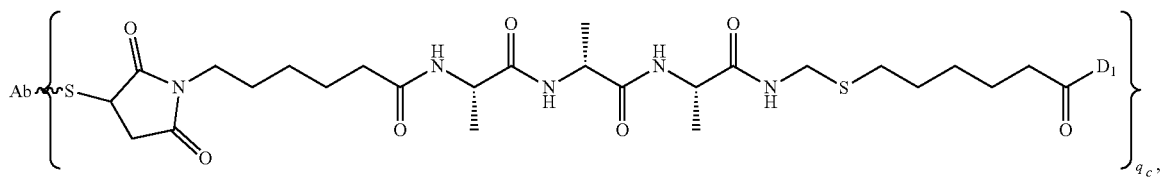

comprising the steps of:
(a) reacting a reducing agent with a capped cysteine-engineered antibody (cCysAb) represented by the following formula:

$$Ab \text{\textasciitilde} \{S\text{-}Cap\}_{q_c},$$

to form a reduced antibody or antigen-binding fragment thereof, wherein the capping agent (Cap) is removed to form a free thiol (—SH) group in the reduced antibody or antigen-binding fragment thereof;
(b) reacting the reduced antibody or antigen-binding fragment thereof with a selective oxidizing agent to form the CysAb, wherein the free thiol group in the engineered cysteine residue is not oxidized; and
(c) reacting the CysAb with a compound represented by the following formula:

(II1)

or a pharmaceutically acceptable salt thereof, thereby forming the ADC, wherein the reduced antibody or antigen-binding fragment thereof in step (a) is used in step (b) without purification, the CysAb or antigen-binding fragment thereof of step (b) is used in step (c) without purification, and steps (a) to (c) are performed continuously, and wherein:

is a cysteine-engineered antibody (CysAb) or antigen-binding fragment thereof covalently linked to the cytotoxic agent through the thiol group located on the engineered cysteine residue; and wherein the CysAb or antigen-binding fragment thereof is a humanized anti-ADAM9 antibody or ADAM9-binding fragment thereof comprising a $CDR_H1$ domain, a $CDR_H2$ domain, and a $CDR_H3$ domain and a $CDR_L1$ domain, a $CDR_L2$ domain, and a $CDR_L3$ domain having the sequences of SEQ ID NOs: 24, 25, and 26 and SEQ ID NOs: 21, 22, 23, respectively;

$q_c$ is 1 or 2;

$D_1$ is represented by the following formula:

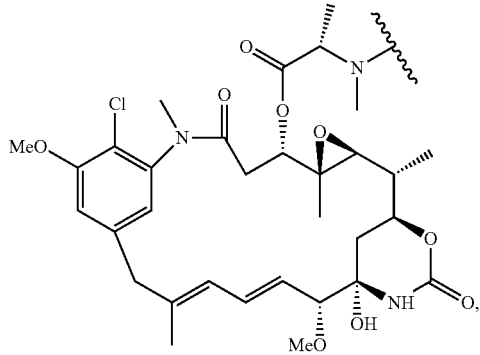 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

and

Cap is a capping agent.

In certain embodiments, the present invention provides a continuous method of preparing an antibody-cytotoxic agent conjugate (ADC) represented by the following formula:

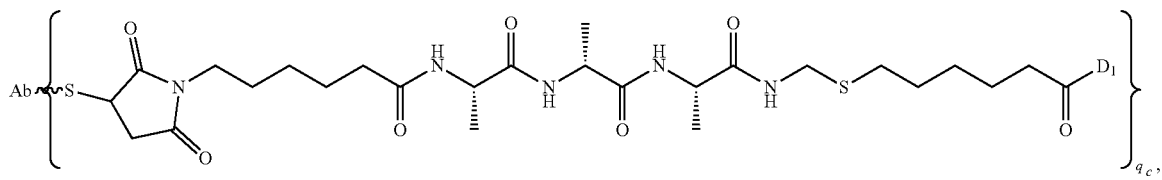

comprising the steps of:
(a) reacting a reducing agent with a capped cysteine-engineered antibody (cCysAb) represented by the following formula:

Ab~S-Cap}$_{q_c}$, to form a reduced antibody or antigen-binding fragment thereof, wherein the capping agent (Cap) is removed to form a free thiol (—SH) group in the reduced antibody or antigen-binding fragment thereof;
(b) reacting the reduced antibody or antigen-binding fragment thereof with a selective oxidizing agent to form the CysAb, wherein the free thiol group in the engineered cysteine residue is not oxidized;
(c) reacting the CysAb with a compound represented by the following formula:

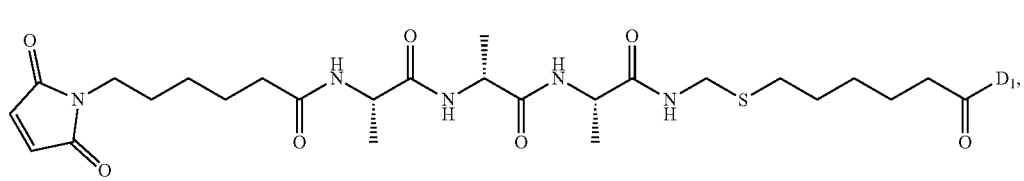
(I11)

or a pharmaceutically acceptable salt thereof, thereby forming the ADC; and
(d) removing the unconjugated compound of formula (I11);
wherein the reduced antibody or antigen-binding fragment thereof in step (a) is used in step (b) without purification, the CysAb or antigen-binding fragment thereof of step (b) is used in step (c) without purification, and steps (a) to (d) are performed continuously, and
wherein:

Ab~S—— is a cysteine-engineered antibody (CysAb) or antigen-binding fragment thereof covalently linked to the cytotoxic agent through the thiol group located on the engineered cysteine residue; and wherein the CysAb or antigen-binding fragment thereof is a humanized anti-ADAM9 antibody or ADAM9-binding fragment thereof comprising a $CDR_H1$ domain, a $CDR_H2$ domain, and a $CDR_H3$ domain and a $CDR_L1$ domain, a $CDR_L2$ domain, and a $CDR_L3$ domain having the sequences of SEQ ID NOs: 24, 25, and 26 and SEQ ID NOs: 21, 22, 23, respectively;
$q_c$ is 1 or 2;

D₁ is represented by the following formula:

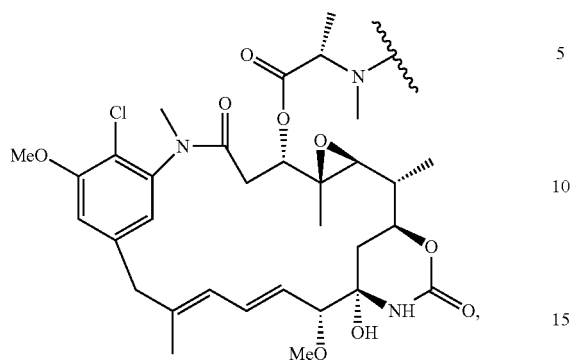

and

Cap is a capping agent.

In certain embodiments, the present invention provides a method of preparing an antibody-cytotoxic agent conjugate (ADC) represented by the following formula:

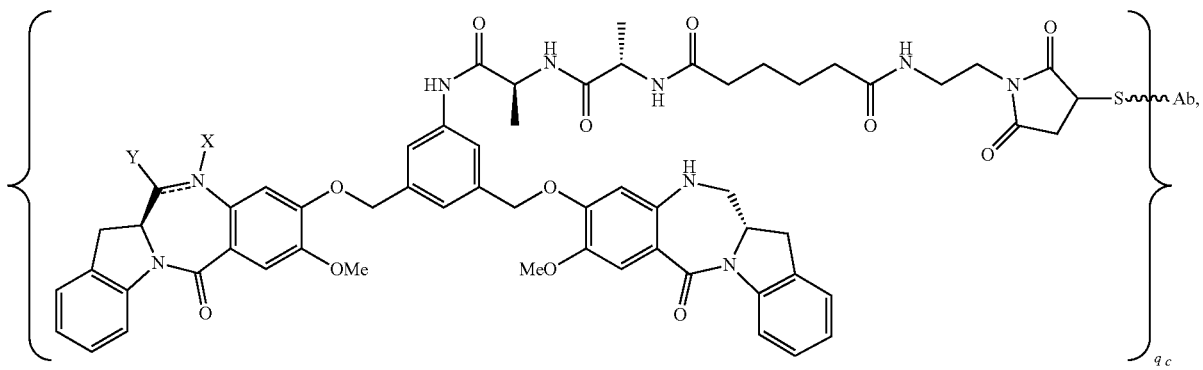

comprising the steps of:

(a) reacting a reducing agent with a capped cysteine-engineered antibody (cCysAb) represented by the following formula:

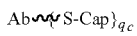

to form a reduced antibody or antigen-binding fragment thereof, wherein the capping agent is removed to form a free thiol (—SH) group in the reduced antibody or antigen-binding fragment thereof;

(b) reacting the reduced antibody or antigen-binding fragment thereof with a selective oxidizing agent to form the CysAb, wherein the free thiol group in the engineered cysteine residue is not oxidized; and (c) reacting the CysAb with a compound represented by the following formula:

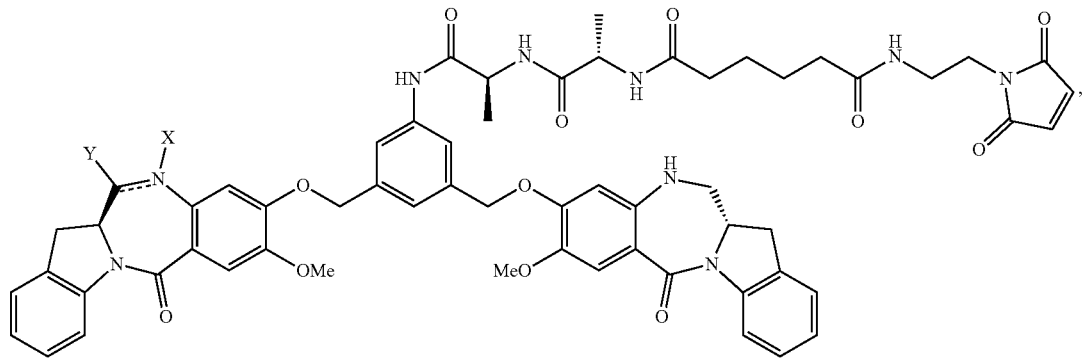

or a pharmaceutical acceptable salt thereof, thereby forming the ADC, wherein the reduced antibody or antigen-binding fragment thereof in step (a) is used in step (b) without purification, and the CysAb or antigen-binding fragment thereof in step (b) is used in step (c) without purification, wherein:

the double line ⚌ between N and C represents a single bond or a double bond, provided that when it is a double bond, X is absent and Y is —H, and when it is a single bond, X is —H, and Y is —SO₃M, and M is H⁺ or a cation;

Ab∿S— is the cysteine-engineered antibody or antigen-binding fragment thereof covalently linked to the cytotoxic agent through the thiol group located on the engineered cysteine residue; wherein the cysteine-engineered antibody is an anti-CD123 antibody or antigen-binding fragment comprising:
  a) an immunoglobulin heavy chain variable region comprising a $CDR_H1$ having an amino acid sequence set forth in SEQ ID NO:4, a $CDR_H2$ having an amino acid sequence set forth in SEQ ID NO:5, and a $CDR_H3$ having an amino acid sequence set forth in SEQ ID NO:6; and
  b) an immunoglobulin light chain variable region comprising a $CDR_L1$ having an amino acid sequence set forth in SEQ ID NO:1, a $CDR_L2$ having an amino acid sequence set forth in SEQ ID NO:2, and a $CDR_L3$ having an amino acid sequence set forth in SEQ ID NO:3;
  $q_c$ is 1 or 2; and
  Cap is a capping agent.

In certain embodiments, the present invention provides a continuous method of preparing an antibody-cytotoxic agent conjugate (ADC) represented by the following formula:

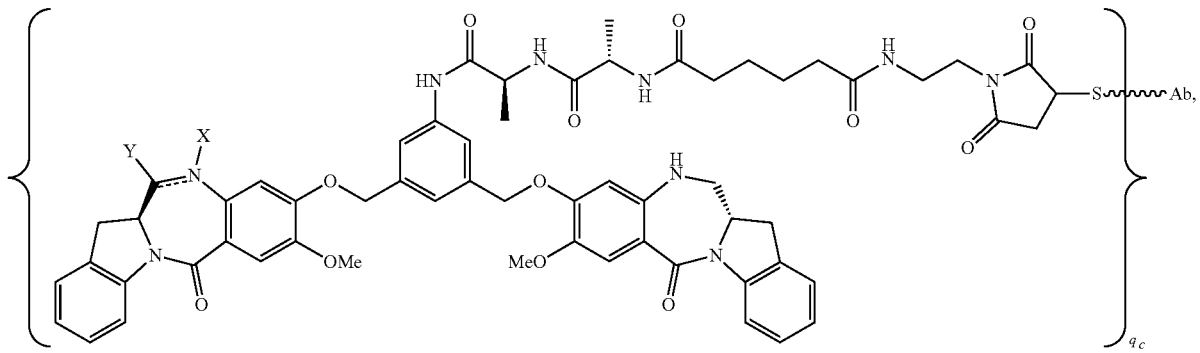

comprising the steps of:
  (a) reacting a reducing agent with a capped cysteine-engineered antibody (cCysAb) represented by the following formula:

Ab∿[S—Cap]$_{q_c}$ to form a reduced antibody or antigen-binding fragment thereof, wherein the capping agent is removed to form a free thiol (—SH) group in the reduced antibody or antigen-binding fragment thereof;
  (b) reacting the reduced antibody or antigen-binding fragment thereof with a selective oxidizing agent to form the CysAb, wherein the free thiol group in the engineered cysteine residue is not oxidized; and
  (c) reacting the CysAb with a compound represented by the following formula:

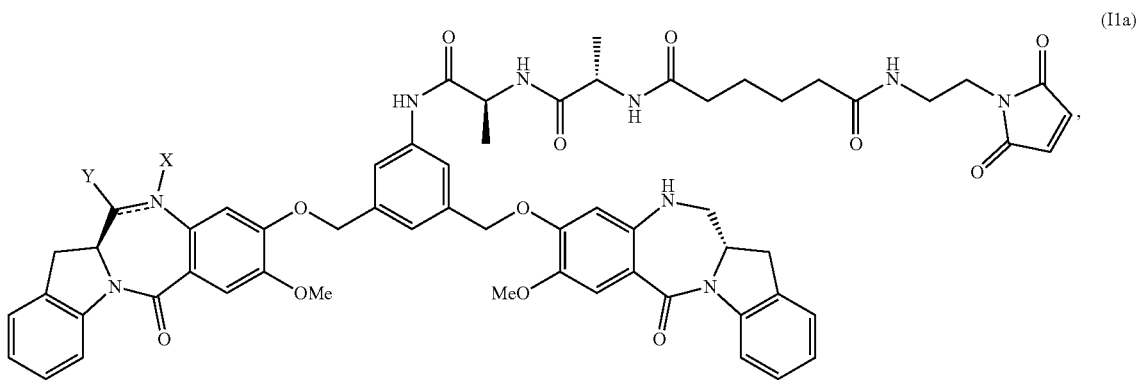

(IIa)

or a pharmaceutical acceptable salt thereof, thereby forming the ADC, wherein the reduced antibody or antigen-binding fragment thereof in step (a) is used in step (b) without purification, and the CysAb or antigen-binding fragment thereof of step (b) is used in step (c) without purification; and steps (a) to (c) are performed continuously, wherein:

the double line ⹀ between N and C represents a single bond or a double bond, provided that when it is a double bond, X is absent and Y is —H, and when it is a single bond, X is —H, and Y is —SO$_3$M, and M is H$^+$ or a cation;

Ab∼S— is the cysteine-engineered antibody or antigen-binding fragment thereof covalently linked to the cytotoxic agent through the thiol group located on the engineered cysteine residue; wherein the cysteine-engineered antibody is an anti-CD123 antibody or antigen-binding fragment comprising:

a) an immunoglobulin heavy chain variable region comprising a CDR$_H$1 having an amino acid sequence set forth in SEQ ID NO:4, a CDR$_H$2 having an amino acid sequence set forth in SEQ ID NO:5, and a CDR$_H$3 having an amino acid sequence set forth in SEQ ID NO:6; and b) an immunoglobulin light chain variable region comprising a CDR$_L$1 having an amino acid sequence set forth in SEQ ID NO:1, a CDR$_L$2 having an amino acid sequence set forth in SEQ ID NO:2, and a CDR$_L$3 having an amino acid sequence set forth in SEQ ID NO:3;

$q_c$ is 1 or 2; and

Cap is a capping agent.

In certain embodiments, the present invention provides a continuous method of preparing an antibody-cytotoxic agent conjugate (ADC) represented by the following formula:

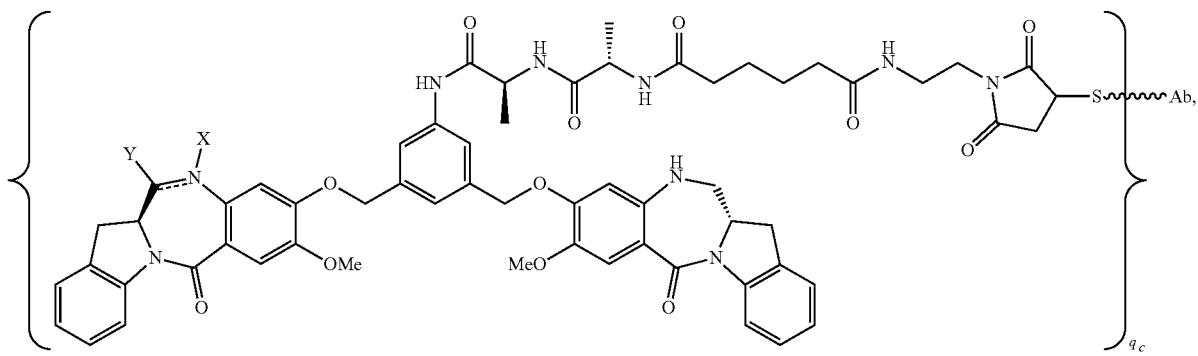

comprising the steps of:

(a) reacting a reducing agent with a capped cysteine-engineered antibody (cCysAb) represented by the following formula:

Ab∼{S—Cap}$_{q_c}$ to form a reduced antibody or antigen-binding fragment thereof, wherein the capping agent is removed to form a free thiol (—SH) group in the reduced antibody or antigen-binding fragment thereof;

(b) reacting the reduced antibody or antigen-binding fragment thereof with a selective oxidizing agent to form the CysAb, wherein the free thiol group in the engineered cysteine residue is not oxidized; and (c) reacting the CysAb with a compound represented by the following formula:

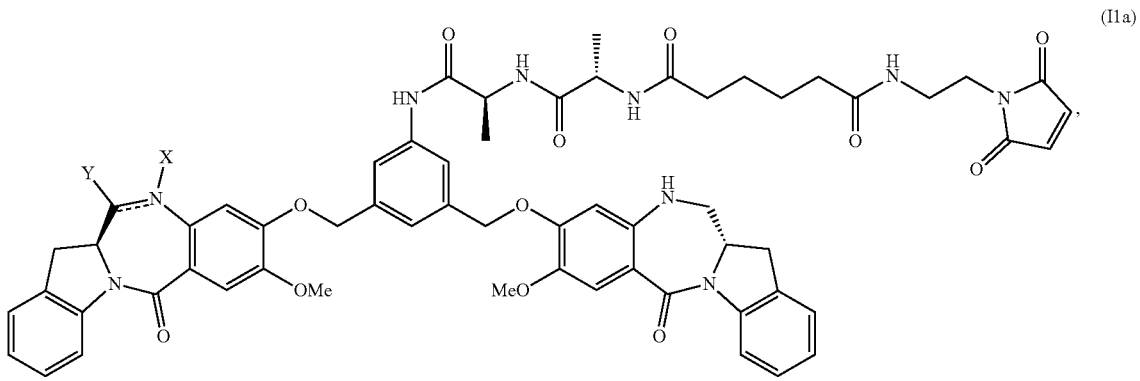

(IIa)

or a pharmaceutical acceptable salt thereof, thereby forming the ADC; and (d) removing unconjugated compound of formula (IIa), wherein the reduced antibody or antigen-binding fragment thereof in step (a) is used in step (b) without purification, and the CysAb or antigen-binding fragment thereof of step (b) is used in step (c) without purification; and steps (a) to (d) are performed continuously, wherein:

the double line ═ between N and C represents a single bond or a double bond, provided that when it is a double bond, X is absent and Y is —H, and when it is a single bond, X is —H, and Y is —$SO_3M$, and M is $H^+$ or a cation;

Ab〰S— is the cysteine-engineered antibody or antigen-binding fragment thereof covalently linked to the cytotoxic agent through the thiol group located on the engineered cysteine residue; wherein the cysteine-engineered antibody is an anti-CD123 antibody or antigen-binding fragment comprising:

a) an immunoglobulin heavy chain variable region comprising a $CDR_H1$ having an amino acid sequence set forth in SEQ ID NO:4, a $CDR_H2$ having an amino acid sequence set forth in SEQ ID NO:5, and a $CDR_H3$ having an amino acid sequence set forth in SEQ ID NO:6; and b) an immunoglobulin light chain variable region comprising a $CDR_L1$ having an amino acid sequence set forth in SEQ ID NO:1, a $CDR_L2$ having an amino acid sequence set forth in SEQ ID NO:2, and a $CDR_L3$ having an amino acid sequence set forth in SEQ ID NO:3;

$q_c$ is 1 or 2; and

Cap is a capping agent.

In certain embodiments, any one of the steps in the methods described herein can be carried out under an inert atmosphere (e.g., $N_2$). In certain embodiments, the methods described herein are carried out under an inert atmosphere (e.g., $N_2$). In certain embodiments, any one of the steps in the methods described herein can be carried out in the presence of $O_2$. In certain embodiments, the methods described herein are carried out in the presence of $O_2$.

It is contemplated that any one embodiment described herein, including those described only in one aspect of the invention (but not in others or not repeated in others), and those described only in the Examples, can be combined with any one or more other embodiments of the invention, unless explicitly disclaimed or inapplicable.

DETAILED DESCRIPTION OF THE INVENTION

1. Definitions

Figure 1:
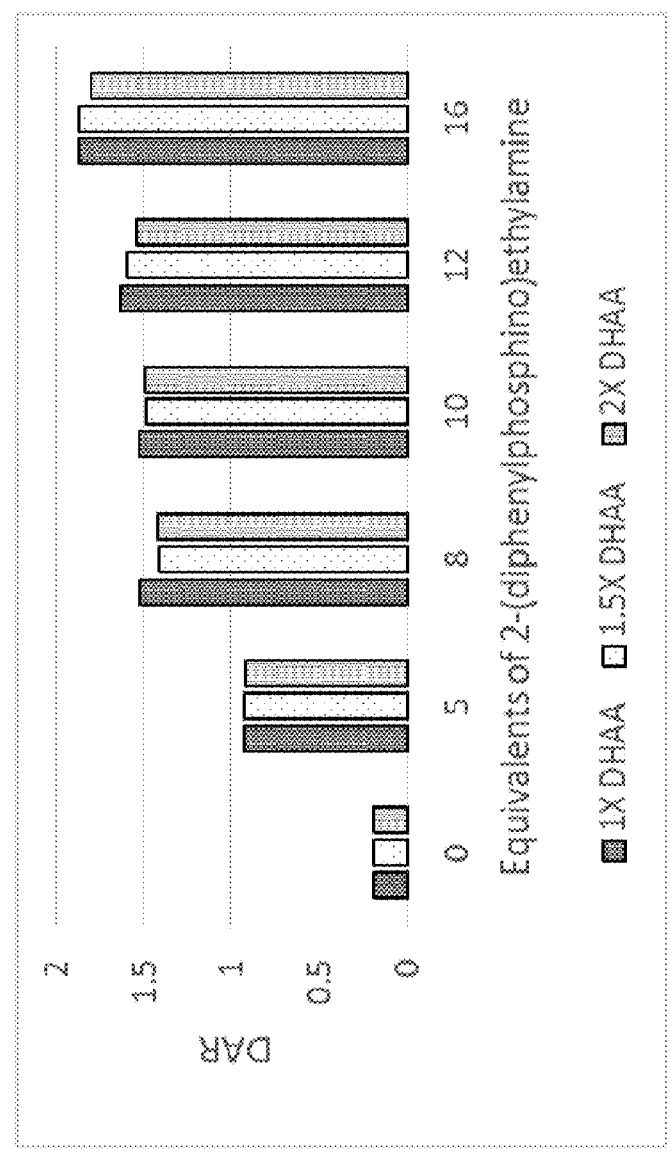
FIG. 1. shows the effects of the amounts of the oxidizing agent DHAA and the reducing agent 2-diphenylphospohinoethylamine used on DAR.

To facilitate an understanding of the present invention, a number of terms and phrases are defined below.

The terms "antibody drug conjugate" (ADC) and "immunoconjugate" as used herein refer to a compound or a derivative thereof that is linked to a cell binding agent (e.g., an antibody or antigen-binding fragment thereof) and is defined by a generic formula: D-L-A, wherein D=cytotoxic drug, L=linker, and A=antibody or antibody fragment. ADCs can also be defined by the generic formula in reverse order: A-L-D. An ADC can comprise multiple drugs and linkers per antibody or antigen-binding fragment thereof, e.g., (D-L)$_4$-A or A-(L-D)$_2$. The terms "antibody drug conjugate" and "immunoconjugate" are used interchangeably herein.

The terms "(human) IL-3Rα," "Interleukine-3 Receptor alpha," or "CD123," as used interchangeably herein, refers to any native (human) IL-3Rα or CD123, unless otherwise indicated. The CD123 protein is an interleukin 3-specific subunit of a heterodimeric cytokine receptor (IL-3 Receptor, or IL-3R). The IL-3R is comprised of a ligand specific alpha subunit, and a signal transducing common beta subunit (also known as CD131) shared by the receptors for interleukin 3 (IL3), colony stimulating factor 2 (CSF2/GM-CSF), and interleukin 5 (IL5). The binding of CD123/IL-3Rα to IL3 depends on the beta subunit. The beta subunit is activated by the ligand binding, and is required for the biological activities of IL3.

All of these above terms for CD123 can refer to either a protein or nucleic acid sequence as indicated herein. The term "CD123/IL-3Rα" encompasses "full-length," unprocessed CD123/IL-3Rα, as well as any form of CD123/IL-3Rα that results from processing within the cell. The term also encompasses naturally occurring variants of CD123/IL-3Rα protein or nucleic acid, e.g., splice variants, allelic variants and isoforms. The CD123/IL-3Rα polypeptides and polynucleotides described herein can be isolated from a variety of sources, such as from human tissue types or from another source, or prepared by recombinant or synthetic methods. Examples of CD123/IL-3Rα sequences include, but are not limited to NCBI reference numbers NP_002174 & NM_002183 (protein and nucleic acid sequences for human CD123 variant 1), and NP_001254642 & NM_001267713 (protein and nucleic acid sequences for human CD123 variant 2).

The term "ADAM9" refers to Disintegrin and Metalloproteinase Domain-containing Protein 9, which a member of the ADAM family of molecules. It is synthesized as an inactive form which is proteolytically cleaved to generate an active enzyme. Processing at the upstream site is particularly important for activation of the proenzyme. ADAM9 is expressed in fibroblasts (Zigrino, P. et al. (2011) *"The Disintegrin-Like And Cysteine-Rich Domains Of ADAM-9 Mediate Interactions Between Melanoma Cells And Fibroblasts,"* J. Biol. Chem. 286:6801-6807), activated vascular smooth muscle cells (Sun, C. et al. (2010) *"ADAM15 Regulates Endothelial Permeability And Neutrophil Migration Via Src/ERK1/2 Signalling,"* Cardiovasc. Res. 87:348-355), monocytes (Namba, K. et al. (2001) *"Involvement Of ADAM9 In Multinucleated Giant Cell Formation Of Blood Monocytes,"* Cell. Immunol. 213:104-113), and activated macrophages (Oksala, N. et al. (2009) *"ADAM-9, ADAM-15, And ADAM-17 Are Upregulated In Macrophages In Advanced Human Atherosclerotic Plaques In Aorta And Carotid And Femoral Arteries—Tampere Vascular Study,"* Ann. Med. 41:279-290). A representative human ADAM9 polypeptide is NCBI Sequence NP_003807. Of the 819 amino acid residues of the ADAM9 polypeptide, residues 1-28 are a signal sequence, residues 29-697 are the Extracellular Domain, residues 698-718 are the Transmembrane Domain, and residues 719-819 are the Intracellular Domain. Three structural domains are located within the Extracellular Domain: a Reprolysin (M12B) Family Zinc Metalloprotease Domain (at approximately residues 212-406); a Disintegrin Domain (at approximately residues 423-497); and an EGF-like Domain (at approximately residues 644-697). A number of post-translational modifications and isoforms have been identified and the protein is proteolytically cleaved in the trans-Golgi network before it reaches the plasma membrane to generate a mature protein. The removal of the pro-domain occurs via cleavage at two different sites. Processing is most likely by a pro-protein convertase such as furin, at the boundary between the pro-domain and the catalytic domain (Arg-205/Ala-206). An additional upstream cleavage pro-protein convertase site (Arg-56/Glu-57) has an important role in the activation of ADAM9. A representative cynomolgus monkey ADAM9 polypeptide is NCBI Sequence XM_005563126.2, including a possible 28 amino acid residue signal sequence. The Reprolysin (M12B) Family Zinc Metalloprotease Domain of the protein is at approximately residues 212-406; the Disintegrin Domain of the protein is at approximately residues 423-497.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')$_2$, and Fv fragments), single chain Fv (scFv) mutants, multispecific antibodies such as bispecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

In some embodiments, an antibody is a non-naturally occurring antibody. In some embodiments, an antibody is purified from natural components. In some embodiments, an antibody is recombinantly produced. In some embodiments, an antibody is produced by a hybridoma.

The term "anti-CD123 antibody," "anti-IL-3Rα antibody" or "an antibody that (specifically) binds to CD123/IL-3Rα" refers to an antibody that is capable of binding CD123/IL-3Rα with sufficient affinity such that the antibody is useful as a diagnostic and/or therapeutic agent in targeting CD123/IL-3Rα. Unless otherwise specified, the extent of binding of an anti-CD123/IL-3Rα antibody to an unrelated, non-CD123/IL-3Rα protein is less than about 10% of the binding of the antibody to CD123/IL-3Rα as measured, e.g., by a radioimmunoassay (RIA). In certain embodiments, an antibody that binds to CD123/IL-3Rα has a dissociation constant ($K_d$) of ≤0.5 nM, ≤0.3 nM, ≤0.1 nM, ≤0.05 nM, or ≤0.01 nM. In one embodiment, the anti-CD123/IL-3Rα antibody does not bind the common beta chain CD131. In one embodiment, the anti-CD123/IL-3Rα antibody does not bind to the same epitope of CD123 that is bound by the known and commercially available CD123 antibodies such as 7G3 (mouse IgG$_{2a}$), 6H6 (mouse IgG$_1$), and 9F5 (mouse IgG$_1$) (Sun et al., *Blood* 87(1): 83-92, 1996).

The sequences of anti-CD123/IL-3Rα antibodies and antigen-binding fragments thereof of the invention are provided herein.

The term "antibody fragment" refers to a portion of an intact antibody and refers to the antigenic determining variable regions of an intact antibody. Examples of antibody fragments include, but are not limited to, Fab, Fab', F(ab')$_2$, and F$_v$ fragments, linear antibodies, single chain antibodies, and multispecific antibodies formed from antibody fragments. The term "antigen-binding fragment" of an antibody includes one or more fragments of an antibody that retain the ability to specifically bind to an antigen. It has been shown that the antigen-binding function of an antibody can be performed by certain fragments of a full-length antibody. Examples of binding fragments encompassed within the term "antigen-binding fragment" of an antibody include (without limitation): (i) an Fab fragment, a monovalent fragment consisting of the V$_L$, V$_H$, C$_L$, and C$_{H1}$ domains (e.g., an antibody digested by papain yields three fragments: two antigen-binding Fab fragments, and one Fc fragment that does not bind antigen); (ii) a F(ab')$_2$ fragment, a bivalent fragment comprising two Fab fragments linked by a disulfide bridge at the hinge region (e.g., an antibody digested by pepsin yields two fragments: a bivalent antigen-binding F(ab')$_2$ fragment, and a pFc' fragment that does not bind antigen) and its related F(ab') monovalent unit; (iii) a F$_d$ fragment consisting of the V$_H$ and C$_H$ domains (i.e., that portion of the heavy chain which is included in the Fab); (iv) a F$_v$ fragment consisting of the V$_L$ and V$_H$ domains of a single arm of an antibody, and the related disulfide linked F$_v$; (v) a dAb (domain antibody) or sdAb (single domain antibody) fragment (Ward et al., *Nature* 341:544-546, 1989), which consists of a V$_H$ domain; and (vi) an isolated complementarity determining region (CDR).

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')$_2$, F$_v$), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, hamster) that have the desired specificity, affinity, and capability (Jones et al., *Nature* 321:522-525, 1986; Riechmann et al., *Nature* 332:323-327, 1988; Verhoeyen et al., *Science* 239:1534-1536, 1988).

In some instances, the F$_v$ framework region (FR) residues of a human immunoglobulin are replaced with the corresponding residues in an antibody from a non-human species that has the desired specificity, affinity, and capability. The humanized antibody can be further modified by the substitution of additional residues either in the F$_v$ framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. Nos. 5,225,539 and 5,639,641, Roguska et al., *Proc. Natl. Acad. Sci. USA* 91(3):969-973, 1994; and Roguska et al., *Protein Eng.* 9(10):895-904, 1996 (all incorporated herein by reference). In some embodiments, a "humanized antibody" is a resurfaced antibody. In some embodiments, a "humanized antibody" is a CDR-grafted antibody.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. *Sequences of Proteins of Immunological Interest,* 5th ed., 1991, National Institutes of Health, Bethesda Md.); and (2) an approach based on crystallographic studies of antigen-antibody complexes (Al-lazikani et al., *J. Molec. Biol.* 273:927-948, 1997). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., *Sequences of Immunological Interest,* 5th Ed., Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., *Sequences of Proteins of Immunological Interest,* 5th Ed., Public Health Service, National Institutes of Health, Bethesda, Md. (1991) (incorporated herein by reference). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk, *J. Mol. Biol.* 196:901-917, 1987). The end of the Chothia CDR-H1 loop when numbered using the Kabat numbering convention varies between H32 and H34 depending on the length of the loop. This is because the Kabat numbering scheme places the insertions at H35A and H35B—if neither 35A nor 35B is present, the loop ends at 32; if only 35A is present, the loop ends at 33; if both 35A and 35B are present, the loop ends at 34. The AbM hypervariable regions represent a compromise between the Kabat CDRs and Chothia structural loops, and are used by Oxford Molecular's AbM antibody modeling software.

| Loop | Kabat | AbM | Chiothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 (Kabat Numbering) |
| H1 | H31-H35 | H26-H35 | H26-H32 (Chothia Numbering) |
| H2 | H50-H65 | H50-H58 | H52-H56 |
| H3 | H9S-H102 | H95-H102 | H95-H102 |

The EU index or EU index as in Kabat or EU numbering scheme refers to the numbering system based on the human IgG1 Eu antibody of Edelman et al., 1969, Proc Natl Acad Sci USA 63:78-85, incorporated herein by reference.

The term "human antibody" means an antibody produced by a human or an antibody having an amino acid sequence corresponding to an antibody produced by a human made using any technique known in the art. In certain embodiments, the human antibody does not have non-human sequence. This definition of a human antibody includes intact or full-length antibodies, or antigen-binding fragments thereof.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid or reduce the chance of eliciting an immune response in that species (e.g., human). In certain embodiments, chimeric antibody may include an antibody or antigen-binding fragment thereof comprising at least one human heavy and/or light chain polypeptide, such as, for example, an antibody comprising murine light chain and human heavy chain polypeptides.

The terms "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_d$) or the half-maximal effective concentration ($EC_{50}$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described herein.

By "specifically binds," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

The term "immunoconjugate," "conjugate," or "ADC" as used herein refers to a compound or a derivative thereof that is linked to a cell binding agent (e.g., an antibody or antigen-binding fragment thereof).

A "linker" is any chemical moiety that is capable of linking a compound, usually a drug, such as a cytotoxic agent described herein (e.g., IGN (indolinobenzodiazepine) compounds), to a cell-binding agent such as an antibody or a fragment thereof in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art.

The term "cysteine-engineered antibody" includes an antibody with at least one Cys that is not normally present at a given residue of the antibody light chain or heavy chain. Such Cys, which may also be referred to as "engineered Cys," can be engineered using any conventional molecular biology or recombinant DNA technology (e.g., by replacing the coding sequence for a non-Cys residue at the target residue with a coding sequence for Cys). For example, if the original residue is Ser with a coding sequence of 5'-UCU-3', the coding sequence can be mutated (e.g., by site-directed mutagenesis) to 5'-UGU-3', which encodes Cys. In certain embodiments, the Cys engineered antibody of the invention has an engineered Cys in the heavy chain. In certain embodiments, the engineered Cys is in or near the CH3 domain of the heavy chain.

The term "unpaired cysteine" refers to a cysteine residue located on the cell-binding agent (e.g., an antibody or antigen-binding fragment thereof) that is not involved in forming a disulfide bond with another cysteine residue of the cell-binding agent. In certain embodiments, the unpaired cysteine of an antibody or antigen-binding fragment thereof is a cysteine residue that is not involved in forming an interchain or intrachain disulfide bond. In certain embodiments, the unpaired cysteine is an engineered cysteine residue.

The term "capping agent" refers to a reagent having a thiol —SH group that can form a disulfide with the unpaired cysteine of the CBA. In certain embodiments, the capping agent is a thiol-containing reagent that is used in the production or purification of the CBA (e.g., an antibody or antigen-binding fragment thereof), such as one or more thiol-containing reagent used in the culture medium for producing an antibody or antigen-binding fragment thereof. In certain embodiments, the capping agent is cysteine, glutathione, homocysteine, or a combination thereof. In certain embodiments, the capping agent is immobilized thiol-containing reagents or thiol-affinity resins (e.g., thiopropyl Sepharose 6B). See Guo, J. et al., Nat Protoc. 2014 January; 9(1): 64-75, incorporated herein by reference.

The term "continuous process" as used herein refers to a process in which one or more reaction reagents continue to be added to a reaction while the reaction proceeds and after at least one reaction product has formed. The reaction products can continue to be removed from the reaction as the reaction proceeds.

The term "flow reactor" as used herein refers to any reactor vessel, typically tube like, that is used for continuous reaction chemistry. Flow reactors can be made of stainless steel, glass, polymers, etc.

The term "filter" as used herein refers to a selective barrier that permits the separation of species in a fluid. Separation is achieved by selectively passing (permeating) one or more species of the fluid through the filter while retarding the passage of one or more other species.

The term "feed stream" as used herein refers to a fluid being fed to a filter or membrane for separation of components in the filter or membrane.

The term "retentate" as used herein refers to the portion of the feed stream that does not pass through the filter.

The term "permeate" as used herein refers to the portion of the feed stream that does pass through the filter.

The term "tangential flow filtration" (TFF) as used herein refers to a membrane-based filtration process in which a feed stream passes parallel to a membrane face. One portion of the feed stream passes through the membrane (permeate) while the remainder (retentate) is recirculated back to the feed reservoir. TFF is also referred to as cross-flow filtration. Systems for performing TFF are known and include, for example, a Pellicon-type system (Millipore, Billerica, Mass.), a Sartocon Cassette system (Sartorius AG, Edgewood, N.Y.), and a Centrasette-type system (Pall Corporation, East Hills, N.Y.).

The term "single-pass tangential flow filtration" (SPTFF) as used herein refers to a tangential flow filtration process in which a feed stream passes over the filtration membrane only once. Systems for performing SPTFF are know and include, for example, a Cadance-type system (Pall Corporation, Westborough, Mass.). Systems and methods for performing SPTFF are disclosed, for example, in U.S. Pat. Nos. 7,384,549, 7,510,654, 7,682,511, 7,967,987, 8,157,999, and 8,231,787, each of which is herein incorporated by reference in its entirety.

The term "continuous diafiltration" as used herein refers to a diafiltration process in which selective separation of solutes is achieved in a continuous fashion by mixing a feed stream with a diluent and pumping it across a membrane with the permeate and retentate being removed. The product is not formed in a vessel as filtration progresses; instead it is continuously withdrawn from the system during the course of the filtration. "Countercurrent diafiltration" refers to a continuous diafiltration process in which a process stream (e.g., permeate or retentate) is recycled in diafiltration steps.

The term "in-line monitoring" refers to monitoring an analyte in real-time, e.g., during a production or purification process. In-line monitoring is distinguished from in-process sampling or offline analysis, which do not provide real-time feedback.

The term "in-line process automation technology" refers to any in-line measurement device used to monitor an analyte during a process.

The term "analyte" as used herein is a broad term, and it refers without limitation to a substance or chemical constituent in a fluid that can be analyzed. Analytes may include naturally occurring substances, artificial substances, metabolites, and/or reaction products. In some embodiments, the analyte for measurement in the methods disclosed herein is an antibody or antigen-binding fragment thereof, drug, linker, linker bound to antibody or antigen-binding fragment thereof, linker bound to drug, antibody-drug conjugate (ADC), drug-to-antibody ratio (DAR), and/or impurity.

The term "formulation buffer" as used herein refers to a buffer that permits biological activity of the active ingredient and which contains no additional components that are unacceptably toxic to a subject to which the formulation would be administered.

The terms "cancer" and "cancerous" refer to or describe the physiological condition in mammals in which a population of cells are characterized by unregulated cell growth. "Tumor" and "neoplasm" refer to one or more cells that result from excessive cell growth or proliferation, either benign (noncancerous) or malignant (cancerous) including pre-cancerous lesions.

Examples of cancer include lung cancer (e.g., non-small-cell lung cancer), colorectal cancer, bladder cancer, gastric cancer, pancreatic cancer, renal cell carcinoma, prostate cancer, esophageal cancer, breast cancer, head and neck cancer, uterine cancer, ovarian cancer, liver cancer, cervical cancer, thyroid cancer, testicular cancer, myeloid cancer, melanoma, and lymphoid cancer. In certain embodiments, the cancer is non-small-cell lung cancer, colorectal cancer, gastric cancer or pancreatic cancer. In certain embodiments, the cancer is non-small-cell lung cancer (squamous cell, nonsquamous cell, adenocarcinoma, or large-cell undifferentiated carcinoma), colorectal cancer (adenocarcinoma, gastrointestinal carcinoid tumors, gastrointestinal stromal tumors, primary colorectal lymphoma, leiomyosarcoma, or squamous cell carcinoma) or breast cancer (e.g., triple negative breast cancer (TNBC)). In certain embodiments, cancer is lymphoma and leukemia. In certain embodiments, examples of cancers include AML, CML, ALL (e.g., B-ALL), CLL, myelodysplastic syndrome, basic plasmacytoid DC neoplasm (BPDCN) leukemia, B-cell lymphomas including non-Hodgkin lymphomas (NHL), precursor B-cell lymphoblastic leukemia/lymphoma and mature B-cell neoplasms, such as B-cell chronic lymphocytic leukemia (B-CLL)/small lymphocytic lymphoma (SLL), B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia (HCL), diffuse large B-cell lymphoma (DLBCL), Burkitt's lymphoma, plasmacytoma, plasma cell myeloma, post-transplant lymphoproliferative disorder, Waldenstrom's macroglobulinemia, anaplastic large-cell lymphoma (ALCL), and Hodgkin's leukemia (HL). In certain embodiments, the cancer is BPDCN leukemia. In certain embodiments, the cancer is ALL. In other embodiments, the cancer is AML.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The term "pharmaceutical composition" refers to a preparation which is in such form as to permit the biological activity of the active ingredient to be effective, and which contains no additional components which are unacceptably toxic to a subject to which the composition would be administered. Such composition can be sterile.

A "therapeutically effective amount" of an immunoconjugate as disclosed herein is an amount sufficient to carry out a specifically stated purpose. A "therapeutically effective amount" can be determined empirically and in a routine manner, in relation to the stated purpose.

"Alkyl' or "linear or branched alkyl" as used herein refers to a saturated linear or branched monovalent hydrocarbon radical. In preferred embodiments, a straight chain or branched chain alkyl has thirty or fewer carbon atoms (e.g., $C_1$-$C_{30}$ for straight chain alkyl group and $C_3$-$C_{30}$ for branched alkyl), and more preferably twenty or fewer carbon atoms. Even more preferably, the straight chain or branched chain alkyl has ten or fewer carbon atoms (i.e., $C_1$-$C_{10}$ for straight chain alkyl group and $C_3$-$C_{10}$ for branched alkyl). In other embodiments, the straight chain or branched chain alkyl has six or fewer carbon atoms (i.e., $C_1$-$C_6$ for straight chain alkyl group or $C_3$-$C_6$ for branched chain alkyl). Examples of alkyl include, but are not limited to, methyl, ethyl, 1-propyl, 2-propyl, 1-butyl, 2-methyl-1-propyl, —$CH_2CH(CH_3)_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Moreover, the term "alkyl" as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. As used herein, ($C_x$-$C_{xx}$)alkyl or $C_{x-xx}$alky means a linear or branched alkyl having x-xx carbon atoms.

"Alkenyl" or "linear or branched alkenyl" refers to linear or branched-chain monovalent hydrocarbon radical of two to twenty carbon atoms with at least one site of unsaturation, i.e., a carbon-carbon double bond, wherein the alkenyl radical includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like. Preferably, the alkenyl has two to ten carbon atoms. More preferably, the alkyl has two to four carbon atoms.

"Alkynyl" or "linear or branched alkynyl" refers to a linear or branched monovalent hydrocarbon radical of two to twenty carbon atoms with at least one site of unsaturation, i.e., a carbon-carbon, triple bond. Examples include, but are not limited to, ethynyl, propynyl, 1-butynyl, 2-butynyl, 1-pentynyl, 2-pentynyl, 3-pentynyl, hexynyl, and the like. Preferably, the alkynyl has two to ten carbon atoms. More preferably, the alkynyl has two to four carbon atoms.

The terms "cyclic alkyl" and "cycloalkyl" can be used interchangeably. As used herein, the term refers to the radical of a saturated carbocyclic ring. In preferred embodiments, cycloalkyls have from 3 to 10 carbon atoms in their ring structure, and more preferably from 5 to 7 carbon atoms in the ring structure. In some embodiments, the two cyclic rings can have two or more atoms in common, e.g., the rings are "fused rings." Suitable cycloalkyls include, but are not limited to cycloheptyl, cyclohexyl, cyclopentyl, cyclobutyl and cyclopropyl. In some embodiments, the cycloalkyl is a monocyclic group. In some embodiments, the cycloalkyl is a bicyclic group. In some embodiments, the cycloalkyl is a tricyclic group.

The term "cycloalklalkyl" refers to an alkyl group described above that is substituted with a cycloalkyl group.

The term "cyclic alkenyl" refers to a carbocyclic ring radical having at least one double bond in the ring structure.

The term "cyclic alkynyl" refers to a carbocyclic ring radical having at least one triple bond in the ring structure.

The term "aryl" or "aromatic ring" as used herein, include substituted or unsubstituted single-ring aromatic groups in which each atom of the ring is carbon. Preferably the ring is a 5- to 7-membered ring, more preferably a 6-membered ring. Aryl groups include, but are not limited to, phenyl, phenol, aniline, and the like. The terms "aryl" also includes "polycyclyl", "polycycle", and "polycyclic" ring systems having two or more rings in which two or more atoms are common to two adjoining rings, e.g., the rings are "fused rings," wherein at least one of the rings is aromatic, e.g., the other cyclic rings can be cycloalkyls, cycloalkenyls, cycloalkynyls, or aromatic rings. In some preferred embodiments, polycycles have 2-3 rings. In certain preferred embodiments, polycyclic ring systems have two cyclic rings in which both of the rings are aromatic. Each of the rings of the polycycle can be substituted or unsubstituted. In certain embodiments, each ring of the polycycle contains from 3 to 10 carbon atoms in the ring, preferably from 5 to 7. For example, aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl, and the like. In some embodiments, the aryl is a single-ring aromatic group. In some embodiments, the aryl is a two-ring aromatic group. In some embodiments, the aryl is a three-ring aromatic group.

The terms "heterocycle," "heterocyclyl," and "heterocyclic ring" as used herein, refers to substituted or unsubstituted non-aromatic ring structures of 3- to 18-membered rings, preferably 3- to 10-membered rings, more preferably 3- to 7-membered rings, whose ring structures include at least one heteroatom, preferably one to four heteroatoms, more preferably one or two heteroatoms. In certain embodiments, the ring structure can have two cyclic rings. In some embodiments, the two cyclic rings can have two or more atoms in common, e.g., the rings are "fused rings." Heterocyclyl groups include, for example, piperidine, piperazine, pyrrolidine, morpholine, lactones, lactams, and the like. Heterocycles are described in Paquette, Leo A.; "Principles of Modem Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Examples of heterocyclic rings include, but are not limited to, tetrahydrofurane, dihydrofuran, tetrahydrothiene, tetrahydropyran, dihydropyran, tetrahydrothiopyran, thiomorpholine, thioxane, homopiperazine, azetidine, oxetane, thietane, homopiperidine, piperidine, piperazine, pyrrolidine, morpholine, oxepane, thiepane, oxazepine, diazepine, thiazepine, 2-pyrroline, 3-pyrroline, indoline, 2H-pyrane, 4H-pyrane, dioxane, 1,3-dioxolane, pyrazoline, dithiane, dithiolane, dihydropyrane, dihydrothiene, dihydrofurane, pyrazolidinylimidazolane, imidazolidine, 3-azabicyco[3.1.0]hexane, 3-azabicyclo [4.1.0]heptane, and azabicyclo[2.2.2]hexane. Spiro moieties are also included within the scope of this definition. Examples of a heterocyclic group wherein ring atoms are substituted with oxo (=O) moieties are pyrimidinone and 1,1-dioxo-thiomorpholine.

The term "heteroaryl" or "heteroaromatic ring" as used herein, refers to substituted or unsubstituted aromatic single ring structures, preferably 6- to 18-member rings, preferably 5- to 7-membered rings, more preferably 5- to 6-membered rings, whose ring structures include at least one heteroatom (e.g., O, N, or S), preferably one to four or one to three heteroatoms, more preferably one or two heteroatoms. When two or more heteroatoms are present in a heteroaryl ring, they may be the same or different. The term "heteroaryl" also includes "polycyclyl", "polycycle", and "polycyclic" ring systems having two or more cyclic rings in which two or more ring atoms are common to two adjoining rings, e.g., the rings are "fused rings," wherein at least one of the rings is heteroaromatic, e.g., the other cyclic rings can be cycloalkyls, cycloalkenyls, cycloalkynyls, aryls, heteroaromatics, and/or heterocyclyls. In some preferred embodiments, polycyclic heteroaryls have 2-3 rings. In certain embodiments, preferred polycyclic heteroaryls have two cyclic rings in which both of the rings are aromatic. In certain embodiments, each ring of the polycycle contains from 3 to 10 atoms in the ring, preferably from 5 to 7 atoms in the ring. For examples, heteroaryl groups include, but are not limited to, pyrrole, furan, thiophene, imidazole, oxazole, thiazole, pyrazole, pyridine, pyrazine, pyridazine, quinoline, pyrimidine, indolizine, indole, indazole, benzimidazole, benzothiazole, benzofuran, benzothiophene, cinnoline, phthalazine, quinazoline, carbazole, phenoxazine, quinoline, purine and the like. In some embodiments, the heteroaryl is a single-ring aromatic group. In some embodiments, the heteroaryl is a two-ring aromatic group. In some embodiments, the heteroaryl is a three-ring aromatic group.

The heterocycle or heteroaryl groups can be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or O-carboline.

The heteroatoms present in heteroaryl or heterocyclyl include the oxidized forms such as NO, SO, and $SO_2$.

In some embodiments, the heteroaromatic ring is a 5- to 18-membered ring.

The term "halo" or "halogen" refers to fluorine (F), chlorine (Cl), bromine (Br) or iodine (I). In some embodiments, the halogen is fluorine. In some embodiments, the halogen is chlorine. In some embodiments, the halogen is bromine. In some embodiments, the halogen is iodine. As used herein, the term "haloalkyl" refers to an alkyl, as defined herein, that is substituted by one or more halo groups as defined herein. The haloalkyl can be monohaloalkyl, dihaloalkyl or polyhaloalkyl. A monohaloalkyl can have one fluoro, chloro, bromo, or iodo substituent. Dihaloalkyl or polyhaloalkyl can be substituted with two or more of the same halo atoms or a combination of different halo groups. Examples of haloalkyl include, but are not limited to, fluoromethyl, difluoromethyl, trifluoromethyl, chloroamethyl, dichloromethyl, trichloromethyl, pentafluoroethyl, heptafluoropropyl, diflurochloromethyl, dichlorofluoromethyl, difluoroehthyl, diflosoropropyl, dichloroethyl and dichloropropyl.

"Alkoxy" used herein refers to alkyl-O—, wherein alkyl is defined herein above. Examples of alkoxy include, not are not limited to, methoxy, ethoxy, propoxy, 2-propoxy, butoxy, tert-butoxy, pentyloxy, hexyloxy, and the like.

The alkyl, haloalkyl, alkoxy, alkenyl, alkynyl, cyclic alkyl, cyclic alkenyl, cyclic alkynyl, carbocyclyl, aryl, heterocyclyl and heteroaryl described above can be optionally substituted with one or more (e.g., 2, 3, 4, 5, 6 or more) substituents.

Unless specifically stated as "unsubstituted," references to chemical moieties herein are understood to also include substituted variants. For example, reference to an "alkyl" group or moiety implicitly includes both substituted and unsubstituted variants. Examples of substituents on chemical moieties includes but is not limited to, halogen, hydroxyl, carbonyl (such as carboxyl, alkoxycarbonyl, formyl, or acyl), thiocarbonyl (such as thioester, thioacetate, or thioformate), alkoxyl, alkylthio, acyloxy, phosphoryl, phosphate, phosphonate, amino, amido, amidine, imine, cyano, nitro, azido, sulfhydryl, alkylthio, sulfate, sulfonate, sulfamoyl, sulfonamido, sulfonyl, heterocyclyl, aralkyl, or aryl or heteroaryl moiety.

"Optional" or "optionally" means that the subsequently described circumstance may or may not occur, so that the application includes instances where the circumstance occurs and instances where it does not. For example, the phrase "optionally substituted" means that a nonhydrogen substituent may or may not be present on a given atom, and, thus, the application includes structures wherein a nonhydrogen substituent is present and structures wherein a nonhydrogen substituent is not present.

The term "substituted" refers to moieties having substituents replacing a hydrogen on one or more carbons, nitrogens, oxygens or sulfurs atoms. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a carbon of a substituent is described as being optionally substituted with one or more of a list of substituents, one or more of the hydrogens on the carbon (to the extent there are any) can separately and/or together be replaced with an independently selected optional substituent. If a nitrogen of a substituent is described as being optionally substituted with one or more of a list of substituents, one or more of the hydrogens on the nitrogen (to the extent there are any) can each be replaced with an independently selected optional substituent. One exemplary substituent can be depicted as —NR'R", wherein R' and R" together with the nitrogen atom to which they are attached, can form a heterocyclic ring. The heterocyclic ring formed from R' and R" together with the nitrogen atom to which they are attached can be partially or fully saturated. In some embodiments, the heterocyclic ring consists of 3 to 7 atoms. In other embodiments, the heterocyclic ring is selected from pyrrolyl, imidazolyl, pyrazolyl, triazolyl, tetrazolyl, isoxazolyl, pyridyl and thiazolyl.

This specification uses the terms "substituent," "radical," and "group" interchangeably.

If a group of substituents are collectively described as being optionally substituted by one or more of a list of substituents, the group can include: (1) unsubstitutable substituents, (2) substitutable substituents that are not substituted by the optional substituents, and/or (3) substitutable substituents that are substituted by one or more of the optional substituents.

If a substituent is described as being optionally substituted with up to a particular number of non-hydrogen substituents, that substituent can be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. Such substituents, in non-limiting examples, can be selected from a linear, branched or cyclic alkyl, alkenyl or alkynyl having from 1 to 10 carbon atoms, aryl, heteroaryl, heterocyclyl, halogen, guanidinium [—NH(C=NH)NH$_2$], —OR$^{100}$, NR$^{101}$R$^{102}$, —NO$_2$, —NR$^{101}$COR$^{102}$, —SR$^{100}$, a sulfoxide represented by —SOR$^{101}$, a sulfone represented by —SO$_2$R$^{101}$, a sulfonate —SO$_3$M, a sulfate —OSO$_3$M, a sulfonamide represented by —SO$_2$NR$^{101}$R$^{102}$, cyano, an azido, —COR$^{101}$, —OCOR$^{101}$, —OCONR$^{101}$R$^{102}$ and a polyethylene glycol unit (—OCH$_2$CH$_2$)$_n$R$^{101}$ wherein M is H or a cation (such as Na$^+$ or K$^+$); R$^{100}$, R$^{102}$ and R$^{103}$ are each independently selected from H, linear, branched or cyclic alkyl, alkenyl or alkynyl having from 1 to 10 carbon atoms, a polyethylene glycol unit (—OCH$_2$CH$_2$)$_n$—R$^{104}$ wherein n is an integer from 1 to 24, an aryl having from 6 to 10 carbon atoms, a heterocyclic ring having from 3 to 10 carbon atoms and a heteroaryl having 5 to 10 carbon atoms; and R$^{104}$ is H or a linear or branched alkyl having 1 to 4 carbon atoms, wherein the alkyl, alkenyl, alkynyl, aryl, heteroaryl and heterocyclyl in the groups represented by R$^{100}$, R$^{101}$, R$^{102}$, R$^{103}$ and R$^{104}$ are optionally substituted with one or more (e.g., 2, 3, 4, 5, 6 or more) substituents independently selected from halogen, —OH, —CN, —NO$_2$ and unsubstituted linear or branched alkyl having 1 to 4 carbon atoms. Preferably, the substituents for the optionally substituted alkyl, alkenyl, alkynyl, cyclic alkyl, cyclic alkenyl, cyclic alkynyl, carbocyclyl, aryl, heterocyclyl and heteroaryl described above include halogen, —CN, —NR$^{102}$R$^{103}$, —CF$_3$, —OR$^{101}$ aryl, heteroaryl, heterocyclyl, —SR$^{101}$, —SOR$^{101}$, —SO$_2$R$^{101}$ and —SO$_3$M.

The number of carbon atoms in a group can be specified herein by the prefix "C$_{x-xx}$" or "C$_x$-C$_{xx}$", wherein x and xx are integers. For example, "C$_{1-4}$alkyl" or "C1-C4 alkyl" is an alkyl group having from 1 to 4 carbon atoms.

The term "compound," "cytotoxic agent," or "cytotoxic compound," are used interchangeably. They are intended to include compounds for which a structure or formula or any derivative thereof has been disclosed in the present invention or a structure or formula or any derivative thereof that has been incorporated by reference. The term also includes, stereoisomers, geometric isomers, tautomers, solvates, metabolites, and salts (e.g., pharmaceutically acceptable salts) of a compound of all the formulae disclosed in the present invention. The term also includes any solvates, hydrates, and polymorphs of any of the foregoing. The specific recitation of "stereoisomers," "geometric isomers," "tautomers," "solvates," "metabolites," "salt", "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms.

The term "chiral" refers to molecules that have the property of non-superimposability of the mirror image partner, while the term "achiral" refers to molecules that are superimposable on their mirror image partner.

The term "stereoisomer" refers to compounds that have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as crystallization, electrophoresis and chromatography.

"Enantiomers" refer to two stereoisomers of a compound that are non-superimposable mirror images of one another.

Stereochemical definitions and conventions used herein generally follow S. P. Parker, Ed., McGraw-Hill, *Dictionary of Chemical Terms* (1984) McGraw-Hill Book Company, New York; and Eliel, E. and Wilen, S., *Stereochemistry of Organic Compounds*, John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and I or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies that are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt can involve the inclusion of another molecule such as an acetate ion, a succinate ion or other counter ion. The counter ion can be any organic or inorganic moiety that stabilizes the charge on the parent compound. Furthermore, a pharmaceutically acceptable salt can have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt can be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt can be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the term "solvate" means a compound that further includes a stoichiometric or non-stoichiometric amount of solvent such as water, isopropanol, acetone, ethanol, methanol, DMSO, ethyl acetate, acetic acid, and ethanolamine dichloromethane, 2-propanol, or the like, bound by non-covalent intermolecular forces. Solvates or hydrates of the compounds are readily prepared by addition of at least one molar equivalent of a hydroxylic solvent such as methanol, ethanol, 1-propanol, 2-propanol or water to the compound to result in solvation or hydration of the imine moiety.

The phrase "pharmaceutically acceptable" indicates that the substance or composition must be compatible chemically and/or toxicologically, with the other ingredients comprising a formulation, and/or the mammal being treated therewith.

The term "amino acid" refers to naturally occurring amino acids or non-naturally occurring amino acid. In one embodiment, the amino acid is represented by $NH_2$—$C(R^{aa}R^{aa'})$—$C(=O)OH$, wherein $R^{aa}$ and $R^{aa'}$ are each independently H, an optionally substituted linear, branched or cyclic alkyl, alkenyl or alkynyl having 1 to 10 carbon atoms, aryl, heteroaryl or heterocyclyl or $R^{aa}$ and the N-terminal nitrogen atom can together form a heterocyclic ring (e.g., as in proline). The term "amino acid residue" refers to the corresponding residue when one hydrogen atom is removed from the amine and/or carboxy end of the amino acid, such as —NH—$C(R^{aa'}R^{aa})$—$C(=O)$—.

The term "cation" refers to an ion with positive charge. The cation can be monovalent (e.g., $Na^+$, $K^+$, $NH_4^+$ etc.), bi-valent (e.g., $Ca^{2+}$, $Mg^{2+}$, etc.) or multi-valent (e.g., $Al^{3+}$ etc.). Preferably, the cation is monovalent.

The term "thiol-reactive group" refers to a group that can react with a thiol (—SH) group to form a covalent bond. Exemplary thiol-reactive groups include, but are not limited to, maleimide, haloacetyl, haloacetamide, vinyl sulfone, vinyl sulfonamide or vinyl pyridine. In one embodiment, the thiol-reactive group is maleimide.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

2. Methods of Preparing Immunoconjugates

In a first aspect, the present invention provides a method of preparing a cell-binding agent-cytotoxic agent conjugate comprising a cell-binding agent (CysCBA) having one or more unpaired cysteine residues covalently linked to a cytotoxic agent, wherein the method comprises the steps of:

(a) reacting a reducing agent with a capped cell-binding agent (cCysCBA) having one or more unpaired cysteine residues capped with a capping agent to form a reduced cell-binding agent, wherein the capping agent is removed to form a free thiol (—SH) group in the reduced cell-binding agent;
(b) reacting the reduced cell-binding agent with a selective oxidizing agent to form the CysCBA, wherein the free thiol group in the unpaired cysteine residue is not oxidized; and
(c) reacting the CysCBA with a compound of formula (I):

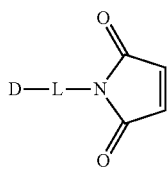

(I)

or a pharmaceutically acceptable salt thereof, thereby forming the conjugate, wherein the reduced cell-binding agent in step (a) is used in step (b) without purification; and the CysCBA step (b) is used in step (c) without purification, wherein:
D is a cytotoxic agent; and
L is a linker.

In a second aspect, the present invention provides a continuous method of preparing a cell-binding agent-cytotoxic agent conjugate (ADC) comprising a cell-binding agent (CysCBA) having one or more unpaired cysteine residues covalently linked to a cytotoxic agent, wherein the method comprises the steps of:
(a) reacting a reducing agent with a capped cell-binding agent (cCysCBA) having one or more unpaired cysteine residues capped with a capping agent to form a reduced cell-binding agent, wherein the capping agent is removed to form a free thiol (—SH) group in the reduced cell-binding agent;
(b) reacting the reduced cell-binding agent with a selective oxidizing agent to form the CysCBA, wherein the free thiol group in the unpaired cysteine residue is not oxidized; and
(c) reacting the CysCBA with a compound of formula (I):

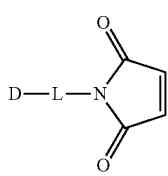

(I)

or a pharmaceutically acceptable salt thereof, thereby forming the conjugate,
wherein the reduced cell-binding agent in step (a) is used in step (b) without purification; the CysCBA step (b) is used in step (c) without purification, and any one or more steps selected from steps (a) to (c) are performed continuously, wherein:
D is a cytotoxic agent; and
L is a linker.

In some embodiments, steps (a) to (c) in methods of the second aspect described above are performed continuously.

In the continuous methods provided herein, components continue to be added to an ongoing process, and products can be removed throughout the process instead of in bulk at the end of the process. For example, in step (a) (reduction step) of the continuous methods described above, the reducing agent and/or the capped cell-binding agent (cCysCBA) continue to be added to the reduction reaction while the reaction proceeds and after at least one product, i.e., the reduced cell-binding agent, has formed. In step (b) (oxidation step) of the continuous methods described above, the reduced cell-binding agent and/or the selective oxidizing agent continue to be added to the oxidation reaction while the reaction proceeds and after at least one product, i.e., the CysCBA has formed. In step (c) (conjugation step) of the continuous methods described above, the CysCBA and/or the compound of formula (I) continue to be added to the conjugation reaction while the reaction proceeds and after at least one conjugation reaction product (ADC) has formed. Similarly, in downstream continuous concentration, purification, and/or buffer exchange processes, ADCs, buffers, and/or other components continue to be added to the concentration purification, and/or buffer exchanges processes as those processes proceed, and concentrated, purified, and buffer exchanged ADCs can be continuously removed from those ongoing processes. Accordingly, an entire ADC process can be continuous (see e.g., FIGS. 5 and 6).

The present inventors have demonstrated that the methods of preparing ADCs described herein can be performed continuously using flow reactors. Flow reactors allow one or more reagents to be continuously added to a reaction while the reaction proceeds and after at least one reaction product has formed. The use of flow reactors in the continuous methods allows for control of the reaction and versatility of the method (e.g., rapid temperature changes/tighter temperature control, mixing mediated by diffusion therefore more uniform, and no constraints by vessels or suite limitations) and improved scalability of the method (i.e., the conventional scale-up risks of batch processing do not apply and space-time yield is optimized (e.g., performing a pseudo scale up (increase output) by running the current process for a longer time)).

In certain embodiments, plug flow reactors (PFRs) are used for the continuous methods of the present invention.

In certain embodiments, a reaction vessel (e.g., a continuously stirred tank reactor (CSTR)) is used for the continuous addition of the reactants before one or more reagents are added to the flow reactor. Use of the reaction vessel (e.g., CSTRs) and flow reactors (e.g., plug flow reactors) in series has the advantage of reducing the overall volume requirements, improving mixing between reactant streams, and increasing risk mitigation capabilities including broader residence time distributions.

In certain embodiments, for reduction step (a) in the continuous method described herein, the reducing agent and the capped cell-binding agent (cCysCBA) are continuously added (e.g., using a feed pump for the reducing agent and a separate feed pump for cCysCBA) to a reaction vessel (e.g., a CSTR) while the reaction proceeds and after at least one product, i.e., the reduced cell-binding agent, has formed. The reaction mixture is withdrew continuously from the reaction vessel (e.g., CSTR) using a pump (e.g., peristaltic pump) and fed through a flow reactor (e.g., PFR). In some embodiments, the volumetric flow rate for withdrawing materials from the reaction vessel (e.g., CSTR) is the same as the combined flow rates for the reducing agent and the cCysCBA being added into the CSTR, i.e., the flow rates in and out of the reaction vessel (e.g., CSTR) are the same.

Similarly, for selective reoxidation step (b) in the continuous method described herein, the reduced cell-binding agent and the selective oxidizing agent are continuously added (e.g., using a feed pump for the reduced cell-binding agent and a separate feed pump for the selective oxidizing agent) to a reaction vessel (e.g., CSTR) while the reaction proceeds and after at least one product, i.e., the CysCBA, has formed. The reaction mixture is withdrew continuously from the reaction vessel (e.g., CSTR) using a pump (e.g., peristaltic pump) and fed through a flow reactor (e.g., PFR). In some embodiments, the volumetric flow rate for withdrawing materials from the reaction vessel (e.g., CSTR) is the same as the combined flow rates for the reduced cell-binding agent and the selective oxidizing agent being added into the CSTR, i.e., the flow rates in and out of the reaction vessel (e.g., CSTR) are the same.

In some embodiments, for conjugation step (c) in the continuous method described herein, the CysCBA and the compound of formula (I) are continuously added (e.g., using a feed pump for the CysCBA and a separate feed pump for the compound of formula (I)) to a reaction vessel (e.g., CSTR) while the reaction proceeds and after at least one product, i.e., the ADC, has formed. The reaction mixture is withdrew continuously from the reaction vessel (e.g., CSTR) using a pump (e.g., peristaltic pump) and fed through a flow reactor (e.g., PFR). In some embodiments, the volumetric flow rate for withdrawing materials from the CSTR is the same as the combined flow rates for the CysCBA and the compound of formula (I) being added into the reaction vessel (e.g., CSTR), i.e., the flow rates in and out of the reaction vessel (e.g., CSTR) are the same.

In some embodiments, kinetic data for each reaction are generated and a desired target conversion for each reaction is specified. Based on these results the CSTR and PFR volumes for each reaction are specified based on the inner diameter of tubing used and volumetric flow rates required to achieve a desired residence time for each reaction step.

In a third aspect, the present invention provides a continuous method of preparing a cell-binding agent-cytotoxic agent conjugate (ADC) comprising a cell-binding agent (CysCBA) having one or more unpaired cysteine residues covalently linked to a cytotoxic agent, wherein the method comprises the steps of:

(a) reacting a reducing agent with a capped cell-binding agent (cCysCBA) having one or more unpaired cysteine residues capped with a capping agent to form a reduced cell-binding agent, wherein the capping agent is removed to form a free thiol (—SH) group in the reduced cell-binding agent;

(b) reacting the reduced cell-binding agent with a selective oxidizing agent to form the CysCBA, wherein the free thiol group in the unpaired cysteine residue is not oxidized; and (c) reacting the CysCBA with a compound of formula (I):

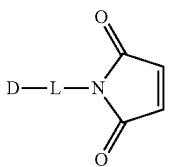

(I)

or a pharmaceutically acceptable salt thereof, thereby forming the conjugate;

(d) removing unconjugated compound of formula (I); and optionally (e) exchanging the conjugate into a stable buffer;

wherein the reduced cell-binding agent in step (a) is used in step (b) without purification; the CysCBA step (b) is used in step (c) without purification, any one or more steps selected from steps (a) to (e) are performed continuously, and single-pass tangential flow filtration (SPTFF) and/or countercurrent diafiltration is used to remove the unconjugated drug and/or exchange the ADC into the stable buffer; and wherein:

D is a cytotoxic agent; and

L is a linker.

In some embodiments, for the continuous method described in the third aspect, the method comprises the steps (a) to (d). In some embodiment, all of the steps (a) to (d) are performed continuously. In some embodiments, only step (d) is performed continuously.

In some embodiments, for the continuous method described in the third aspect, the method comprises the steps (a) to (e). In some embodiments, all of the steps (a) to (e) are performed continuously. In some embodiments, only steps (d) and (e) are performed continuously.

The present inventors have also demonstrated that continuous ADC processing can be accomplished using single-pass tangential flow filtration (SPTFF), which can successfully separate unconjugated drug (i.e., compound of formula (I)) from ADCs). ADC processing can involve conjugation (formation) of the ADC (i.e., step (c) described above), concentration of the ADC, purification of the ADC, and/or formulation of the ADC. Although it is particularly useful for the entire process from ADC conjugation to formulation to be continuous, it is also possible to combine continuous processing steps with batch processing steps. In addition, it is possible for upstream processing steps (e.g., the preparation of an antibody, i.e., steps (a) and (b) in the methods describes here) to be continuous and to feed continuously into the ADC conjugation.

Bulk (conventional) diafiltration involves priming a tangential flow filtration (TFF) system with a first buffer A (the buffer that a product is initially in). The product is then added to a retentate vessel where it mixes with the prime volume. A feed pump for the retentate vessel pumps product from the retentate over the TFF membrane, where it is either retained (and returns to the retentate) or discarded to waste. Another pump (the diafiltration pump) would feed from the vessel to buffer B contained in a separate vessel (the buffer into which the product will be exchanged) with a feed line from the vessel into the retentate vessel. Both pumps are started and the product in the retentate vessel begins passing over the TFF membrane. As buffer is removed via the waste stream, the volume in the retentate is maintained by adding Buffer B (in equal volume) to the retentate vessel. As a result, the product slowly is exchanged into Buffer B.

SPTFF uses a related concept of exchanging the product initially in Buffer A into Buffer B. However, the product only ever makes a single-pass over the membrane so all of the appropriate volume of Buffer B to achieve complete buffer exchange must be achieved. To do this, SPTFF can add Buffer B over stacked stages. The product, therefore, passes through the membranes only once: entering in Buffer A and exiting the module in Buffer B.

Figure 6:
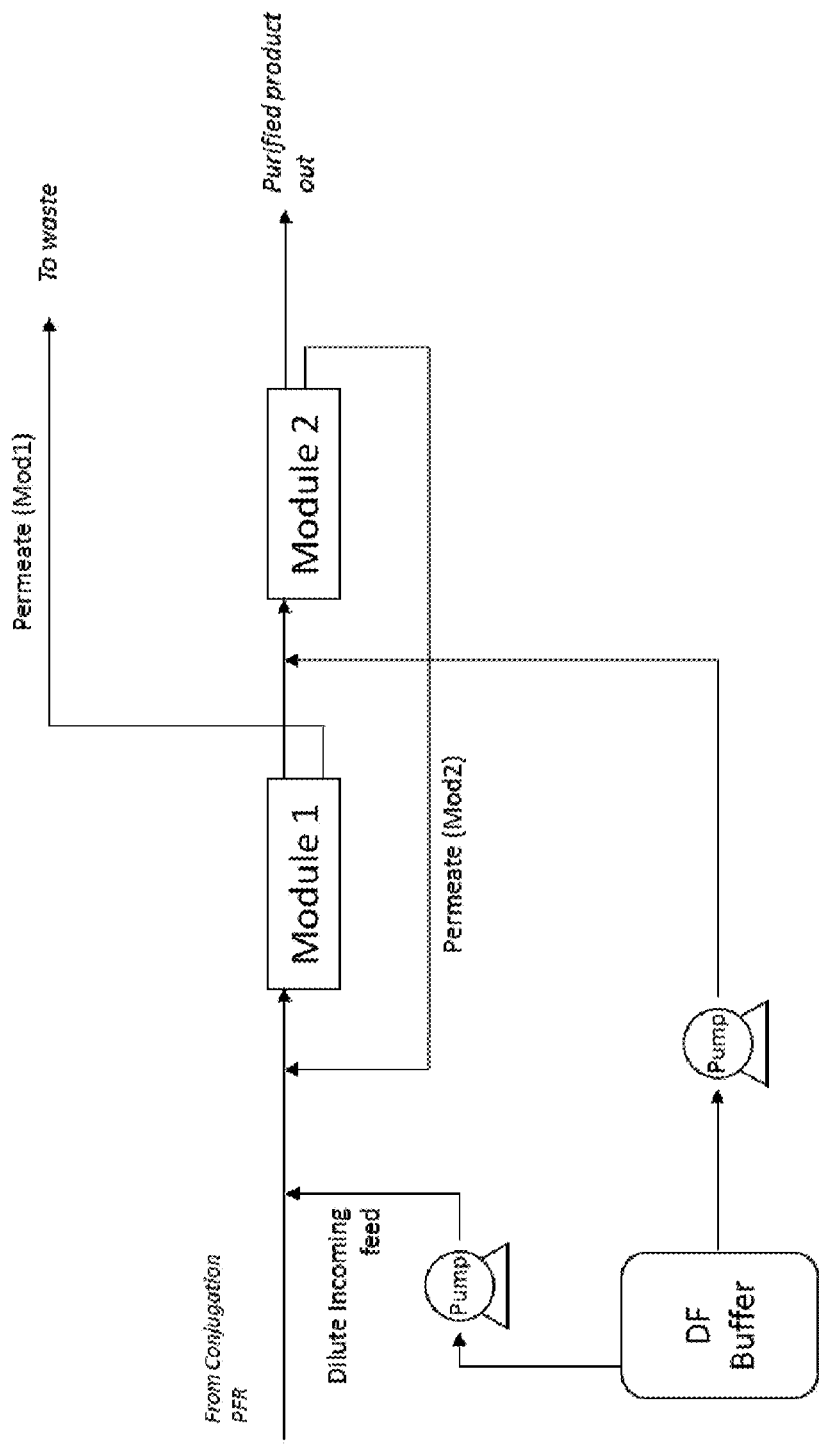
FIG. 6 shows countercurrent TFF purification for integrated manufacturing process of the CD123-targeting ADC described in Example 5.
Figure 7:
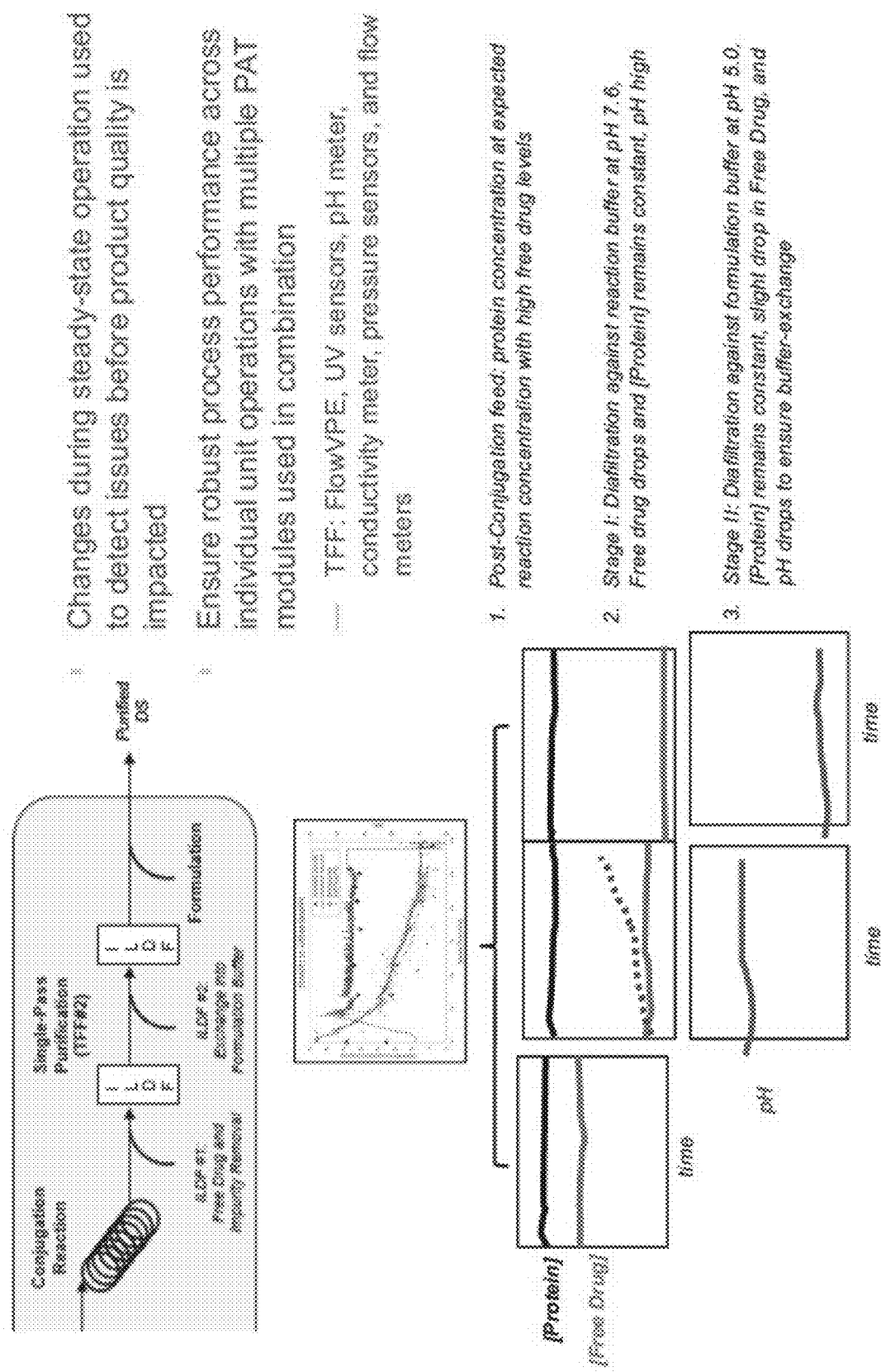
FIG. 7 shows how the use of in-line process automation technology (PAT) can be used to increase control and detectability.
Figure 8:
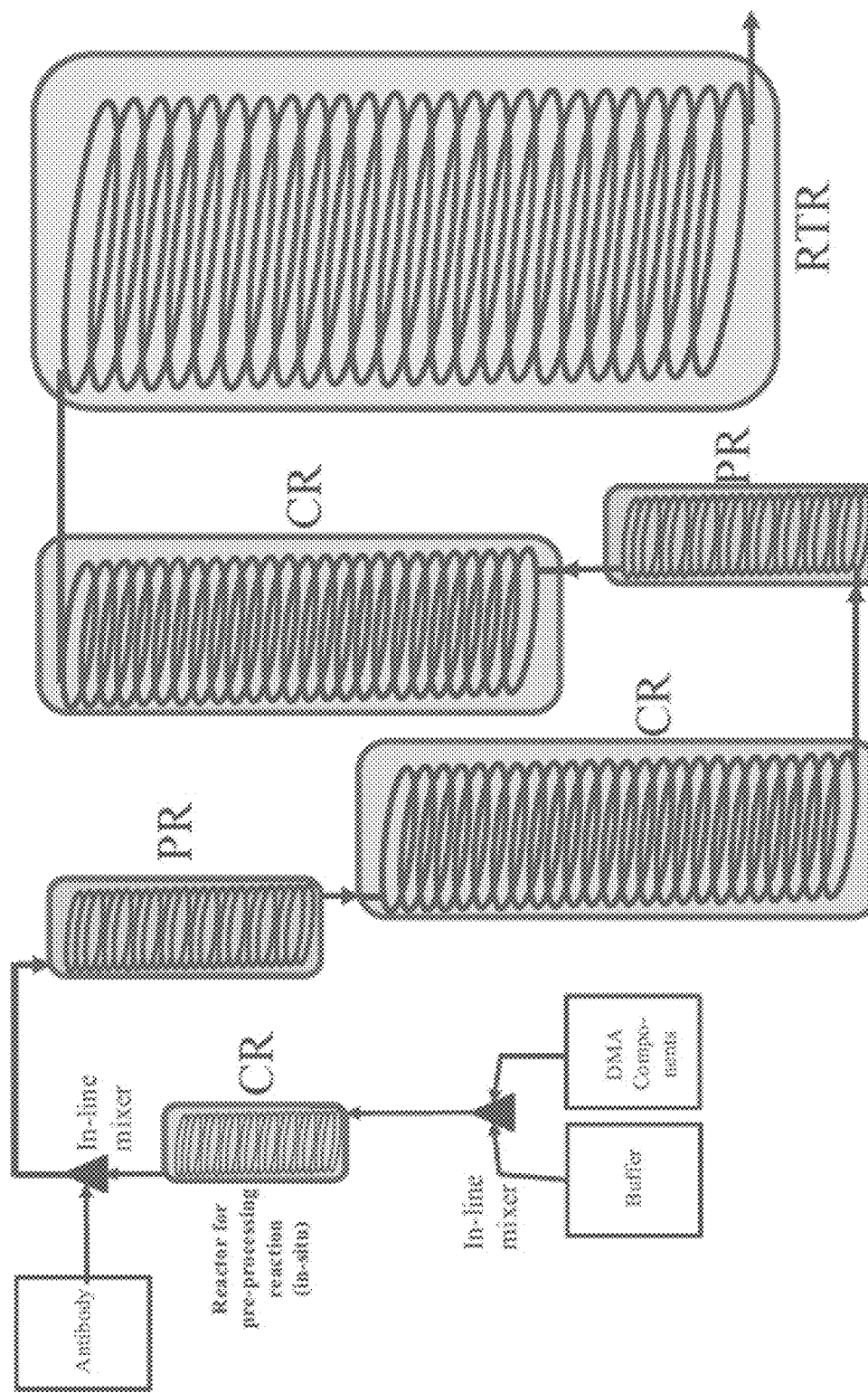
FIG. 8 shows a schematic of heating and cooling reactors that could be used to pulse a conjugation reaction with an elevated temperature. In the Pulsing Reactors (labeled "PR"), the jacket temperature is elevated so that the reaction components contained within the coil are heated temporarily to induce a short temperature excursion. Then, in the Cooling Reactors (labeled "CR"), the jacket temperature is kept at a cooler temperature to let the reaction components within the coil cool back down from the elevated temperature. This can reduce the amount of aggregation occurring during the reaction. The Residence Time Reactor (RTR) maintains the desired reaction temperature after pulsing is complete, and its volume can be based on the desired reaction time.

Similarly, continuous ADC processing can be accomplished using countercurrent diafiltration. Countercurrent diafiltration involves two or more SPTFF (e.g., Module 1, Module 2 etc.). In some embodiments, countercurrent diafiltration involves two modules of SPTFF, in which the retentate from Module 1 is combined with an additional feed of the diafiltration buffer and then directly fed into Module 2 and the permeate from Module 2 is recycled and combined with the feed to Module 1. An exemplary countercurrent diafiltration is shown in FIG. 6. The unpurified crude ADC product is combined with a stream of diafiltration (DF) buffer and then fed through Module 1 of the countercurrent TFF purification unit. The permeate from Module 1 is removed via the waste stream and the retentate from Module 1 is combined with an additional feed of DF buffer and then fed through Module 2. The purified ADC is recovered from the retentate of Module 2 and the permeate from Module 2 is recycled and combined with the feed to Module 1.

Accordingly, continuous ADC processing methods provided herein (e.g., using SPTFF and/or countercurrent diafiltration) can reduce processing time, improve yield, and/or improve product consistency as compared to batch ADC processing. Continuous ADC processing methods provided herein (e.g., using SPTFF and/or countercurrent diafiltration) can also eliminate hold steps used in batch conjugation processes. Continuous ADC processing methods provided herein (e.g., using SPTFF and/or countercurrent diafiltration) can also allow for use of smaller equipment. SPTFF is also advantageous because antibodies that are sensitive to oxidation, potentially caused by shear forces, may be better suited for SPTFF.

The use of SPTFF can allow for continuous addition and/or removal of components from the conjugation reaction. Thus, SPTFF can be used to prepare reagents for ADC conjugation and for processing assembled ADCs. SPTFF can enable continuous ADC processing so that all (or a subset) of the processing steps for a particular ADC (e.g., production, concentration, purification, and/or formulation) can occur simultaneously. Countercurrent diafiltration can also be used to prepare reagents for ADC conjugation and for processing assembled ADCs.

According to the methods provided herein, SPTFF can be used to concentrate an ADC, to purify an ADC, and/or to formulate an ADC (e.g., by exchanging an ADC into a formulation buffer). SPTFF can be used to transfer an ADC from a first buffer to a second buffer. Countercurrent diafiltration can also be used to concentrate an ADC, to purify an ADC, and/or to formulate an ADC (e.g., by exchanging an ADC into a formulation buffer), and countercurrent diafiltration can also be used to transfer an ADC from a first buffer to a second buffer.

In some methods provided herein, SPTFF is used throughout ADC production, purification, and formulation, making the entire process from ADC production to formulation continuous. In some methods provided herein, countercurrent diafiltration is used throughout ADC production, purification, and formulation, making the entire process from ADC production to formulation continuous.

In some methods provided herein, SPTFF is used in combination with conventional TFF such that some portions of the processes are continuous, whereas other portions are performed in batches. For example, an antibody or antigen-binding fragment thereof can be buffer-exchanged prior to conjugation using conventional (batch) TFF and then fed into a continuous process, wherein SPTFF is used for downstream processes. Countercurrent diafiltration can be used in place of or in combination with SPTFF in such methods.

Regardless of whether the process for putting an antibody in buffer for conjugation is performed in a batch or continuous fashion, the ADC concentration and purification processes in the downstream of the conjugation reaction can use SPTFF and be performed in a continuous fashion or can use conventional TFF and be performed in a batch fashion. Similarly, regardless of whether the process for putting an antibody in buffer for conjugation is performed in a batch or continuous process, and regardless of whether the ADC is concentrated and purified using a batch or continuous process, the ADC can be formulated using SPTFF in a continuous fashion or using conventional TFF in a batch fashion. Countercurrent diafiltration can be used in place of or in combination with SPTFF in such methods.

In some embodiments, at least two steps in an ADC process are performed using SPTFF. For example, in some embodiments, SPTFF is used to transfer an antibody or antigen-binding fragment thereof into a conjugation buffer and used to concentrate and purify the ADC after it is formed, while either SPTFF or TFF is used to exchange the ADC into formulation buffer. In some embodiments, SPTFF is used to transfer an antibody or antigen-binding fragment thereof into a conjugation buffer and used to exchange a purified ADC into formulation buffer, while either SPTFF or TFF is used to concentrate and purify the ADC after it is formed. In some embodiments, SPTFF is used to concentrate and purify the ADC and is used to exchange the concentrated and purified ADC into formulation buffer, wherein either SPTFF or TFF is used to transfer the antibody or antigen-binding fragment thereof into a conjugation buffer.

SPTFF can use an ultrafiltration membrane, e.g., in methods of concentrating an ADC. SPTFF can use a diafiltration membrane, e.g., in methods of purifying an ADC and/or in methods of transferring an ADC to a buffer (e.g., a formulation buffer).

In some embodiments, at least two steps in an ADC process are performed using SPTFF and/or countercurrent diafiltration. For example, in some embodiments, SPTFF and/or countercurrent diafiltration is used to transfer an antibody or antigen-binding fragment thereof into a conjugation buffer and used to concentrate and purify the ADC after it is formed, while SPTFF, countercurrent diafiltration, and/or TFF is used to exchange the ADC into formulation buffer. In some embodiments, SPTFF and/or countercurrent diafiltration is used to transfer an antibody or antigen-binding fragment thereof into a conjugation buffer and used to exchange a purified ADC into formulation buffer, while SPTFF, countercurrent diafiltration, and/or TFF is used to concentrate and purify the ADC after it is formed. In some embodiments, SPTFF and/or countercurrent diafiltration is used to concentrate and purify the ADC and used to exchange the concentrated and purified ADC into formulation buffer, wherein SPTFF, countercurrent diafiltration, and/or TFF is used to transfer the antibody or antigen-binding fragment thereof into a conjugation buffer.

Column chromatography can also be used in a flow-through mode in the continuous ADC processing methods provided herein (e.g., in combination with SPTFF and/or countercurrent diafiltration). For example, a conjugation reaction (e.g., a continuous conjugation reaction) can feed into flow-through column chromatography to remove unconjugated drug from the conjugation reaction. The ADCs purified via the flow-through column chromatography can then feed into an SPTFF process for buffer exchange into a formulation buffer. The ADCs purified via the flow-through column chromatography can also feed into a countercurrent diafiltration process for buffer exchange into a formulation buffer.

In some instances, the reaction parameters of the continuous methods provided herein can be rapidly changed or "pulsed". For example, in a continuous method described herein, temperature can be rapidly altered, e.g., by using a water bath, encapsulated reactor, heater, thermoelectric source, and/or insulating a section of coils and/or tubes through which the reaction flows. In addition, in a continuous flow conjugation, pH can be rapidly altered, e.g., by addition of an acid or base. Accordingly, in certain instances, a continuous reaction is performed using a pulsed parameter. The use of a pulsed parameter can, for example, decrease reaction time (i.e., increase reaction speed), without compromising product quality, quench or stop a reaction temporarily by rapidly dropping the temperature, stabilize the conjugate in solution before another perturbation (e.g., addition of another chemical reagent) is introduced, whereas longer exposures to the same parameter can dramatically decrease product quality or product stability.

In certain instances, the continuous reaction is exposed to an altered temperature (e.g., increased or decreased) for a specified time increment for a specified number of times. For example, in one instance, temperature is increased by at least 2° C., at least 3° C., at least 4° C., or at least 5° C. Accordingly, the temperature can be increased or decreased by at least 5° C., 10° C., 15° C., 20° C., 25° C., 30° C., or 35° C. For instance, the temperature can be increased or decreased by 5° C., 10° C., 15° C., 20° C., 25° C., 30° C., or 35° C. The temperature can also be increased or decreased by 5° C. to 10° C., by 10° C. to 15° C., by 15° C. to 20° C., by 20° C. to 25° C., by 25° C. to 30° C., or by 30° C. to 35° C. Thus, for example, temperature can be increased (e.g., from about 20° C.) to an elevated temperature of 25° C., 30° C., 35° C., 40° C., 45° C., 50° C., or 55° C. Temperature can be also increased (e.g., from about 25° C.) to an elevated temperature of 30° C., 35° C., 40° C., 45° C., 50° C., or 55° C. In certain instances, the temperature does not exceed 55° C. In certain instance, the temperature is increased (e.g., from 20° C.) to an elevated temperature in the range of 35° C. to 55° C. or to an elevated temperature in the range of 40° C. to 50° C. In certain instances, the temperature is increased (e.g., from 20° C.) to an elevated temperature of 60° C., to 70° C., to 80° C., to 90° C., or to 100° C. (e.g., for a short time increment such as 10 seconds). In certain instances, the temperature is increased (e.g., from 20° C.) to an elevated temperature in the range of 60° C. to 70° C., in the range of 70° C. to 80° C., in the range of 80° C. to 90° C., or in the range of 90° C. to 100° C. (e.g., for a short time increment such as 10 seconds). In certain instances, the time it takes to increase or decrease the temperature to the elevated or reduced temperature is no more than 2 minutes. In certain instances, the time it takes to increase or decrease the temperature to the elevated or reduced temperature is no more than 1 minute.

In certain instances, the continuous reaction is exposed to an altered pH (e.g., increased or decreased) for a specified time increment for a specified number of times. For example, in one instance, pH is increased or decreased by 1, 2, 3, 4, or 5. In one instance, pH is increased by 1 to 2, by 2 to 3, by 3 to 4, or by 4 to 5. Thus, for example, pH can be increased (e.g., from 4) to 5, 6, 7, 8, or 9. PH can also be increased (e.g., from 5) to 6, 7, 8, or 9. PH can also be decreased (e.g., from 9) to 8, 7, 6, 5, or 4.

In certain instances, the pulse (e.g., exposure to altered temperature and/or pH) occurs for 30 seconds, 1 minute, 2 minutes, 3 minutes, 4 minutes, 5 minutes, 6 minutes, 7 minutes, 8 minutes, 9 minutes, 10 minutes, 15 minutes, 30 minutes, an hour, 1.5 hours, or 2 hours. The pulse (e.g., exposure to altered temperature and/or) can also occur, for example, for 30 seconds to 1 minute, for 1 minute to 2 minutes, for 2 minutes to 3 minutes, for 3 minutes to 4 minutes, for 4 minutes to 5 minutes, for 6 minutes to 7 minutes, for 7 minutes to 8 minutes, for 8 minutes to 9 minutes, or for 9 minutes to 10 minutes. The pulse (e.g., exposure to altered temperature and/or) can also occur, for example, for 1 to 10 minutes, for 1 to 15 minutes, for 1 to 30 minutes, for 1 minute to 1 hour, for 1 minute to 1.5 hours, or for 1 minute to 2 hours. The pulse (e.g., exposure to altered temperature and/or) can also occur, for example, for 1 to 5 minutes, or 5 to 10 minutes, 10 to 15 minutes, 15 minutes to 30 minutes, 30 minutes to 1 hour, 1 hour to 1.5 hours, or 1.5 hours to 2 hours. In certain instances, the pulse (e.g., exposure to altered temperature and/or pH) does not exceed 2 hours, 1 hour, 30 minutes, 20 minutes, or 15 minutes.

In certain instances, the pulse (e.g., exposure to altered temperature and/or pH) occurs once. In certain instances, the pulse (e.g., exposure to altered temperature and/or) is repeated twice, three times, four times, five times, six times, seven times, eight times, nine times, or ten times. In certain instances, the pulse (e.g., exposure to altered temperature and/or) occurs one to five times. In certain instances, the pulse (e.g., exposure to altered temperature and/or) occurs two to twenty times or five to ten times.

Continuous methods (e.g., using SPTFF and/or countercurrent diafiltration) can be used with or without in-line monitoring processes (discussed below).

In a first embodiment, the CysCBA in the first, second or third aspect or any embodiments described therein is a cysteine-engineered antibody (CysAb) or antigen-binding fragment thereof and the method comprises the steps of:

(a) reacting a reducing agent with a capped cysteine-engineered antibody (cCysAb) or antigen-binding fragment thereof having one or more engineered cysteine residues capped with a capping agent to form a reduced antibody or antigen-binding fragment thereof, wherein the capping agent is removed to form a free thiol (—SH) group in the reduced antibody or antigen-binding fragment thereof;

(b) reacting the reduced antibody or antigen-binding fragment thereof with a selective oxidizing agent to form the CysAb, wherein the free thiol group in the engineered cysteine residue is not oxidized; and (c) reacting the CysAb with the compound of formula (I):

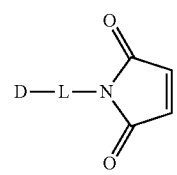

or a pharmaceutically acceptable salt thereof, thereby forming the antibody-cytotoxic agent conjugate (ADC), wherein the reduced antibody or antigen-binding fragment thereof in step (a) is used in step (b) without purification; and the CysAb or antigen-binding fragment thereof in step (b) is used in step (c) without purification, wherein:

D is a cytotoxic agent; and

L is a linker.

In certain embodiments, the steps (a), (b) and (c) in the method of the first aspect or first embodiment are carried out in the same reaction vessel.

In certain embodiments, for the method of the first embodiment or any embodiments described therein, one or more interchain disulfide bonds in the capped cysteine-engineered antibody (cCysAb) or antigen-binding fragment thereof are reduced in step (a). In certain embodiments, the one or more interchain disulfide bonds are re-formed in step (b).

In certain embodiments, for the method of the first, second or third aspect or the first embodiment or any embodiments described therein, any suitable reducing agent can be used in the reaction of step (a). Treatment of the cCysCBA (e.g., cCysAb or antigen-binding fragment thereof) with the reducing agent can remove the capping agent from the unpaired cysteine residue to form a free thiol (—SH) group and may also reduce disulfide bonds formed between two cysteine residues of the cell-binding agent, for example, the interchain and/or intrachain disulfide bonds of an antibody or antigen-binding fragment thereof. Exemplary reducing agents include, but are not limited to, (i) phosphine based reducing agents, such as tris(2-carboxyethyl)phosphine hydrochloride (TCEP), trishydroxypropyl phosphine (THPP), tris (2-cyanoethyl)phosphine, dicyclohexylphosphino)benzenesulfonic acid, bis(p-sulfonatophenyl)phenylphosphine, (diphenylphosphino)benzenesulfonic acid, (diphenylphosphino)benzoic acid, 2-(diphenylphosphino)-N,N,N-trimethylbenzylammonium triflate, (diphenylphosphino)ethylamine, 2-(diisopropylphosphino)ethylamine, 3-(diphenylphosphino)propylamine (DPPA), sodium 3,3',3"-phosphinetriyltribenzenesulfonate, sodium 3-(diphenylphosphino)benzenesulfonate, sodium 4-(diphenylphosphino)benzenesulfonate, bis(p-sulfonatophenyl) phenylphosphine dihydrate dipotassium salt, bis(p-sulfonatophenyl)phenylphosphine dihydrate dipotassium salt, propanoic acid, 3,3',3"-phosphinidynetris-1,1',1"-trimethyl ester (TmTCEP), propanenitrile 3,3'-(phenylphosphinidene)bis-benzenamine (also known as N,N-bis(cyanoethlyl)aniline), 4-(diethylphosphino)-N,N-dimethyl-tris(3-methoxypropyl)phosphine, 2-(diphenylphosphino)acetic acid, (S) 2-[2-(diphenylphosphino)ethyl]-pyridine, 2-2-(diphenylphosphino)-1-phenylethylamine, 2-(diphenylphosphino)ethanaminium tetrafluoroborate, 3-(diphenylphosphino)-propanoic acid, (acetic acid, 2-(diphenylphosphino)-, ethyl ester), or 4-(diphenylphosphanyl)butanoic acid; (i) thiol based reducing agents, such as dithiothreitol (DTT), 1,4-dithioerythritol (DTE), 1,4-butanedithiol, L-1,4-dithiothreitol, (S)-2-aminobutane-1,4-dithiol hydrochloride, (2S)-2-aminobutane-1,4-dithiol (DTBA), 2-aminoethane thiol (MEA) (or hydrochloride salt thereof), or any one of the following:

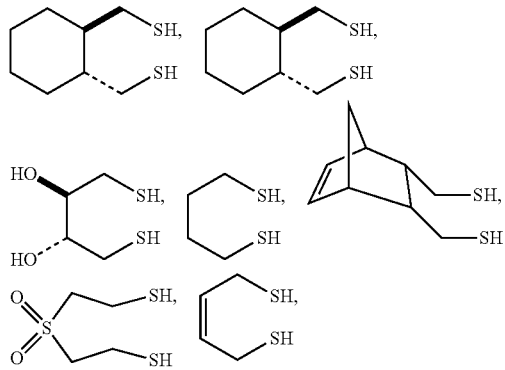

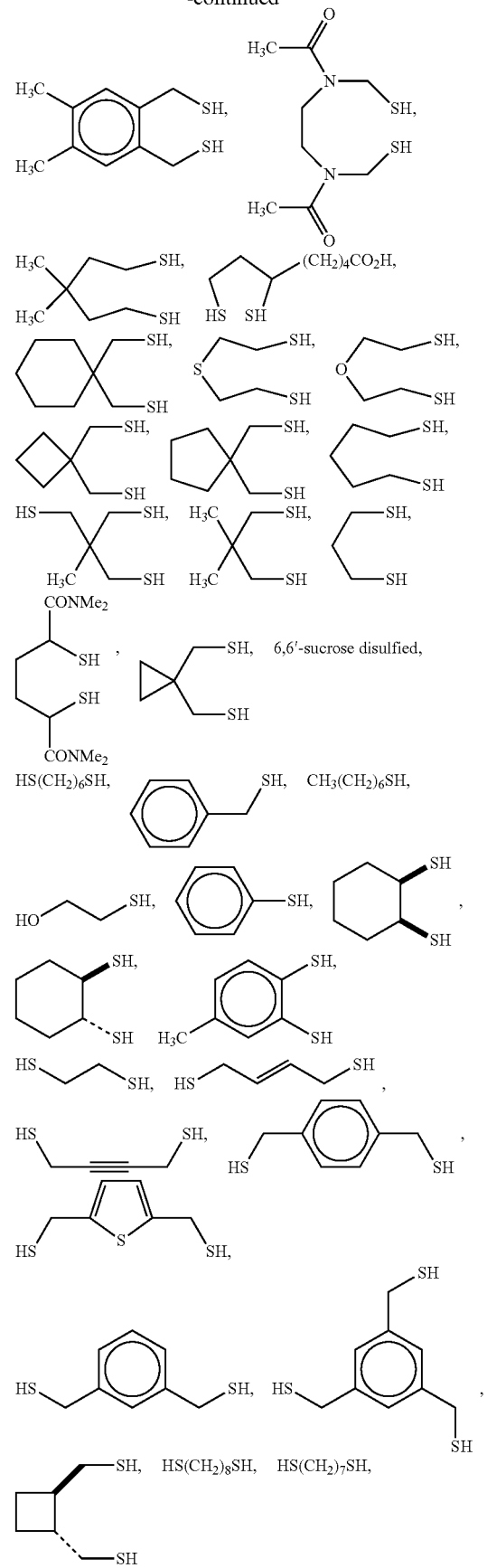

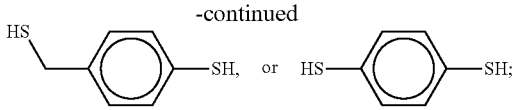

(iii) immobilized disulfide reducing agents, such as immobilized TCEP disulfide reducing gel or resins, immobilized reductant column containing beaded resin to which a thiol-based reducing agent has been immobilized, or (iv) other reducing agents, such as selenol, guanidine-HCl, or urea.

In certain embodiments, the reducing agent is selected based on the isoelectric point (pI) of the CBA (e.g., an antibody or an antigen-binding fragment thereof).

In certain embodiments, the method of the first aspect, second aspect or third aspect or the first embodiment or any embodiments described therein, further comprises determining the pI of the CBA (e.g., an antibody or an antigen-binding fragment thereof) and selecting the reducing agent based on the pI of the CBA. The pI of the CBA can be determined using any suitable methods known.

In certain embodiments, for the method of the first aspect, second aspect, or third aspect or the first embodiment or any embodiments described therein, any suitable oxidizing agent can be used in the reaction of step (b). The oxidizing agent selectively oxidizes and re-forms the disulfide bonds formed between two cysteine residues of the CBA, without re-oxidizing the free thiol of the unpaired cysteine residue. In certain embodiments, the oxidizing agent selectively re-forms the interchain and/or intrachain disulfide bonds of an antibody or antigen-binding fragment thereof, without re-oxidizing the free thiol of the unpaired cysteine residue. Exemplary oxidizing agent includes, but is not limited to, dehydroascorbic acid (DHAA), copper sulfate, oxygen, air, or $Cu(II)$-$(1,10$-phenanthroline$)_3$ and iodine solutions (see Hamdan, F. F. et al., Biochemistry, 2002, 41(24), pp 7647-7658, incorporated herein by reference).

In a second embodiment, for the method of the first aspect, second aspect, or third aspect or the first embodiment or any embodiments described therein, the reducing agent is step (a) is TCEP or DPPA.

In a third embodiment, for the method of the first aspect, second aspect or third aspect or the first embodiment, the second embodiment, or any embodiments described therein, the oxidizing agent is DHAA.

In a fourth embodiment, for the method of the first aspect, second aspect, or third aspect or the first, second or third embodiment, or any embodiments described therein, the reaction of step (a) is carried out at a pH between 5.0 and 8.5. More specifically, the reaction of step (a) is carried out at a pH between 6.0 and 7.5.

In certain embodiments, for the method of the first aspect, second aspect, or third aspect or the first, second, third or fourth embodiment, or any embodiments described therein, the reaction of step (b) is carried out at a pH between 5.0 and 8.5. More specifically, the reaction of step (b) is carried out at a pH between 6.0 and 7.5.

In certain embodiments, for the method of the first aspect, second aspect, or third aspect or the first, second, third or fourth embodiment, or any embodiments described therein, the reaction of step (c) is carried out at a pH between 5.0 and 8.5. More specifically, the reaction of step (c) is carried out at a pH between 6.0 and 7.5. Even more specifically, the reaction of step (c) is carried out at a pH between 5.5 and 6.5. In another specific embodiment, the reaction of step (c) is carried out at pH 6.0. In another specific embodiment, the reaction of step (c) is carried out at pH 6.5.

In certain embodiments, for the method of the first aspect, second aspect, or third aspect or the first, second, third or fourth embodiment, or any embodiments described therein, the method further comprises adjusting the pH of the reaction mixture after step (b) before reacting the CysCBA with the cytotoxic agent in step (c).

In certain embodiments, for the method of the first aspect, second aspect, or third aspect or the first, second, third or fourth embodiment, or any embodiments described therein, the pH of the reaction mixture after step (b) is not adjusted before reacting the CysCBA with the cytotoxic agent in step (c).

In a fifth embodiment, for the method of the first aspect, second aspect, or third aspect or the first, second, third or fourth embodiment, or any embodiments described therein, the reducing agent in step (a) is TCEP and the reaction of step (a) is carried out at a pH between 7.0 and 8.0, more specifically, between 7.3 and 7.7, and even more specifically, at pH 7.5.

In certain embodiments, for the method of the fifth embodiment, the oxidizing agent is DHAA and the reaction of step (b) is carried out at a pH between 7.0 and 8.0, more specifically, between 7.3 and 7.7, and even more specifically, at pH 7.5.

In certain embodiments, for the method of the fifth embodiment or any embodiments described therein, the pH of the reaction mixture after step (b) is adjusted from a pH between 7.3 and 7.7 (e.g., pH 7.5) to a pH between 5.8 to 6.2 (e.g., pH 6.0) before reacting the CysCBA with the cytotoxic agent in step (c).

In a sixth embodiment, for the method of the first aspect, second aspect, or third aspect or the first, second, third or fourth embodiment, or any embodiments described therein, the reducing agent in step (a) is DPPA and the reaction of step (a) is carried out at a pH between 6.0 and 7.0, more specifically, between 6.3 and 6.7, even more specifically, at pH 6.5.

In certain embodiments, for the method of the sixth embodiment, the oxidizing agent is DHAA and the reaction of step (b) is carried out at a pH between 6.0 and 7.0, more specifically, between 6.3 and 6.7, even more specifically, at pH 6.5.

In certain embodiments, for the method of the sixth embodiment or any embodiments described therein, the pH of the reaction mixture after step (b) is not adjusted before reacting the CysCBA with the cytotoxic agent in step (c) and the reaction of step (c) is carried out at a pH between 6.0 and 7.0, more specifically, between 6.3 and 6.7, even more specifically, at pH 6.5.

In a seventh embodiment, for the method of the first or second aspect, or the first, second, third, fourth, fifth or sixth embodiment, or any embodiments described therein, the conjugate is purified by tangential flow filtration (TFF), adsorptive chromatograph, non-adsorptive chromatography, adsorptive filtration, selective precipitation or a combination thereof. More specifically, the conjugate is purified by TFF.

Any suitable TFF systems may be utilized for purification, including a Pellicon type system (Millipore, Billerica, Mass.), a Sartocon Cassette system (Sartorius AG, Edgewood, N.Y.), TangenX cassette (TangenX Technology Corporation, Shrewsbury, Mass.) and a Centrasette type system (Pall Corp., East Hills, N.Y.)

Any suitable adsorptive chromatography resin may be utilized for purification, wherein the resin may retain either the cell-binding agent-cytotoxic agent conjugate and permit elution of the impurities or retain the impurities and permit elution of the cell-binding agent-cytotoxic agent conjugate.

Preferred adsorptive chromatography resins include hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof. Examples of suitable hydroxyapatite resins include ceramic hydroxyapatite (CHT Type I and Type II, Bio-Rad Laboratories, Hercules, Calif.), HA Ultrogel hydroxyapatite (Pall Corp., East Hills, N.Y.), and ceramic fluoroapatite (CFT Type I and Type II, Bio-Rad Laboratories, Hercules, Calif.). An example of a suitable HCIC resin is MEP Hypercel resin (Pall Corp., East Hills, N.Y.). Examples of suitable HIC resins include Butyl-Sepharose, Hexyl-Sepaharose, Phenyl-Sepharose, and Octyl Sepharose resins (all from GE Healthcare, Piscataway, N.J.), as well as Macro-prep Methyl and Macro-Prep t-Butyl resins (Biorad Laboratories, Hercules, Calif.). Examples of suitable ion exchange resins include SP-Sepharose, CM-Sepharose, and Q-Sepharose resins (all from GE Healthcare, Piscataway, N.J.), and Unosphere S resin (Bio-Rad Laboratories, Hercules, Calif.). Examples of suitable mixed mode ion exchangers include Bakerbond ABx resin (JT Baker, Phillipsburg N.J.) Examples of suitable IMAC resins include Chelating Sepharose resin (GE Healthcare, Piscataway, N.J.) and Profinity IMAC resin (Bio-Rad Laboratories, Hercules, Calif.). Examples of suitable dye ligand resins include Blue Sepharose resin (GE Healthcare, Piscataway, N.J.) and Affi-gel Blue resin (Bio-Rad Laboratories, Hercules, Calif.). Examples of suitable affinity resins include Protein A Sepharose resin (e.g., MabSelect, GE Healthcare, Piscataway, N.J.), where the cell-binding agent is an antibody, and lectin affinity resins, e.g. Lentil Lectin Sepharose resin (GE Healthcare, Piscataway, N.J.), where the cell-binding agent bears appropriate lectin binding sites. Alternatively an antibody specific to the cell-binding agent may be used. Such an antibody can be immobilized to, for instance, Sepharose 4 Fast Flow resin (GE Healthcare, Piscataway, N.J.). Examples of suitable reversed phase resins include C4, C8, and C18 resins (Grace Vydac, Hesperia, Calif.).

Any suitable non-adsorptive chromatography resin may be utilized for purification. Examples of suitable non-adsorptive chromatography resins include, but are not limited to, SEPHADEX™ G-25, G-50, G-100, SEPHACRYL™ resins (e.g., S-200 and S-300), SUPERDEX™ resins (e.g., SUPERDEX™ 75 and SUPERDEX™ 200), BIO-GEL® resins (e.g., P-6, P-10, P-30, P-60, and P-100), and others known to those of ordinary skill in the art.

In some embodiments, the conjugate is purified by single-pass tangential flow filtration (SPTFF). In some embodiments, the conjugate is purified by countercurrent diafiltration.

In some embodiments, the SPTFF is used to remove the unconjugated drug and/or to exchange the ADC into the stable buffer. In some embodiments, flow-through column chromatography is used to remove the unconjugated drug and SPTFF is used to exchange the ADC into the stable buffer.

In some embodiments, countercurrent diafiltration is used to remove the unconjugated drug and/or to exchange the ADC into the stable buffer. In some embodiments, flow-through column chromatography is used to remove the unconjugated drug and countercurrent diafiltration is used to exchange the ADC into the stable buffer.

In some embodiments, the SPTFF uses an ultrafiltration membrane. In some embodiments, the SPTFF uses a diafiltration membrane.

In some embodiments, the method improves the consistency of the ADC production. In some embodiments, the method decreases the time for ADC production.

In some embodiments, the SPTFF improves the consistency of the ADC production. In some embodiments, the SPTFF decreases the time for ADC concentration, purification, or transfer. In some embodiments, the SPTFF decreases the amount of buffer used.

In some embodiments, the countercurrent diafiltration improves the consistency of the ADC production. In some embodiments, the countercurrent diafiltration decreases the time for ADC concentration, purification, or transfer. In some embodiments, the countercurrent diafiltration decreases the amount of buffer used.

In certain embodiments, for the method of the first aspect, second aspect, or third aspect or the first, second, third, fourth, fifth, sixth or seventh embodiment or any embodiments described therein, the method further comprises adjusting the pH of the reaction mixture after step (c) before the conjugate is purified. In some embodiments, the pH of the reaction mixture after step (c) is adjusted to a pH between 4.0 and 6.0, between 4.0 and 5.5, between 4.0 and 5.0, between 4.5 and 5.0, or between 4.6 and 4.8. In a specific embodiment, the pH is adjusted to 4.5, 4.6, 4.7, 4.8, 4.9 or 5.0. In another specific embodiment, the pH is adjusted to 4.7.

In an eighth embodiment, for the method of the first aspect, second aspect or third aspect or the first, second, third, fourth, fifth, sixth or seventh embodiment, or any embodiments described therein, excess amount of the reducing agent relative to the cCysCBA is used in step (a). More specifically, the molar ratio of the reducing agent to the cCysCBA (e.g., an antibody or antigen-binding fragment thereof) is between 1:1 and 50:1, between 2:1 and 30:1, between 5:1 and 25:1, or between 10:1 and 25:1. Even more specifically, the molar ratio is between 15:1 and 20:1.

In a ninth embodiment, for the method of the first aspect, second aspect or third aspect or the first, second, third, fourth, fifth, sixth, seventh or eighth embodiment, or any embodiments described therein, the molar ratio of the reducing agent in step (a) to the oxidizing agent in step (b) is between 20:1 and 1:20, between 10:1 and 1:10, between 5:1 and 1:5, between 2:1 and 1:2, between 1.2:1 and 1:1.5, between 1:1 and 1:20, or between 1:1 and 1:10. More specifically, the molar ratio of the reducing agent to the oxidizing agent is between 1:1 and 1:1.5. Even more specifically, the molar ratio of the reducing agent to the oxidizing agent is 1:1. Alternatively, the molar ratio of the reducing agent to the oxidizing agent is 1:1.5.

In a tenth embodiment, for the method of the first aspect, second aspect or third aspect or the first, second, third, fourth, fifth, sixth, seventh, eighth or ninth embodiment, or any embodiments described therein, excess amount of the compound of formula (I) relative to CysCBA (e.g., an antibody or antigen-binding fragment thereof) or antigen-binding fragment thereof is used in step (c). More specifically, between 1.1 and 20, between 1.5 and 20, between 2 and 20, between 2 and 10, between 2 and 5, between 3.5 and 5, between 4.2 and 5, between 4.3 and 4.9, between 4.4 and 4.8, or between 4.5 and 4.7 molar equivalents of the compound of formula (I) is used for each equivalent of CysCBA. In a specific embodiment, 4.0, 4.1, 4.2, 4.3, 4.4, 4.5, 4.6, 4.7, 4.8, 4.9 or 5.0 molar equivalents of the compound of formula (I) is used for each equivalent of CysCBA. In another specific embodiment, 4.6 molar equivalents of the compound of formula (I) is used for each equivalent of CysCBA.

In certain embodiments, for the methods described herein (e.g., the method of the first, second, third, fourth, fifth, sixth, seventh, eighth, ninth or tenth embodiment, or any embodiments described therein), CysAb is an antibody having an engineered cysteine residue at one or more positions selected from the EU/OU numbering positions 40, 43, 84, 88, 103, 112, 113, 114, 115, 118, 131, 132, 133, 134, 135, 136, 137, 138, 139, 140, 161, 168, 172, 179, 187, 209, 234, 235, 236, 237, 238, 239, 244, 245, 248, 249, 250, 251, 252, 253, 254, 255, 256, 257, 258, 260, 262, 265, 267, 270, 272, 274, 279, 280, 282, 283, 284, 285, 286, 288, 289, 293, 295, 297, 298, 303, 305, 307, 308, 309, 311, 312, 313, 314, 315, 316, 317, 318, 325, 326, 327, 328, 329, 330, 332, 334, 338, 339, 340, 341, 343, 345, 360, 361, 362, 371, 373, 375, 376, 377, 378, 380, 382, 384, 385, 386, 387, 389, 390, 391, 413, 422, 423, 424, 427, 428, 430, 431, 433, 434, 435, 436, 437, 438, 440, 442, 443 and 446 of the antibody. In other embodiments, CysAb is an antibody having an engineered cysteine residue at one or more positions selected from the Kabat numbering positions 15, 43, 106, 108, 110, 112, 113, 119, 120, 121, 142, 144, 149, 153, 156, 158, 168, 173, 175, 205 and 207. In certain embodiments, the CysAb is an antibody having an engineered cysteine residue at one or more positions described in WO 2016/040856 and U.S. Pat. No. 7,521,541, each of which is incorporated herein by reference. More specifically, the CysAb is an antibody having an engineered cysteine residue at the EU/OU numbering position 442 of a heavy chain of the antibody. Even more specifically, the CysAb is an antibody having an engineered cysteine residue at the EU/OU numbering position 442 of both heavy chains.

In an eleventh embodiment, the present invention provides a method of preparing an antibody-cytotoxic agent conjugate (ADC) represented by the following formula:

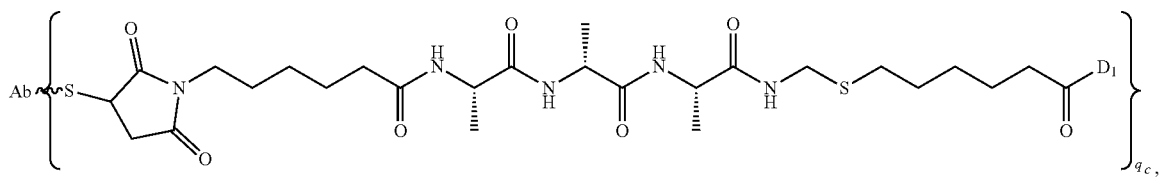

comprising the steps of:
(a) reacting a reducing agent with a capped cysteine-engineered antibody (cCysAb) represented by the following formula:

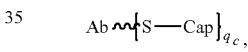

to form a reduced antibody or antigen-binding fragment thereof, wherein the capping agent (Cap) is removed to form a free thiol (—SH) group in the reduced antibody or antigen-binding fragment thereof;
(b) reacting the reduced antibody or antigen-binding fragment thereof with a selective oxidizing agent to form the CysAb, wherein the free thiol group in the engineered cysteine residue is not oxidized; and
(c) reacting the CysAb with a compound represented by the following formula:

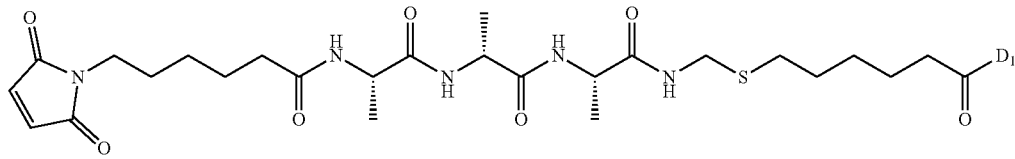

or a pharmaceutically acceptable salt thereof, thereby forming the ADC, wherein the reduced antibody or antigen-binding fragment thereof in step (a) is used in step (b) without purification, and the CysAb or antigen-binding fragment thereof of step (b) is used in step (c) without purification, wherein:

Ab〰S— is a cysteine-engineered antibody (CysAb) or antigen-binding fragment thereof covalently linked to the cytotoxic agent through the thiol group located on the engineered cysteine residue; and wherein the CysAb or antigen-binding fragment thereof is a humanized anti-ADAM9 antibody or ADAM9-binding fragment thereof comprising a $CDR_H1$ domain, a $CDR_H2$ domain, and a $CDR_H3$ domain and a $CDR_L1$ domain, a $CDR_L2$ domain, and a $CDR_L3$ domain having the sequences of SEQ ID NOs: 24, 25, and 26 and SEQ ID NOs: 21, 22, 23, respectively;

$q_c$ is 1 or 2;

Cap is a capping agent; and $D_1$ is represented by the following formula:

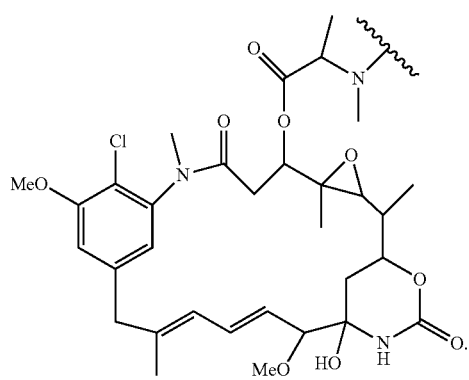 [SMILES: *N(C)C(C)C(=O)OC1CC(=O)N(C)c2cc(cc(OC)c2Cl)C/C(C)=C/C=C/C(OC)C2(O)CC(OC(=O)N2)C(C)C2OC12C]

Preferably, $D_1$ is represented by the following formula:

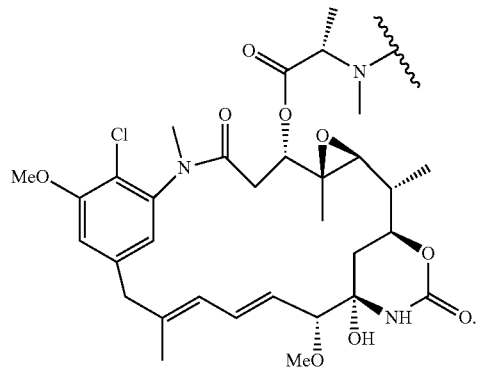 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In a twelfth embodiment, the present invention provides a continuous method of preparing an antibody-cytotoxic agent conjugate (ADC) represented by the following formula:

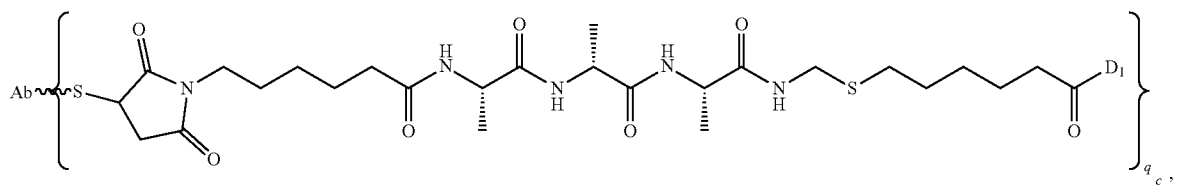

comprising the steps of:
(a) reacting a reducing agent with a capped cysteine-engineered antibody (cCysAb) represented by the following formula:

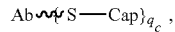

to form a reduced antibody or antigen-binding fragment thereof, wherein the capping agent (Cap) is removed to form a free thiol (—SH) group in the reduced antibody or antigen-binding fragment thereof;
(b) reacting the reduced antibody or antigen-binding fragment thereof with a selective oxidizing agent to form the CysAb, wherein the free thiol group in the engineered cysteine residue is not oxidized; and
(c) reacting the CysAb with a compound represented by the following formula:

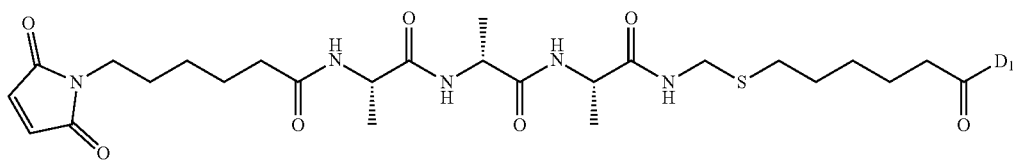

(I11)

or a pharmaceutically acceptable salt thereof, thereby forming the ADC, wherein the reduced antibody or antigen-binding fragment thereof in step (a) is used in step (b) without purification, and the CysAb or antigen-binding fragment thereof of step (b) is used in step (c) without purification, and steps (a) to (c) are performed continuously, and wherein:

Ab~~S— is a cysteine-engineered antibody (CysAb) or antigen-binding fragment thereof covalently linked to the cytotoxic agent through the thiol group located on the engineered cysteine residue; and wherein the CysAb or antigen-binding fragment thereof is a humanized anti-ADAM9 antibody or ADAM9-binding fragment thereof comprising a $CDR_H1$ domain, a $CDR_H2$ domain, and a $CDR_H3$ domain and a $CDR_L1$ domain, a $CDR_L2$ domain, and a $CDR_L3$ domain having the sequences of SEQ ID NOs: 24, 25, and 26 and SEQ ID NOs: 21, 22, 23, respectively;

$q_c$ is 1 or 2;

Cap is a capping agent; and $D_1$ is represented by the following formula:

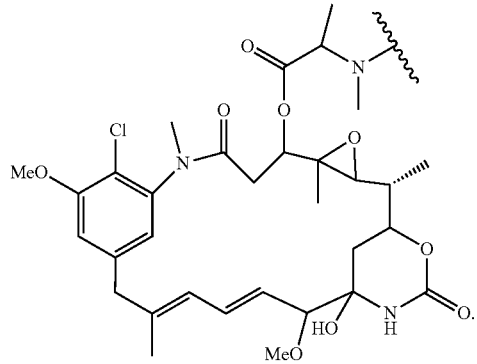 [SMILES: *N(C)C(C)C(=O)OC1CC(=O)N(C)c2cc(cc(OC)c2Cl)C/C(C)=C/C=C/C(OC)C2(O)CC(OC(=O)N2)[C@@H](C)C2OC12C]

Preferably, $D_1$ is represented by the following formula:

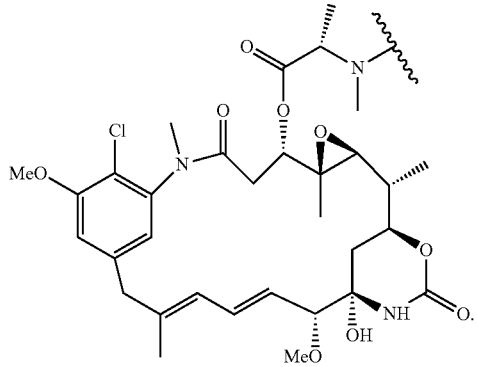 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In a thirteenth embodiment, the method of the eleventh or twelfth embodiment as described herein, further comprises the steps of: (d) removing unconjugated compound of formula (I11); and optionally (e) exchanging the ADC into a stable buffer.

In some embodiments, SPTFF is used to remove the unconjugated drug and/or to exchange the ADC into the stable buffer. In some embodiments, countercurrent diafiltration is used to remove the unconjugated drug and/or to exchange the ADC into the stable buffer.

In certain embodiments, steps (d) and (e) are performed continuously.

In a fourteenth embodiment, the present invention provides a continuous method of preparing an antibody-cytotoxic agent conjugate (ADC) represented by the following formula:

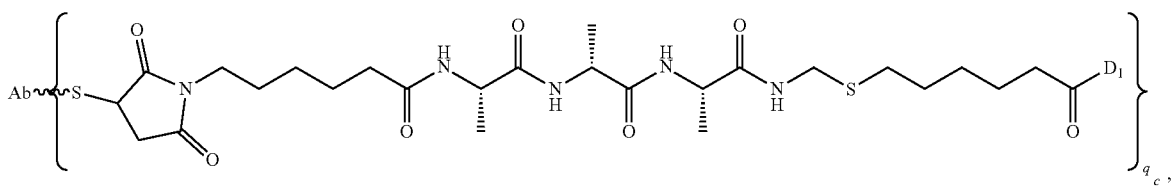

comprising the steps of:
(a) reacting a reducing agent with a capped cysteine-engineered antibody (cCysAb) represented by the following formula:

Ab~~S—Cap}$_{q_c}$, to form a reduced antibody or antigen-binding fragment thereof, wherein the capping agent (Cap) is removed to form a free thiol (—SH) group in the reduced antibody or antigen-binding fragment thereof;

(b) reacting the reduced antibody or antigen-binding fragment thereof with a selective oxidizing agent to form the CysAb, wherein the free thiol group in the engineered cysteine residue is not oxidized; and (c) reacting the CysAb with a compound represented by the following formula:

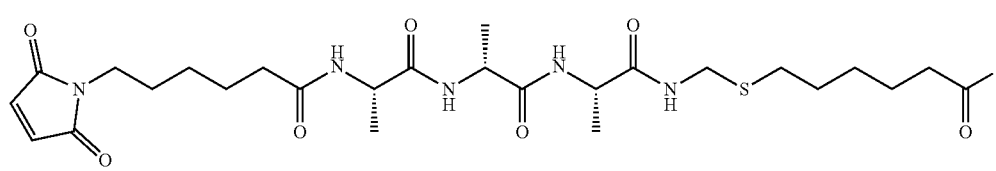

(I11)

or a pharmaceutically acceptable salt thereof, thereby forming the ADC; and (d) removing unconjugated compound of formula (I11) by countercurrent diafiltration;

wherein the reduced antibody or antigen-binding fragment thereof in step (a) is used in step (b) without purification, and the CysAb or antigen-binding fragment thereof of step (b) is used in step (c) without purification, and steps (a) to (d) are performed continuously, and wherein:

Ab~~~S— is a cysteine-engineered antibody (CysAb) or antigen-binding fragment thereof covalently linked to the cytotoxic agent through the thiol group located on the engineered cysteine residue; and wherein the CysAb or antigen-binding fragment thereof is a humanized anti-ADAM9 antibody or ADAM9-binding fragment thereof comprising a $CDR_H1$ domain, a $CDR_H2$ domain, and a $CDR_H3$ domain and a $CDR_L1$ domain, a $CDR_L2$ domain, and a $CDR_L3$ domain having the sequences of SEQ ID NOs: 24, 25, and 26 and SEQ ID NOs: 21, 22, 23, respectively;

$q_c$ is 1 or 2;

Cap is a capping agent; and $D_1$ is represented by the following formula:

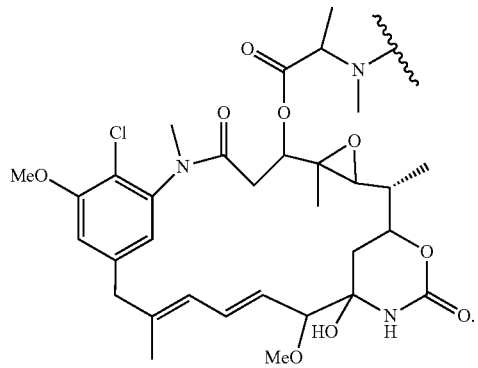 [SMILES: *N(C)C(C)C(=O)OC1CC(=O)N(C)c2cc(cc(OC)c2Cl)C/C(C)=C/C=C/C(OC)C2(O)CC(OC(=O)N2)[C@@H](C)C2OC12C]

Preferably, $D_1$ is represented by the following formula:

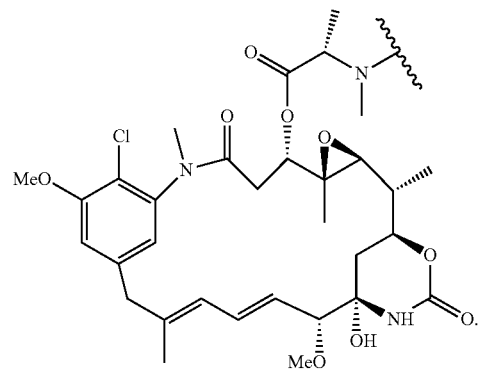 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In certain embodiments, for the method of the eleventh, twelfth, thirteenth, or fourteenth embodiment or any embodiments described herein, the humanized anti-ADAM9 antibody or ADAM9-binding fragment thereof comprises a heavy chain variable domain ($V_H$) and a light chain variable domain ($V_L$) having sequences of SEQ ID NO:27 and SEQ ID NO:28, respectively.

In certain embodiments, for the method of the eleventh, twelfth, thirteenth, or fourteenth embodiment or any embodiments described herein, the humanized anti-ADAM9 antibody comprises a heavy chain and a light chain having the sequences of SEQ ID NO:29 and SEQ ID NO:30, respectively.

In certain embodiments, for the method of the eleventh, twelfth, thirteenth, or fourteenth embodiment or any embodiments described herein, the reducing agent is DPPA. In certain embodiments, between 10 and 20 molar equivalents of DPPA is used in step (a) for each equivalent of cCysAb. More specifically, between 15 and 17 molar equivalents of DPPA is used in step (a) for each equivalent of cCysAb. Even more specifically, 16 molar equivalents of DPPA is used in step (a) for each equivalent of cCysAb.

In certain embodiments, for the method of the eleventh, twelfth, thirteenth, or fourteenth embodiment or any embodiments described herein, the reaction in step (a) is carried out at a pH between 6.0 and 7.0 or a pH between 6.3 and 6.7. More specifically, the reaction in step (a) is carried out at pH 6.5.

In certain embodiments, for the method of the eleventh, twelfth, thirteenth, or fourteenth embodiment or any embodiments described herein, the oxidizing agent is DHAA. In certain embodiments, between 20 and 30 molar equivalents of DHAA is used in step (b) for each equivalent of cCysAb. More specifically, between 23 and 25 molar equivalents of DHAA is used in step (b) for each equivalent of cCysAb. Even more specifically, between 23 and 25 molar equivalents of DHAA is used in step (b) for each equivalent of cCysAb. Even more specifically, 24 molar equivalents of DHAA is used in step (b) for each equivalent of cCysAb.

In certain embodiments, for the method of the eleventh, twelfth, thirteenth, or fourteenth embodiment or any embodiments described herein, the reaction in step (b) is carried out at a pH between 6.0 and 7.0 or a pH between 6.3 and 6.7. More specifically, the reaction in step (b) is carried out at pH 6.5.

In certain embodiments, for the method of the eleventh, twelfth, thirteenth, or fourteenth embodiment or any embodiments described herein, the reaction in step (c) is carried out at a pH between 6.0 and 7.0 or a pH between 6.3 and 6.7. More specifically, the reaction in step (c) is carried out at pH 6.5.

In certain embodiments, for the method of the eleventh, twelfth, thirteenth, or fourteenth embodiment or any embodiments described herein, excess amount of the compound of formula (I11) relative to CysAb (e.g., an antibody or antigen-binding fragment thereof) or antigen-binding fragment thereof is used in step (c). More specifically, between 1.1 and 20, between 1.5 and 20, between 2 and 20, between 2 and 10, between 2 and 5, between 3.5 and 5, between 4.2 and 5, between 4.3 and 4.9, between 4.4 and 4.8, or between 4.5 and 4.7 molar equivalents of the compound of formula (I11) is used for each equivalent of CysAb. In a specific embodiment, 4.0, 4.1, 4.2, 4.3, 4.4, 4.5, 4.6, 4.7, 4.8, 4.9 or 5.0 molar equivalents of the compound of formula (I11) is used for each equivalent of CysAb. In another specific embodiment, 4.6 molar equivalents of the compound of formula (I11) is used for each equivalent of CysAb.

In certain embodiments, for the method of the eleventh, twelfth, thirteenth, or fourteenth embodiment or any embodiments described herein, between 15 and 17 molar equivalents of DPPA is used in step (a) for each equivalent of cCysAb; the reaction in step (a) is carried out at a pH between 6.3 and 6.7; between 23 and 25 molar equivalents of DHAA is used in step (b) for each equivalent of cCysAb; the reaction in step (b) is carried out at a pH between 6.3 and 6.7; and the reaction in step (c) is carried out at a pH between 6.3 and 6.7.

In certain embodiments, for the method of the eleventh, twelfth, thirteenth, or fourteenth embodiment or any embodiments described herein, 16 molar equivalents of DPPA is used in step (a) for each equivalent of cCysAb; the reaction in step (a) is carried out at pH 6.5; 24 molar equivalents of DHAA is used in step (b) for each equivalent of cCysAb; the reaction in step (b) is carried out at pH 6.5; and the reaction in step (c) is carried out at pH 6.5.

In certain embodiments, for the method of the eleventh, twelfth, thirteenth, or fourteenth embodiment or any embodiments described herein, the method further comprises adjusting the pH of the reaction mixture after step (c) before the conjugate is purified (e.g., before step (d)). In some embodiments, the pH of the reaction mixture after step (c) is adjusted to a pH between 4.0 and 6.0, between 4.0 and 5.5, between 4.0 and 5.0, between 4.5 and 5.0, or between 4.6 and 4.8. In a specific embodiment, the pH is adjusted to 4.5, 4.6, 4.7, 4.8, 4.9 or 5.0. In another specific embodiment, the pH is adjusted to 4.7.

In certain embodiments, for the method of the eleventh, twelfth, thirteenth, or fourteenth embodiment or any embodiments described herein, the capping agent is cysteine, glutathione or a combination thereof.

In certain embodiments, for the method of the eleventh, twelfth, thirteenth, or fourteenth embodiment or any embodiments described herein, $q_c$ is 2.

In certain embodiments, a composition (e.g., a pharmaceutical composition) comprising the immunoconjugates prepared by the method of the eleventh embodiment or any embodiments described therein has a DAR value in the range of 1.0 to 2.5, 1.5 to 2.5, 1.8 to 2.2, or 1.9 to 2.1. In some embodiments, the DAR is 1.8, 1.9, 2.0 or 2.1.

In a fifteenth embodiment, the present invention provides a method of preparing an antibody-cytotoxic agent conjugate (ADC) represented by the following formula:

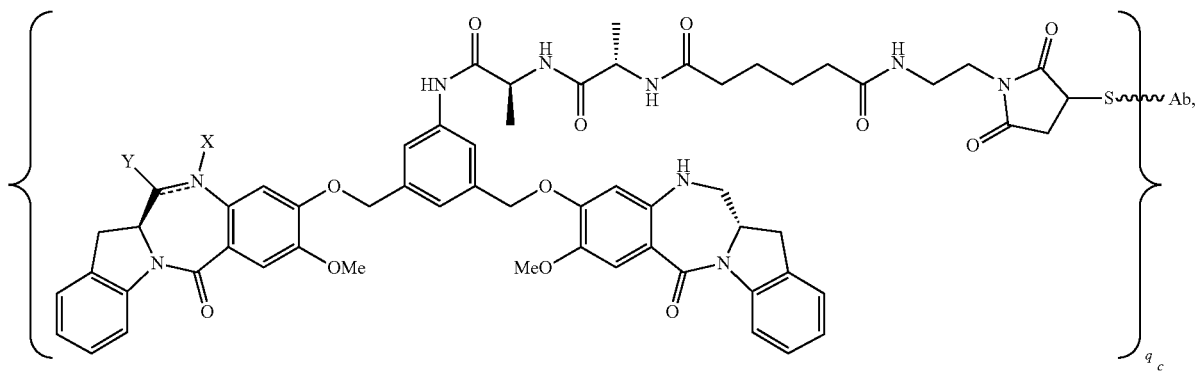

comprising the steps of:
(a) reacting a reducing agent with a capped cysteine-engineered antibody (cCysAb) represented by the following formula:

$$Ab\text{\textasciitilde}\!\!\{S-Cap\}_{q_c}$$

to form a reduced antibody or antigen-binding fragment thereof, wherein the capping agent is removed to form a free thiol (—SH) group in the reduced antibody or antigen-binding fragment thereof;
(b) reacting the reduced antibody or antigen-binding fragment thereof with a selective oxidizing agent to form the CysAb, wherein the free thiol group in the engineered cysteine residue is not oxidized; and
(c) reacting the CysAb with a compound represented by the following formula:

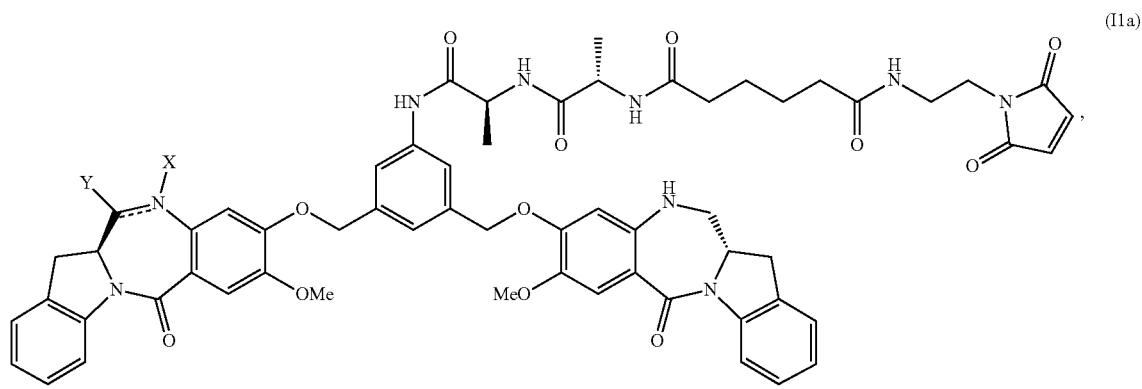

or a pharmaceutical acceptable salt thereof, thereby forming the ADC, wherein the reduced antibody or antigen-binding fragment thereof in step (a) is used in step (b) without purification, and the CysAb or antigen-binding fragment thereof of step (b) is used in step (c) without purification, wherein:

the double line = between N and C represents a single bond or a double bond, provided that when it is a double bond, X is absent and Y is —H, and when it is a single bond, X is —H, and Y is —SO₃M, and M is H⁺ or a cation;

Ab~S— is the cysteine-engineered antibody or antigen-binding fragment thereof covalently linked to the cytotoxic agent through the thiol group located on the engineered cysteine residue; wherein the cysteine-engineered antibody is an anti-CD123 antibody or antigen-binding fragment comprising:

a) an immunoglobulin heavy chain variable region comprising a $CDR_H1$ having an amino acid sequence set forth in SEQ ID NO:4, a $CDR_H2$ having an amino acid sequence set forth in SEQ ID NO:5, and a $CDR_H3$ having an amino acid sequence set forth in SEQ ID NO:6; and b) an immunoglobulin light chain variable region comprising a $CDR_L1$ having an amino acid sequence set forth in SEQ ID NO:1, a $CDR_L2$ having an amino acid sequence set forth in SEQ ID NO:2, and a $CDR_L3$ having an amino acid sequence set forth in SEQ ID NO:3;

$q_c$ is 1 or 2; and

Cap is a capping agent.

In a sixteenth embodiment, the present invention provides a continuous method of preparing an antibody-cytotoxic agent conjugate (ADC) represented by the following formula:

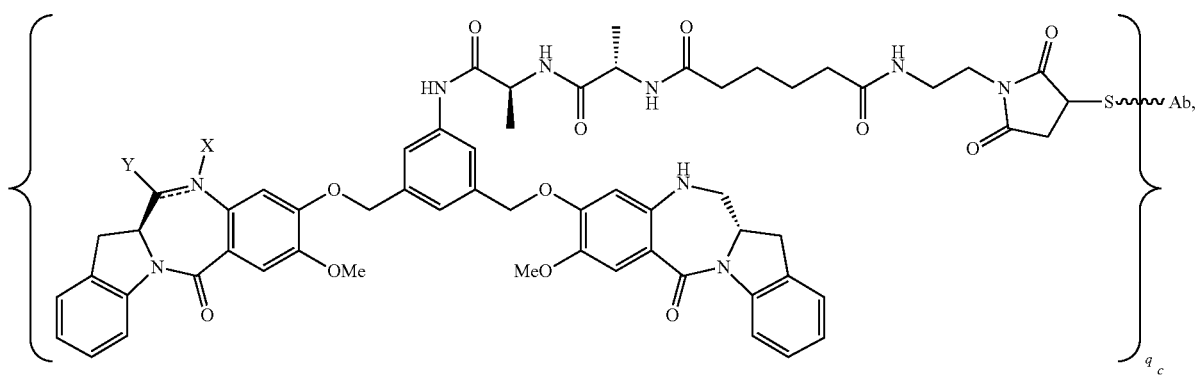

comprising the steps of:

(a) reacting a reducing agent with a capped cysteine-engineered antibody (cCysAb) represented by the following formula:

Ab~S—Cap}$_{q_c}$ to form a reduced antibody or antigen-binding fragment thereof, wherein the capping agent is removed to form a free thiol (—SH) group in the reduced antibody or antigen-binding fragment thereof;

(b) reacting the reduced antibody or antigen-binding fragment thereof with a selective oxidizing agent to form the CysAb, wherein the free thiol group in the engineered cysteine residue is not oxidized; and (c) reacting the CysAb with a compound represented by the following formula:

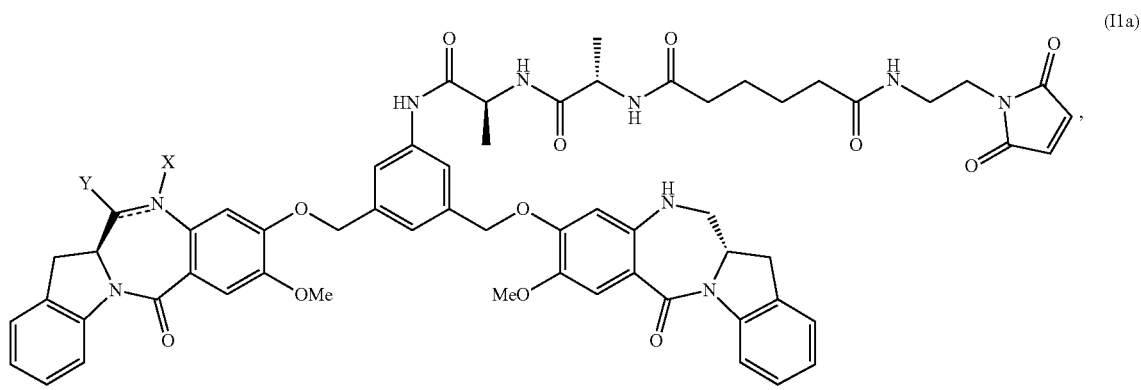 (I1a)

or a pharmaceutical acceptable salt thereof, thereby forming the ADC, wherein the reduced antibody or antigen-binding fragment thereof in step (a) is used in step (b) without purification, and the CysAb or antigen-binding fragment thereof of step (b) is used in step (c) without purification, and steps (a) to (c) are performed continuously, wherein:

the double line ═ between N and C represents a single bond or a double bond, provided that when it is a double bond, X is absent and Y is —H, and when it is a single bond, X is —H, and Y is —SO$_3$M, and M is H$^+$ or a cation;

Ab〜S— is the cysteine-engineered antibody or antigen-binding fragment thereof covalently linked to the cytotoxic agent through the thiol group located on the engineered cysteine residue; wherein the cysteine-engineered antibody is an anti-CD123 antibody or antigen-binding fragment comprising:

a) an immunoglobulin heavy chain variable region comprising a CDR$_H$1 having an amino acid sequence set forth in SEQ ID NO:4, a CDR$_H$2 having an amino acid sequence set forth in SEQ ID NO:5, and a CDR$_H$3 having an amino acid sequence set forth in SEQ ID NO:6; and b) an immunoglobulin light chain variable region comprising a CDR$_L$1 having an amino acid sequence set forth in SEQ ID NO:1, a CDR$_L$2 having an amino acid sequence set forth in SEQ ID NO:2, and a CDR$_L$3 having an amino acid sequence set forth in SEQ ID NO:3;

$q_c$ is 1 or 2; and

Cap is a capping agent.

In a seventeenth embodiment, the method of the fifteenth or sixteenth embodiment as described herein, further comprises the steps of: (d) removing unconjugated compound of formula (I1a); and optionally (e) exchanging ADC into a stable buffer.

In some embodiments, SPTFF is used to remove the unconjugated drug and/or to exchange the ADC into the stable buffer. In some embodiments. In some embodiments, countercurrent diafiltration is used to remove the unconjugated compound of formula (I1a); and/or to exchange the ADC into the stable buffer.

In certain embodiments steps (d) and (e) are performed continuously.

In an eighteenth embodiment, the present invention provides a continuous method of preparing an antibody-cytotoxic agent conjugate (ADC) represented by the following formula:

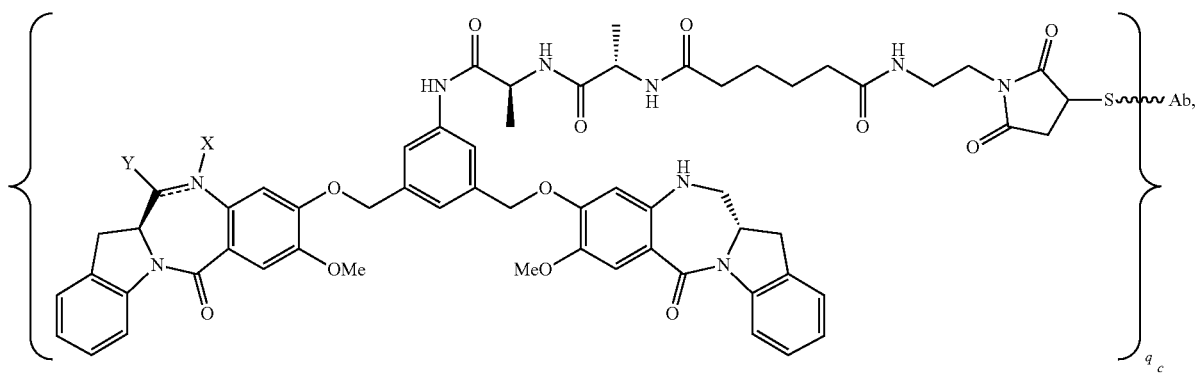

comprising the steps of:

(a) reacting a reducing agent with a capped cysteine-engineered antibody (cCysAb) represented by the following formula:

Ab〜S—Cap$\}_{q_c}$ to form a reduced antibody or antigen-binding fragment thereof, wherein the capping agent is removed to form a free thiol (—SH) group in the reduced antibody or antigen-binding fragment thereof;
(b) reacting the reduced antibody or antigen-binding fragment thereof with a selective oxidizing agent to form the CysAb, wherein the free thiol group in the engineered cysteine residue is not oxidized; and
(c) reacting the CysAb with a compound represented by the following formula:

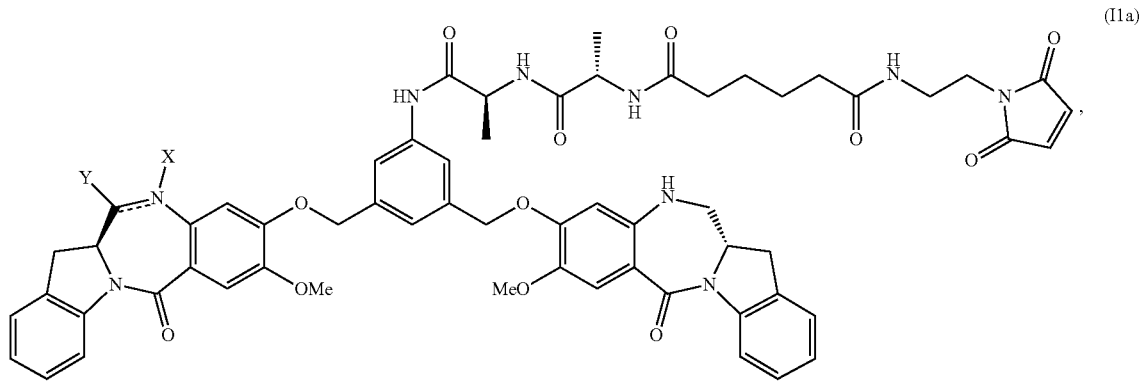

or a pharmaceutical acceptable salt thereof, thereby forming the ADC; and
(d) removing unconjugated compound of formula (I1a) by countercurrent diafiltration;
wherein the reduced antibody or antigen-binding fragment thereof in step (a) is used in step (b) without purification, and the CysAb or antigen-binding fragment thereof of step (b) is used in step (c) without purification, and steps (a) to (d) are performed continuously, wherein:
the double line $=$ between N and C represents a single bond or a double bond, provided that when it is a double bond, X is absent and Y is —H, and when it is a single bond, X is —H, and Y is —SO$_3$M, and M is H$^+$ or a cation;

Ab〜〜S— is the cysteine-engineered antibody or antigen-binding fragment thereof covalently linked to the cytotoxic agent through the thiol group located on the engineered cysteine residue; wherein the cysteine-engineered antibody is an anti-CD123 antibody or antigen-binding fragment comprising:

a) an immunoglobulin heavy chain variable region comprising a CDR$_H$1 having an amino acid sequence set forth in SEQ ID NO:4, a CDR$_H$2 having an amino acid sequence set forth in SEQ ID NO:5, and a CDR$_H$3 having an amino acid sequence set forth in SEQ ID NO:6; and b) an immunoglobulin light chain variable region comprising a CDR$_L$1 having an amino acid sequence set forth in SEQ ID NO:1, a CDR$_L$2 having an amino acid sequence set forth in SEQ ID NO:2, and a CDR$_L$3 having an amino acid sequence set forth in SEQ ID NO:3;

q$_c$ is 1 or 2; and

Cap is a capping agent.

In certain embodiments, the conjugate prepared by the method of the fifteenth, sixteenth, seventeenth and eighteenth embodiments is represented by the following formula:

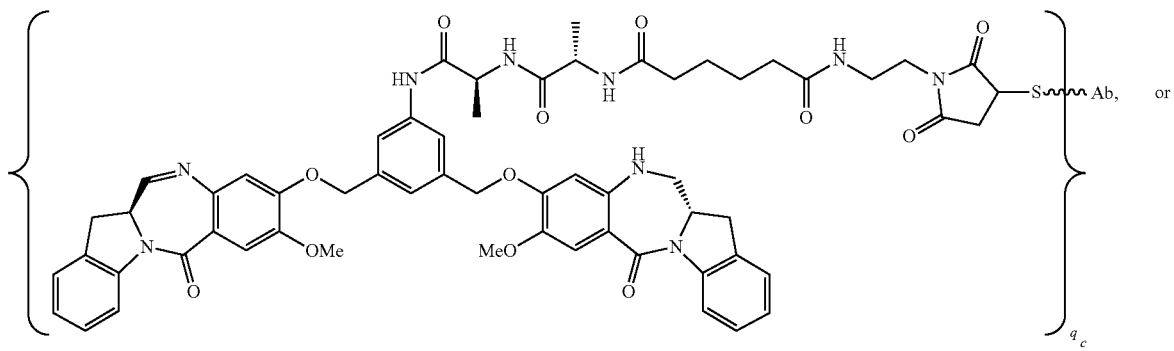

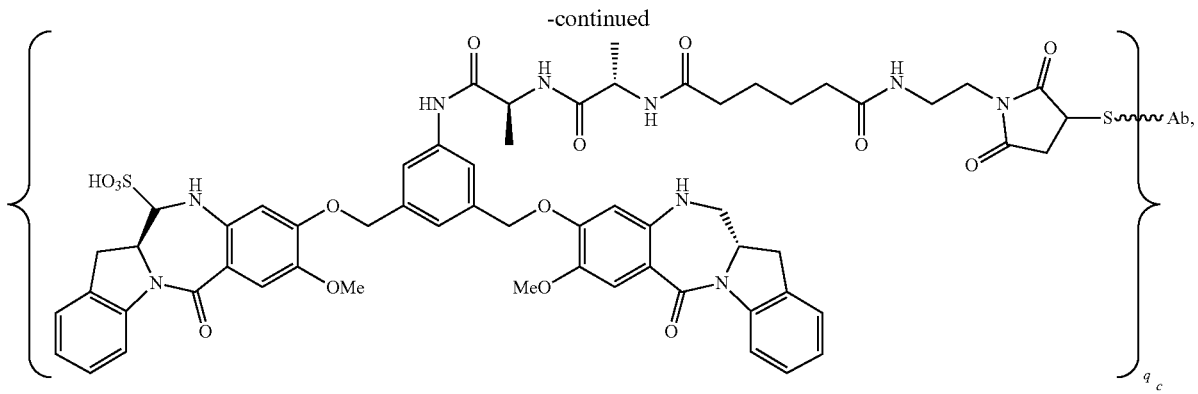

or a pharmaceutically acceptable salt thereof, and the compound is represented by the following formula:

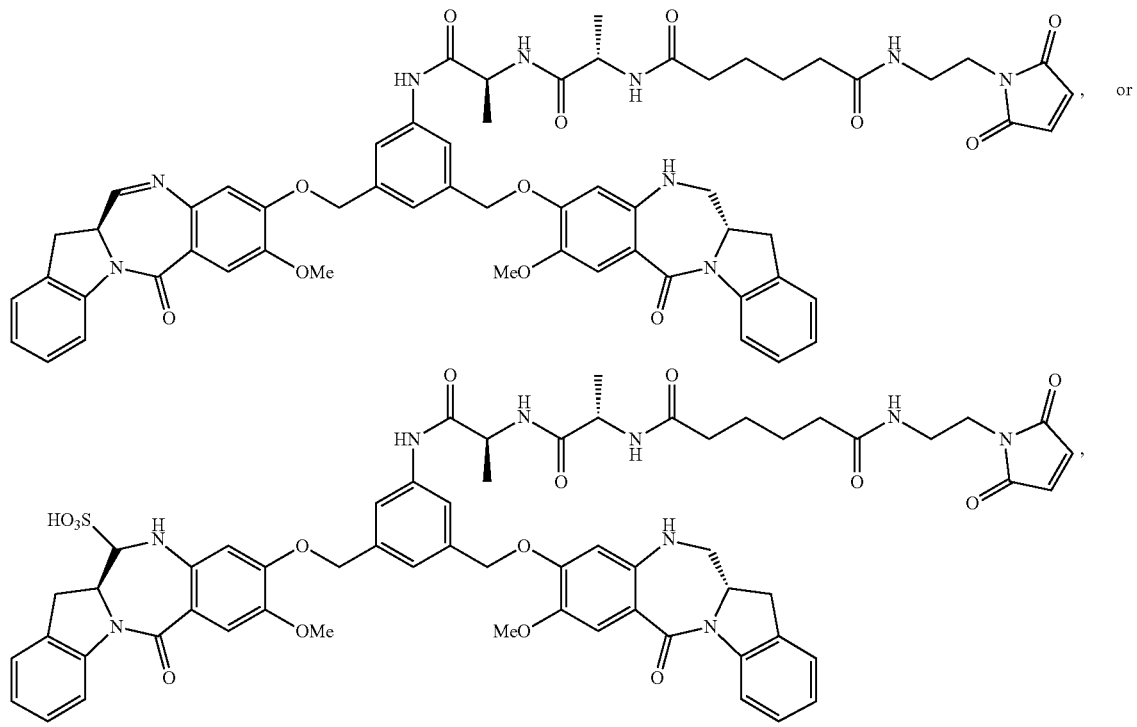

or a pharmaceutically acceptable salt thereof.

In certain embodiments, the pharmaceutically acceptable salt is a sodium salt or a potassium salt. In certain embodiment, the pharmaceutically acceptable salt is a sodium salt.

In certain embodiments, for the method of the fifteenth, sixteenth, seventeenth or eighteenth embodiment, the anti-CD123 antibody or antigen-binding fragment thereof comprises a $V_H$ sequence of SEQ ID NO: 7 and a $V_L$ sequence of SEQ ID NO:9.

In certain embodiments, for the method of the fifteenth, sixteenth, seventeenth or eighteenth embodiment, the anti-CD123 antibody comprises:

a) a heavy chain having the amino acid sequence set forth in SEQ ID NO:8; and b) a light chain having the amino acid sequence set forth in SEQ ID NO:10.

In certain embodiments, for the method of the fifteenth, sixteenth, seventeenth or eighteenth embodiment, the reducing agent is DPPA or TCEP. In certain embodiments, the reducing agent is TCEP.

In certain embodiments, for the method of the fifteenth, sixteenth, seventeenth or eighteenth embodiment, the reaction in step (a) is carried out at a pH between 5.0 and 8.5, between 7.0 and 8.0 or between 7.3 and 7.7. More specifically, the reaction of step (a) is carried out at pH 7.5.

In certain embodiments, for the method of the fifteenth, sixteenth, seventeenth or eighteenth embodiment, the oxidizing agent is DHAA.

In certain embodiments, for the method of the fifteenth, sixteenth, seventeenth or eighteenth embodiment, the reaction in step (b) is carried out at a pH between 5.0 and 8.5, between 7.0 and 8.0 or between 7.3 and 7.7. More specifically, the reaction of step (b) is carried out at pH 7.5.

In certain embodiments, for the method of the fifteenth, sixteenth, seventeenth or eighteenth embodiment, the reaction of step (c) is carried out at a pH between 5.0 and 8.5, between 5.5 and 6.5 or between 5.8 and 6.2. More specifically, the reaction of step (c) is carried out at pH 6.0.

In certain embodiments, for the method of the fifteenth, sixteenth, seventeenth or eighteenth embodiment or any embodiments described herein, excess amount of the compound of formula (I1a) relative to CysAb (e.g., an antibody or antigen-binding fragment thereof) or antigen-binding fragment thereof is used in step (c). More specifically, between 1.1 and 20, between 1.5 and 20, between 2 and 20, between 2 and 10, between 2 and 5, between 3.5 and 5, between 4.2 and 5, between 4.3 and 4.9, between 4.4 and 4.8, or between 4.5 and 4.7 molar equivalents of the compound of formula (I1a) is used for each equivalent of CysAb. In a specific embodiment, 4.0, 4.1, 4.2, 4.3, 4.4, 4.5, 4.6, 4.7, 4.8, 4.9 or 5.0 molar equivalents of the compound of formula (I1a) is used for each equivalent of CysAb. In another specific embodiment, 4.6 molar equivalents of the compound of formula (I11) is used for each equivalent of CysAb.

In certain embodiments, for the method of the fifteenth, sixteenth, seventeenth or eighteenth embodiment, the reducing agent is TCEP; the reaction in step (a) is carried out at a pH between 7.3 and 7.7; the oxidizing agent is DHAA; the reaction in step (b) is carried out at a pH between 7.3 and 7.7; and the pH of the reaction mixture after step (b) is adjusted from a pH between 7.3 and 7.7 to a pH between 5.8 and 6.2 before reacting the CysAb with the cytotoxic agent in step (c).

In certain embodiments, for the method of the fifteenth, sixteenth, seventeenth or eighteenth embodiment, the reducing agent is TCEP; the reaction in step (a) is carried out at pH 7.5; the oxidizing agent is DHAA; the reaction in step (b) is carried out at pH 7.5; and the pH of the reaction mixture after step (b) is adjusted from pH 7.5 to pH 6.0 before reacting the CysAb with the cytotoxic agent in step (c).

In certain embodiments, for the method of the fifteenth, sixteenth, seventeenth or eighteenth embodiment, the method further comprises adjusting the pH of the reaction mixture after step (c) before the conjugate is purified (e.g., before step (d)). In some embodiments, the pH of the reaction mixture after step (c) is adjusted to a pH between 4.0 and 6.0, between 4.0 and 5.5, between 4.0 and 5.0, between 4.5 and 5.0, or between 4.6 and 4.8. In a specific embodiment, the pH is adjusted to 4.5, 4.6, 4.7, 4.8, 4.9 or 5.0. In another specific embodiment, the pH is adjusted to 4.7.

In certain embodiments, for the method of the fifteenth, sixteenth or seventeenth embodiment, the capping reagent is cysteine, glutathione or a combination thereof.

In certain embodiments, a composition (e.g., a pharmaceutical composition) comprising the immunoconjugates prepared by the method of the fifteenth, sixteenth or seventeenth embodiment or any embodiments described therein has a DAR value in the range of 1.0 to 2.5, 1.5 to 2.5, 1.8 to 2.2, or 1.9 to 2.1. In some embodiments, the DAR is 1.8, 1.9, 2.0 or 2.1.

The conjugates prepared by the methods of the present invention has substantially high purity and stability. In certain embodiments, the conjugates prepared by the methods of the present invention has monomer percentage of greater than 90%, 95%, 96%, 97%, 98%, 99%, or 99.5%. In certain embodiments, the conjugate prepared by the methods of the present invention has less than about 10%, less than about 5% (e.g., less than or equal to about 4%, 3%, 2%, 1% or 0%) of high molecular weight species. As used herein, the term "high molecular weight species" or "HMW" refers to antibody-containing or conjugate-containing species that are high in molecular weight. The high molecular weight species can be dimer, trimer, other higher order oligomers formed by aggregation of the antibody or conjugate or the combination thereof. The high molecular weight species can be identified and its amount determined by SEC-HPLC.

In certain embodiments, the average molar ratio of the cytotoxic agent to the CysCBA (i.e, DAR) in a composition of the conjugate is from 1.0 to 2.5, from 1.5 to 2.5, from 1.7 to 2.3, from 1.8 to 2.2, or from 1.9 to 2.1. In another embodiment, the DAR for a composition of the conjugates prepared by the methods of the present invention is 1.5, 1.6, 1.7, 1.8, 1.9, 2.0, 2.1, 2.2, 2.3, 2.4, or 2.5. In one embodiment, the DAR is 2.0. The DAR value can be determined by any methods known in the art. In one embodiment, the DAR value can be determined by UV/Vis spectroscopy using the absorbance values at wavelengths for antibodies and cytotoxic agent, respectively. Alternatively, the DAR value can be determined by mass spectrometry and/or HPLC.

In certain embodiments, for the methods described herein (e.g., the method of the first, second, third, fourth, fifth, sixth, seventh, eighth, ninth, tenth, eleventh, twelfth, thirteenth fourteenth, fifteenth, sixteenth, seventeenth or eighteenth embodiment, or any embodiments described therein), the reaction of step (a), step (b) or step (c) is carried out in a buffer solution. Any suitable buffer can be used in the methods of the present invention. Exemplary buffers include, but are not limited to, a citrate buffer, an acetate buffer, a succinate buffer, a phosphate buffer, MES ((2-(N-morpholino)ethanesulfonic acid)) buffer, bis-tris methane (2-[Bis(2-hydroxyethyl)amino]-2-(hydroxymethyl)propane-1,3-diol) buffer, ADA (N-(2-Acetamido)iminodiacetic acid) buffer, ACES (N-2-aminoethanesulfonic acid) buffer, PIPES (piperazine-N,N'-bis(2-ethanesulfonic acid)), MOPSO (0-Hydroxy-4-morpholinepropanesulfonic acid) buffer, bistris propane (1,3-bis(tris(hydroxymethyl)methylamino)propane) buffer, BES (N,N-bis(2-hydroxyethyl)-2-aminoethanesulfonic acid), TES (N-[tris(hydroxymethyl)methyl]-2-aminoethanesulfonic acid) buffer, HEPES (4-(2-hydroxyethyl)piperazine-1-ethanesulfonic acid) buffer, DIPSO, (3-(N,N-Bis[2-hydroxyethyl]amino)-2-hydroxypropanesulfonic acid or N,N-Bis(2-hydroxyethyl)-3-amino-2-hydroxypropanesulfonic acid), MOBS (4-(N-morpholino) butanesulfonic acid) buffer, TAPSO (3-[[1,3-dihydroxy-2-(hydroxymethyl)propan-2-yl]amino]-2-hydroxypropane-1-sulfonic acid) buffer, trizma (Tris or 2-Amino-2-(hydroxymethyl)-1,3-propanediol) buffer, HEPPSO (N-(2-hydroxyethyl)piperazine-N'-(2-hydroxypropanesulfonic acid)) buffer, POPSO (piperazine-1,4-bis-(2-hydroxy-propane-sulfonic acid) dehydrate) buffer, EPPS (4-(2-hydroxyethyl)piperazine-1-propanesulfonic acid) buffer, tricine (N-(2-Hydroxy-1,1-bis(hydroxymethyl)ethyl)glycine) buffer, gly-gly, bicine (2-(Bis(2-hydroxyethyl)amino)acetic acid) buffer, HEPBS (N-(2-hydroxyethyl)piperazine-N'-(4-butanesulfonic acid)) buffer, TAPS (3-[[1,3-dihydroxy-2-(hydroxymethyl)propan-2-yl]amino]propane-1-sulfonic acid) buffer, AMPD (2-amino-2-methyl-1,3-propanediol) buffer, TABS (N-tris(Hydroxymethyl)methyl-4-aminobutanesulfonic acid) buffer, AMPSO (N-(1,1-Dimethyl-2-hydroxyethyl)-3-amino-2-hydroxypropanesulfonic acid) buffer, or a combination thereof. In certain embodiments, the buffer is a phosphate buffer.

In certain embodiments, for the methods described herein (e.g., the method of the first, second, third, fourth, fifth, sixth, seventh, eighth, ninth, tenth, eleventh, twelfth, thirteenth fourteenth, fifteenth, sixteenth, seventeenth or eighteenth embodiment, or any embodiments described therein), the reaction of step (a), step (b) or step (c) is carried out in the presence of small amount of organic solvent. More specifically, the organic solvent is dimethylacetamide (DMA). The organic solvent (e.g., DMA) can be present in the amount of 1%-20%, 1-15%, 2-15%, 5-15%, or 5-10% by volume of the total volume of the reaction mixture.

In certain embodiments, for the methods of the present invention described above, the reaction of step (a), step (b) or step (c) is allowed to proceed to completion or substantial completion, for example, for a period of 2 minutes to 1 week, 1 hour to 48 hours, 1 hour to 36 hours, 1 hour to 24 hours, 1 hour to 12 hours, 1 hour to 8 hours, 5 hours to 15 hours, 5 hours to 10 hours, 1 hours to 5 hours, 30 minutes to 2 hour, or 5 minutes to 30 minutes. In certain embodiments, the reaction of step (a) is allowed to proceed for a period of 1 hour to 12 hours, 1 hour to 8 hours, 2 hours to 8 hours, 3 hours to 7 hours, or 4 hours to 6 hours. In a specific embodiment, the reaction of step (a) is allowed to proceed for 5 hours. In certain embodiments, the reaction of step (b) is allowed to proceed for a period of 1 hour to 12 hours, 1 hour to 8 hours, 3 hours to 9 hours, 4 hours to 8 hours, or 5 hours to 7 hours. In a specific embodiment, the reaction of step (b) is allowed to proceed for 6 hours. In certain embodiments, the reaction of step (c) is allowed to proceed for a period of 1 hour to 24 hours, 5 hours to 15 hours, 6 hours to 14 hours, 7 hours to 13 hours, 8 hours to 12 hours or 9 hours to 11 hours. In a specific embodiment, the reaction of step (c) is allowed to proceed for 10 hours.

In certain embodiments, for the methods of the present invention described above, the reaction of step (a), step (b) or step (c) can be carried out at any suitable temperature. In certain embodiments, the reaction can be carried out at a temperature from 10° C. to 50° C., from 10° C. to 40° C., or from 10° C. to 30° C. In certain embodiments, the reaction can be carried out at a temperature from 15° C. to 30° C., 20° C. to 30° C., 15° C. to 25° C., from 16° C. to 24° C., from 17° C. to 23° C., from 18° C. to 22° C. or from 19° C. to 21° C. In certain embodiments, the reaction can be carried out at 15° C., 16° C., 17° C., 18° C., 19° C., 20° C., 21° C., 22° C., 23° C., 24° C. or 25° C.

In certain embodiments, for the reaction of step (a), step (b) or step (c) in the methods of the present invention described above, the concentration for the cell-binding agent (e.g., antibody) can be in the range of 1 mg/mL to 50 mg/mL, 1 mg/mL to 20 mg/mL, 1 mg/mL to 15 mg/mL, 1 mg/mL to 10 mg/mL, 1 mg/mL to 6 mg/mL, or 2 mg/mL to 5 mg/mL. In certain embodiments, the concentration for the cell-binding agent (e.g., antibody) is in the range of 3 mg/mL to 5 mg/mL.

In certain embodiments, for the methods described herein, the stable buffer is a formulation buffer for the ADC.

3. In-Line Process Automation Technology (In-Line PAT)

Provided herein are in-line process automation technologies used for continuous methods described herein, e.g., methods for forming and processing antibody drug conjugates (ADCs) described in the first, second or third aspects or any embodiments described therein. Such technologies provide for direct measurements, which can eliminate off-line assays and decrease handling of materials by operators. In-line monitoring can be used to monitor ADC (protein) concentration as well as the removal of free drug. This can allow targeting a final ADC concentration based on data obtained from in-line readings instead of based on a specific volume or number of diavolumes used in the processes (e.g., purification processes). PAT implementation allows for increase control and detectability (e.g., changes during steady-state operation can be used to detect issues before product quality is impacted) and use of multiple PAT modules (e.g., FlowVPE, UV sensors, pH meter, conductivity meter, pressure sensors, or flow meters) can ensure robust process performance across individual unit operations.

In-line monitoring can be used, for example, to monitor the flow rates in a feed stream from any pump in, for example, an antibody reduction and/or oxidation reaction and/or an ADC conjugation reaction (e.g., a reaction described in the method described in the first, second or third aspects or any embodiments described therein). In-line monitoring can be used, for example, to monitor the concentration of a component added to an antibody reduction and/or oxidation reaction and/or an ADC conjugation reaction (e.g., a reaction described in the method described in the first, second or third aspects or any embodiments described therein). Such monitoring can ensure adequate control over the stoichiometry of the reactions. The in-line monitoring can monitor the flow rate or concentration of, for example, an antibody or antigen-binding fragment thereof, a reducing agent, an oxidation agent, a cytotoxic agent or a cytotoxic agent-linker compound (e.g., a compound represented by formula (I)), and/or a conjugation buffer. The in-line monitoring can monitor the flow rate of concentration of an antibody or antigen-binding fragment thereof into a conjugation reaction buffer.

In-line monitoring can also be used, for example, to determine when to stop a conjugation reaction, e.g., by stopping to add conjugation buffer, by stopping the circulation of conjugation buffer, and/or starting to rinse or remove conjugation buffer. In some embodiments provided herein, in-line monitoring of an unconjugated drug (e.g., a compound of formula (I)) can be used. Measurements of unconjugated drug can be used to infer the average number of drugs per antibody (DAR) achieved in a conjugation reaction. Thus, a conjugation reaction can be stopped when the targeted DAR is reached.

In-line monitoring can also be used to monitor the concentration and/or purification of an ADC. The concentration and/or purification can use filtration (e.g., ultrafiltration, diafiltration). The filtration can be tangential flow filtration, including SPTFF. The filtration can be countercurrent diafiltration. When used to monitor filtration, in-line monitoring can be used to measure an analyte in either the retentate or the permeate. Thus, for example, in-line monitoring of an unconjugated drug or unconjugated drug-linker compound in a retentate can be used to assess the degree of purification of the ADC. Levels of unconjugated drug or unconjugated drug-linker compound can be high in a retentate shortly after a conjugation reaction but low in a retentate after purification. In-line monitoring of an ADC in a retentate or a permeate can be used to assess ADC loss during concentration and/or purification processes.

The purification can also use chromatography (e.g., flow through column chromatography). In-line monitoring at the end of a chromatography column can, for example, measure ADC levels and can be used to determine when a column is overloaded or when there is ADC breakthrough.

In-line monitoring can also be used to measure pH, which can be used, for example, to determine the completeness of a buffer exchange.

Exemplary in-line monitoring technologies include the use of, for example, a Fourier Transform Infared (FTIR) flow cell, High Performance Liquid Chromatography (HPLC), or Ultra Performance Liquid Chromatography (UPLC).

In-line monitoring technologies can use, for example, a FlowVPE or UV sensor. In some embodiments, FlowVPE is used to perform in-line monitoring. FlowVPE uses a flow cell for continuous monitoring.

The efficacy of tangential flow filtration (e.g., single-pass tangential flow filtration (SPTFF) can be monitored in-line using FlowVPE, a UV sensor, a pH meter, a conductivity meter, a pressure sensor, a flow meter, etc. The efficacy of countercurrent diafiltration can also be monitored in-line using FlowVPE, a UV sensor, a pH meter, a conductivity meter, a pressure sensor, a flow meter, etc.

In-line monitoring processes can be used in combination with continuous methods of the present invention (discussed above), e.g., continuous conjugation processes using single-pass tangential flow filtration and/or countercurrent diafiltration, or with batch conjugation processes (which are known in the art)

4. Cell-Binding Agents (CysCBA)

Cell-binding agents in the immunoconjugates of the present invention can be of any kind presently known, or that become known, including peptides and non-peptides. Generally, these can be antibodies (such as polyclonal antibodies and monoclonal antibodies, especially monoclonal antibodies), lymphokines, hormones, growth factors, vitamins (such as folate etc., which can bind to a cell surface receptor thereof, e.g., a folate receptor), nutrient-transport molecules (such as transferrin), or any other cell-binding molecule or substance.

In certain embodiments, the cell-binding agent is an antibody, a single chain antibody, an antibody fragment that specifically binds to the target cell, a monoclonal antibody, a single chain monoclonal antibody, a monoclonal antibody fragment (or "antigen-binding portion" or "antigen-binding fragment") that specifically binds to a target cell, a chimeric antibody, a chimeric antibody fragment (or "antigen-binding portion" or "antigen-binding fragment") that specifically binds to the target cell, a domain antibody (e.g., sdAb), or a domain antibody fragment that specifically binds to the target cell.

In certain embodiments, the cell-binding agent is a humanized antibody, a humanized single chain antibody, or a humanized antibody fragment (or "antigen-binding portion" or "antigen-binding fragment").

In certain embodiments, the cell-binding agent is a resurfaced antibody, a resurfaced single chain antibody, or a resurfaced antibody fragment (or "antigen-binding portion" or "antigen-binding fragment").

In certain embodiments, the cell-binding agent is an antibody or an antigen-binding portion thereof (including antibody derivatives), the CBA may bind to a ligand on the target cell, such as a cell-surface ligand, including cell-surface receptors.

In certain embodiments, the cell-binding agent is a cysteine-engineered antibody or antigen-binding fragment thereof. In certain embodiments, the cysteine-engineered antibody or antigen-binding fragment thereof is an anti-folate receptor antibody or an antigen-binding fragment thereof, an anti-EGFR antibody or an antigen-binding fragment thereof, an anti-CD33 antibody or an antigen-binding fragment thereof, an anti-CD19 antibody or an antigen-binding fragment thereof, an anti-Muc1 antibody or an antigen-binding fragment thereof, an anti-CD37 antibody an antigen-binding fragment thereof, anti-cMet antibody or an antigen-binding fragment thereof, or anti-EpCAM antibody or an antigen-binding fragment thereof.

In certain embodiments, the cell-binding agent is an antibody or antigen-binding fragment thereof that: (a) binds an epitope within amino acids 101 to 346 of human CD123/IL3-Rα antigen, and (b) inhibits IL3-dependent proliferation in antigen-positive TF-1 cells (see WO2017/004026, incorporated herein by reference in their entirety).

In certain embodiments, the cell-binding agent is an anti-CD123 antibody or antigen-binding fragment thereof as described in WO2017/004026, which is incorporated herein by reference.

In certain embodiments, the anti-CD123 antibody or antigen-binding fragment thereof may comprise: a) at least one light chain variable region or fragment thereof comprising three sequential complementarity-determining regions (CDR) $CDR_L1$, $CDR_L2$, and $CDR_L3$, respectively, wherein $CDR_L1$ has the amino acid sequence of RASQDINSYLS (SEQ ID NO:1), $CDR_L2$ has the amino acid sequence of RVNRLVD (SEQ ID NO:2), and, $CDR_L3$ has the amino acid sequence of LQYDAFPYT (SEQ ID NO:3); and b) at least one heavy chain variable region or fragment thereof comprising three sequential complementarity-determining regions (CDR) $CDR_H1$, $CDR_H2$, and $CDR_H3$, respectively, wherein, $CDR_H1$ has the amino acid sequence of SSIMH (SEQ ID NO:4), $CDR_H2$ has the amino acid sequence of YIKPYNDGTKYNEKFKG (SEQ ID NO:5), and, $CDR_H3$ has the amino acid sequence of EGGNDYYDTMDY (SEQ ID NO:6).

In certain embodiments, the anti-CD123 antibody or antigen-binding fragment thereof comprises a heavy chain variable region ($V_H$) having the amino acid sequence of

```
                                      (SEQ ID NO: 7)
QVQLVQSGAEVKKPGASVKVSCKASGYIFTWVRQAPGQGLEWIGYIKPY

NDGTKYNEKFKGRATLTSDRSTSTAYMELSSLRSEDTAVYYCAREGGND

YYDTMDYWGQGTLVTVSS
``` and a light chain variable region ($V_L$) having the amino acid sequence of

```
                                      (SEQ ID NO: 9)
DIQMTQSPSSLSASVGDRVTITCRASQDINSYLSWFQQKPGKAPKTLIY

RVNRLVDGVPSRFSGSGSGNDYTLTISSLQPEDFATYYCLQYDAFPYTF

GQGTKVEIKR.
```

In certain embodiments, the anti-CD123 antibody has a heavy chain full length sequence of

```
                                      (SEQ ID NO: 8)
QVQLVQSGAEVKKPGASVKVSCKASGYIFTSSIMHWVRQAPGQGLEWIG

YIKPYNDGTKYNEKFKGRATLTSDRSTSTAYMELSSLRSEDTAVYYCAR

EGGNDYYDTMDYWGQGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYT

QKSLCLSPG
``` and a light chain full length sequence of (SEQ ID NO: 10)
DIQMTQSPSSLSASVGDRVTITC<u>RASQDINSYLS</u>WFQQKPGKAPKTLIY <u>RVNRLVD</u>GVPSRFSGSGSGNDYTLTISSLQPEDFATYYC<u>LQYDAFPYTF</u>

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

In certain embodiments, the cell-binding agent is an anti-CD33 antibody or an antigen-binding fragment thereof as described in U.S. Pat. Nos. 7,342,110 and 7,557,189, which are incorporated herein by reference.

In certain embodiments, the anti-CD33 antibody or antigen-binding fragment thereof may comprise: a) at least one light chain variable region or fragment thereof comprising three sequential complementarity-determining regions (CDR) CDR$_L$1, CDR$_L$2, and CDR$_L$3, respectively, wherein CDR$_L$1 has the amino acid sequence of KSSQSVFFSSSQK-NYLA (SEQ ID NO:11), CDR$_L$2 has the amino acid sequence of WASTRES (SEQ ID NO:12), and, CDR$_L$3 has the amino acid sequence of HQYLSSRT (SEQ ID NO:13); and b) at least one heavy chain variable region or fragment thereof comprising three sequential complementarity-determining regions (CDR) CDR$_H$1, CDR$_H$2, and CDR$_H$3, respectively, wherein, CDR$_H$1 has the amino acid sequence of SYYIH (SEQ ID NO:14), CDR$_H$2 has the amino acid sequence of VIYPGNDDISYNQKFQG (SEQ ID NO:15), and, CDR$_H$3 has the amino acid sequence of EVRLRYFDV (SEQ ID NO:16).

In certain embodiments, the anti-CD33 antibody or antigen-binding fragment thereof comprises a heavy chain variable region (V$_H$) having the amino sequence of (SEQ ID NO: 17)
QVQLQQPGAEVVKPGASVKMSCKASGYTFT<u>SYYIH</u>WIKQTPGQGLEWVG <u>VIYPGNDDISYNQKFQG</u>KATLTADKSSTTAYMQLSSLTSEDSAVYYCAR <u>EVRLRYFDV</u>WGQGTTVTVSS and a light chain variable region (V$_L$) having the amino acid sequence of (SEQ ID NO: 19)
EIVLTQSPGSLAVSPGERVTMSC<u>KSSQSVFFSSSQKNYLA</u>WYQQIPGQSP RLLIY<u>WASTRES</u>GVPDRFTGSGSGTDFTLTISSVQPEDLAIYYC<u>HQYLSS</u>

<u>RT</u>FGQGTKLEIKR.

In certain embodiments, the anti-CD33 antibody has a heavy chain full length sequence of (SEQ ID NO: 18)
QVQLQQPGAEVVKPGASVKMSCKASGYTFT<u>SYYIH</u>WIKQTPGQGLEWVG <u>VIYPGNDDISYNQKFQG</u>KATLTADKSSTTAYMQLSSLTSEDSAVYYCAR <u>EVRLRYFDV</u>WGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKS

LXLSPG and a light chain full length sequence of (SEQ ID NO: 20)
EIVLTQSPGSLAVSPGERVTMSC<u>KSSQSVFFSSSQKNYLA</u>WYQQIPGQS PRLLIY<u>WASTRES</u>GVPDRFTGSGSGTDFTLTISSVQPEDLAIYYC<u>HQYL</u>

<u>SSRT</u>FGQGTKLEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC, wherein X in SEQ ID

NO: 18 is S or C. In one embodiment, X is C.

In certain embodiments, the anti-CD33 antibody is huMy9-6 antibody.

In certain embodiment, the cell-binding agent is an anti-ADAM9 antibody or an antigen-binding fragment thereof as described in WO2018/119196 and U.S. Provisional Application Nos. 62/690,052 and 62/691,342, each of which are incorporated herein by reference.

In certain embodiments, the anti-ADAM9 antibody or antigen-binding fragment thereof is a humanized anti-ADAM9 antibody or antigen-binding fragment thereof that specifically binds to human ADAM9 and cyno ADAM9.

In certain embodiments, the humanized anti-ADAM9 antibody or ADAM9-binding fragment thereof is optimized to have at least a 100-fold enhancement in binding affinity to cyno ADAM9 and retains high affinity binding to human ADAM9 as compared to the chimeric or murine parental antibody.

In certain embodiments, the anti-ADAM9 antibody or antigen-binding fragment thereof (e.g., the humanized anti-ADAM9 antibody or antigen-binding fragment thereof) comprises: a) at least one light chain variable region or fragment thereof comprising three sequential complementarity-determining regions (CDR) CDR$_L$1, CDR$_L$2, and CDR$_L$3, respectively, wherein CDR$_L$1 has the amino acid sequence of KASQSVDYSGDSYMN (SEQ ID NO:21), CDR$_L$2 has the amino acid sequence of AASDLES (SEQ ID NO:22), and, CDR$_L$3 has the amino acid sequence of QQSHEDPFT (SEQ ID NO:23); and b) at least one heavy chain variable region or fragment thereof comprising three sequential complementarity-determining regions (CDR) CDR$_H$1, CDR$_H$2, and CDR$_H$3, respectively, wherein, CDR$_H$1 has the amino acid sequence of SYWMH (SEQ ID NO:24), CDR$_H$2 has the amino acid sequence of EIIP-IFGHTNYNEKFKS (SEQ ID NO:25), and, CDR$_H$3 has the amino acid sequence of GGYYYYPRQGFLDY (SEQ ID NO:26).

In certain embodiments, the anti-ADAM9 antibody or antigen-binding fragment thereof (e.g., the humanized anti-ADAM9 antibody or antigen-binding fragment thereof) comprises a heavy chain variable region (V$_H$) having the amino sequence of (SEQ ID NO: 27)
EVQLVESGGG LVKPGGSLRLSCAASGFTFS <u>SYWMH</u>WVRQA -continued

```
PGKGLEWVGE IIPIFGHTNY NEKFKSRFTI SLDNSKNTLY

LQMGSLRAED TAVYYCARGG YYYYPRQGFL DYWGQGTTVT VSS
``` and a light chain variable region (V$_L$) having the amino acid sequence of (SEQ ID NO: 28)
```
DIVMTQSPDSLAVSLGERATISCKASQSVDYSGDSYMNWYQQKPGQPPKL

LIYAASDLES GIPARFSGSG SGTDFTLTIS

SLEPEDFATYYCQQSHEDPFTFGQGTKLEI K.
```

In certain embodiments, the anti-ADAM9 antibody has a heavy chain full length sequence of (SEQ ID NO:29)
```
EVQLVESGGG LVKPGGSLRL SCAASGFTFS SYWMHWVRQA PGKGLEWVGE

IIPIFGHTNY NEKFKSRFTI SLDNSKNTLY LQMGSLRAED TAVYYCARGG

YYYYPRQGFL DYWGQGTTVT VSSASTKGPS VFPLAPSSKS TSGGTAALGC

LVKDYFPEPV TVSWNSGALT SGVHTFPAVL QSSGLYSLSS VVTVPSSSLG

TQTYICNVNH KPSNTKVDKR VEPKSCDKTH TCPPCPAPEL LGGPSVFLFP

PKPKDTLYIT REPEVTCVVV DVSHEDPEVK FNWYVDGVEV HNAKTKPREE

QYNSTYRVVS VLTVLHQDWL NGKEYKCKVS NKALPAPIEK TISKAKGQPR

EPQVYTLPPS REEMTKNQVS LTCLVKGFYP SDIAVEWESN GQPENNYKTT

PPVLDSDGSF FLYSKLTVDK SRWQQGNVFS CSVMHEALHN HYTQKSLCLS PG
``` and a light chain full length sequence of (SEQ ID NO: 30)
```
DIVMTQSPDSLAVSLGERATISCKASQSVDYSGDSYMNWYQQKPGQPPKL

LIYAASDLESGIPARFSGSGSGTDFTLTISSLEPEDFATYYCQQSHEDPF

TFGQGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.
```

In certain embodiment, the cell-binding agent is an anti-EpCAM antibody or an antigen-binding fragment thereof as described in U.S. Provisional Application No. 62/751,530, incorporated herein by reference.

In certain embodiments, the anti-EpCAM antibody or antigen-binding fragment thereof may comprise: a) at least one light chain variable region or fragment thereof comprising three sequential complementarity-determining regions (CDR) CDR$_L$1, CDR$_L$2, and CDR$_L$3, respectively, wherein CDR$_L$1 has the amino acid sequence of RSSRSLLHSDGFTYLY (SEQ ID NO:31), CDR$_L$2 has the amino acid sequence of QTSNLAS (SEQ ID NO:32), and, CDR$_L$3 has the amino acid sequence of AQNLELPNT (SEQ ID NO:33); and b) at least one heavy chain variable region or fragment thereof comprising three sequential complementarity-determining regions (CDR) CDR$_H$1, CDR$_H$2, and CDR$_H$3, respectively, wherein, CDR$_H$1 has the amino acid sequence of NYYIH (SEQ ID NO:34), CDR$_H$2 has the amino acid sequence of WIYPGNVYIQYNEKFKG (SEQ ID NO:35), and, CDR$_H$3 has the amino acid sequence of DGPWFAY (SEQ ID NO:36).

In certain embodiments, the anti-EpCAM antibody or antigen-binding fragment thereof comprises a heavy chain variable region (V$_H$) having the amino sequence of (SEQ ID NO: 37)
```
QVQLVQSGAEVKKPGASVKVSCKASGYTFTNYYIHWVRQAPGQRLEYIGW

IYPGNVYIQYNEKFKGRATLTADKSASTAYMELSSLRSEDTAVYYCARDG

PWFAYWGQGTLVTVSS
``` and a light chain variable region (V$_L$) having the amino acid sequence of (SEQ ID N: 38)
```
DIVLTQTPLSLSVTPGQPASISCRSSRSLLHSDGFTYLYWFLQKPGQSP

QLLIYQTSNLASGVPDRFSSSGSGTDFTLKISRVEAEDVGVYYCAQNLE

LPNTFGQGTKLEIK.
```

In certain embodiments, the anti-EpCAM antibody has a heavy chain full length sequence of (SEQ ID NO: 39)
```
QVQLVQSGAEVKKPGASVKVSCKASGYTFTNYYIHWVRQAPGQRLEYIG

WIYPGNVYIQYNEKFKGRATLTADKSASTAYMELSSLRSEDTAVYYCAR

DGPWFAYWGQGTLVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLX

LSPG
``` and a light chain full length sequence of (SEQ ID NO: 40)
DIVLTQTPLSLSVTPGQPASISCRSSRSLLHSDGFTYLYWFLQKPGQSPQ

LLIYQTSNLASGVPDRFSSSGSGTDFTLKISRVEAEDVGVYYCAQNLELP

NTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC, wherein X in SEQ ID NO: 39 is

S or C. In one embodiment, X is C.

In certain embodiments, the cell-binding agent is an anti-folate receptor antibody. In certain embodiments, the cell-binding agent is an anti-human folate receptor 1 (FOLR1) antibody or an antigen-binding fragment thereof as described in U.S. Pat. Nos. 8,709,432, 8,557,966, and WO2011106528, all of which are incorporated herein by reference.

In certain embodiments, the anti-FOLR1 antibody or antigen-binding fragment thereof may comprise: a) at least one light chain variable region or fragment thereof comprising three sequential complementarity-determining regions (CDR) $CDR_L1$, $CDR_L2$, and $CDR_L3$, respectively, wherein $CDR_L1$ has the amino acid sequence of KASQSVSFAGTSLMH (SEQ ID NO:41), $CDR_L2$ has the amino acid sequence of RASNLEA (SEQ ID NO:42), and, $CDR_L3$ has the amino acid sequence of QQSREYPYT (SEQ ID NO:43); and b) at least one heavy chain variable region or fragment thereof comprising three sequential complementarity-determining regions (CDR) $CDR_H1$, $CDR_H2$, and $CDR_H3$, respectively, wherein, $CDR_H1$ has the amino acid sequence of GYFMN (SEQ ID NO:44) or GYTFTGYFMN (SEQ ID NO:47), $CDR_H2$ has the amino acid sequence of RIHPYDGDTFYNQKFQG (SEQ ID NO:45) or RIHPYDGDTF (SEQ ID NO:48), and, $CDR_H3$ has the amino acid sequence of YDGSRAMDY (SEQ ID NO:46). In certain embodiments, the anti-FOLR1 antibody or antigen-binding fragment thereof comprises a) a light chain variable region comprising a $CDR_L1$ having an amino sequence set forth in SEQ ID NO:41, a $CDR_L2$ having an amino sequence set forth in SEQ ID NO:42, and a $CDR_L3$ having an amino sequence set forth in SEQ ID NO:43; and b) a heavy chain variable region comprising a $CDR_H1$ having an amino sequence set forth in SEQ ID NO:44, a $CDR_H2$ having an amino sequence set forth in SEQ ID NO:45, and a $CDR_H3$ having an amino sequence set forth in SEQ ID NO:46. In certain embodiments, the anti-FOLR1 antibody or antigen-binding fragment thereof comprises a) a light chain variable region comprising a $CDR_L1$ having an amino sequence set forth in SEQ ID NO:41, a $CDR_L2$ having an amino sequence set forth in SEQ ID NO:42, and a $CDR_L3$ having an amino sequence set forth in SEQ ID NO:43; and b) a heavy chain variable region comprising a $CDR_H1$ having an amino sequence set forth in SEQ ID NO:47, a $CDR_H2$ having an amino sequence set forth in SEQ ID NO:48, and a $CDR_H3$ having an amino sequence set forth in SEQ ID NO:46.

In certain embodiments, the anti-FOLR1 antibody or antigen-binding fragment thereof comprises a heavy chain variable region ($V_H$) having the amino sequence of (SEQ ID NO: 49)
QVQLVQSGAEVVKPGASVKISCKASGYTFTGYFMNWVKQSPGQSLEWIG

RIHPYDGDTFYNQKFQGKATLTVDKSSNTAHMELLSLTSEDFAVYYCTR

YDGSRAMDYWGQGTTVTVSS and a light chain variable region ($V_L$) having the amino acid sequence of (SEQ ID NO: 50)
DIVLTQSPLSLAVSLGQPAIISCKASQSVSFAGTSLMHWYHQKPGQQPRL

LIYRASNLEAGVPDRFSGSGSKTDFTLNISPVEAEDAATYYCQQSREYPY

TFGGGTKLEIKR,
or (SEQ ID NO: 51)
DIVLTQSPLSLAVSLGQPAIISCKASQSVSFAGTSLMHWYHQKPGQQPRL

LIYRASNLEAGVPDRFSGSGSKTDFTLTISPVEAEDAATYYCQQSREYPY

TFGGGTKLEIKR.

In certain embodiments, the anti-FOLR1 antibody has a heavy chain full length sequence of (SEQ ID NO: 52)
QVQLVQSGAEVVKPGASVKISCKASGYTFTGYFMNWVKQSPGQSLEWIGR

IHPYDGDTFYNQKFQGKATLTVDKSSNTAHMELLSLTSEDFAVYYCTRYD

GSRAMDYWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLXLSPGY and a light chain full length sequence of (SEQ ID NO: 53)
DIVLTQSPLSLAVSLGQPAIISCKASQSVSFAGTSLMHWYHQKPGQQPRL

LIYRASNLEAGVPDRFSGSGSKTDFTLNISPVEAEDAATYYCQQSREYPY

TFGGGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC,
or (SEQ ID NO: 54)
DIVLTQSPLSLAVSLGQPAIISCKASQSVSFAGTSLMHWYHQKPGQQPRL

LIYRASNLEAGVPDRFSGSGSKTDFTLTISPVEAEDAATYYCQQSREYPY

TFGGGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC, wherein X in SEQ ID NO: 52 is

C or S and Y in SEQ ID NO: 52 is K or absent. In one embodiment, X is C.

In certain embodiments, the anti-FOLR1 antibody is huMov19 or M9346A antibody.

In certain embodiments, the antibody described herein is a murine, non-human mammal, chimeric, humanized, or human antibody. For example, the humanized antibody may be a CDR-grafted antibody or resurfaced antibody. In certain embodiments, the antibody is a full-length antibody. In certain embodiments, the antigen-binding fragment thereof is an Fab, Fab', F(ab')$_2$, F$_d$, single chain Fv or scFv, disulfide linked F$_v$, V-NAR domain, IgNar, intrabody, IgGΔCH$_2$, minibody, F(ab')$_3$, tetrabody, triabody, diabody, single-domain antibody, DVD-Ig, Fcab, mAb$_2$, (scFv)$_2$, or scFv-Fc.

In certain embodiments, the cell-binding agent is an alternative protein scaffold, such as a Centyrin (a protein scaffold based on a consensus sequence of fibronectin type III (FN3) repeats; see U.S. Patent Publication 2010/0255056, 2010/0216708 and 2011/0274623 incorporated herein by reference), an Ankyrin Repeat Protein (e.g., a designed ankyrin repeat protein, known as DARPin; see U.S. Patent Publication Nos. 2004/0132028, 2009/0082274, 2011/0118146, and 2011/0224100, incorporated herein by reference, and also see C. Zahnd et al., *Cancer Res.* (2010) 70:1595-1605; Zahnd et al., *J. Biol. Chem.* (2006) 281(46): 35167-35175; and Binz, H. K., Amstutz, P. & Pluckthun, A., *Nature Biotechnology* (2005) 23:1257-1268, incorporated herein by reference), an ankyrin-like repeats protein or synthetic peptide (see e.g., U.S. Patent Publication No. 2007/0238667; U.S. Pat. No. 7,101,675; WO 2007/147213; and WO 2007/062466, incorporated herein by reference), an Adnectin (a fibronectin domain scaffold protein; see US Patent Publication Nos. 2007/0082365; 2008/0139791, incorporated herein by reference), Avibody (including diabodies, triabodies, and tetrabodies; see U.S. Publication Nos. 2008/0152586 and 2012/0171115), dual receptor retargeting (DART) molecules (P. A. Moore et al., *Blood*, 2011; 117(17):4542-4551; Veri M C, et al., *Arthritis Rheum*, 2010 Mar. 30; 62(7):1933-43; Johnson S, et al. *J Mol Biol*, 2010 Apr. 9; 399(3):436-49), and cell penetrating supercharged proteins (*Methods in Enzymol.* 502, 293-319 (2012).

In certain embodiments, the cell-binding agent is an activatable antibody or an activatable antigen-binding antibody fragment (collectively as AA). In some embodiments, the activatable antibody or activatable antigen-binding antibody fragment comprises an antibody or antigen-binding antibody fragment (e.g., antibodies or antigen-binding antibody fragments described herein) specifically binds to a ligand on the target cell (or "a target") coupled to a masking moiety (MM), such that coupling of the MM reduces the ability of the antibody or antigen-binding antibody fragment to bind the target. In some embodiments, the MM is coupled via a sequence that includes a substrate for a protease, for example, a protease that is active in diseased tissue and/or a protease that is co-localized with the target at a treatment site in a subject. The activatable antibodies are preferably stable in circulation, activated at intended sites of therapy and/or diagnosis but not in normal, e.g., healthy tissue or other tissue not targeted for treatment and/or diagnosis, and, when activated, exhibit binding to the target that is at least comparable to the corresponding, unmodified antibody. In some embodiments, the AAs are those described in WO 2009/025846, WO 2010/081173, WO 2015/048329, WO 2015/116933 and WO 2016/118629, each of which is incorporated by reference in its entirety.

In some embodiments, the activatable antibody or antibody fragment comprises:
(a) a cleavable moiety (CM) coupled to the antibody or antibody fragment (collectively as "AB"), wherein the CM is a polypeptide that functions as a substrate for a protease; and (b) a masking moiety (MM) coupled to the antibody or antibody fragment, wherein the MM inhibits the binding of the antibody or antibody fragment to the ligand when the activatable antibody is in an uncleaved state, wherein the activatable antibody in the uncleaved state has the structural arrangement from N-terminus to C-terminus as follows: (MM)-(CM)-(AB) or (AB)-(CM)-(MM).

In some embodiments, the masking moiety (or "mask") is an amino acid sequence that is coupled or otherwise attached to the antibody and is positioned within the activatable antibody construct such that the masking moiety reduces the ability of the antibody to specifically bind the target. Suitable masking moieties are identified using any of a variety of known techniques. For example, peptide masking moieties are identified using the methods described in WO 2009/025846, the contents of which is herein incorporated by reference in its entirety.

The $K_d$ of the AB modified with a NM towards the target can be at least 5, 10, 25, 50, 100, 250, 500, 1,000, 2,500, 5,000, 10,000, 50,000, 100,000, 500,000, 1,000,000, 5,000, 10,000,000, 50,000,000 or greater, or between 5-10, 10-100, 10-1,000, 10-10,000, 10-10,000, 10-1,00,000, 10-10,000,000, 100-1,000, 100-10,000, 100-100,000, 100-1,000,000, 100-10,000,000, 1,000-10,000, 1,000-100,000, 1,000-1,000, 000, 1,000-10,000,000, 10,000-10000, 10,000-1,00,000, 10,000-100,000, 100,000-1,000,000, or 100,000-1,00000 times greater than the $K_d$ of the AB not modified with an MM or the parental AB towards the target, Conversely, the binding affinity of the AB modified with a MM towards the target can be at least 5, 10, 25, 50, 100, 250, 500, 1,000, 2,500, 5,000, 10,000, 50,000, 100,000, 500,000, 1,1000,000, 5,000,000, 10,000,000, 50,00,000 or greater, or between 5-10, 10-100, 10-1,000, 10-10,000, 10-100,000, 10-1,000, 000, 10-10,000,000, 100-1,000, 100-10,000, 100-100,000, 100-1,000,000, 100-1,000,000, 1,000-10,000, 1,000-100, 000, 1,000-1,000,000, 1,000-10,000,000, 10,000-100,000, 10,000-1,000,000, 10,000-10,000,000, 100,000-1,000,000, or 100,000-10,000,000 times lower than the binding affinity of the AB not modified with an MM or the parental AB towards the target.

The dissociation constant ($K_d$) of the MM towards the AB is generally greater than the $K_d$ of the AB towards the target. The $K_d$ of the MM towards the AB can be at least 5, 10, 25, 50, 100, 250, 500, 1,000, 2,500, 5,000, 10,000, 100,000, 1,000,000 or even 10,000,000 times greater than the $K_d$ of the AB towards the target. Conversely, the binding affinity of the MM towards the AB is generally lower than the binding affinity of the AB towards the target. The binding affinity of MM towards the AB can be at least 5, 10, 25, 50, 100, 250, 500, 1,000, 2,500, 5,000, 10,000, 100,000, 1,000,000 or even 10,000,000 times lower than the binding affinity of the AB towards the target.

When the AB is modified with a MM and is in the presence of the target, specific binding of the AB to its target can be reduced or inhibited, as compared to the specific binding of the AB not modified with an MM or the specific binding of the parental AB to the target. When compared to the binding of the AB not modified with an MM or the binding of the parental AB to the target, the AB's ability to bind the target when modified with an MM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, 96, hours, or 5, 10, 15, 30, 45, 60, 90, 120, 150, 180 days, or 1, 2, 3, 4, 5, 6, 7, 8, 9, 10, 11, 12 months or greater when measured in vivo or in a Target Displacement in vitro immunoabsorbent assay, as described WO 2010/081173.

The MM can inhibit the binding of the AB to the target. The MM can bind the antigen binding domain of the AB and inhibit binding of the AB to its target. The MM can sterically inhibit the binding of the AB to the target. The MM can allosterically inhibit the binding of the AB to its target. In these embodiments when the AB is modified or coupled to a MM and in the presence of target, there is no binding or substantially no binding of the AB to the target, or no more than 0.001%, 01%, 0.1%, 1%, 2%, 3%, 4%, 5%, 6%, 7%, 8%, 9%, 10%, 15%, 20%, 25%, 30%, 35%, 40%, or 50% binding of the AB to the target, as compared to the binding of the AB not modified with an MM, the parental AB, or the AB not coupled to an MM to the target, for at least 4, 6, 8, 12, 28, 24, 30, 36, 48, 60, 72, 84, 96, hours, or 5, 10, 15, 30, 45, 60, 90, 120, 150, 180 days or 1, 2, 3, 4, 5, 6, 7, 8, 9, 10, 11, 12 months or greater when measured in vivo or in a Target Displacement n vitro immunoabsorbent assay, as described WO 2010/081173.

When an AB is coupled to or modified by a MM, the MM can 'mask' or reduce, or inhibit the specific binding of the AB to its target. When an AB is coupled to or modified by a MM, such coupling or modification can effect a structural change which reduces or inhibits the ability of the AB to specifically bind its target.

An AB coupled to or modified with an MM can be represented by the following formulae (in order from an amino (N) terminal region to carboxyl (C) terminal region):

(MM)-(AB)

(AB)-(MM)

(MM)-L-(AB)

(AB)-L-(MM)

where MM is a masking moiety, the Ab is an antibody or target-binding antigen fragment, and L is a linker. In many embodiments, it may be desirable to insert one or more linkers, e.g., flexible linkers, into the composition so as to provide for flexibility.

In certain embodiments, the MM is not a natural binding partner of the Ab. In some embodiments, the MM contains no or substantially no homology to any natural binding partner of the Ab. In some embodiments, the MM is no more than 5%, 10%, 15%, 20%, 25%, 30%, 35%, 40%, 45%, 50%, 55%, 60%, 65%, 70%, 75%, or 80% similar to any natural binding partner of the Ab. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the Ab. In some embodiments, the MM is no more than 25% identical to any natural binding partner of the Ab. In some embodiments, the MM is no more than 50% identical to any natural binding partner of the Ab. In some embodiments, the MM is no more than 20% identical to any natural binding partner of the Ab. In some embodiments, the MM is no more than 10% identical to any natural binding partner of the Ab.

The activatable antibodies provided herein can also include a cleavable moiety (CM). Such AAs exhibit activatable/switchable binding, to the AB's target. AAs generally include an antibody or antibody fragment (AB), modified by or coupled to a masking moiety (MM) and a modifiable or cleavable moiety (CM). In some embodiments, the CM contains an amino acid sequence that serves as a substrate for a protease of interest. In other embodiments, the CM provides a cysteine-cysteine disulfide bond that is cleavable by reduction. In yet other embodiments the CM provides a photolytic substrate that is activatable by photolysis.

In some embodiments, the cleavable moiety (or "substrate") includes an amino acid sequence that is a substrate for a protease, usually an extracellular protease. Suitable substrates are identified using any of a variety of known techniques. For example, peptide substrates are identified using the methods described in U.S. Pat. Nos. 7,666,817 and 8,563,269; and WO 2014/026136, the contents of each of which is herein incorporated by reference in its entirety. (See also, Boulware et al., Biotechnol Bioeng. 106(3):339-346 (2010)). Optionally, the CM comprises a cysteine-cysteine pair capable of forming a disulfide bond, which can be cleaved by action of a reducing agent. The CM is positioned such that when the CM is cleaved by a cleaving agent (e.g., a protease substrate of a CM is cleaved by the protease and/or the cysteine-cysteine disulfide bond is disrupted via reduction by exposure to a reducing agent), in the presence of a target, resulting in a cleaved state, the Ab binds the target, and in an uncleaved state, in the presence of the target, binding of the Ab to the target is inhibited by the MM. It should be noted that the amino acid sequence of the CM may overlap with or be included within the MM, such that all or a portion of the CM facilitates "masking" of the Ab when the activatable antibody is in the uncleaved conformation.

In some embodiments, the CM may be selected based on a protease that is co-localized in tissue with the desired target of the activatable antibody. A variety of different conditions are known in which a target of interest is co-localized with a protease, where the substrate of the protease is known in the art. For example, the target tissue can be a cancerous tissue, particularly cancerous tissue of a solid tumor. There are many reports in the literature of increased levels of proteases having known substrates in a number of cancers, e.g., solid tumors. See, e.g., La Rocca et al. (2004) British J. of Cancer 90(7): 1414-1421.

Exemplary substrates can include but are not limited to substrates cleavable by one or more of the following enzymes: MMP-1, MMP-2, MMP-3, MMP-8, MMP-9, MMP-14, PLASMIN, PSA, PSMA, CATHEPSIN D, CATHEPSIN K, CATHEPSIN S, ADAMIO, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE.

In some embodiments, the CM is a polypeptide of up to 15 amino acids in length.

In some embodiments, the CM is a polypeptide that includes a first cleavable moiety (CM1) that is a substrate for at least one matrix metalloprotease (MMP) and a second cleavable moiety (CM2) that is a substrate for at least one serine protease (SP). In some embodiments, each of the CM1 substrate sequence and the CM2 substrate sequence of the CM1-CM2 substrate is independently a polypeptide of up to 15 amino acids in length.

In some embodiments the CM is a substrate for legumain, plasmin, TMPRSS-3/4, MMP-9, MT1-MMP, cathepsin, caspase, human neutrophil elastase, beta-secretase, uPA, or PSA.

The $K_d$ of the Ab modified with a MM and a CM towards the target can be at least 5, 10, 25, 50, 100, 250, 500, 1,000, 2,500, 5,000, 10,000, 50,000, 100,000, 500,000, 1,000,000, 5,000,000, 10,000,000, 50,000000 or greater, or between 5-10, 10-100, 10-1,000, 10-10,000, 10-100,000, 10-1,000,000, 10-10,00000, 100-1,000, 100-10,000, 100-100,000, 100-1,000,000, 100-10,000,000, 1,000-10,000, 1,000-100,000, 1,000-1,000,000, 1,000-10,000,000, 10,000-100,000, 10,000-1,000,000, 10,000-110,000,000, 100,000-1,000,000, or 100000-10,000,000 times greater than the $K_d$ of the Ab not modified with an MM and a CM or the parental Ab towards the target. Conversely, the binding affinity of the Ab modified with a MM and a CM towards the target can be at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1,000-10,000,000, 10,000-100,000, 10,000-1,000,000, 10,000-10,000,000, 100,000-1,0000,0000 or 100,000-10,00,000 tines lower than the binding affinity of the Ab not modified with an MM and a CM or the parental Ab towards the target.

When the Ab is modified with a MM and a CM and is in the presence of the target but not in the presence of a modifying agent (for example an enzyme, protease, reduction agent, light), specific binding of the Ab to its target can be reduced or inhibited, as compared to the specific binding of the Ab not modified with an MM and a CM or the parental Ab to the target. When compared to the binding of the parental Ab or the binding of an Ab not modified with an MM and a CM to its target, the Ab's ability to bind the target when modified with an MM and a CM can be reduced by at least 50%, 60%, 70%, 80%, 90%, 92% 93%, 94%, 95%, 96%, 97%, 98%, 99% and even 100% for at least 2, 4, 6, 8, 12, 28, 24, 30, 36, 48, 60, 72, 84, 96 hours, or 5, 10, 15, 30, 45, 60, 90, 120, 150, 180 days, or 1, 2, 3, 4, 5, 6, 7, 8, 9, 10, 11, 12 months or greater when measured in vivo or in a Target Displacement in vitro immunoabsorbent assay, as described in WO201008117, incorporated herein by reference in its entirety.

As used herein, the term cleaved state refers to the condition of the AA following modification of the CM by a protease and/or reduction of a cysteine-cysteine disulfide, bond of the CM, and/or photoactivation. The term uncleaved state, as used herein, refers to the condition of the AA in the absence of cleavage of the CM by a protease and/or in the absence reduction of a cysteine-cysteine disulfide bond of the CM, and/or in the absence of light. As discussed above, the term AA is used herein to refer to an AA in both its uncleaved (native) state, as well as in its cleaved state. It will be apparent to the ordinarily skilled artisan that in some embodiments a cleaved AA may lack an MM due to cleavage of the CM by protease, resulting in release of at least the MM (e.g. where the MM is not joined to the A by a covalent bond (e.g., a disulfide bond between cysteine residues.

By activatable or switchable is meant that the AA exhibits a first level of binding to a target when in a inhibited, masked or uncleaved state (i.e. a first conformation), and a second level of binding to the target in the uninhibited, unmasked and/or cleaved state (i.e., a second conformation), where the second level of target binding is greater than the first level of binding. In general the access of target to the Ab of the AA is greater in the presence of a cleaving agent capable of cleaving the CM than in the absence of such a cleaving agent. Thus, when the AA is in the uncleaved state, the Ab is inhibited from target binding and can be masked from target binding (i.e., the first conformation is such the Ab can not bind the target) and in the cleaved state the AB is not inhibited or is unmasked to target binding.

The CM and AB of the AA may be selected so that the AB represents a binding moiety for a target of interest, and the CM represents a substrate for a protease that is co-localized with the target at a treatment site in a subject. Alternatively or in addition, the CM is a cysteine-cysteine disulfide bond that is cleavable as a result of reduction of this disulfide bond. AAs contain at least one of a protease-cleavable CM or a cysteine-cysteine disulfide bond, and in some embodiments include both kinds of CMs. The AAs can alternatively or further include a photolabile substrate, activatable by a light source. The AAs disclosed herein find particular use where, for example, a protease capable of cleaving a site in the CM is present at relatively higher levels in target-containing tissue of a treatment site (for example diseased tissue; for example for therapeutic treatment or diagnostic treatment) than in tissue of non-treatment sites (for example in healthy tissue). The AAs disclosed herein also find particular use where, for example, a reducing agent capable of reducing a site in the CM is present at relatively higher levels in target-containing tissue of a treatment or diagnostic site than in tissue of non-treatment non-diagnostic sites. The AAs disclosed herein also find particular use where, for example, a light source, for example, by way of laser, capable of photolysing a site in the CM is introduced to a target-containing tissue of a treatment or diagnostic site.

In some embodiments AAs can provide for reduced toxicity and/or adverse side effects that could otherwise result from binding of the Ab at non-treatment sites if the Ab were not masked or otherwise inhibited from binding its target. Where the AA contains a CM that is cleavable by a reducing agent that facilitates reduction of a disulfide bond, the ABs of such AAs may selected to exploit activation of an Ab where a target of interest is present at a desired treatment site characterized by elevated levels of a reducing agent, such that the environment is of a higher reduction potential than, for example, an environment of a non-treatment site.

In general, an AA can be designed by selecting an Ab of interest and constructing the remainder of the AA so that, when conformationally constrained, the MM provides for masking of the Ab or reduction of binding of the Ab to its target. Structural design criteria to be taken into account to provide for this functional feature.

AAs exhibiting a switchable phenotype of a desired dynamic range for target binding in an inhibited versus an uninhibited conformation are provided. Dynamic range generally refers to a ratio of (a) a maximum detected level of a parameter under a first set of conditions to (b) a minimum detected value of that parameter under a second set of conditions. For example, in the context of an AA, the dynamic range refers to the ratio of (a) a maximum detected level of target protein binding to an AA in the presence of protease capable of cleaving the CM of the AA to (b) a minimum detected level of target protein binding to an AA in the absence of the protease. The dynamic range of an AA can be calculated as the ratio of the equilibrium dissociation constant of an AA cleaving agent (e.g., enzyme) treatment to the equilibrium dissociation constant of the AA cleaving agent treatment. The greater the dynamic range of an AA, the better the switchable phenotype of the AA. AAs having relatively higher dynamic range values (e.g., greater than 1) exhibit more desirable switching phenotypes such that target protein binding by the AA occurs to a greater extent (e.g., predominantly occurs) in the presence of a cleaving agent (e.g., enzyme) capable of cleaving the CM of the AA than in the absence of a cleaving agent.

AAs can be provided in a variety of structural configurations. Exemplary formulae for AAs are provided below. It is specifically contemplated that the N- to C-terminal order of the AB. MM and CM may be reversed within an AA. It is also specifically contemplated that the CM and MM may overlap in amino acid sequence. e.g., such that the CM is contained within the MM.

For example, AAs can be represented by the following formula (in order from an amino (N) terminal region to carboxyl (C) terminal region:

(MM)-(CM)-(A B)

(AB)-(CM)-(MM) where MM is a masking moiety. CM is a cleavable moiety, and AB is an antibody or fragment thereof. It should be noted that although MM and CM are indicated as distinct components in the formula above, in all exemplary embodiments (including formulae) disclosed herein it is contemplated that the amino acid sequences of the MM and the CM could overlap, e.g., such that the CM is completely or partially contained within the MM. In addition, the formulae above provide for additional amino acid sequences that may be positioned N-terminal or C-terminal to the AA elements.

In certain embodiments, it may be desirable to insert one or more linkers, e.g., flexible linkers, into the AA construct so as to provide for flexibility at one or more of the MM-CM junction, the CM-AB junction, or both. For example, the AB, MM, and/or CM may not contain a sufficient number of residues (e.g., Gly, Ser, Asp. Asn, especially Gly and Ser, particularly Gly) to provide the desired flexibility. As such, the switchable phenotype of such AA constructs may benefit from introduction of one or more amino acids to provide for a flexible linker. In addition, as described below, where the AA is provided as a conformationally constrained construct, a flexible linker can be operably inserted to facilitate formation and maintenance of a cyclic structure in the uncleaved AA.

For example, in certain embodiments an AA comprises one of the following formulae (where the formula below represent an amino acid sequence in either N- to C-terminal direction or C- to N-terminal direction):

(MM)-$L_1$-(CM)-(AB)

(MM)-(CM)-$L_1$-(AB)

(MM)-$L_1$-(CM)-$L_2$-(AB)

CyClo[$L_1$-(MM)-$L_2$-(CM)-$L_3$-(AB)]

wherein MM, CM, and AB are as defined above; wherein $L_1$, $L_2$ and $L_3$ are each independently and optionally present or absent, are the same or different flexible linkers that include at least 1 flexible amino acid (e.g., Gly); and wherein cyclo where present, the AA is in the form of a cyclic structure due to the presence of a disulfide bond between a pair of cysteines in the AA. In addition, the formulae above provide for additional amino acid sequences that may be positioned N-terminal or C-terminal to the AA elements. It should be understood that in the formula CyClo[$L_1$-(MM)-$L_2$-(CM)-$L_3$-(AB)], the cysteines responsible for the disulfide bond may be positioned in the AA to allow for one or two tails, thereby generating a lasso or omega structure when the AA is in a disulfide-bonded structure (and thus conformationally constrained state). The amino acid sequence of the tail(s) can provide for additional AA features, such as binding to a target receptor to facilitate localization of the AA, increasing serum half-life of the AA, and the like. Targeting moieties (e.g., a ligand for a receptor of a cell present in a target tissue) and serum half-life extending moieties (e.g., polypeptides that bind serum proteins, such as immunoglobulin (e.g., IgG) or serum albumin (e.g., human serum albumin (HSA)).

Linkers suitable for use in the AAs described herein are generally ones that provide flexibility of the modified AB or the AA to facilitate the inhibition of the binding of the AB to the target. Such linkers are generally referred to as flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $(GSGGS)_n$ and $(GGGS)_n$, where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev, Computational Chem, 11173-142 (1992)), Exemplary flexible linkers include, but are not limited to Gly-Gly-Ser-Gly, Gly-Gly-Ser-Gly-Gly, Gly-Ser-Gly-Ser-Gly, Gly-Ser-Gly-Gly, Gly-Gly-Gly-Ser-Gly, Gly-Ser-Ser-Ser-Gly, and the like. The ordinarily skilled artisan will recognize that design of an AA can include linkers that are all or partially flexible, such that the linker can include a flexible linker as well as one or more portions that confer less flexible structure to provide for a desired AA structure.

In addition to the elements described above, the modified ABs and AAs can contain additional elements such as, for example, amino acid sequence N- or C-terminal of the AA. For example, AAs can include a targeting moiety to facilitate delivery to a cell or tissue of interest. Moreover, the AA can be provided in the context of a scaffold protein to facilitate display of the AA on a cell surface In some embodiments, the activatable antibody, also includes a signal peptide. In some embodiments, the signal peptide is conjugated to the activatable antibody, via a spacer. In some embodiments, the spacer is conjugated to the activatable antibody, in the absence of a signal peptide. In some embodiments, the spacer is joined directly to the MM of the activatable antibody. In some embodiments, the spacer is joined directly to the MM of the activatable antibody, in the structural arrangement from N-terminus to C-terminus of spacer-MM-CM-AB.

Suitable spacers and spacer technology is known in the art and can routinely be used to incorporate spacers in some embodiments of the provided activatable antibodies. See, for example, WO 2016/179285 (e.g., at pages 52-53), the contents of which is herein incorporated by reference in its entirety.

In some embodiments, the activatable antibody is exposed to and cleaved by a protease such that, in the activated or cleaved state, the activated antibody includes a light chain sequence that includes at least a portion of LP2 and/or CM sequence after the protease has cleaved the CM.

The CM is specifically cleaved by at least one protease at a rate of about $0.001\text{-}1500\times10^4$ $M^{-1}S^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or $1500\times10^4$ $M^{-1}S^{-1}$. In some embodiments, the CM is specifically cleaved at a rate of about 100,000 $M^{-1}S^{-1}$. In some embodiments, the CM is specifically cleaved at a rate from about $1 \times 10^2$ to about $1 \times 10^6$ $M^{-1}$ $S^{-1}$ (i.e., from about $1 \times 10^2$ to about $1 \times 10^6$ $M^{-1}S^{-1}$).

For specific cleavage by an enzyme, contact between the enzyme and CM is made. When the activatable antibody, comprising an Ab (e.g., an antibody or EpCAM-binding antibody fragment) coupled to a MM and a CM is in the presence of the target and sufficient enzyme activity, the CM can be cleaved. Sufficient enzyme activity can refer to the ability of the enzyme to make contact with the CM and effect cleavage. It can readily be envisioned that an enzyme may be in the vicinity of the CM but unable to cleave because of other cellular factors or protein modification of the enzyme.

5. Cytotoxic Agents (D) or Cytotoxic Agent-Linker Compounds (Compound of Formula (I)

In certain embodiments, for step (c) in the methods described herein (e.g., the method of the first, second, third, fourth, fifth, sixth, seventh, eighth, ninth or tenth embodiment, or any embodiments described therein), the CysCBA (e.g., CysAb or antigen-binding fragment thereof) is reacted with a compound of formula (I):

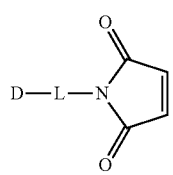
(I)

or a pharmaceutically acceptable salt thereof, thereby forming the conjugate, wherein D is a cytotoxic agent, and L is a linker.

In certain embodiments, D is a benzodiazepine compound, such as a pyrrolobenzodiazepine (PBD), oxazolidinobenzodiazepine (OBD) or an indolinobenzodiazepine (IGN) compound.

As used herein, a "benzodiazepine" compound is a compound having a benzodiazepine core structure. The benzodiazepine core can be substituted or unsubstituted, and/or fused with one or more ring structures. It also includes a compound having two benzodiazepine core linked by a linker. The imine functionality (—C═N—) as part of benzodiazepine core can be reduced.

As used herein, a "pyrrolobenzodiazepine" (PBD) compound is a compound having a pyrrolobenzodiazepine core structure. The pyrrolobenzodiazepine can be substituted or unsubstituted. It also includes a compound having two pyrrolobenzodiazepine core linked by a linker. The imine functionality (—C═N—) as part of indolinobenzodiazepine core can be reduced.

In certain embodiments, the pyrrolobenzodiazepine compound comprises a core structure represented by

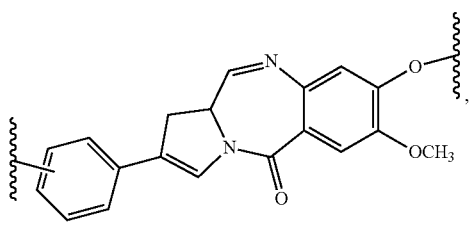

which can be optionally substituted.

In certain embodiments, the pyrrolobenzodiazepine compounds comprises a core structure represented by

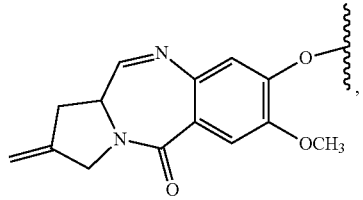 [SMILES: *Oc1cc2c(cc1OC)C(=O)N1CC(=C)CC1C=N2]

which can be optionally substituted.

As used herein, an "indolinobenzodiazepine" (IGN) compound is a compound having an indolinobenzodiazepine core structure. The indolinobenzodiazepine can be substituted or unsubstituted. It also includes a compound having two indolinobenzodiazepine core linked by a linker. The imine functionality (—C═N—) as part of indolinobenzodiazepine core can be reduced.

In certain embodiments, the indolinobenzodiazepine compound comprises a core structure represented by

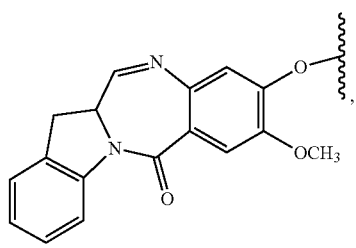 [SMILES: *Oc1cc2c(cc1OC)C(=O)N1c3ccccc3CC1C=N2]

which can be optionally substituted.

In some embodiments, the indolinobenzodiazepine compound comprises a core structure represented by

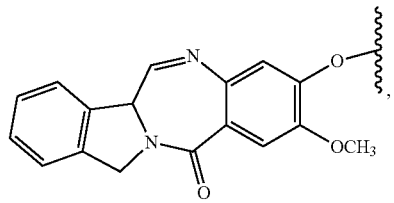 [SMILES: *Oc1cc2c(cc1OC)C(=O)N1Cc3ccccc3C1C=N2]

which can be optionally substituted.

As used herein, an "oxazolidinobenzodiazepine" (OBD) compound is a compound having an oxazolidinobenzodiazepine core structure. The oxazolidinobenzodiazepine can be substituted or unsubstituted. It also includes a compound having two oxazolidinobenzodiazepine cores linked by a linker. The imine functionality (—C═N—) as part of an oxazolidinobenzodiazepine core can be reduced.

In some embodiments, the oxazolidinobenzodiazepine compound comprises a core structure represented by

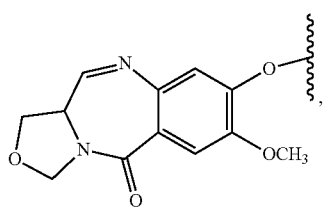 [SMILES: *Oc1cc2c(cc1OC)C(=O)N1COCC1C=N2]

which can be optionally substituted.

In certain embodiments, D is a maytansinoid compound.

In a 1$^{st}$ specific embodiment, for the compound of formula (I) in the methods described herein (e.g., the method of the first, second, third, fourth, fifth, sixth, seventh, eighth, ninth or tenth embodiment, or any embodiments described therein), D is represented by the following formula:

or a pharmaceutically acceptable salt thereof, wherein:

the double line $=$ between N and C represents a single bond or a double bond, provided that when it is a double bond, X is absent and Y is —H or a ($C_1$-$C_4$) alkyl; and when it is a single bond, X is —H or an amine protecting moiety, Y is —OH or —$SO_3$H or a pharmaceutically acceptable salt thereof;

one of L', L", and L''' is represented by the following formula:

$$-Z_1-P_1-Z_2-R_{x1}-C(=O)- \quad (A'), or$$

$$-N(R^e)-R_{x1}-C(=O)- \quad (D');$$

and the other two are each independently selected from —H, an optionally substituted linear, branched or cyclic alkyl, alkenyl or alkynyl, a polyethylene glycol unit —($CH_2CH_2O$)$_n$—$R^c$, halogen, guanidinium [—NH

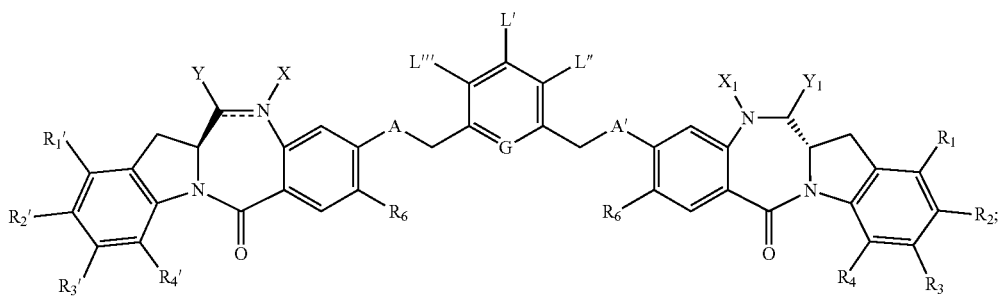
(D-IA)

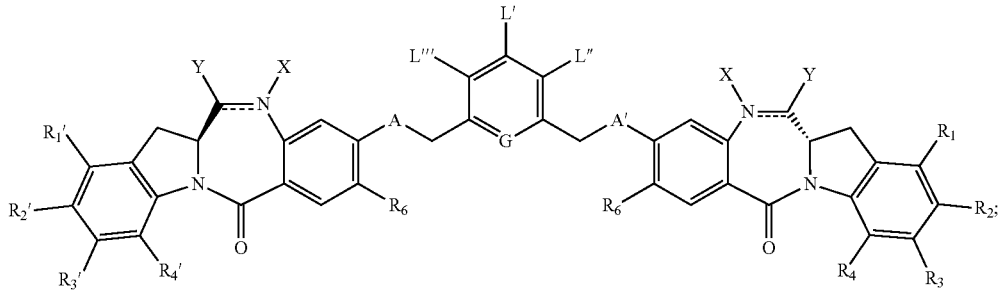
(D-IB)

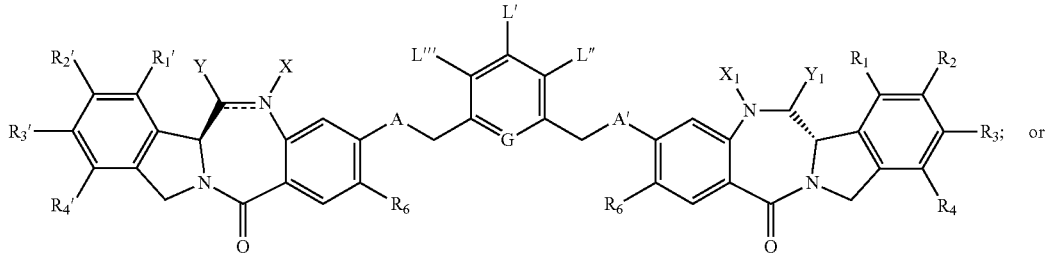
(D-IC) or

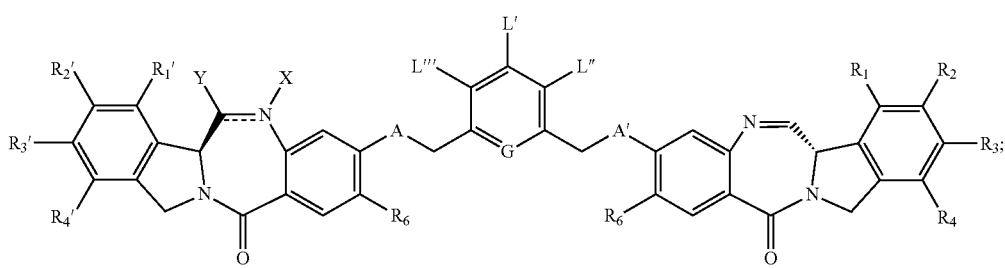
(D-ID)

(C=NH)NH$_2$], —OR, —NR'R", —NO$_2$, —NR'COR", —SR, —SOR', —SO$_2$R', —SO$_3$H, —OSO$_3$H, —SO$_2$NR'R", cyano, an azido, —COR', —OCOR', and —OCONR'R";

one of the $Z_1$ and $Z_2$ is —C(=O)—, and the other is —NR$_5$—;

P$_1$ is an amino acid residue or a peptide containing between 2 to 20 amino acid residues;

R$_{x1}$ is an optionally substituted linear, branched or cyclic alkyl, alkenyl or alkynyl;

R$^e$ is —H, a linear, branched or cyclic alkyl, alkenyl or alkynyl or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, wherein R$^{101}$ and R$^{102}$ are each independently a linear, branched, or cyclic alkyl, alkenyl or alkynyl;

R, for each occurrence, is independently selected from the group consisting of —H, an optionally substituted linear, branched or cyclic alkyl, alkenyl or alkynyl, a polyethylene glycol unit —(CH$_2$CH$_2$O)$_n$—R', an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl, a polyethylene glycol unit —(CH$_2$CH$_2$O)$_n$—R', and an optionally substituted 3- to 18-membered heterocyclic ring having 1 to 6 heteroatoms independently selected from O, S, N and P;

R$^c$ is —H or an optionally substituted linear or branched alkyl having 1 to 4 carbon atoms;

n is an integer from 1 to 24;

X$_1$ is selected from —H, an amine-protecting group, an optionally substituted linear, branched or cyclic alkyl, alkenyl or alkynyl, a polyethylene glycol unit —(CH$_2$CH$_2$O)$_n$—R, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y$_1$ is selected from —H, an oxo group, an optionally substituted linear, branched or cyclic alkyl, alkenyl or alkynyl, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

R$_1$, R$_2$, R$_3$, R$_4$, R$_1$', R$_2$', R$_3$' and R$_4$' are each independently selected from the group consisting of —H, an optionally substituted linear, branched or cyclic alkyl, alkenyl or alkynyl, a polyethylene glycol unit —(CH$_2$CH$_2$O)$_n$—R', halogen, guanidinium [—NH(C=NH)NH$_2$], —OR, —NR'R", —NO$_2$, —NCO, —NR'COR", —SR, —SOR', —SO$_2$R', —SO$_3^-$H, —OSO$_3$H, —SO$_2$NR'R", cyano, an azido, —COR', —OCOR', and —OCONR'R";

R$_6$ is —H, —R, —OR, —SR, —NR'R", —NO$_2$, or halogen;

G is —CH— or —N—;

A and A' are the same or different, and are independently selected from —O—, oxo (—C(=O)—), —CRR'O—, —CRR'—, —S—, —CRR'S—, —NR$_5$ and —CRR'N(R$_5$)—; and R$_5$ for each occurrence is independently —H or an optionally substituted linear or branched alkyl.

In certain embodiments, D is represented by formula (D-IA) or a pharmaceutically acceptable salt thereof.

In certain embodiments, for formula (D-IA), (D-IB), (D-IC) or (D-ID), X$_1$ is —H, —OH, (C$_1$-C$_3$)alkyl, halo(C$_1$-C$_3$)alkyl, or phenyl; Y$_1$' is —H, an oxo group, (C$_1$-C$_3$)alkyl or halo(C$_1$-C$_3$)alkyl, and the remaining variables are as described in the 1$^{st}$ specific embodiment or any embodiments described therein. More specifically, X$_1$ is —H, —OH or -Me; and Y$_1$ is —H or oxo. Even more specifically, X$_1$ is —H; and Y$_1$ is —H.

In certain embodiments, for formula (D-IA), (D-IB), (D-IC) or (D-TD), A and A' are the same or different, and are selected from —O— and —S—, and the remaining variables are as described in the 1$^{st}$ specific embodiment or any embodiments described therein. More specifically, A and A' are —O—.

In certain embodiments, for formula (D-IA), (D-IB), (D-IC) or (D-ID), R$_6$ is —OMe, and the remaining variables are as described in the 1$^{st}$ specific embodiment or any embodiments described therein.

In certain embodiments, for formula (D-IA), (D-IB), (D-IC) or (D-ID), R$_1$, R$_2$, R$_3$, R$_4$, R$_1$', R$_2$', R$_3$' and R$_4$' are independently —H, halogen, —NO$_2$, —OH, (C$_1$-C$_3$)alkyl, halo(C$_1$-C$_3$)alkyl or (C$_1$-C$_3$)alkoxy, and the remaining variables are as described in the 1$^{st}$ specific embodiment or any embodiments described therein. More specifically, R$_1$, R$_2$, R$_3$, R$_4$, R$_1$', R$_2$', R$_3$' and R$_4$' are all —H.

In certain embodiments, for formula (D-IA), (D-IB), (D-IC) or (D-TD), R, R', R" and R$_5$ are each independently —H or (C$_1$-C$_3$)alkyl, and the remaining variables are as described in the 1$^{st}$ specific embodiment or any embodiments described therein.

In certain embodiments, for formula (D-IA), (D-IB), (D-IC) or (D-ID), G is —CH—.

In certain embodiments, D is represented by formula (D-IA), (D-IB), (D-IC) or (D-ID), wherein:
R$_1$, R$_2$, R$_3$, R$_4$, R$_1$', R$_2$', R$_3$' and R$_4$' are all —H;
R$_6$ is —OMe;
X$_1$ and Y$_1$ are both —H;
A and A' are —O—; and the remaining variables are as described in the 1 specific embodiment or any embodiments described therein. In certain embodiments, G is —CH—; and
the remaining variables as described above.

In a 2$^{nd}$ specific embodiment, for formula (D-IA), (D-IB), (D-IC) or (D-ID), one of L', L" and L'" is represented by formula (A') or (D'), and the others are —H, an linear or branched alkyl having from 1 to 6 carbon atoms, halogen, —OH, (C$_1$-C$_6$)alkoxy, or —NO$_2$, and the remaining variables are as described in the 1$^{st}$ specific embodiment or any embodiments described therein. In certain embodiments, L' is represented by formula (A'); and L" and L'" are both —H. In other embodiments, L' is represented by formula (D'); and L" and L'" are both —H.

In certain embodiments, R$_{x1}$ in formula (A') or (D') is a linear, branched or cyclic alkyl having 1 to 6 carbon atoms optionally substituted with halogen, —OH, (C$_1$-C$_3$)alkyl, (C$_1$-C$_3$)alkoxy, halo(C$_1$-C$_3$)alkyl, or a charged substituent or an ionizable group Q; and the remaining variables are as described in the 1 or 2$^{nd}$ specific embodiment or any embodiments described therein.

In a 3rd specific embodiments, for formula (D-IA), (D-IB), (D-IC) or (D-ID) described in the $1^{st}$ or $2^{nd}$ specific embodiment or any embodiments described therein, L' is represented by the following formula:

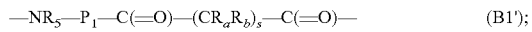  (B1');

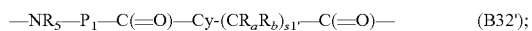  (B32');

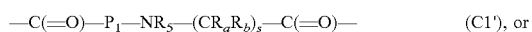  (C1'), or

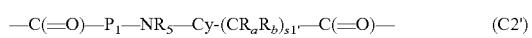  (C2')

wherein:

$R_a$ and $R_b$, for each occurrence, are each independently —H, $(C_1-C_3)$alkyl or a charged substituent or an ionizable group Q;

s is an integer from 1 to 6;

s1' is 0 or an integer from 1 to 6;

Cy is a cyclic alkyl having 5 or 6 ring carbon atoms optionally substituted with halogen, —OH, $(C_1-C_3)$alkyl, $(C_1-C_3)$alkoxy, or halo$(C_1-C_3)$alkyl; and the remaining variables are as described in the $1^{st}$ or $2^{nd}$ specific embodiment or any embodiments described therein.

In certain embodiments, Cy in formulas (B2') and (C2') is cyclohexane; and s1' is 0 or 1.

In a $4^{th}$ specific embodiment, for the compound of formula (I), D is represented by the following formula:

In certain embodiments, for compounds described in the $1^{st}$, $2^{nd}$, $3^{rd}$ or $4^{th}$ specific embodiment or any embodiments described therein, the charged substituent or an ionizable group Q is i) —SO$_3$H, —Z'—SO$_3$H, —OPO$_3$H$_2$, —Z'—OPO$_3$H$_2$, —PO$_3$H$_2$, —Z'—PO$_3$H$_2$, —CO$_2$H, —Z'—CO$_2$H, —NR$_{11}$R$_{12}$, or —Z'—NR$_{11}$R$_{12}$, or a pharmaceutically acceptable salt thereof; or, ii) —N$^+$R$_{14}$R$_{15}$R$_{16}$X$^-$ or —Z'—N$^+$R$_{14}$R$_{15}$R$_{16}$X$^-$; Z' is an optionally substituted alkylene, an optionally substituted cycloalkylene or an optionally substituted phenylene; R$_{14}$ to R$_{16}$ are each independently an optionally substituted alkyl; and X$^-$ is a pharmaceutically acceptable anion. More specifically, Q is —SO$_3$H or a pharmaceutically acceptable salt thereof.

In a $6^{th}$ specific embodiment, for formula (D-IA), (D-IB), (D-IC), (D-ID) or (D-IE), P$_1$ is a peptide containing 2 to 10 amino acid residues, and the remaining variables are as described in the $1^{st}$, $2^{nd}$, $3^{rd}$, $4^{th}$ or $5^{th}$ specific embodiment or any embodiments described therein. In certain embodiments, P$_1$ is a peptide containing 2 to 5 amino acid residues. In certain embodiments, P$_1$ is a peptide cleavable by a protease. More specifically, P$_1$ is a peptide cleavable by a protease expressed in tumor tissue. In certain embodiments, P$_1$ is Gly-Gly-Gly, Ala-Val, Val-Cit, Val-Lys, Phe-Lys, Lys-Lys, Ala-Lys, Phe-Cit, Leu-Cit, Ile-Cit, Trp, Cit, Phe-Ala, Phe-N$^9$-tosyl-Arg, Phe-N$^9$-nitro-Arg, Phe-Phe-Lys, D-Phe-

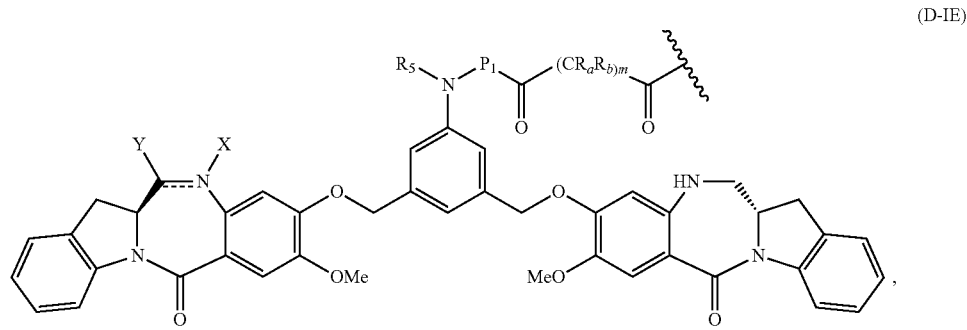

(D-IE)

or a pharmaceutically acceptable salt thereof, and the remaining variables are as described in the $3^{rd}$ specific embodiment or any embodiments described therein.

In a $5^{th}$ specific embodiment, for formula (D-IA), (D-IB), (D-IC), (D-ID) or (D-IE), R$_a$ and R$_b$ are both H; and R$_5$ is H or Me, and the remaining variables are as described in the 3rd or $4^{th}$ specific embodiment or any embodiments described therein.

Phe-Lys, Gly-Phe-Lys, Leu-Ala-Leu, Ile-Ala-Leu, Val-Ala-Val, Ala-Leu-Ala-Leu (SEQ ID NO: 56), p-Ala-Leu-Ala-Leu (SEQ ID NO: 57), Gly-Phe-Leu-Gly (SEQ ID NO: 58), Val-Arg, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, Gln-Val, Asn-Ala, Gln-Phe and Gln-Ala. More specifically, P$_1$ is Gly-Gly-Gly, Ala-Val, Ala-Ala, Ala-D-Ala, D-Ala-Ala, or D-Ala-D-Ala.

In a 7th specific embodiment, for compound of formula (I), D is represented by the following structural formula:
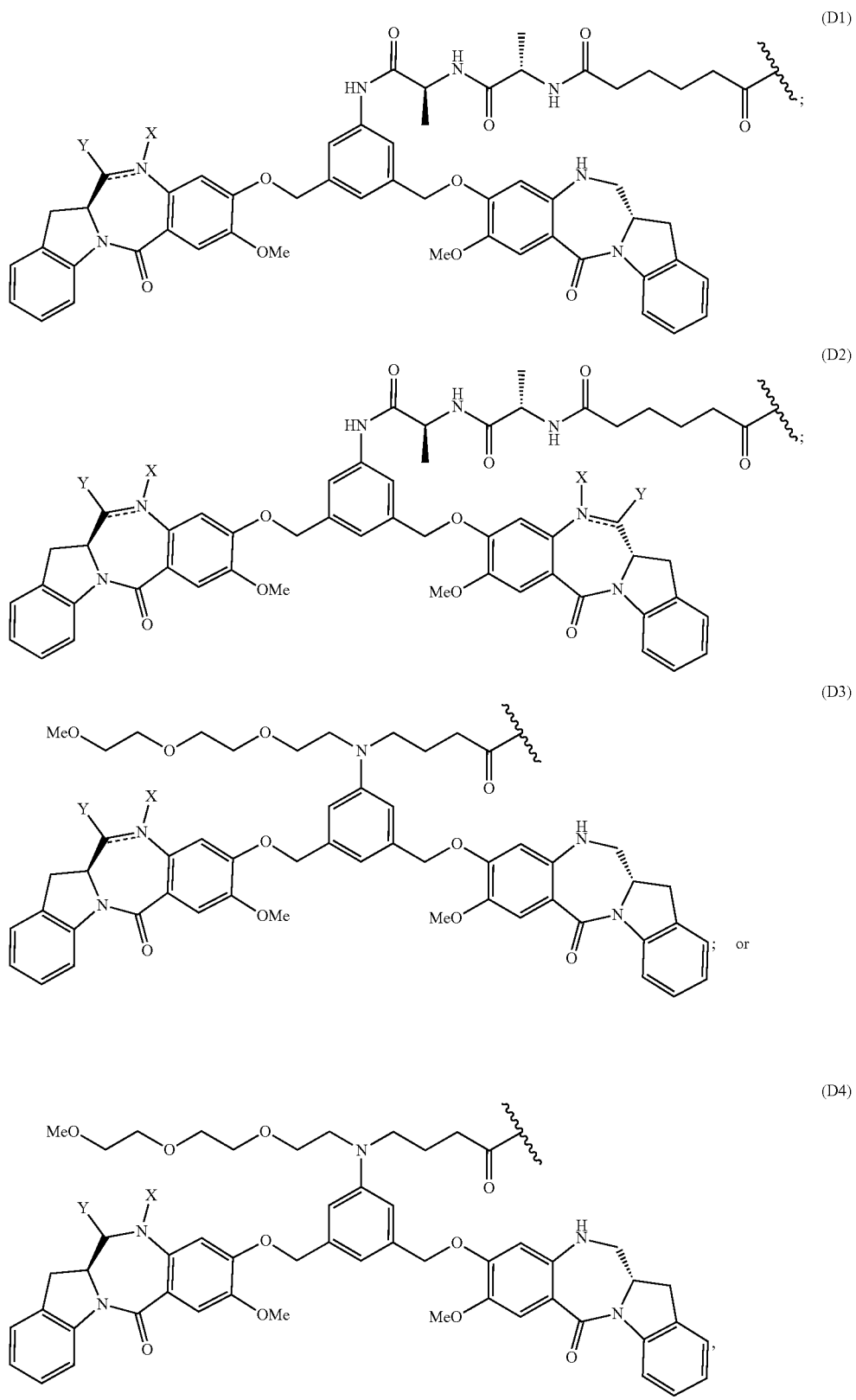

or a pharmaceutically acceptable salt thereof, wherein the double line ⚌ between N and C represents a single bond or a double bond, provided that when it is a double bond, X is absent and Y is —H; and when it is a single bond, X is —H, Y is —SO₃H or a pharmaceutically acceptable salt thereof, and the remaining variables are as described in the 1 specific embodiment or any embodiments described therein.

In a 8$^{th}$ specific embodiment, for compound of formula (I) in the methods described herein (e.g., the method of the first, second, third, fourth, fifth, sixth, seventh, eighth, ninth or tenth embodiment, or any embodiments described therein), -L- is represented by the following structural formula:

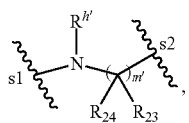

(L-I)

or a pharmaceutically acceptable salt thereof, wherein:
s1 is the site covalently linked to D; s2 is the site covalently linked to the maleimide group;
$R_{23}$ and $R_{24}$, for each occurrence, are independently H or an optionally substituted alkyl;
m' is an integer between 0 and 10;
Rh' is H or an optionally substituted alkyl;

In certain embodiments, $R_{23}$ and $R_{24}$ are both H; and m' is an integer between 1 and 6, and the remaining variables are as described in the 8th specific embodiment or any embodiments described therein.

In certain embodiments, Rh' is H, and the remaining variables are as described in the 8$^{th}$ specific embodiment or any embodiments described therein.

In a 9$^{th}$ specific embodiment, for compound of formula (I) in the methods described herein (e.g., the method of the first, second, third, fourth, fifth, sixth, seventh, eighth, ninth or tenth embodiment, or any embodiments described therein), -L- is represented by the following structural formula:

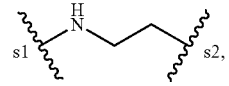

(L1)

or a pharmaceutically acceptable salt thereof, and the remaining variables are as described in the 1$^{st}$, 2$^{nd}$, 3$^{rd}$, 4$^{th}$, 5$^{th}$, 6$^{th}$ or 7$^{th}$ specific embodiment or any embodiments described therein.

In a 10$^{th}$ specific embodiment, the compound of formula (I) in the methods described herein (e.g., the method of the first, second, third, fourth, fifth, sixth, seventh, eighth, ninth or tenth embodiment, or any embodiments described therein) is represented by the following formula:

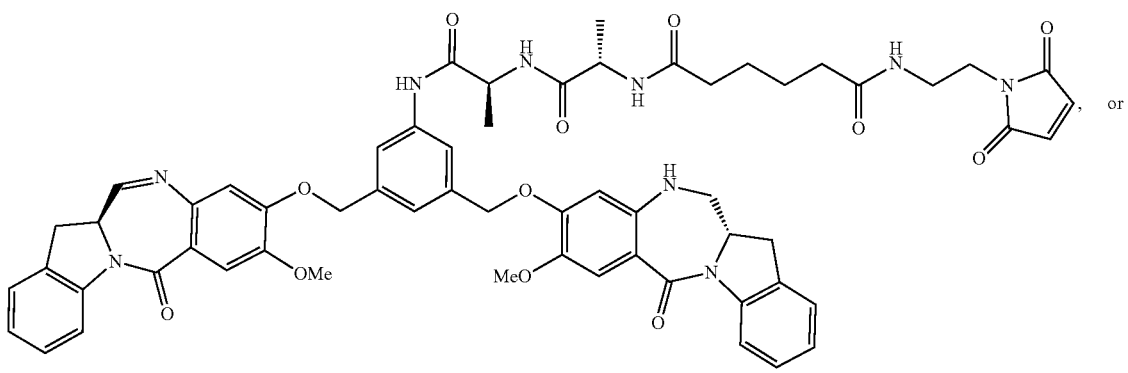

(I1), or

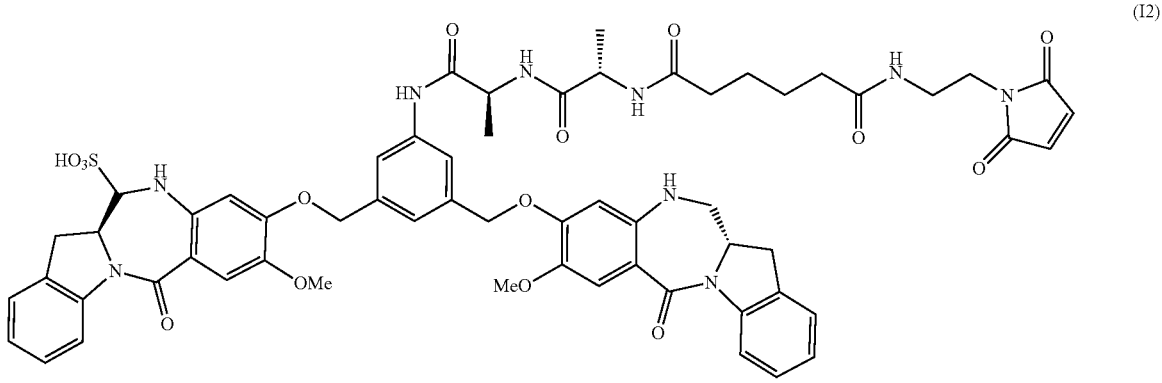

(I2)

and the remaining variables are as described in the 1$^{st}$, 2$^{nd}$, 3$^{rd}$, 4$^{th}$, 5$^{th}$, 6$^{th}$ or 7$^{th}$ specific embodiment or any embodiments described therein.

or a pharmaceutically acceptable salt thereof.

In certain embodiments, the compound of formula (I) is represented by the following formula:

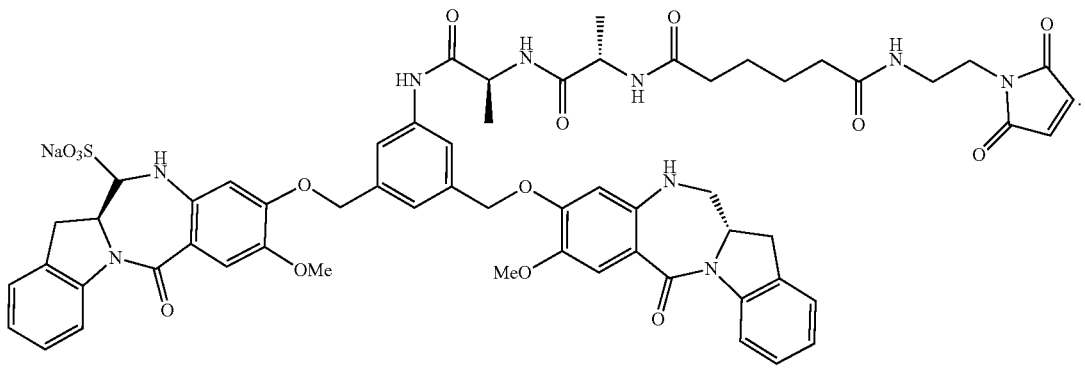
(I3)
In a 11th specific embodiment, for compound of formula (I) in the methods described herein (e.g., the method of the first, second, third, fourth, fifth, sixth, seventh, eighth, ninth or tenth embodiment, or any embodiments described therein), D is represented by the following formula:
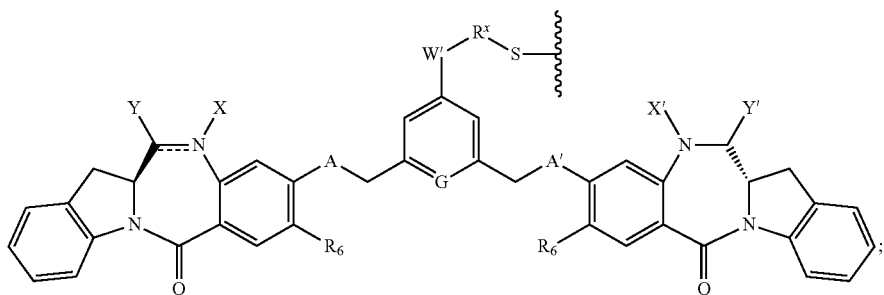
(D-IIA)
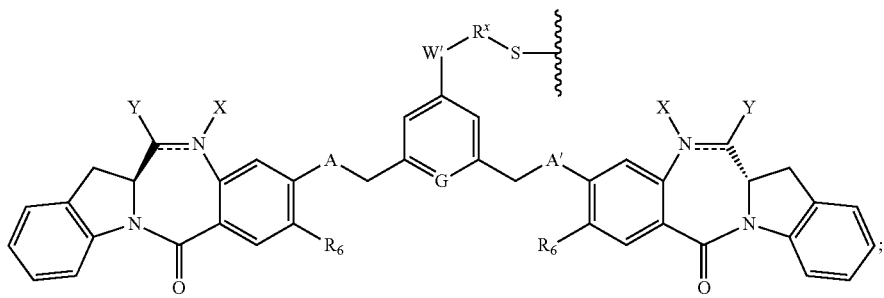
(D-IIB)
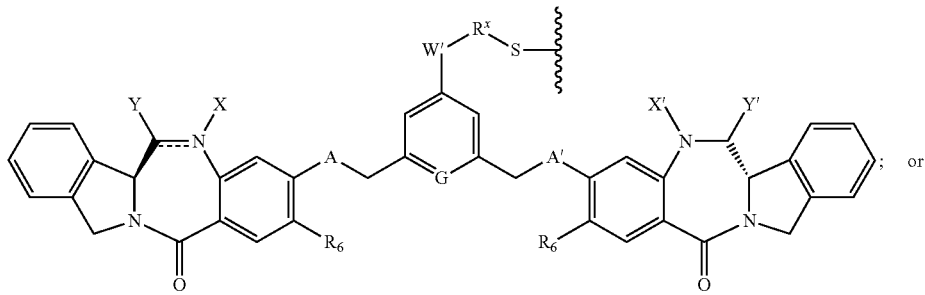
(D-IIC)
; or

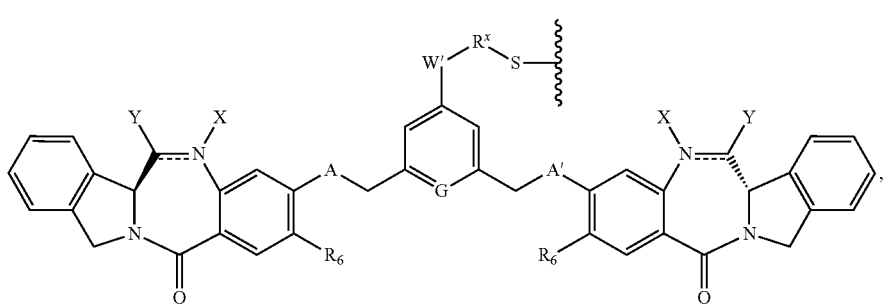

(D-IID)

or a pharmaceutically acceptable salt thereof, wherein:

the double line ═ between N and C represents a single bond or a double bond, provided that when it is a double bond, X is absent and Y is —H or a ($C_1$-$C_4$)alkyl; and when it is a single bond, X is —H or an amine protecting moiety, Y is —OH or —$SO_3$H or a pharmaceutically acceptable salt thereof;

X' is selected from the group consisting of —H, —OH, a substituted or unsubstituted linear, branched or cyclic alkyl, alkenyl or alkynyl, phenyl, and an amine-protecting group;

Y' is selected from the group consisting of —H, an oxo group, a substituted or unsubstituted linear, branched or cyclic alkyl, alkenyl or alkynyl;

A and A' are selected from —O— and —S—;

W' is absent, or selected from —O—, —N($R^e$)—, —N($R^e$)—C(═O)—, —N(C(═O)$R^e$)—, —S— or —$CH_2$—S—, —$CH_2$NR—;

$R^x$ is absent or selected from a linear, branched or cyclic alkyl;

$R^e$ is —H, a linear, branched or cyclic alkyl, alkenyl or alkynyl or —($CH_2$—$CH_2$—O)$_n$—$R^k$, wherein $R^k$ is a —H, a linear, branched cyclic alkyl having 1 to 6 carbon atoms, optionally bearing a secondary amino (e.g., —$NHR^{101}$) or tertiary amino (—$NR^{101}R^{102}$) group or a 5- or 6-membered nitrogen containing heterocycle, wherein $R^{101}$ and $R^{102}$ are each independently a linear, branched, or cyclic alkyl, alkenyl or alkynyl;

n is an integer from 1 to 24;

G is selected from —CH— or —N—;

$R_6$ is —H, —R, —OR, —SR, —NR'R'', —$NO_2$, or halogen; and

R, for each occurrence, is independently selected from the group consisting of —H, an optionally substituted linear, branched or cyclic alkyl, alkenyl or alkynyl, a polyethylene glycol unit —($CH_2CH_2O$)$_n$—R', an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R'' are each independently selected from —H, —OH, —OR, —NHR, —$NR_2$, —COR, an optionally substituted linear, branched or cyclic alkyl, alkenyl or alkynyl, a polyethylene glycol unit —($CH_2CH_2O$)$_n$—R', and an optionally substituted 3- to 18-membered heterocyclic ring having 1 to 6 heteroatoms independently selected from O, S, N and P;

$R^c$ is —H or an optionally substituted linear or branched alkyl having 1 to 4 carbon atoms; and L is a linker.

In certain embodiments, D is represented by formula (D-IIA) or a pharmaceutically acceptable salt thereof.

In certain embodiments, D is represented by formula (D-IIA), (D-IIB), (D-IIC) or (D-IID), wherein:

X' and Y' are both —H;

A and A' are both —O—;

$R_6$ is —OMe;

W' is —N($R^e$)— or —N($R^e$)—C(═O)—;

$R^e$ is —H, a linear or branched alkyl having 1 to 4 carbon atoms or —($CH_2$—$CH_2$—O)$_n$—$R^k$, wherein $R^k$ is a —H, a linear or branched alkyl having 1 to 4 carbon atoms;

n is an integer from 2 to 6;

$R^x$ is a linear or branched alkyl having 1 to 6 carbon atoms; and the remaining variables are as described in the 11th specific embodiment or any embodiments described therein.

In a 12$^{th}$ specific embodiment, for compound of formula (I), D is represented by the following structural formula:

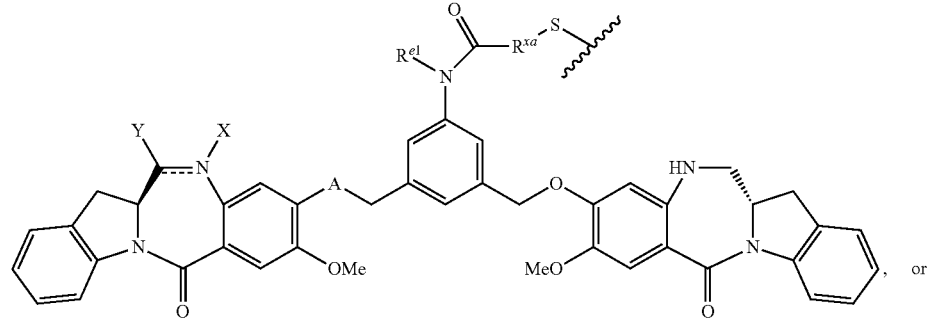

(D-IIE)

(D-IIF)

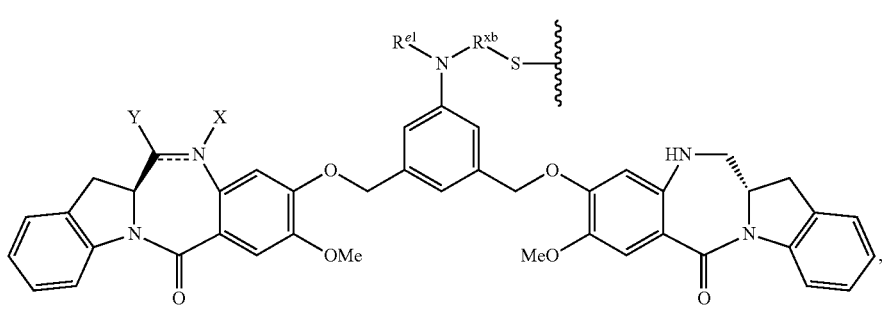

or a pharmaceutically acceptable salt thereof, wherein:
$R^{e1}$ is H or a $(C_1\text{-}C_6)$alkyl;
$R^{xa}$ is a $(C_1\text{-}C_6)$alkyl;
$R^{e2}$ is $-(CH_2-CH_2-O)_n-R^k$;
n is an integer from 2 to 6;
$R^k$ is —H or -Me;

$R^{xb}$ is a $(C_1\text{-}C_6)$alkyl; and the remaining variables are as described in the 11$^{th}$ Specific embodiment or any embodiments described therein.

In a 13$^{th}$ specific embodiment, for compound of formula (I), D is represented by the following formula:

(D5)

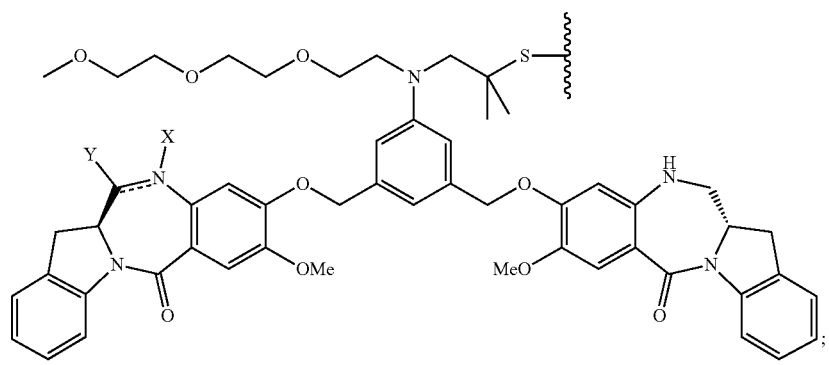

or a pharmaceutically acceptable salt thereof, and the remaining variables are as described in the 11$^{th}$ specific embodiment or any embodiments described therein.

In a 14$^{th}$ specific embodiment, for compound of formula (I) in the methods described herein (e.g., the method of the first, second, third, fourth, fifth, sixth, seventh, eighth, ninth or tenth embodiment, or any embodiments described therein), D is represented by the following formula:

(D-III)

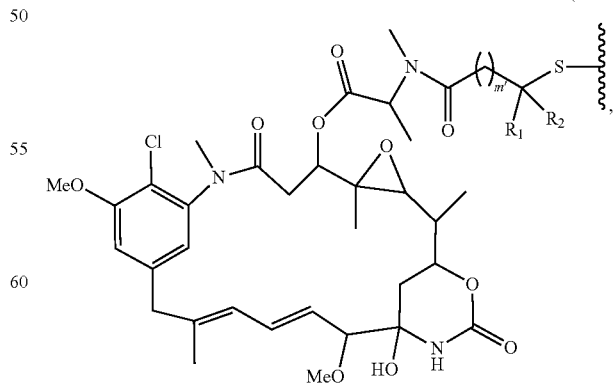

wherein m' is 1 or 2; $R_1$ and $R_2$, are each independently —H or a $(C_1\text{-}C_3)$alkyl; and L is a linker.

In certain embodiments, D is represented by the following formula:

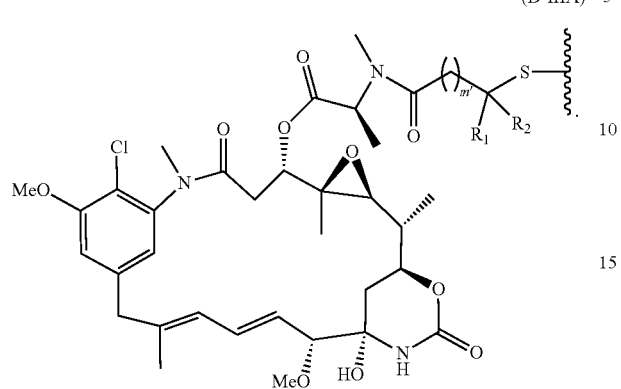

(D-IIIA)

In a 15th specific embodiment, for compound of formula (I) in the methods described herein (e.g., the method of the first, second, third, fourth, fifth, sixth, seventh, eighth, ninth or tenth embodiment, or any embodiments described therein), L is represented by the following structural formula:

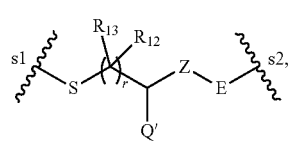

(L-II)

or a pharmaceutically acceptable salt thereof, wherein:

s1 is the site covalently linked to D, and s2 is the site covalently linked to the maleimide group;

E is —$(CR_{10}R_{11})_q$—, cycloalkyl, or cycloalkylalkyl;

Z is absent, —$SO_2NR_9$—, —$NR_9SO_2$—, —C(=O)—$NR_9$—, —$NR_9$—C(=O)—, —C(=O)—O—, —O—C(=O)—, —C(=O)—$NR_9$—$(CH_2CH_2O)_p$—, —$NR_9$—C(=O)—$(CH_2CH_2O)_p$—, —$(OCH_2CH_2)_p$—C(=O)$NR_9$—, or —$(OCH_2CH_2)_p$—$NR_9$—C(=O)—;

p is an integer from 1 to 24;

Q is H, a charged substituent, or an ionizable group;

$R_9$, $R_{10}$, $R_{11}$, $R_{12}$, and $R_{13}$, for each occurrence, are independently H or an optionally substituted alkyl;

q and r, for each occurrence, are independently an integer between 0 and 10; and, the remaining variables are as described in the 11th, 12th, 13th or 14th specific embodiment or any embodiments described therein.

In certain embodiments, E is —$(CR_{10}R_{11})_q$—, and the remaining variables are as described in the 15th specific embodiment.

In certain embodiments, E is

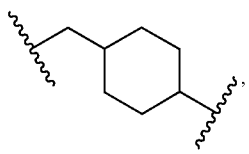 [SMILES: *CC1CCC(*)CC1]

and the remaining variables are as described in the 15th specific embodiment.

In certain embodiment, Z is —C(=O)—$NR_9$— or —$NR_9$—C(=O)—, and the remaining variables are as described in the 15th specific embodiment or any embodiments described therein.

In a 16th specific embodiment, for compound of formula (I), L is represented by the following structural formula:

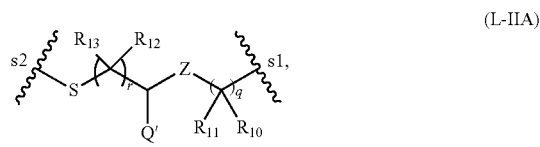

(L-IIA)

wherein $R_9$, $R_{10}$, $R_{11}$, $R_{12}$, and $R_{13}$, for each occurrence, are independently —H or a ($C_1$-$C_3$)alkyl; and the remaining variables are as described in the 15th specific embodiment or any embodiments described therein.

In certain embodiments, $R_9$ is —H, and the remaining variables are as described in the 16th specific embodiment.

In certain embodiments, Q' is:
i) H;
ii) —$SO_3H$, —Z'—$SO_3H$, —$OPO_3H_2$, —Z'—$OPO_3H_2$, —$PO_3H_2$, —Z'—$PO_3H_2$, —$CO_2H$, —Z'—$CO_2H$, —$NR_{11}R_{12}$, or —Z'—$NR_{14}R_{15}$, or a pharmaceutically acceptable salt thereof; or,
iii) —$N^+R_{14}R_{15}R_{16}X^-$ or —Z'—$N^+R_{14}R_{15}R_{16}X^-$;

Z' is an optionally substituted alkylene, an optionally substituted cycloalkylene, or an optionally substituted phenylene;

$R_{14}$, $R_{15}$ and $R_{16}$ are each independently an optionally substituted alkyl; and, $X^-$ is a pharmaceutically acceptable anion, and the remaining variables are as described in the 16th specific embodiment or any embodiments described therein.

In certain embodiments, Q' is H or —$SO_3H$ or a pharmaceutically acceptable salt thereof, and the remaining variables are as described in the 16th specific embodiment or any embodiments described therein.

In certain embodiments, $R_9$, $R_{10}$, $R_{11}$, $R_{12}$, and $R_{13}$ are all H; and q and r are each independently an integer between 1 and 6, and the remaining variables are as described in the 16th specific embodiment or any embodiments described therein.

In certain embodiments, L is represented by formula (L-IIA), wherein:

$R_{12}$ and $R_{13}$, for each occurrence, are each independently H or ($C_1$-$C_3$)alkyl;

Q is H or —$SO_3H$ or a pharmaceutically acceptable salt thereof

Z is —C(=O)—$NR_9$— or —$NR_9$—C(=O)—;

$R_9$ is H or ($C_1$-$C_3$)alkyl;

$R_{10}$ and $R_{11}$, for each occurrence, are independently H or ($C_1$-$C_3$)alkyl; and q and r are each an integer from 1 to 5; and the remaining variables are as described in the 16th specific embodiment or any embodiments described therein.

In a 17th specific embodiment, for compound of formula (I), L is represented by any one of the following structural formulae:

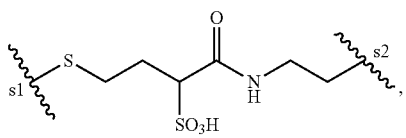
(L2)

and

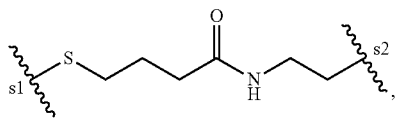
(L3)

or a pharmaceutically acceptable salt thereof, and the remaining variables are as described in the 11$^{th}$, 12$^{th}$, 13$^{th}$ or 14$^{th}$ specific embodiment or any embodiments described therein.

In a 18$^{th}$ specific embodiment, for compound of formula (I), L is represented by the following structural formula:

(L-III)

or a pharmaceutically acceptable salt thereof, wherein:

s1 is the site covalently linked to D; s2 is the site covalently linked to the maleimide group;

$R_{19}$, $R_{20}$, $R_{21}$ and $R_{22}$, for each occurrence, are independently H or an optionally substituted alkyl;

u and v are each independently an integer between 0 and 10;

$R^h$ is H or an optionally substituted alkyl;

$P_L$ is an optionally substituted alkylene, —(CH$_2$—CH$_2$—O)$_j$— (wherein the oxygen atom is connected to the —(C=O)— group connected to $P_L$), an amino acid residue or a peptide containing 2 to 20 amino acid residues; and j is an integer from 1 to 24; and the remaining variables are as described in the 11$^{th}$, 12$^{th}$, 13$^{th}$ or 14$^{th}$ specific embodiment or any embodiments described therein.

In certain embodiments, $R_{19}$, $R_{20}$, $R_{21}$ and $R_{22}$ are each H; and u and v are each independently an integer between 1 and 6; and the remaining variables are as described above in the 18$^{th}$ specific embodiment.

In certain embodiments, $P_L$ is an amino acid residue or a peptide containing 2 to 10 amino acid residues and the remaining variables are as described above in the 18$^{th}$ specific embodiment or any embodiments described therein. More specifically, $P_L$ is a peptide containing 2 to 5 amino acid residues. In another more specific embodiment, $P_L$ is selected from the group consisting of: Ala-Val, Val-Ala, Val-Cit, Cit-Val. Val-Lys, Phe-Lys, Lys-Lys, Ala-Lys, Phe-Cit, Leu-Cit, Ile-Cit, Trp-Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO:55), β-Ala-Leu-Ala-Leu (SEQ ID NO:56), Gly-Phe-Leu-Gly (SEQ ID NO:57), Val-Arg, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, Met-Ala, Gln-Val, Asn-Ala, Gln-Phe, Gln-Ala, Gly-Gly-Gly, Ala-Ala-Ala, D-Ala-Ala-Ala, Ala-D-Ala-Ala, Ala-Ala-D-Ala, Ala-Val-Cit, Ala-Val-Ala, and β-Ala-Gly-Gly-Gly (SEQ ID NO:58). Even more specifically, $P_L$ is Gly-Gly-Gly, Ala-Ala-Ala, D-Ala-Ala-Ala, Ala-D-Ala-Ala, Ala-Val-Ala, or β-Ala-Gly-Gly-Gly.

In a 19$^{th}$ specific embodiment, for compound of formula (I), L is represented by the following structural formula:

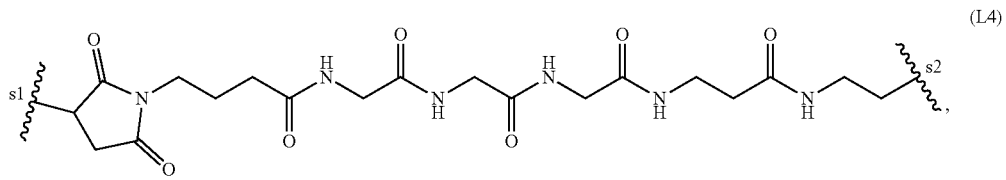 [SMILES: *CCNC(=O)CCNC(=O)CNC(=O)CNC(=O)CNC(=O)CCCN1C(=O)CC(*)C1=O]
(L4)

or a pharmaceutically acceptable salt thereof, and the remaining variables are as described in the 11$^{th}$, 12$^{th}$, 13$^{th}$ or 14$^{th}$ specific embodiment or any embodiments described therein.

In a 20$^{th}$ specific embodiment, the compound of formula (I) in the methods described herein (e.g., the method of the first, second, third, fourth, fifth, sixth, seventh, eighth, ninth or tenth embodiment, or any embodiments described therein) is represented by the following formula:

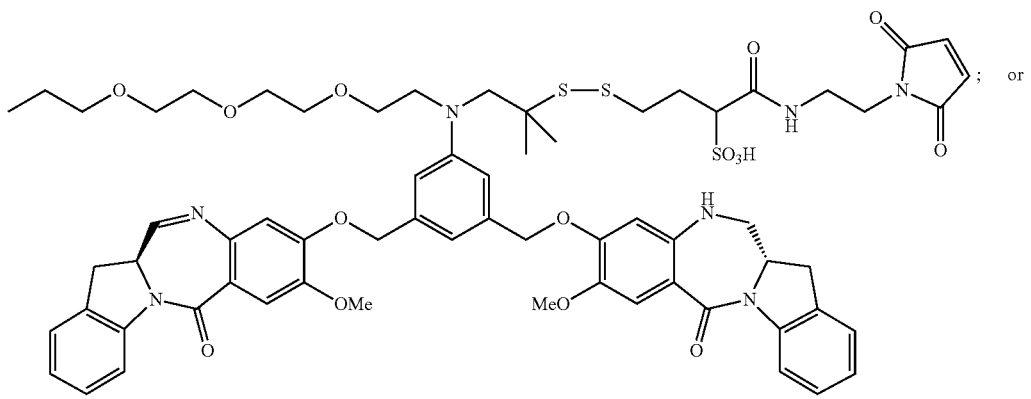

(I4)

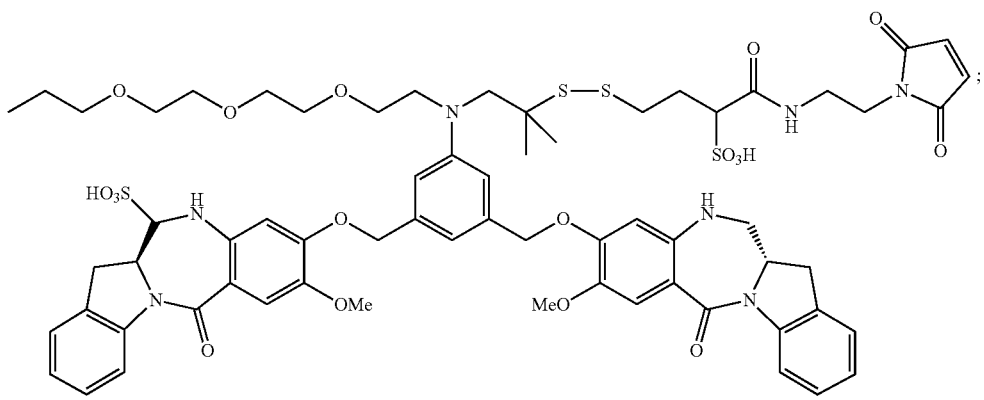

(I5)

or a pharmaceutically acceptable salt thereof.

In certain embodiments, the compound of formula (I) in the 20th specific embodiment is represented by the following formula:

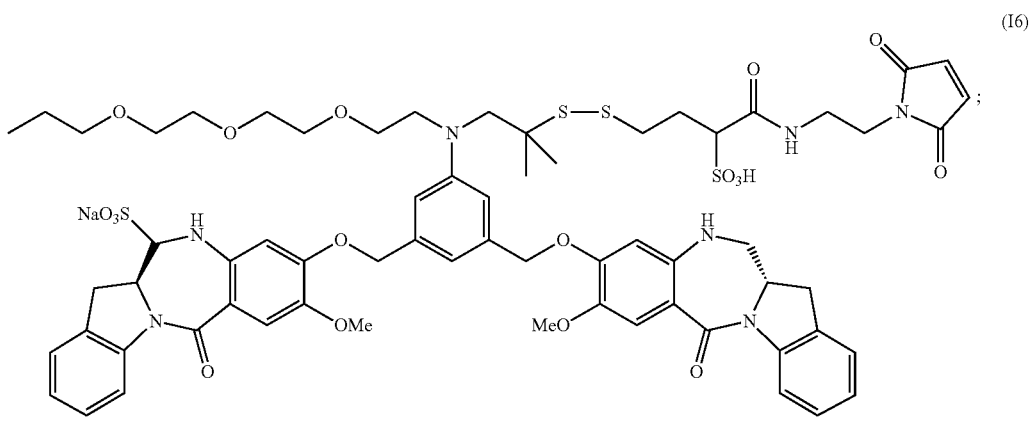

(I6)

In a 21st specific embodiment, the compound of formula (I) in the methods described herein (e.g., the method of the first, second, third, fourth, fifth, sixth, seventh, eighth, ninth or tenth embodiment, or any embodiments described therein) is represented by the following formula:

(I7)

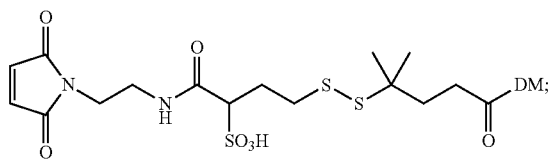

(I8)

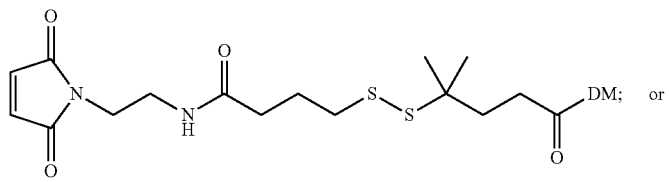

(I9)

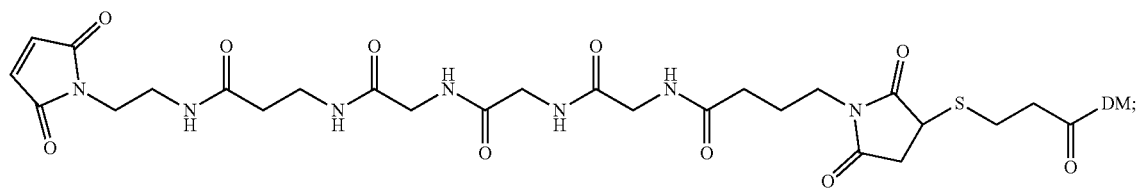

or a pharmaceutically acceptable salt thereof, wherein DM is a drug moiety represented by the following formula:

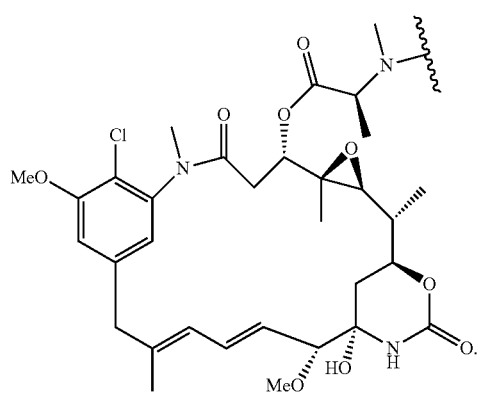 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In a 22$^{nd}$ specific embodiment, the compound of formula (I) in the methods described herein (e.g., the method of the first, second, third, fourth, fifth, sixth, seventh, eighth, ninth or tenth embodiment, or any embodiments described therein) is represented by the following formula:

$$L_2'\text{-A-NH}—CR^{1A}R^{2A}—S-L_1\text{-D} \quad (I\text{-a}),$$

or a pharmaceutically acceptable salt thereof, wherein:
$L_2'$ is a spacer bearing a maleimide moiety;
A is an amino acid or a peptide comprising 2 to 20 amino acids;
$R^{1A}$ and $R^{2A}$ are each independently H or a $C_{1-3}$alkyl;
$L_1$ is a spacer; and
$D-L_1\text{-SH}$ is a cytotoxic agent.

In certain embodiments, at least of $R^{1A}$ and $R^{2A}$ is H, and the remaining variables are as described in the 22$^{nd}$ specific embodiment.

In certain embodiments, $R^{1A}$ and $R^{2A}$ are each independently H or Me, and the remaining variables are as described in the 22$^{nd}$ specific embodiment.

In certain embodiments, $R^{1A}$ and $R^{2A}$ is H; and the other one is Me, and the remaining variables are as described in the 22$^{nd}$ specific embodiment.

In certain embodiments, $R^{1A}$ and $R^{2A}$ are both H, and the remaining variables are as described in the 22$^{nd}$ specific embodiment.

In certain embodiments, $L_1$ is $-L_1'—C(=O)—$; and $L_1'$ is an alkylene or a cycloalkylene, and the remaining variables are as described in the 22$^{nd}$ specific embodiment or any embodiments described therein. More specifically, $L_1'$ is $C_{1-10}$alkylene. Even more specifically, $L_1$ is $—CR^{3A}R^{4A}—(CH_2)_{1-8}—C(=O)—$; $R^{3A}$ and $R^{4A}$ are each independently H or Me. In another more specific embodiment, $L_1$ is $—CR^{3A}R^{4A}—(CH_2)_{3-5}—C(=O)—$. In a even more specific embodiment, $R^{3A}$ and $R^{4A}$ are both Me.

In certain embodiments, $L_1$ is $—(CH_2)_{4-6}—C(=O)—$, and the remaining variables are as described in the 22$^{nd}$ specific embodiment or any embodiments described therein.

In a 23$^{rd}$ specific embodiment, for formula (I-a), $L_2'$ is represented by the following structural formula:

$$J_{CB}'\text{-}R^A\text{-V}—W—R^B—V'—R^C\text{-}J_{A'};$$

wherein:
$R^A$ is an alkylene, a cycloalkylalkylene or an arylene;
$R^B$ and $R^C$ are each independently absent, an alkylene, a cyclalkylene, or an arylene;
V and V' are each independently $—(O—CH_2—CH_2)_{p1}—$, or $—(CH_2—CH_2—O)_{p1}—$;
p1 is 0 or an integer from 1 to 10;
W is absent,

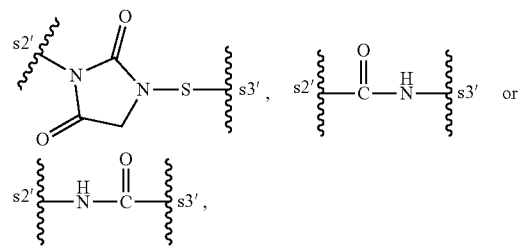

wherein s2' indicates the site connected to V, $R^A$ or $J_{CB}'$ and s3' indicates the site connected to $R^B$, V', $R^C$ or $J_A$;

$J_{CB}'$ is

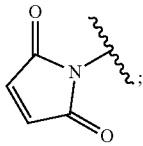

and $J_A$ is —C(=O)—; and the remaining variables are as described in the 22$^{nd}$ specific embodiment or any embodiments described therein.

In certain embodiments, p1 is 0 and $R^C$ is absent, and the remaining variables are as described in the 23$^{rd}$ specific embodiment.

In a 24$^{th}$ specific embodiment, for formula (I-a), $L_2'$ is represented by the following structural formula:

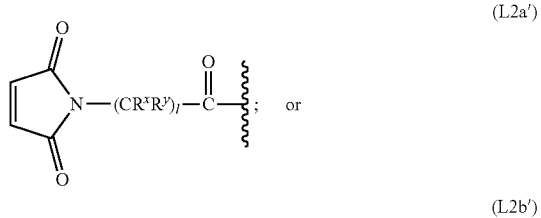

(L2a')

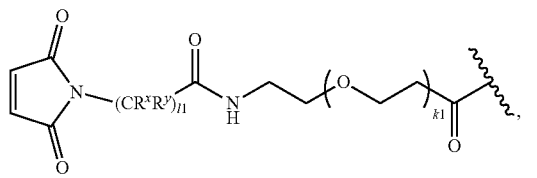

(L2b')

wherein:

$R^x$ and $R^y$ for each occurrence, are independently H, —OH, halogen, —O—($C_{1-4}$ alkyl), —SO$_3$H, —NR$_{40}$R$_{41}$R$_{42}^+$, or a $C_{1-4}$ alkyl optionally substituted with —OH, halogen, —SO$_3$H or NR$_{40}$R$_{41}$R$_{42}^+$, wherein R$_{40}$, R$_{41}$ and R$_{42}$ are each independently H or a $C_{1-4}$ alkyl;

l and l1 are each independently an integer from 1 to 10;

k1 is an integer from 1 to 12; and the remaining variables are as described in the 22$^{nd}$ specific embodiment or any embodiments described therein.

In certain embodiments, $R^x$ and $R^y$ are all H, and the remaining variables are as described above in the 24$^{th}$ specific embodiment.

In certain embodiments, l and l1 are each an integer an integer from 2 to 6, and the remaining variables are as described above in the 24$^{th}$ specific embodiment or any embodiments described therein.

In a 25$^{th}$ specific embodiment, for formula (I-a), A is a peptide cleavable by a protease, and the remaining variables are as described in the 22$^{nd}$, 23$^{rd}$ or 24$^{th}$ specific embodiment or any embodiments described therein. More specifically, A is a peptide cleavable by a protease expressed in tumor tissue. In another more specific embodiment, A is a peptide having an amino acid that is covalent linked with —NH—CR$^1$R$^2$—S-L$_1$-D selected from the group consisting of Ala, Arg, Asn, Asp, Cit, Cys, selino-Cys, Gln, Glu, Gly, Ile, Leu, Lys, Met, Phe, Pro, Ser, Thr, Trp, Tyr and Val, each independently as L or D isomer. More specifically, the amino acid connected to —NH—CR$^1$R$^2$—S-L$_1$-D is an L amino acid.

In certain embodiments, A is a peptide containing 2 to 5 amino acid residues, and the remaining variables are as described in the 25$^{th}$ specific embodiment or any embodiments described therein. More specifically, A is selected from the group consisting of Gly-Gly-Gly, Ala-Val, Val-Ala, D-Val-Ala, Val-Cit, D-Val-Cit, Val-Lys, Phe-Lys, Lys-Lys, Ala-Lys, Phe-Cit, Leu-Cit, Ile-Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Ala-Ala, D-Ala-Ala-Ala, Ala-D-Ala-Ala, Ala-Ala-D-Ala, Ala-Leu-Ala-Leu (SEQ ID NO:55), β-Ala-Leu-Ala-Leu (SEQ ID NO:56), Gly-Phe-Leu-Gly (SEQ ID NO:57), Val-Arg, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, Gln-Val, Asn-Ala, Gln-Phe, Gln-Ala, D-Ala-Pro, and D-Ala-tBu-Gly, wherein the first amino acid in each peptide is connected to $L_2$ group and the last amino acid in each peptide is connected to —NH—CR$^1$R$^2$—S-L-D. Even more specifically, A is Ala-Ala-Ala, Ala-D-Ala-Ala, Ala-Ala, D-Ala-Ala, Val-Ala, D-Val-Ala, D-Ala-Pro, or D-Ala-tBu-Gly.

In a 26$^{th}$ specific embodiment, for formula (I-a), D is a maytansinoid and the remaining variables are as described in the 22$^{nd}$, 23$^{rd}$, 24$^{th}$ or 25$^{th}$ specific embodiment or any embodiments described therein. More specifically, D is represented by the following formula:

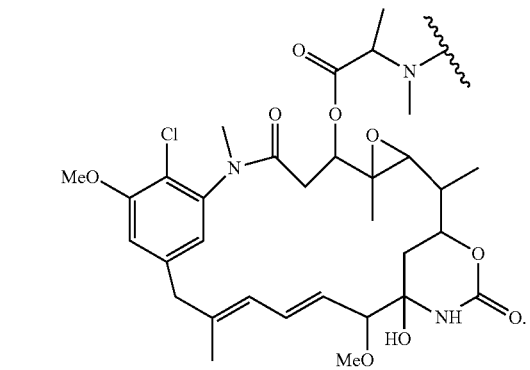 [SMILES: *N(C)C(C)C(=O)OC1CC(=O)N(C)c2cc(cc(OC)c2Cl)C/C(C)=C/C=C/C(OC)C2(O)CC(OC(=O)N2)C(C)C2OC12C]

Even more specifically, D is represented by the following formula:

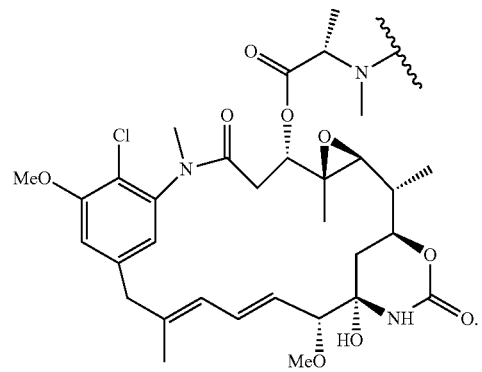 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In a 27th specific embodiment, the compound of formula (I) in the methods described herein (e.g., the method of the first, second, third, fourth, fifth, sixth, seventh, eighth, ninth or tenth embodiment, or any embodiments described therein) is represented by the following formula:

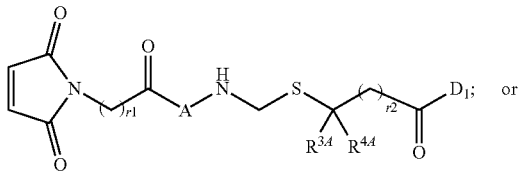
(I-b)

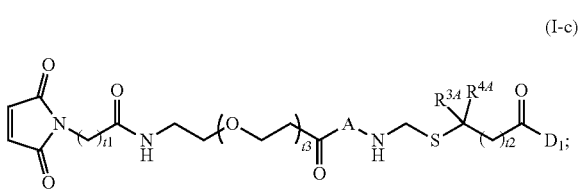
(I-c)

or a pharmaceutically acceptable salt thereof, wherein:
$R^{3A}$ and $R^{4A}$ are each independently H or Me;
r1 and t1 are each independently an integer from 1 to 6;
r2 and t2 are each independently an integer from 1 to 7;
t3 is an integer from 1 to 12;
$D_1$ is represented by the following formula:

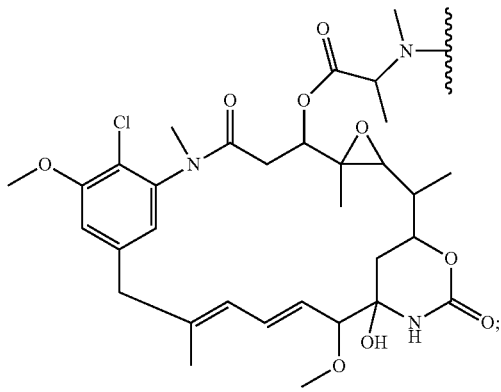 [SMILES: *N(C)C(C)C(=O)OC1CC(=O)N(C)c2cc(cc(OC)c2Cl)C/C(C)=C/C=C/C(OC)C2(O)CC(OC(=O)N2)C(C)C2OC12C]

and the remaining variables are as described in the 25th or 26th specific embodiment or any embodiments described therein.

In certain embodiment, A is Ala-Ala-Ala, Ala-D-Ala-Ala, Ala-Ala, D-Ala-Ala, Val-Ala, D-Val-Ala, D-Ala-Pro, or D-Ala-tBu-Gly, and the remaining variables are as described in the 28th specific embodiment.

In certain embodiment, r1 is an integer from 2 to 4; and r2 is an integer from 3 to 5, and the remaining variables are as described in the 27th specific embodiment or any embodiments described therein.

In a 28th specific embodiment, the compound of formula (I) in the methods described herein (e.g., the method of the first, second, third, fourth, fifth, sixth, seventh, eighth, ninth or tenth embodiment, or any embodiments described therein) is represented by the following formula:

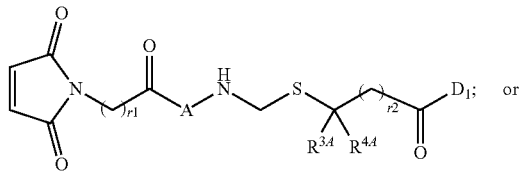
(I-d)

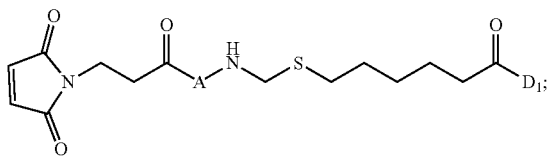
(I-e)

wherein:
r1 and t1 are each an integer from 2 to 6;
r2 and t2 are each an integer from 2 to 5; and
t3 is an integer from 2 to 12; and the remaining variables are as described in the 27th specific embodiment or any embodiments described therein.

In certain embodiments, $R^{3A}$ and $R^{4A}$ are both Me, and the remaining variables are as described in the 28th specific embodiment.

In certain embodiments, $R^{3A}$ and $R^{4A}$ are both H, and the remaining variables are as described in the 28th specific embodiment.

In a 29th specific embodiment, the compound of formula (I) in the methods described herein (e.g., the method of the first, second, third, fourth, fifth, sixth, seventh, eighth, ninth or tenth embodiment, or any embodiments described therein) is represented by the following formula:

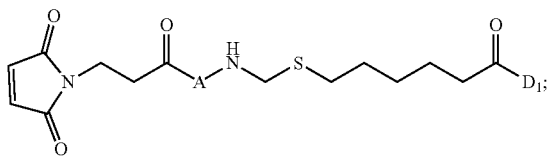
(I-f)

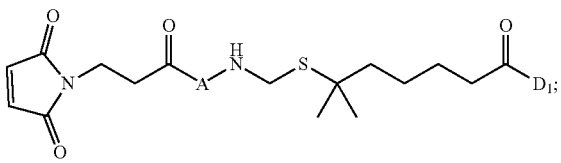
(I-g)

-continued
(I-h)
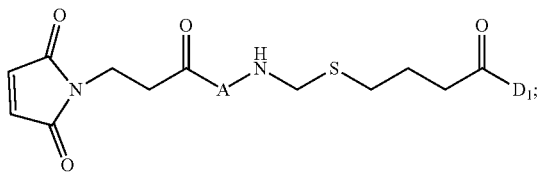
(I-i)
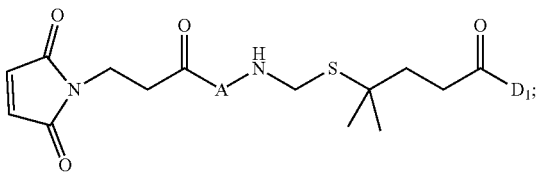
(I-j)
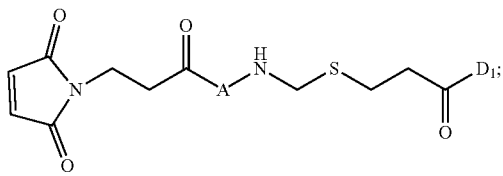
(I-k)
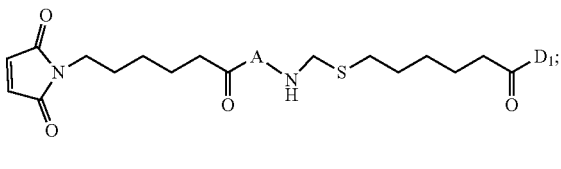
(I-l)
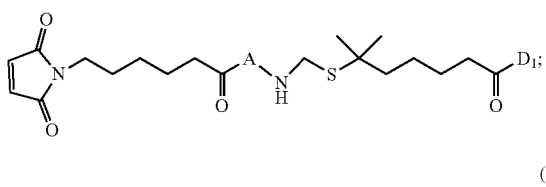
(I-m)
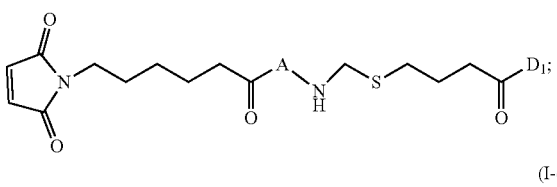
(I-n)
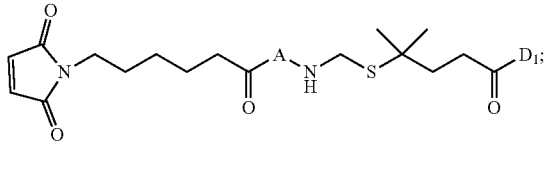
(I-o)
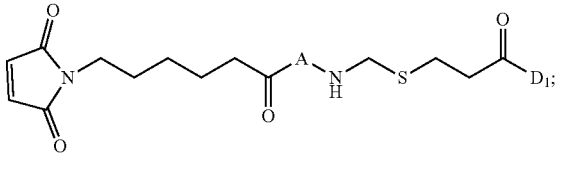
(I-p)
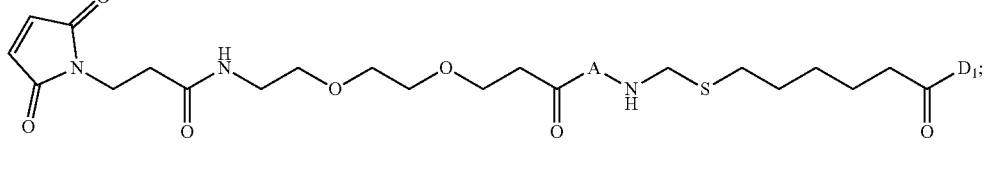
(I-q)
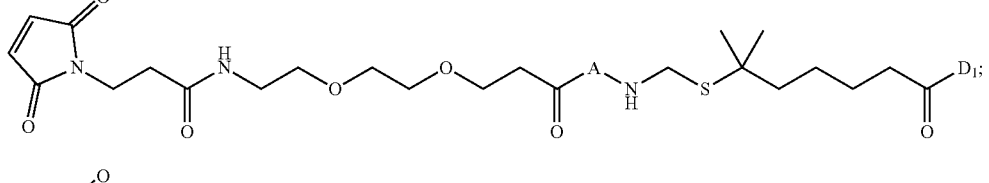
(I-r)
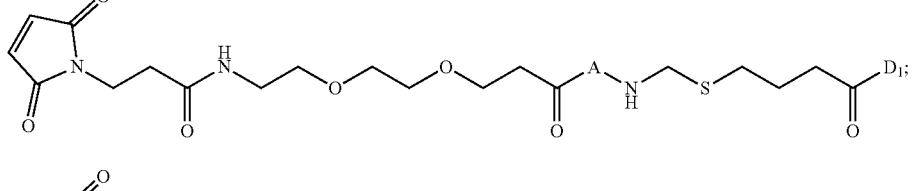
(I-s)
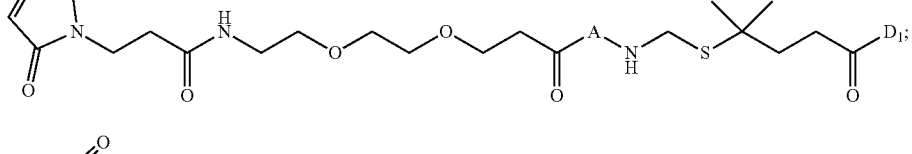
(I-t)
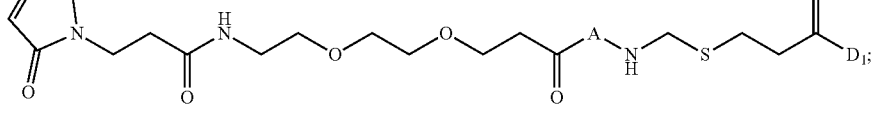

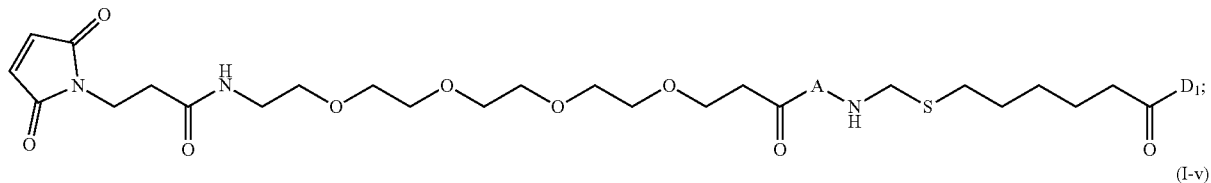
(I-u)
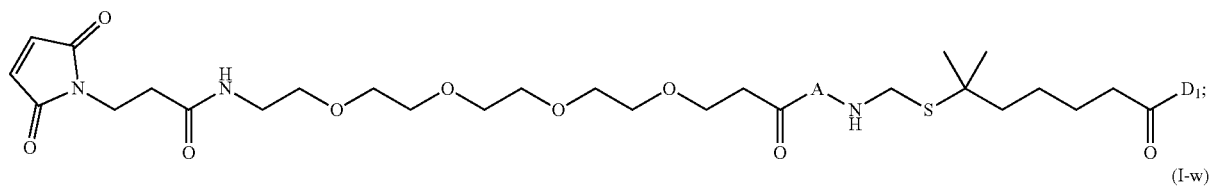
(I-v)
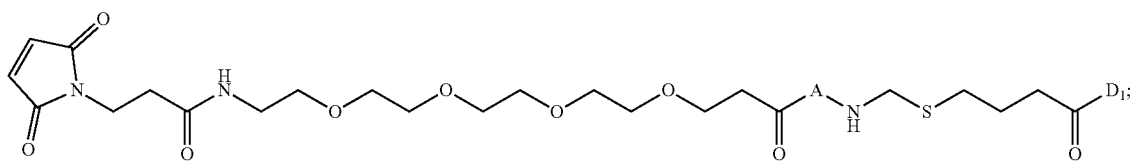
(I-w)
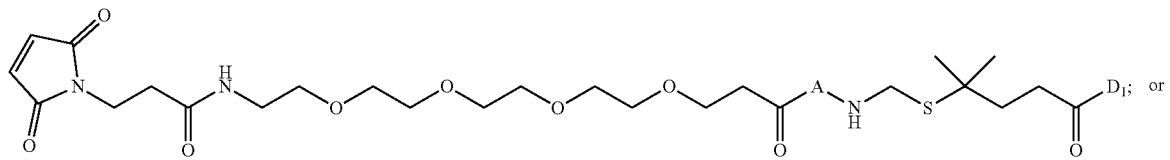
(I-x) or
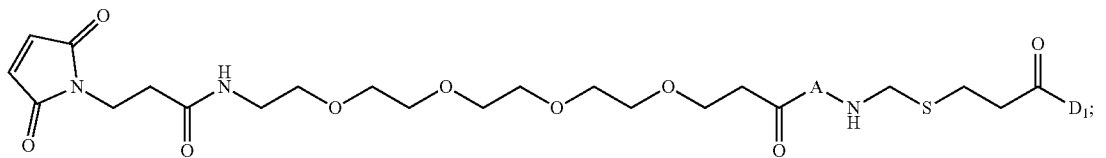
(I-y)
or a pharmaceutically acceptable salt thereof, wherein:
A is Ala-Ala-Ala, Ala-D-Ala-Ala, Ala-Ala, D-Ala-Ala, Val-Ala, D-Val-Ala, D-Ala-Pro, or D-Ala-tBu-Gly; and
$D_1$ is represented by the following formula:
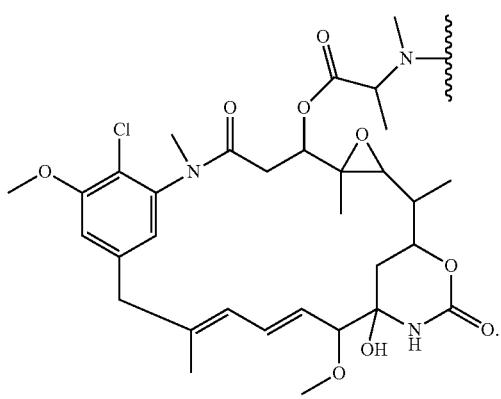 [SMILES: *N(C)C(C)C(=O)OC1CC(=O)N(C)c2cc(cc(OC)c2Cl)C/C(C)=C/C=C/C(OC)C2(O)CC(OC(=O)N2)C(C)C2OC12C]

In a 30th specific embodiment, the compound of formula (I) in the methods described herein (e.g., the method of the first, second, third, fourth, fifth, sixth, seventh, eighth, ninth or tenth embodiment, or any embodiments described therein) is represented by the following formula:
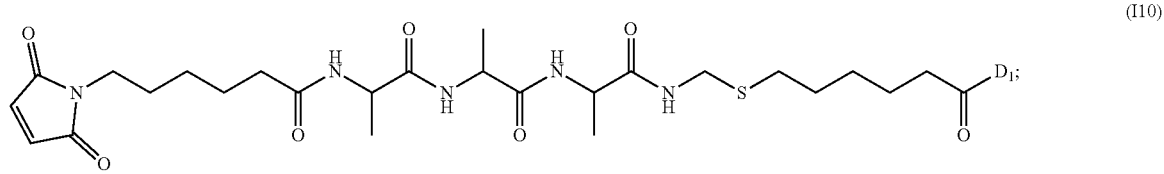
(I10)
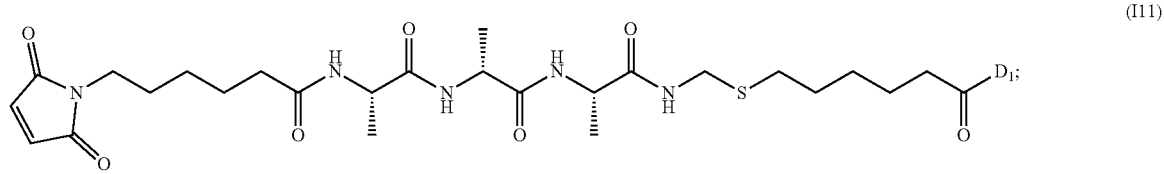
(I11)
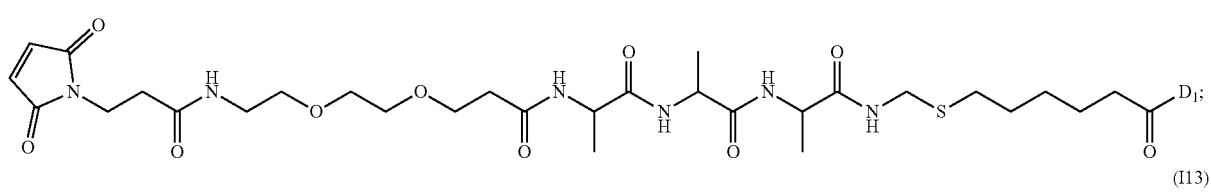
(I12)
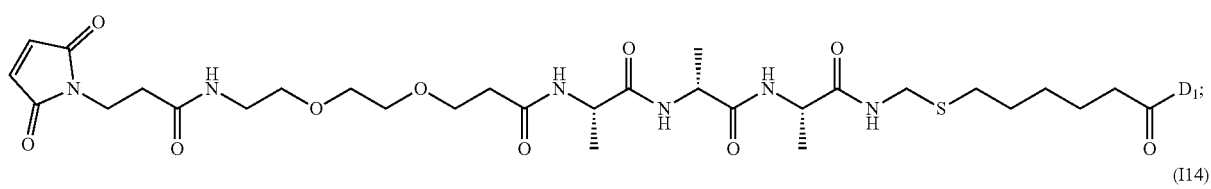
(I13)
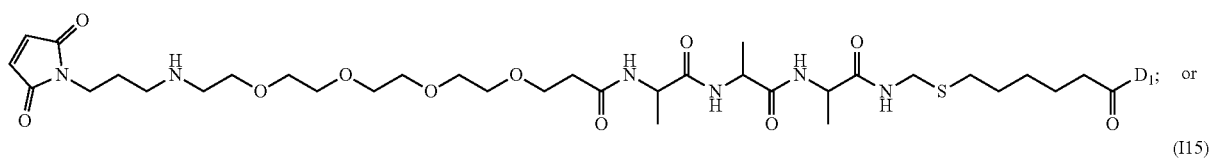
(I14) or
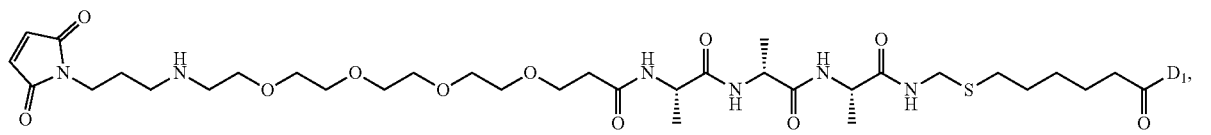
(I15)
wherein $D_1$ is represented by the following formula:
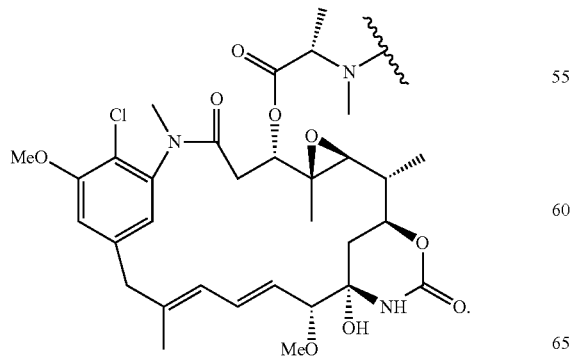

In certain embodiment, the compound of formula (I) is represented by formula (I11):

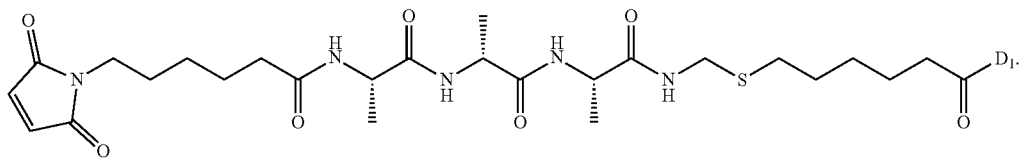

(I11)

The compound of formula (I11) is also refereed as DM21-C or Mal-LDL-DM or MalC5-LDL-DM.

In certain embodiments, for the compound of formula (I) described above, the pharmaceutically acceptable salt is a sodium salt or a potassium salt. In certain embodiments, for the compound of formula (I) described above, the pharmaceutically acceptable salt is a sodium salt.

5. Immunoconjugates, Pharmaceutical Compositions and Methods of Use

The present invention also provide conjugates described herein prepared by the methods of the present invention. Also provided is a pharmaceutical composition comprising a conjugates described herein.

The pharmaceutical compositions described herein can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration. In some particular embodiments, the administration is intravenous. The pharmaceutical compositions described herein can also be used in vitro or in ex vivo.

The present invention includes a method of inhibiting abnormal cell growth or treating a proliferative disorder in a mammal (e.g., human) comprising administering to said mammal a therapeutically effective amount of the immunoconjugate or the pharmaceutical composition of the present invention.

In certain embodiments, the abnormal cell growth or proliferative disorder in a mammal is cancer, including hematologic cancer, leukemia, or lymphoma. In certain embodiments, the proliferative disorder is a cancer of a lymphatic organ, or a hematological malignancy.

For example, the cancer may be selected from the group consisting of: acute myeloid leukemia (AML, including CD33-low AML, P-glycoprotein positive AML, relapsed AML, or refractory AML), chronic myelogenous leukemia (CML), including blastic crisis of CML and Abelson oncogene associated with CML (Bcr-ABL translocation), myelodysplastic syndrome (MDS), acute lymphoblastic leukemia (ALL), including, but not limited to, acute B lymphoblastic leukemia or B-cell acute lymphoblastic leukemia (B-ALL), chronic lymphocytic leukemia (CLL), including Richter's syndrome or Richter's transformation of CLL, hairy cell leukemia (HCL), acute promyelocytic leukemia (APL), B-cell chronic lymphoproliferative disease (B-CLPD), atypical chronic lymphocytic leukemia (preferably with a marked CD11c expression), diffuse large B-cell lymphoma (DLBCL), blastic plasmacytoid dendritic cell neoplasm (BPDCN), non-Hodgkin lymphomas (NHL), including mantel cell leukemia (MCL), and small lymphocytic lymphoma (SLL), Hodgkin's lymphoma, systemic mastocytosis, and Burkitt's lymphoma.

In certain embodiments, the cancer has at least one negative prognostic factor, e.g., overexpression of P-glycoprotein, overexpression of EVI1, a p53 alteration, DNMT3A mutation, FLT3 internal tandem duplication.

In certain embodiments, the cancer may be selected form the group consisting of lung cancer (e.g., non-small-cell lung cancer), colorectal cancer, bladder cancer, gastric cancer, pancreatic cancer, renal cell carcinoma, prostate cancer, esophageal cancer, breast cancer, head and neck cancer, uterine cancer, ovarian cancer, liver cancer, cervical cancer, thyroid cancer, testicular cancer, myeloid cancer, melanoma, and lymphoid cancer. In certain embodiments, the cancer is non-small-cell lung cancer, colorectal cancer, gastric cancer, breast cancer (e.g., triple negative breast cancer (TNBC)) or pancreatic cancer. In further embodiments, immunoconjugates of the present invention may be useful in the treatment of non-small-cell lung cancer (squamous cell, nonsquamous cell, adenocarcinoma, or large-cell undifferentiated carcinoma), colorectal cancer (adenocarcinoma, gastrointestinal carcinoid tumors, gastrointestinal stromal tumors, primary colorectal lymphoma, leiomyosarcoma, or squamous cell carcinoma) or breast cancer (e.g., triple negative breast cancer (TNBC))

Example 1. Reducing Agent Screening and Antibody Pre-Processing

Reducing Agent Screening

Various reducing agents were screened for the ability to reduce engineered cysteines in an anti-CD123 antibody containing site-specific conjugation sites. For all reactions, a 50 mg/mL stock solution of antibody in 20 mM Histidine, pH 6.0 was diluted into potassium phosphate, pH 6.0 buffer to achieve a final potassium phosphate concentration of 50 mM. The required volumes of DMA and the appropriate phosphine stocks solubilized in DMA were subsequently added to the reaction solution to achieve a 2.0 mg/mL antibody concentration, 10% (v/v) DMA, and the indicated number of equivalents of phosphine (mol:mol) with respect to the antibody. The reaction mixtures were subsequently allowed to react at 25° C. for 4 h. Upon completion of the reduction reaction, 40 (mol:mol) equivalents of Alexa Fluor 488-maleimide with respect to the antibody was introduced into the reaction using a 10 mM stock of the Alexa Fluor 488 maleimide in DMA. After incubation overnight at 25° C., the degree of labeling was determined by SEC chromatography employing the known extinction coefficients of the antibody at 280 nm and of the AF488-mal at 280 and 493 nm. The results are shown in Table A below.

TABLE A

| Phosphine Equiv | Bis(p-sulfonatophenyl)phenylphosphine dihydrate | 2-(Diphenylphosphino)benzenesulfonic acid | 2-(Diphenylphosphino)benzoic acid |
|---|---|---|---|
| 0 | 0.5 | 0.5 | 0.5 |
| 2 | 0.835 | 0.78 | 2.08 |
| 3 | 0.845 | 0.74 | 2.605 |
| 5 | 0.88 | N/A | 4.5 |
| 10 | 1.02 | 0.65 | 7.1 |

| Phosphine Equiv | TCEP·HCl | 2-(diphenylphosphinoethylamine |
|---|---|---|
| 0 | 0.5 | 0.5 |
| 2 | 2.41 | 1.97 |
| 3 | 3.36 | 2.14 |
| 5 | 3.94 | 2.62 |
| 10 | 7.24 | 5.16 |

| Phosphine Equiv | 2-(diphenylphosphino)-N,N,N-trimethylbenzeylammonium triflate | 2-(Dicyclohexylphosphino)benzenesulfonic acid |
|---|---|---|
| 0 | 0.5 | 0.5 |
| 2 | 0.514 | 0.69 |
| 3 | 0.48 | 0.86 |
| 5 | 0.51 | 0.63 |
| 10 | 0.633 | 0.05 |

Results from these data indicate the phosphines 2-(diphenylphosphino)benzoic acid, TCEP, and 2-(diphenylphosphino)ethylamine are capable of reducing the disulfides of the antibody making them available for subsequent labeling with AF488 maleimide.

In a separate experiment, two specific phosphines were screened for their ability to reduce engineered cysteines in an anti-CD123 antibody containing site-specific conjugation sites. The antibody was first diluted into 50 mM potassium phosphate buffer, pH 6.0. To this solution was added the appropriate number of equivalents (mol:mol) with respect to the antibody of the indicated reducing agent and DMA to achieve a final concentration of 5 mg/mL of antibody and 5% (v/v) DMA. This mixture was allowed to react for 4 h at 25° C. Upon completion of this step, aliquots of the reduced antibody were removed, diluted with pH 6.0 potassium phosphate buffer and allowed to react with 20 mol:mol equivalents of AF488-mal vs. antibody at 2.5 mg/mL antibody and 10% (v/v) DMA. The degree of labeling was monitored by SEC at 280 and 493 nm after allowing the mixture to react for 18 h at 25° C. The remainder of the reduction solution was also diluted with pH 6.0 potassium phosphate buffer maintaining a 50 mM buffer concentration. DMA and DHAA, as a DMA stock solution, at a 1.5:1 molar ratio of DHAA to reducing agent, were then added to the reaction. The final composition of the re-oxidation reaction mixture is 2.5 mg/mL antibody with the indicated number of DHAA equivalents, and 5% (v/v) DMA. After incubating this solution for 18 h at 25° C., the conjugation reaction was set up. The reaction mixture was diluted with pH 6.0 potassium phosphate maintaining the 50 mM buffer concentration. To this solution was added DMA and 10 molar equivalents of AF488-mal with respect to the antibody. The final composition of the conjugation reaction mixture was 2.0 mg/mL antibody, 10 molar equivalents of AF488-mal, and 10% (v/v) DMA. This reaction mixture was allowed to react for 18 h at 25° C. Upon completion of the reaction, the degree of labeling with AF488-mal was determined by SEC chromatography employing the known extinction coefficients of the antibody at 280 nm and of the AF488-mal at 280 and 493 nm. The results of this study are shown in Table B below.

TABLE B

| | 2-(Diphenylphosphino) ethylamine | | 3-(Diphenylphosphino) Propylamine | |
|---|---|---|---|---|
| No of Equiv. | Reduction DAR (20 equiv. Alexa) | DAR post-conjugation (1.5X DHAA; 5 equiv. Alexa) | Reduction DAR (20 equiv. Alexa) | DAR post-conjugation (1.5X DHAA; 5 equiv. Alexa) |
| 5 | 3.25 | 0.93 | 6.82 | 1.62 |
| 10 | 5.96 | 1.49 | 9.38 | 2.26 |
| 16/15 | 7.17 | 1.88 | 9.49 | 2.39 |

These studies indicate both 2-(diphenylphosphino)ethylamine and 3-(diphenylphosphino)propylamine are effective reducing agents capable of reducing the native inter-chain disulfides and engineered cysteine disulfides of the antibody. Additionally upon re-oxidation in the one-pot reaction with an excess of DHAA, the expected DAR 2 conjugates can be obtained.

In a separate experiment, the process was tested with reduction at pH 7.5 using phosphine and non-phosphine reducing agents. An anti-CD123 antibody was first diluted into 50 mM potassium phosphate buffer, pH 7.5. To this solution was added the appropriate number of equivalents (mol:mol) with respect to the antibody of the indicated reducing agent and DMA to achieve a final concentration of 5 mg/mL of antibody and 5% (v/v) DMA. This mixture was allowed to react for 4 h at 25° C. Upon completion of this step, the reaction solution was further diluted with pH 7.5 potassium phosphate buffer maintaining a 50 mM buffer concentration. DMA and DHAA, as a DMA stock solution, at a 1.5:1 molar ratio of DHAA to reducing agent, were then added to the reaction. The final composition of the re-oxidation reaction mixture was 2.5 mg/mL antibody, the indicated number of DHAA equivalents, and 5% (v/v) DMA. After incubating this solution for 18 h at 25° C., the conjugation reaction was set up. The reaction mixture pH was reduced by dilution with pH 6.0 potassium phosphate maintaining the 50 mM buffer concentration. To this solution was added DMA and 10 molar equivalents of AF488-mal with respect to the antibody. The final composition of the conjugation reaction mixture was 2.0 mg/mL antibody, 10 molar equivalents of AF488-mal, and 10% (v/v) DMA. This reaction mixture was allowed to react for 18 h at 25° C. Upon completion of the reaction, the degree of labeling with AF488-mal was determined by SEC chromatography employing the known extinction coefficients of the antibody at 280 nm and of the AF488-mal at 280 and 493 nm. Results of this study are shown in Table C below.

TABLE C

| | Reaction Reducing Agent | DTT (equiv. vs Ab) | DHAA (equiv. vs DTT) | AF488-mal (equiv. vs Ab) | AF488 labels per Ab |
|---|---|---|---|---|---|
| 1 | DTT | 5 | 1.5 | 10 | 1.3 |
| 2 | DTT | 10 | 1.5 | 10 | 1.6 |
| 3 | DTT | 20 | 1.5 | 10 | 1.4 |
| 4 | TCEP | 10 | 1.5 | 10 | 1.7 |
| 5 | TCEP | 15 | 1.5 | 10 | 1.8 |
| 6 | TCEP | 20 | 1.5 | 10 | 2.0 |
| 7 | 2-(Diphenylphosphino)ethylamine | 5 | 1.5 | 10 | 1.3 |
| 8 | 2-(Diphenylphosphino)ethylamine | 10 | 1.5 | 10 | 1.7 |
| 9 | 2-(Diphenylphosphino)ethylamine | 15 | 1.5 | 10 | 1.8 |
| 10 | 3-(Diphenylphosphino)propylamine | 5 | 1.5 | 10 | 2.0 |
| 11 | 3-(Diphenylphosphino)propylamine | 10 | 1.5 | 10 | 1.6 |
| 12 | 3-(Diphenylphosphino)propylamine | 15 | 1.5 | 10 | 2.1 |

Oxidizing and Reducing Agent Concentrations and Effects on DAR

The ratio of DHAA to 2-Diphenylphosphinoethylamine was examined for effects on DAR. An anti-CD123 antibody was first diluted into 50 mM potassium phosphate buffer, pH 6.0. To this solution was added the appropriate number of equivalents (mol:mol) of 2-(diphenylphosphino)ethylamine with respect to the antibody and DMA to achieve a final concentration of 5 mg/mL of antibody and 5% (v/v) DMA. This mixture was allowed to react for 4 h at 25° C. Upon completion of this step, aliquots of the reduced antibody were removed, diluted with pH 6.0 potassium phosphate buffer and allowed to react with 20 mol:mol equivalents of AF488-mal vs antibody at 2.5 mg/mL antibody and 10% (v/v) DMA. The degree of labeling was monitored by SEC at 280 and 493 nm after allowing the mixture to react for 18 h at 25° C. The remainder of the reduction solution was also diluted with pH 6.0 potassium phosphate buffer maintaining a 50 mM buffer concentration. DMA and DHAA, as a DMA stock solution, at the indicated molar ratio of DHAA to reducing agent, were then added to the reaction. The final composition of the re-oxidation reaction mixture was 2.5 mg/mL antibody with the indicated number of DHAA equivalents, and 5% (v/v) DMA. After incubating this solution for 18 h at 25° C., the conjugation reaction was set up. The reaction mixture was diluted with pH 6.0 potassium phosphate maintaining the 50 mM buffer concentration. To this solution was added DMA and 10 molar equivalents of AF488-mal with respect to the antibody. The final composition of the conjugation reaction mixture was 2.0 mg/mL antibody, 10 molar equivalents of AF488-mal, and 10% (v/v) DMA. This reaction mixture was allowed to react for 18 h at 25° C. Upon completion of the reaction, the degree of labeling with AF488-mal was determined by SEC chromatography employing the known extinction coefficients of the antibody at 280 nm and of the AF488-mal at 280 and 493 nm. Results of this study are shown in Table D below and in FIG. 1.

TABLE D

| Equivalents of 2-Diphenylphosphino ethylamine | DAR Post Reduction; 20 equiv. AF488-Mal) |
|---|---|
| 0 | 0.53 |
| 5 | 3.25 |
| 6 | 4.19 |
| 8 | 5.51 |
| 10 | 5.96 |
| 12 | 6.44 |
| 16 | 7.17 |

These data indicate that effective conjugation occurs with 2-(diphenylphosphino)ethylamine. In particular, as the equivalents of phosphine increase, higher degrees of AF-488 labeling are observed. Additionally, in the 1.0 to 2.0 mol:mol excess of DHAA to phosphine, no significant difference in AF-488 labeling was observed, indicating full re-oxidation of the native interchain disulfide bonds of the antibody.

Antibody Concentration Study

The effect of high antibody concentration on DAR was evaluated using the one-pot conjugation method. An anti-ADAM9 antibody was first diluted into 50 mM potassium phosphate buffer, pH 6.0. To this solution was added the 25 equivalents (mol:mol) of the indicated phosphine with respect to the antibody and DMA to achieve a final concentration of 10 mg/mL of antibody and 5% (v/v) DMA. This mixture was allowed to react for 4 h at 25° C. Upon completion of this step, aliquots of the reduced antibody were removed, diluted with pH 6.0 potassium phosphate buffer and allowed to react with 25 mol:mol equivalents of AF488-mal vs antibody at 4.0 or 7.5 mg/mL antibody, for the low and high concentration reactions, respectively, and 10% (v/v) DMA. The degree of labeling was monitored by SEC at 280 and 493 nm after allowing the mixture to react for 4 h at 25° C. The remainder of the reduction solution was also diluted with pH 6.0 potassium phosphate buffer maintaining a 50 mM buffer concentration. DMA and DHAA, as a DMA stock solution, at a 1:1 molar ratio of DHAA to reducing agent, were then added to the reaction. The final composition of the re-oxidation reaction mixture was 4 or 7.5 mg/mL antibody, as indicated, with 25 mol:mol equivalents DHAA with respect to antibody, and 7.5% (v/v) DMA. After incubating this solution for 18 h at 25° C., the conjugation reaction was set up. The reaction mixture was diluted with pH 6.0 potassium phosphate maintaining the 50 mM buffer concentration. To this solution was added DMA and 5 molar equivalents of AF488-mal with respect to the antibody. The final composition of the conjugation reaction mixture was 3.5 or 7 mg/mL antibody for the low and high concentration reactions, respectively, 5 molar equivalents of AF488-mal, and 10% (v/v) DMA. This reaction mixture was allowed to react for 18 h at 25° C. Upon completion of the reaction, the degree of labeling with AF488-mal was determined by SEC chromatography employing the known extinction coefficients of the antibody at 280 nm and of the AF488-mal at 280 and 493 nm. Results of this study are shown in Table E below.

TABLE E

| Reaction | Phosphine | Reduction Concentration (mg/mL) | Re-oxidation Concentration (mg/mL) | Conjugation Concentration (mg/mL) | AF488-mal labeling after reduction reaction | AF488-mal labeling of final conjugate |
|---|---|---|---|---|---|---|
| 1 | TCEP | 10 | 4 | 3.5 | 8.45 | 1.53 |
| 2 | Tris(hydroxypropyl) phosphine | 10 | 4 | 3.5 | 9.72 | 1.88 |
| 3 | Tris(hydroxypropyl) phosphine | 10 | 7.5 | 7 | 9.63 | 1.97 |
| 4 | 2-(diphenylphosphino) ethylamine | 10 | 4 | 3.5 | 8.76 | 1.93 |
| 5 | 2-(diphenylphosphino) ethylamine | 10 | 7.5 | 7 | 8.67 | 1.85 |

TABLE E-continued

| Reaction | Phosphine | Reduction Concentration (mg/mL) | Re-oxidation Concentration (mg/mL) | Conjugation Concentration (mg/mL) | AF488-mal labeling after reduction reaction | AF488-mal labeling of final conjugate |
|---|---|---|---|---|---|---|
| 6 | 3-(diphenylphosphino) propylamine | 10 | 4 | 3.5 | 9.37 | 1.94 |
| 7 | 3-(diphenylphosphino) propylamine | 10 | 7.5 | 7 | 8.98 | 2.15 |
| 8 | Bis(3-aminopropyl) phenylphosphine | 10 | 4 | 3.5 | 9.51 | 1.91 |
| 9 | Bis(3-aminopropyl) phenylphosphine | 10 | 7.5 | 7 | 8.28 | 2.05 |

After reduction, re-oxidation, and conjugation at low or high concentration, with different phosphines, all reactions showed AF488-mal labeling approaching the target of 2.0 labels per antibody.

Effect of Time and Temperature on TCEP Reduction

Figure 2:
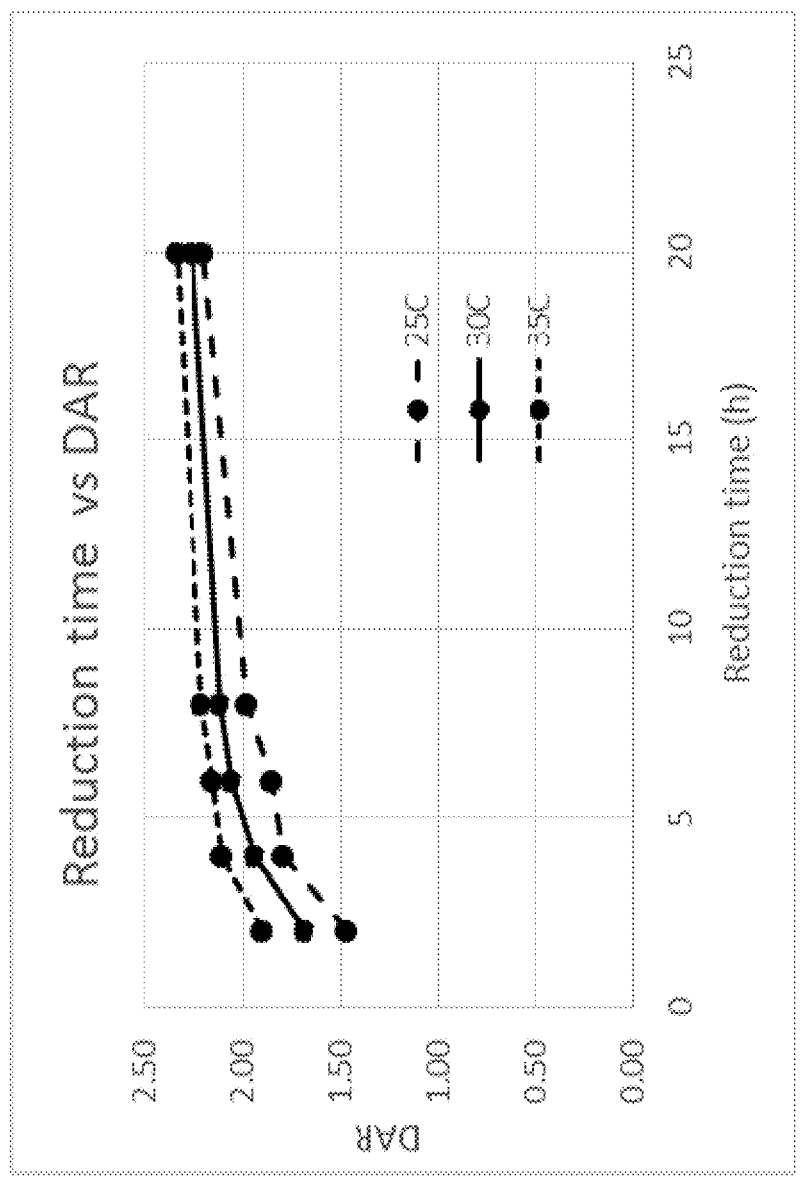
FIG. 2 shows the effects of reaction time and temperature for the TCEP reduction on DAR.
Figure 3:
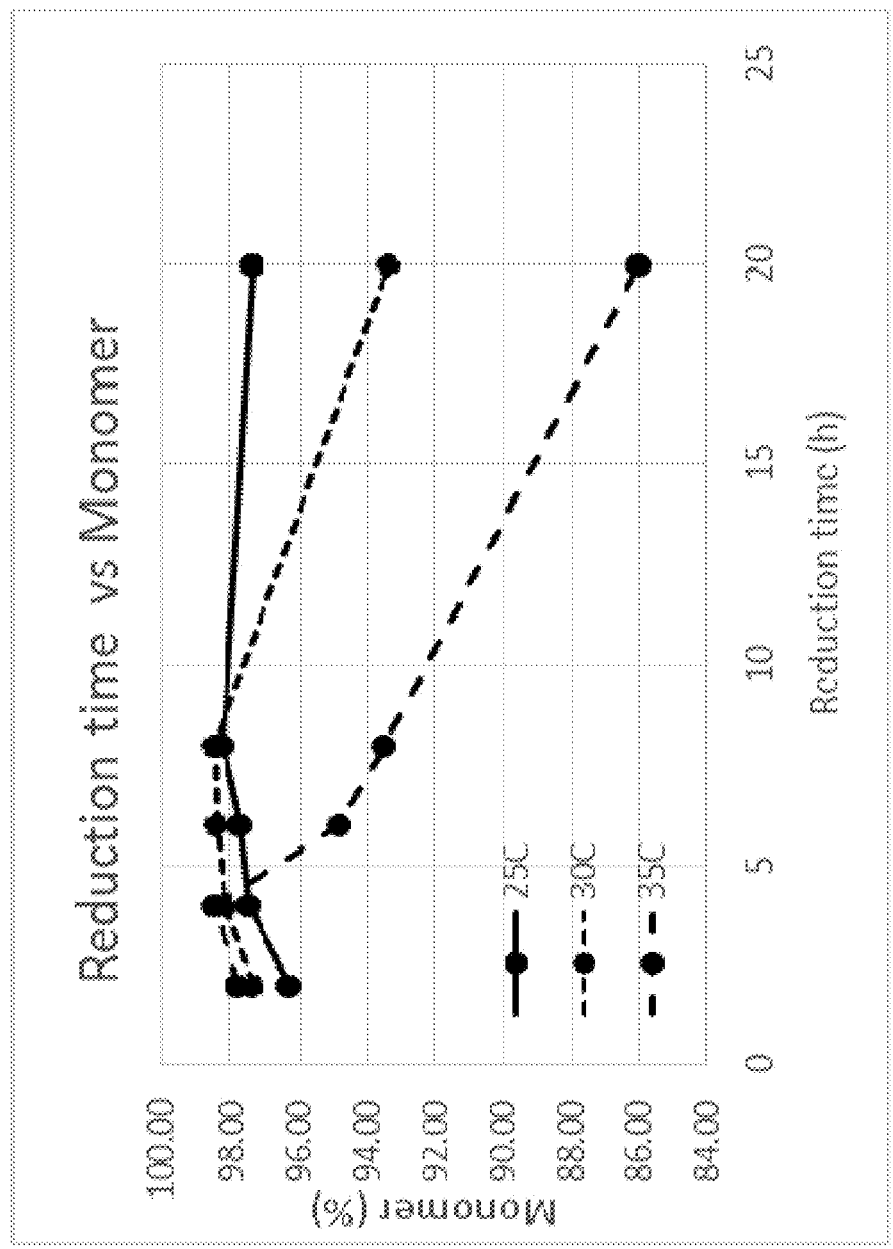
FIG. 3 shows the effects of reaction time and temperature for the TCEP reduction on monomer percentage.

The effect of time and temperature on TCEP reduction was examined using the one-pot conjugation method. Reduction reactions were performed at an anti-ADAM9 antibody concentration of 10 mg/mL in pH 6.0, 25 mM succinate with 5% DMA. Reactions were set up with 25 mol:mol equivalents of TCEP and were performed at either 25° C., 30° C. or 35° C. for either 2, 4, 6, 8, or 20 hours. Re-oxidation reactions were performed at an antibody concentration of 7 mg/mL in pH 6.0, 25 mM succinate with 8% DMA. Reactions were set up with a 1.5 fold excess of DHAA with respect to TCEP and were performed at 25° C. for 16-20 hours. The re-oxidized antibody was used directly to set up conjugation reactions with AF488-mal payload. These conjugation reactions were performed at an antibody concentration of 5 mg/mL in pH 6.0, 25 mM succinate with 10% DMA. Reactions were set up with 5.0 mol:mol equivalents of AF488-mal and were performed at 25° C. for 16-20h. At the end of each AF488-mal reaction, samples were analyzed via SEC for monomer and degree of AF488-mal labeling. The degree of labeling with AF488-mal was determined by employing the known extinction coefficients of the antibody at 280 nm and of the AF488-mal at 280 and 493 nm. Details of these reactions are shown in Table F and FIGS. 2 and 3.

TABLE F

| Sample | Reduction Time (h) | Reduction Temperature (C) | % Monomer | SEC DAR |
|---|---|---|---|---|
| 1 | 2 | 25 | 96.30 | 1.53 |
| 2 | 4 | 25 | 97.44 | 1.86 |
| 3 | 6 | 25 | 97.74 | 1.92 |
| 4 | 8 | 25 | 98.20 | 2.05 |
| 5 | 20 | 25 | 97.13 | 2.28 |
| 6 | 2 | 30 | 97.32 | 1.75 |
| 7 | 4 | 30 | 98.17 | 2.01 |
| 8 | 6 | 30 | 98.41 | 2.13 |
| 9 | 8 | 30 | 98.46 | 2.19 |
| 10 | 20 | 30 | 93.36 | 2.34 |
| 11 | 2 | 35 | 97.79 | 1.97 |
| 12 | 4 | 35 | 98.45 | 2.18 |
| 13 | 6 | 35 | 94.81 | 2.24 |
| 14 | 8 | 35 | 93.51 | 2.29 |
| 15 | 20 | 35 | 85.99 | 2.42 |

This study demonstrates TCEP reduction reaction times and temperature have an impact on the final conjugate degree of labeling, with the shortest reduction times translating into lower degrees of labeling with AF488-mal. An additional impact on conjugate stability was observed at elevated temperature where the % monomer of the conjugate was found to decrease as a function of time.

TCEP Equivalents Screening

Figure 4:
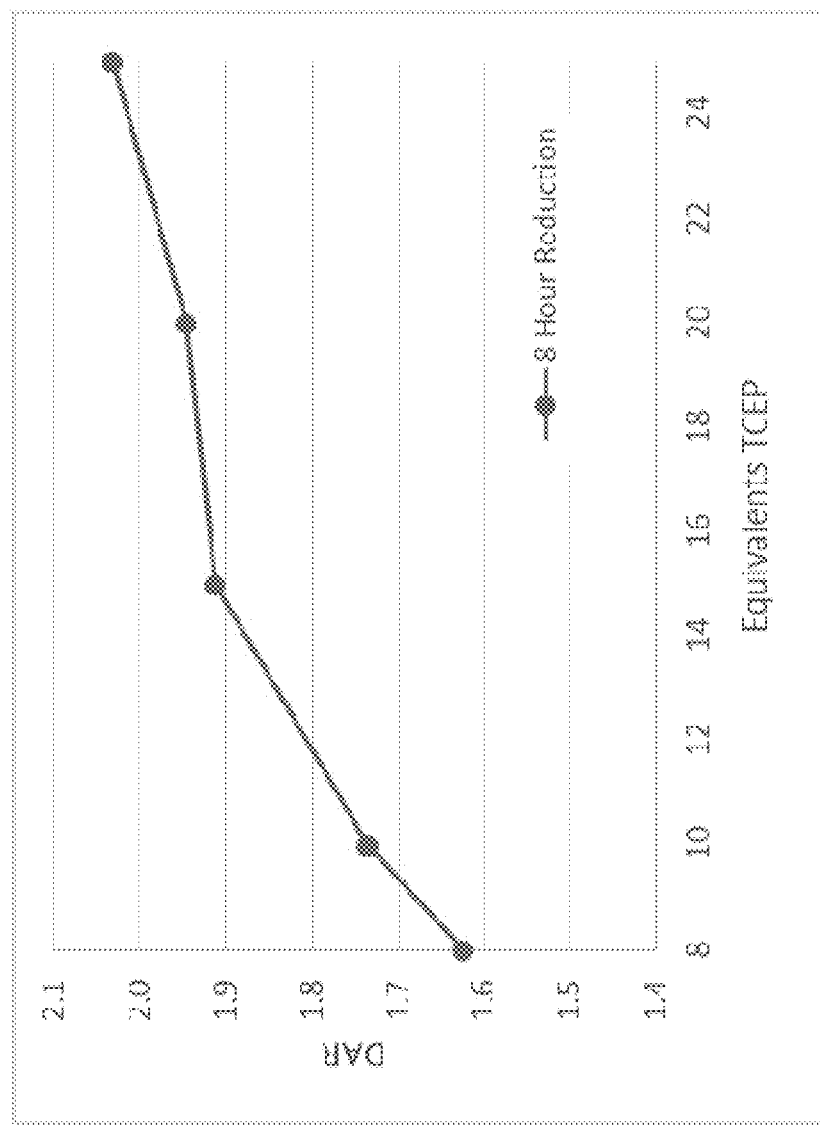
FIG. 4 shows the effects of the amount of TCEP used in the reduction reaction on DAR.

The effect of TCEP concentration on cysteine reduction was examined using the one-pot conjugation method and the anti-ADAM9 antibody. Reduction reactions were performed at an antibody concentration of 10 mg/mL in pH 6.0, 25 mM succinate with 5% DMA. These reduction reactions were set up with either 8, 10, 15, 20 or 25 equivalents of TCEP with respect to the antibody and were performed at 25° C. for 8 hours. Re-oxidation reactions were performed at an antibody concentration of 7 mg/mL in pH 6.0, 25 mM succinate with 8% DMA in the presence of 1.5 fold excess of DHAA with respect to TCEP and were performed at 25° C. for 16-20 hours. The re-oxidized antibody reaction mixture was used directly to set up conjugation reactions with AF-488Mal labeling. These conjugation reactions were performed at an antibody concentration of 5 mg/mL in pH 6.0, 25 mM succinate with 10% DMA. Reactions were set up with 5 molar equivalents of AF-488Mal with respect to the antibody and were performed at 25° C. for 16-20h. Upon completion of the reaction, the degree of labeling with AF488-mal was determined by SEC chromatography employing the known extinction coefficients of the antibody at 280 nm and of the AF488-mal at 280 and 493 nm. Results of this study are shown in Table G below and in FIG. 4.

TABLE G

| Sample | Equiv TCEP | Reduction Time (h) | SEC DAR |
|---|---|---|---|
| 1 | 8 | 8 | 1.62 |
| 2 | 10 | 8 | 1.73 |
| 3 | 15 | 8 | 1.91 |
| 4 | 20 | 8 | 1.95 |
| 5 | 25 | 8 | 2.03 |

These data indicate that the final conjugate payload loading is dependent on the molar excess of phosphine. With TCEP at pH 6.0, 15 or greater equivalents of reducing agent is required to achieve a degree of labeling greater than 1.9.

Example 2: Comparison of one-pot conjugation process using TCEP and 3-(Diphenylphosphino) Propylamine (DPPA)

These experiments were designed to confirm and compare the efficacy of the pH 7.5 reduction with TCEP and pH 6.0 reduction with DPPA at a 25 mg Ab scale using an anti-ADAM9 antibody.

For the TCEP one-pot process, the reduction reaction was performed at an antibody concentration of 12 mg/mL in pH 7.5, 50 mM KPi with 5% DMA. The reaction was set up with 27 molar equivalents of TCEP with respect to antibody and was performed at 25° C. for 4 hours. This reduced antibody was used to set up the re-oxidation reaction, which was performed at an antibody concentration of 10 mg/mL in pH 7.5, 50 mM KPi with 7.5% DMA. The re-oxidation reaction was set up with a 1:1 molar ratio of DHAA to TCEP and was performed at 25° C. for 4 hours. The re-oxidized antibody was pH adjusted to 6.0 with 1 M acetic acid prior to conjugation. The conjugation reaction was performed at an antibody concentration of 8 mg/mL in pH 6.0, 50 mM KPi with 15% DMA. The conjugation reaction was set up with 5.4 molar equivalents of DM21-C with respect to antibody and was performed at 25° C. for 8-12 hours.

For the DPPA one-pot process, the reduction reaction was performed at an antibody concentration of 12 mg/mL in pH 6.0, 25 mM succinate with 5% DMA in the presence of 16 molar equivalents of DPPA with respect to antibody and was performed at 25° C. for 4 hours. The reduced antibody was used to set up the re-oxidation reaction, which was performed at an antibody concentration of 10 mg/mL in pH 6.0, 25 mM succinate with 7.5% DMA. The re-oxidation reaction was set up with a 1:1 molar ratio of DHAA to DPPA and was performed at 25° C. for 13 hours. The conjugation reaction was performed at an antibody concentration of 8 mg/mL in pH 6.0, 25 mM succinate with 15% DMA. The conjugation reaction was set up with 5.4 molar equivalents of DM21-C with respect to antibody and was performed at 25° C. for 8-12 hours. The crude conjugates were analyzed via SEC for monomer and DAR. The results for the one-pot conjugation process using TCEP and DPPA are detailed in Table H.

TABLE H

| Sample | Reducing Agent | Reduction pH | Re-oxidation pH | Conjugation pH | Equivalents Phosphine | % Monomer | SEC DAR |
|---|---|---|---|---|---|---|---|
| 1 | TCEP | 7.5 | 7.5 | 6 | 27.17 | 98.0 | 1.82 |
| 2 | DPPA | 6 | 6 | 6 | 16.30 | 97.7 | 1.98 |

This data supports the findings of the previous set of reactions, confirming that conjugation with a pH 6.0 DPPA reduction results in a higher DAR value than conjugation featuring a pH 7.5 TCEP reduction. The monomer level was comparable for these two reduction conditions, with the pH 7.5 TCEP reduction yielding a 0.3% higher monomer level.

Example 3: Reduction Reaction pH Screening for the One-Pot Process Using TCEP as a Reducing Agent This experiment was designed to screen reduction reaction pH for the one-pot process using TCEP as a reducing agent, an anti-ADAM9 antibody, and DM21-C payload.

The incoming anti-ADAM9 antibody solution (25 mg/mL antibody in 10 mM sodium acetate, pH 5.0, 9% sucrose) was diluted with the appropriate pH 200 mM potassium phosphate buffer to prepare different pH antibody stock solutions that were pH 7.0, 8.0, and 8.5 with a final potassium phosphate concentration of 50 mM. These antibody solutions were subsequently used to set up the corresponding pH reduction reactions. Reduction reactions were performed at an antibody concentration of 10 mg/mL in 50 mM potassium phosphate at pH 7.0, 8.0, or 8.5, and 5% DMA. Reactions were set up with 27 molar equivalents of TCEP with respect to antibody and were performed at 25° C. for 4 hours. The reduced antibody solution was pH adjusted to 6.0 using 1M acetic acid and then used without purification to set up re-oxidation reactions that were performed at an antibody concentration of 9 mg/mL in pH 6.0, 50 mM potassium phosphate with 8% DMA. Reactions were set up with a 1.5 fold molar excess of DHAA with respect to TCEP and were performed at 25° C. for 12-16 hours. The re-oxidized antibody was then used directly to set up conjugation reactions that were performed at an antibody concentration of 8 mg/mL in pH 6.0, 50 mM potassium phosphate containing 15% DMA. Reactions were set up with 5.4 equivalents of DM21-C and were performed at 25° C. for 8 hours. The crude conjugates were analyzed via SEC for % monomer and DAR.

The results of this experiment are shown in Table I below. In particular, these results indicate that increasing the reduction reaction pH from 7.0 to 8.5 does not significantly impact the final conjugate.

TABLE I

| Reaction | Reduction pH | oxidation pH | Conjugation pH | % Monomer | SEC DAR |
|---|---|---|---|---|---|
| 1 | 7.0 | 6.0 | 6.0 | 97.39 | 1.81 |
| 2 | 8.0 | 6.0 | 6.0 | 96.42 | 1.76 |
| 3 | 8.5 | 6.0 | 6.0 | 96.00 | 1.78 |

Example 4: One-Pot Conjugation Process Development for Conjugation of an Anti-ADAM9 Drug Conjugate One-Pot Process at pH 5.0 without pH Adjustment This experiment was designed to determine if an anti-ADAM9 antibody at 25 mg/mL in pH 5.0, 10 mM acetate buffer containing 9% sucrose is suitable for direct conjugation at pH 5.0 without a pH adjustment in the one-pot process.

Reduction reactions were performed at an antibody concentration of 12 mg/mL in pH 5, 10 mM acetate+9% sucrose with 5% DMA. Reactions were set up with the indicated molar excess DPPA with respect to the antibody and were performed at 25° C. for 10 hours. The reduced antibody was used without purification to set up re-oxidation reactions, which were performed at 10 mg/mL in pH 5.0, 10 mM acetate+9% sucrose containing 7.5% DMA. Reactions were set up with a 1:1 molar ratio of DHAA to DPPA phosphine and were performed at 25° C. for 12 hours. The re-oxidized antibody was used without purification to set up conjugation reactions with DM21-C. These conjugation reactions were performed at an antibody concentration of 8 mg/mL in pH 5, 10 mM acetate+9% sucrose containing 15% DMA. Reactions were set up with 5.4 equivalents of DM21-C and were performed at 25° C. for 12h. At the end of the conjugation reactions, samples were analyzed via SEC for % monomer and DAR.

The results of this experiment are shown in Table J below. In particular, these results indicate that DPPA can be used as the reducing agent in the one-pot process at pH 5.0 to prepare DAR 2 conjugates.

TABLE J

| Re-action | Reducing Agent | DPPA Equivalents | % Monomer | SEC DAR |
|---|---|---|---|---|
| 1 | DPPA | 11 | 98.12 | 2.11 |
| 2 | DPPA | 16 | 97.54 | 2.07 |
| 3 | DPPA | 22 | 97.05 | 2.17 |
| 4 | DPPA | 27 | 95.72 | 2.26 |

Reaction Temperature Screen for One-Pot Process Using DPPA

This experiment was designed to screen the reaction temperature for the one-pot process using DPPA as the reducing agent, an anti-ADAM9 antibody, and DM21-C payload.

For all reactions, the incoming anti-ADAM9 antibody (~25 mg/mL antibody in 10 mM sodium acetate, pH 5.0 with 9% sucrose) was diluted into pH 6.5 potassium phosphate buffer to give a final potassium phosphate buffer concentration of 50 mM. These antibody solutions were subsequently used to set-up the reduction reactions at a final antibody concentration of 4.1 mg/mL antibody. DPPA phosphine at 16 molar equivalents with respect to the antibody was added to the antibody solution with a final DMA co-solvent concentration of 5%. The reduction reaction was allowed to proceed for 4 h at the indicated temperature. The reaction temperature was maintained at the indicated value for the duration of the one-pot process. The reduced antibody solution was then used without purification to set-up the re-oxidation reaction. Re-oxidation reactions were performed at a final antibody concentration of 3.7 mg/mL with a 1.5-fold molar excess of DHAA oxidant with respect to DPPA and a final DMA co-solvent concentration of 7%. The re-oxidation reaction was allowed to proceed for 8 h prior to initiation of the conjugation reaction. To the re-oxidized antibody solution was added 5.4 molar equivalents of DM21-C with respect to the antibody at a concentration of 2.8 mg/mL after dilution with additional 50 mM pH 6.5 potassium phosphate. After reacting for 8 h at a final DMA concentration of 15%, the crude reaction mixture was analyzed via SEC for % monomer and DAR. The results of these experiments are shown in Table K below. Based on these data, temperatures between 18° and 27° C. in the one-pot process were found to have no impact on DAR and % monomer.

TABLE K

| Re-action | Temperature (C.) | DAR (SEC) | % Monomer |
|---|---|---|---|
| 1 | 27 | 1.97 | 98.46 |
| 2 | 25 | 1.96 | 98.47 |
| 3 | 23 | 1.98 | 98.46 |
| 4 | 21 | 2.00 | 98.45 |
| 5 | 22 | 2.04 | 98.52 |
| 6 | 20 | 2.01 | 98.44 |
| 7 | 18 | 2.02 | 98.56 | pH Screen for One-Pot Process Using DPPA

This experiment was designed to screen the reaction pH for the one-pot process using DPPA as the reducing agent, an anti-ADAM9 antibody, and DM21-C payload at 25° C.

For all reactions, the incoming anti-ADAM9 antibody (~25 mg/mL antibody in 10 mM sodium acetate, pH 5.0 with 9% sucrose) was diluted into the indicated pH potassium phosphate buffer to give a final potassium phosphate buffer concentration of 50 mM. These antibody solutions were subsequently used to set-up the reduction reactions at a final antibody concentration of 4.1 mg/mL antibody. DPPA phosphine at 16 molar equivalents with respect to the antibody was added to the antibody solution with a final DMA co-solvent concentration of 5%. The reduction reaction was allowed to proceed for 4 h. The reaction pH was maintained at the indicated value for the duration of the one-pot process with no pH adjustments. The reduced antibody solution was then used without purification to set-up the re-oxidation reaction. Re-oxidation reactions were performed at a final antibody concentration of 3.7 mg/mL with a 1.5-fold molar excess of DHAA oxidant with respect to DPPA and a final DMA co-solvent concentration of 7%. A potassium phosphate stock buffer of the appropriate pH was used for dilution of the reaction to achieve the target antibody concentration. The re-oxidation reaction was allowed to proceed for 8 h prior to initiation of the conjugation reaction. To the re-oxidized antibody solution was added 5.4 molar equivalents of DM21-C with respect to the antibody at a concentration of 2.8 mg/mL after dilution with additional 50 mM potassium phosphate buffer of the appropriate pH. After reacting for 8 h at a final DMA concentration of 15%, the crude reaction mixture was analyzed via SEC for % monomer and DAR. The results of these experiments are shown in Table L below.

TABLE L

| Re-action | pH | DAR (SEC) | % Monomer |
|---|---|---|---|
| 1 | 6.6 | 1.98 | 98.43 |
| 2 | 6.5 | 1.96 | 98.47 |
| 3 | 6.4 | 1.99 | 98.47 |
| 4 | 6.3 | 1.99 | 98.53 |

Phosphine Concentration Screen for One-Pot Process Using DPPA

This experiment was designed to screen the quantity of phosphine in the one-pot process using DPPA as the reducing agent, an anti-ADAM9 antibody, and DM21-C payload at 25° C.

For all reactions, the incoming anti-ADAM9 antibody (~25 mg/mL antibody in 10 mM sodium acetate, pH 5.0 with 9% sucrose) was diluted into pH 6.5 potassium phosphate buffer to give a final potassium phosphate buffer concentration of 50 mM. These antibody solutions were subsequently used to set-up the reduction reactions at a final antibody concentration of 4.1 mg/mL antibody. DPPA phosphine at the indicated number of molar equivalents with respect to the antibody was added to the antibody solution with a final DMA co-solvent concentration of 5%. The reduction reaction was allowed to proceed for 4 h, and the reaction pH was maintained at 6.5 for the duration of the one-pot process with no pH adjustments. The reduced antibody solution was then used without purification to set-up the re-oxidation reaction. Re-oxidation reactions were performed at a final antibody concentration of 3.7 mg/mL with a 1.5-fold molar excess of DHAA oxidant with respect to DPPA and a final DMA co-solvent concentration of 7%. A pH 6.5 potassium phosphate stock buffer was used for dilution of the reaction to achieve the target antibody concentration. The re-oxidation reaction was allowed to proceed for 8 h prior to initiation of the conjugation reaction. To the re-oxidized antibody solution was added 5.4 molar equivalents of DM21-C with respect to the antibody at a concentration of 2.8 mg/mL after dilution with additional 50 mM pH 6.5 potassium phosphate buffer. After reacting for 8 h at a final DMA concentration of 15%, the crude reaction mixture was analyzed via SEC for % monomer and DAR. The results of these experiments are shown in Table M below.

TABLE M

| Reaction | DPPA equivalents | DAR (SEC) | % Monomer |
|---|---|---|---|
| 1 | 19 | 2.03 | 98.44 |
| 2 | 16 | 1.96 | 98.47 |
| 3 | 14 | 1.95 | 98.43 |

DHAA Oxidant Concentration Screen for One-Pot Process Using DPPA

This experiment was designed to screen the quantity of DHAA oxidant in the one-pot process using DPPA as the reducing agent, anti-ADAM9 antibody, and DM21-C payload at 25° C.

For all reactions, the incoming anti-ADAM9 antibody (~25 mg/mL antibody in 10 mM sodium acetate, pH 5.0 with 9% sucrose) was diluted into pH 6.5 potassium phosphate buffer to give a final potassium phosphate buffer concentration of 50 mM. These antibody solutions were subsequently used to set-up the reduction reactions at a final antibody concentration of 4.1 mg/mL antibody. DPPA phosphine at 16 molar equivalents with respect to the antibody was added to the antibody solution with a final DMA co-solvent concentration of 5%. The reduction reaction was allowed to proceed for 4 h, and the reaction pH was maintained at 6.5 for the duration of the one-pot process with no pH adjustments. The reduced antibody solution was then used without purification to set-up the re-oxidation reaction. Re-oxidation reactions were performed at a final antibody concentration of 3.7 mg/mL with the indicated fold molar excess of DHAA oxidant with respect to DPPA and a final DMA co-solvent concentration of 7%. A pH 6.5 potassium phosphate stock buffer was used for dilution of the reaction to achieve the target antibody concentration. The re-oxidation reaction was allowed to proceed for 8 h prior to initiation of the conjugation reaction. To the re-oxidized antibody solution was added 5.4 molar equivalents of DM21-C with respect to the antibody at a concentration of 2.8 mg/mL after dilution with additional 50 mM pH 6.5 potassium phosphate buffer. After reacting for 8 h at a final DMA concentration of 15%, the crude reaction mixture was analyzed via SEC for % monomer and DAR. The results of these experiments are shown in Table N below.

TABLE N

| Reaction | DHAA equivalents (vs. DPPA) | DAR (SEC) | % Monomer |
|---|---|---|---|
| 1 | 1.7 | 1.96 | 98.43 |
| 2 | 1.5 | 1.96 | 98.47 |
| 3 | 1.4 | 1.98 | 98.43 |

Payload Concentration Screen for One-Pot Process Using DPPA

This experiment was designed to screen the required quantity of DM21-C payload in the one-pot process using DPPA as the reducing agent, anti-ADAM9 antibody, at 25° C.

For all reactions, the incoming anti-ADAM9 antibody (~25 mg/mL antibody in 10 mM sodium acetate, pH 5.0 with 9% sucrose) was diluted into pH 6.5 potassium phosphate buffer to give a final potassium phosphate buffer concentration of 50 mM. These antibody solutions were subsequently used to set-up the reduction reactions at a final antibody concentration of 4.1 mg/mL antibody. DPPA phosphine at 16 molar equivalents with respect to the antibody was added to the antibody solution with a final DMA co-solvent concentration of 5%. The reduction reaction was allowed to proceed for 4 h, and the reaction pH was maintained at 6.5 for the duration of the one-pot process with no pH adjustments. The reduced antibody solution was then used without purification to set-up the re-oxidation reaction. Re-oxidation reactions were performed at a final antibody concentration of 3.7 mg/mL with a 1.5 fold molar excess of DHAA oxidant with respect to DPPA and a final DMA co-solvent concentration of 7%. A pH 6.5 potassium phosphate stock buffer was used for dilution of the reaction to achieve the target antibody concentration. The re-oxidation reaction was allowed to proceed for 8 h prior to initiation of the conjugation reaction. To the re-oxidized antibody solution was added the indicated molar equivalents of DM21-C with respect to the antibody at a concentration of 2.8 mg/mL after dilution with additional 50 mM pH 6.5 potassium phosphate buffer. After reacting for 8 h at a final DMA concentration of 15%, the crude reaction mixture was analyzed via SEC for % monomer and DAR. The results of these experiments are shown in Table O below.

TABLE O

| Reaction | DM21-C equivalents (vs. Ab) | DAR (SEC) | % Monomer |
|---|---|---|---|
| 1 | 5.4 | 1.96 | 98.47 |
| 2 | 5.2 | 1.94 | 98.48 |
| 3 | 5.0 | 1.93 | 98.50 |
| 4 | 4.8 | 1.96 | 98.45 |
| 5 | 4.6 | 1.93 | 98.46 |
| 6 | 4.3 | 1.93 | 98.44 |
| 7 | 4.1 | 1.92 | 98.40 |
| 8 | 3.9 | 2.00 | 98.52 |
| 9 | 3.7 | 2.01 | 98.47 |
| 10 | 3.5 | 2.01 | 98.44 |

Conjugation Reaction Time Screen for One-Pot Process Using DPPA

This experiment was designed to screen the required conjugation reaction time in the one-pot process using DPPA as the reducing agent, an anti-ADAM9 antibody, at 25° C.

For this reaction, the incoming anti-ADAM9 antibody (~25 mg/mL antibody in 10 mM sodium acetate, pH 5.0 with 9% sucrose) was diluted into pH 6.5 potassium phosphate buffer to give a final potassium phosphate buffer concentration of 50 mM. This antibody solution was subsequently used to set-up the reduction reaction at a final antibody concentration of 4.1 mg/mL antibody. DPPA phosphine at 16 molar equivalents with respect to the antibody was added to the antibody solution with a final DMA co-solvent concentration of 5%. The reduction reaction was allowed to proceed for 4 h, and the reaction pH was maintained at 6.5 for the duration of the one-pot process with no pH adjustments. The reduced antibody solution was then used without purification to set-up the re-oxidation reaction. This re-oxidation reaction was performed at a final antibody concentration of 3.7 mg/mL with a 1.5 fold molar excess of DHAA oxidant with respect to DPPA and a final DMA co-solvent concentration of 7%. A pH 6.5 potassium phosphate stock buffer was used for dilution of the reaction to achieve the target antibody concentration. The re-oxidation reaction was allowed to proceed for 8 h prior to initiation of the conjugation reaction. To the re-oxidized antibody solution was added 5.4 molar equivalents of DM21-C with respect to the antibody at a concentration of 2.8 mg/mL after dilution with additional 50 mM pH 6.5 potassium phosphate buffer. The final DMA concentration for the conjugation reaction is 15%. Reaction progress was monitored by repeat SEC chromatography reactions of the reaction held at 25° C. in an instrument sample chamber for 1.5 to 10.5 h. SEC % monomer and conjugate DAR data were collected and are summarized in Table P below.

TABLE P

| Re-action | Conjugation time (h) | DAR (SEC) | % Monomer |
|---|---|---|---|
| 1 | 1.5 | 1.86 | 98.58 |
| 2 | 2.5 | 1.90 | 98.56 |
| 3 | 3.5 | 1.93 | 98.50 |
| 4 | 4.5 | 1.91 | 98.52 |
| 5 | 5.5 | 1.93 | 98.51 |
| 6 | 6.5 | 1.95 | 98.54 |
| 7 | 7.5 | 1.97 | 98.53 |
| 8 | 8.5 | 1.96 | 98.50 |
| 9 | 9.5 | 1.95 | 98.47 |
| 10 | 10.5 | 1.94 | 98.46 |

Organic Co-Solvent Condition Screen for the One-Pot Process Using DPPA

This experiment was designed to screen the % organic co-solvent content during the final conjugation step of the one-pot process using DPPA as the reducing agent, an anti-ADAM9 antibody, and DHAA oxidant at a constant temperature of 25° C.

For all reactions, the incoming anti-ADAM9 antibody (~25 mg/mL antibody in 10 mM sodium acetate, pH 5.0 with 9% sucrose) was diluted into pH 6.5 potassium phosphate buffer to give a final potassium phosphate buffer concentration of 50 mM. These antibody solutions were subsequently used to set-up the reduction reactions at a final antibody concentration of 4.1 mg/mL antibody. DPPA phosphine at 16 molar equivalents with respect to the antibody was added to the antibody solution with a final DMA co-solvent concentration of 5%. The reduction reaction was allowed to proceed for 4 h, and the reaction pH was maintained at 6.5 for the duration of the one-pot process with no pH adjustments. The reduced antibody solution was then used without purification to set-up the re-oxidation reaction. Re-oxidation reactions were performed at a final antibody concentration of 3.7 mg/mL with a 1.5 fold molar excess of DHAA oxidant with respect to DPPA and a final DMA co-solvent concentration of 7%. A pH 6.5 potassium phosphate stock buffer was used for dilution of the reaction to achieve the target antibody concentration. The re-oxidation reaction was allowed to proceed for 8 h prior to initiation of the conjugation reaction. To the re-oxidized antibody solution was added 5.4 molar equivalents of DM21-C with respect to the antibody at a concentration of 2.8 mg/mL after dilution with additional 50 mM pH 6.5 potassium phosphate buffer. After reacting for 8 h at the indicated final DMA concentration, the crude reaction mixture was analyzed via SEC for % monomer and DAR. The results of these experiments are shown in Table Q below.

TABLE Q

| Re-action | Conjugation reaction DMA content (%) | DAR (SEC) | % Monomer |
|---|---|---|---|
| 1 | 16 | 1.97 | 98.44 |
| 2 | 15 | 1.96 | 98.47 |
| 3 | 13 | 1.98 | 98.48 |
| 4 | 12 | 1.97 | 98.47 |
| 5 | 11 | 1.97 | 98.47 |
| 6 | 10 | 1.96 | 98.46 |
| 7 | 9 | 1.96 | 98.46 |

Reduction Reaction Time Screen for One-Pot Process Using DPPA

This experiment was designed to screen the required time for the reduction reaction step of the one-pot process using DPPA as the reducing agent, an anti-ADAM9 antibody, and DHAA oxidant at a constant temperature of 23° C.

For all reactions, the incoming anti-ADAM9 antibody (~25 mg/mL antibody in 10 mM sodium acetate, pH 5.0 with 9% sucrose) was diluted into pH 6.5 potassium phosphate buffer to give a final potassium phosphate buffer concentration of 30 mM. These antibody solutions were subsequently used to set-up the reduction reactions at a final antibody concentration of 4.5 mg/mL antibody. DPPA phosphine at 16 molar equivalents with respect to the antibody was added to the antibody solution with a final DMA co-solvent concentration of 5%. The reduction reaction was allowed to proceed for the indicated time between 1 and 5 h, and the reaction pH was maintained at 6.5 for the duration of the one-pot process with no pH adjustments. The reduced antibody solution was then used without purification to set-up the re-oxidation reaction. Re-oxidation reactions were performed at a final antibody concentration of 4.0 mg/mL with a 1.5 fold molar excess of DHAA oxidant with respect to DPPA and a final DMA co-solvent concentration of 7%. A pH 6.5 potassium phosphate stock buffer was used for dilution of the reaction to achieve the target antibody concentration. The re-oxidation reaction was allowed to proceed for 6 h prior to initiation of the conjugation reaction. To the re-oxidized antibody solution was added 4.6 molar equivalents of DM21-C with respect to the antibody at a concentration of 3.5 mg/mL after dilution with additional 30 mM pH 6.5 potassium phosphate buffer. After reacting for 13 h at a final DMA concentration of 10%, the crude reaction mixture was analyzed via SEC for % monomer and DAR. The results of these experiments are shown in Table R below.

TABLE R

| Re-action | Reduction time (h) | DAR (SEC) | % Monomer |
|---|---|---|---|
| 1 | 1 | 1.96 | 98.74 |
| 2 | 2 | 1.97 | 98.73 |
| 3 | 3 | 2.00 | 98.66 |
| 4 | 4 | 2.05 | 98.70 |
| 5 | 5 | 2.03 | 98.65 |

Re-Oxidation Reaction Time Screen for One-Pot Process Using DPPA

This experiment was designed to screen the required time for the re-oxidation reaction step of the one-pot process using DPPA as the reducing agent, an anti-ADAM9 antibody, and DHAA oxidant at a constant temperature of 23° C.

For all reactions, the incoming anti-ADAM9 antibody (~25 mg/mL antibody in 10 mM sodium acetate, pH 5.0 with 9% sucrose) was diluted into pH 6.5 potassium phosphate buffer to give a final potassium phosphate buffer concentration of 30 mM. These antibody solutions were subsequently used to set-up the reduction reactions at a final antibody concentration of 4.5 mg/mL antibody. DPPA phosphine at 16 molar equivalents with respect to the antibody was added to the antibody solution with a final DMA co-solvent concentration of 5%. The reduction reaction was allowed to proceed for 4 h, and the reaction pH was maintained at 6.5 for the duration of the one-pot process with no pH adjustments. The reduced antibody solution was then used without purification to set-up the re-oxidation reaction. Re-oxidation reactions were performed at a final antibody concentration of 4.0 mg/mL with a 1.5 fold molar excess of DHAA oxidant with respect to DPPA and a final DMA co-solvent concentration of 7%. A pH 6.5 potassium phosphate stock buffer was used for dilution of the reaction to achieve the target antibody concentration. The re-oxidation reaction was allowed to proceed for the indicated time between 1 and 7 h prior to initiation of the conjugation reaction. To the re-oxidized antibody solution was added 4.6 molar equivalents of DM21-C with respect to the antibody at a concentration of 3.5 mg/mL after dilution with additional 30 mM pH 6.5 potassium phosphate buffer. After reacting for 13 h at a final DMA concentration of 10%, the crude reaction mixture was analyzed via SEC for % monomer and DAR. The results of these experiments are shown in Table S below.

TABLE S

| Re-action | Re-oxidation time (h) | DAR (SEC) | % Monomer |
|---|---|---|---|
| 1 | 1 | 2.02 | 98.69 |
| 2 | 2 | 2.05 | 97.88 |
| 3 | 3 | 2.03 | 98.65 |
| 4 | 4 | 2.01 | 98.08 |
| 5 | 5 | 1.97 | 98.09 |
| 6 | 6 | 1.98 | 98.61 |
| 7 | 7 | 1.96 | 98.65 |

Scale Up Conditions for One-Pot Process Using DPPA

This experiment was designed test performance of the one-pot reaction process at a 1.2 g antibody scale using DPPA as the reducing agent, an anti-ADAM9 antibody, and DHAA oxidant at a constant temperature of 23° C.

For this reaction, the incoming anti-ADAM9 antibody (~25 mg/mL antibody in 10 mM sodium acetate, pH 5.0 with 9% sucrose) was diluted into pH 6.5 potassium phosphate buffer to give a final potassium phosphate buffer concentration of 30 mM. The antibody solution was subsequently used to set-up the reduction reaction at a final antibody concentration of 4.5 mg/mL antibody. DPPA phosphine at 16 molar equivalents with respect to the antibody was added to the antibody solution with a final DMA co-solvent concentration of 5%. The reduction reaction was allowed to proceed for 5 h, and the reaction pH was maintained at 6.5 for the duration of the one-pot process with no pH adjustments. The reduced antibody solution was then used without purification to set-up the re-oxidation reaction. Re-oxidation reactions were performed at a final antibody concentration of 4.0 mg/mL with a 1.5 fold molar excess of DHAA oxidant with respect to DPPA and a final DMA co-solvent concentration of 7%. A pH 6.5 potassium phosphate stock buffer was used for dilution of the reaction to achieve the target antibody concentration. The re-oxidation reaction was allowed to proceed for 6 h prior to initiation of the conjugation reaction. To the re-oxidized antibody solution was added 4.6 molar equivalents of DM21-C with respect to the antibody at a concentration of 3.5 mg/mL after dilution with additional 30 mM pH 6.5 potassium phosphate buffer. After reacting for 12 h at a final DMA concentration of 10%, the crude reaction mixture was purified and formulated. Upon completion of the reaction, the homogenous reaction mixture was first filtered with a 0.5/0.2 um dual layer polyethersulfone filter. Following filtration, the reaction mixture was purified by TFF for 14 diavolumes against 10 mM sodium succinate, pH 4.7 buffer containing 9 w/v % sucrose. Following recovery, the buffer exchanged conjugate was filtered with a 0.5/0.2 um dual layer polyethersulfone filter and formulated at a final concentration of 7 mg/mL conjugate in 10 mM sodium succinate, pH 4.7 with 9 w/v % sucrose and 0.01% polysorbate-20. The overall yield of the process at the 1.2 g scale was 93%. SEC chromatography of the final conjugate was used to determine the % monomer and DAR as 98.71% and 1.99, respectively.

Example 5: Comparison of One-Pot Conjugation Process Using DPPA and the Multi-Step Process Using TCEP For the multi-step process at a 500 mg antibody scale, reduction was performed at 10 mg/mL anti-ADAM9 antibody and 27 (mol:mol) equivalents of TCEP with respect to the antibody in 50 mM pH 7.6 potassium phosphate reduction buffer at 37° C. for 1 h. Following reduction, TFF was performed diafiltering against 50 mM pH 7.6 potassium phosphate buffer for 10 diavolumes to remove residual phosphine, phosphine oxide and small molecule thiol containing capping molecules. This purified, reduced antibody was used without further treatment to prepare the selective re-oxidation reaction. Re-oxidation was performed at a final antibody concentration of 7 mg/mL, 15 (mol:mol) equivalents of DHAA with respect to antibody, and 1% (v/v) DMA, for 4 h at 25° C. After holding the re-oxidized reaction solution overnight at 4° C., the conjugation reaction with DM21-C was prepared without any additional processing of the re-oxidized antibody solution. Conjugation was performed at a final antibody concentration of 6 mg/mL in 50 mM pH 7.6 potassium phosphate with 4.4 (mol:mol) equivalents of DM21-C payload with respect to the antibody, and 10% (v/v) DMA at 25 C for 18 h. Following conjugation, the crude reaction mixture was purified by TFF with diafiltration against 10 mM sodium succinate, pH 5.0 buffer containing 9% (w/v) sucrose for 12 diavolumes.

For the one-pot process at a 500 mg antibody scale, reduction was performed at 12 mg/mL anti-ADAM9 antibody with 16 (mol:mol) equivalents of 3-(diphenylphosphino)propylamine (DPPA) with respect to the antibody in 25 mM pH 6.0 sodium succinate buffer, and 5% (v/v) DMA at 25° C. for 4 h. The crude reduced antibody solution was then carried forward without purification into the selective re-oxidation reaction. Re-oxidation was conducted at 10 mg/mL antibody with 16 (mol:mol) equivalents of DHAA with respect to the antibody and 7.5% (v/v) DMA at 25° C. for 23 h. The crude re-oxidized antibody solution was then carried forward without purification into the conjugation reaction. Conjugation was performed at a final antibody concentration of 8 mg/mL in 25 mM pH 6.0 sodium succinate buffer with 5.4 (mol:mol) equivalents of DM21-C with respect to the antibody at 25° C. for 20 h. Following conjugation the crude reaction mixture was purified by TFF with diafiltration against 10 mM sodium succinate, pH 5.0 buffer containing 9% (w/v) sucrose for 12 diavolumes.

The monomer and DAR values for both reactions were determined by SEC chromatography of the final conjugates. DAR values were calculated using the extinction coefficients of the antibody at 280 nm, the 252 to 280 nm absorbance ratio of the antibody, and payload extinction coefficient at 252 nm. Results of this study are given in Table T.

TABLE T

| Reaction | % Monomer | SEC DAR |
|---|---|---|
| Multi-step TCEP Process | 86.2 | 1.7 |
| One-pot DPPA Process | 98.2 | 1.9 |

Example 6: Continuous One-Pot Conjugation Process

An end-to-end integrated continuous manufacturing run was demonstrated for the one-pot process. G4723A antibody was used for the study. The demonstrated was designed to integrate continuous-stirred tank reactors (CSTRs) and plug flow reactors (PFRs) as a proof of concept for scaling up the one-pot continuous process.

Figure 5:
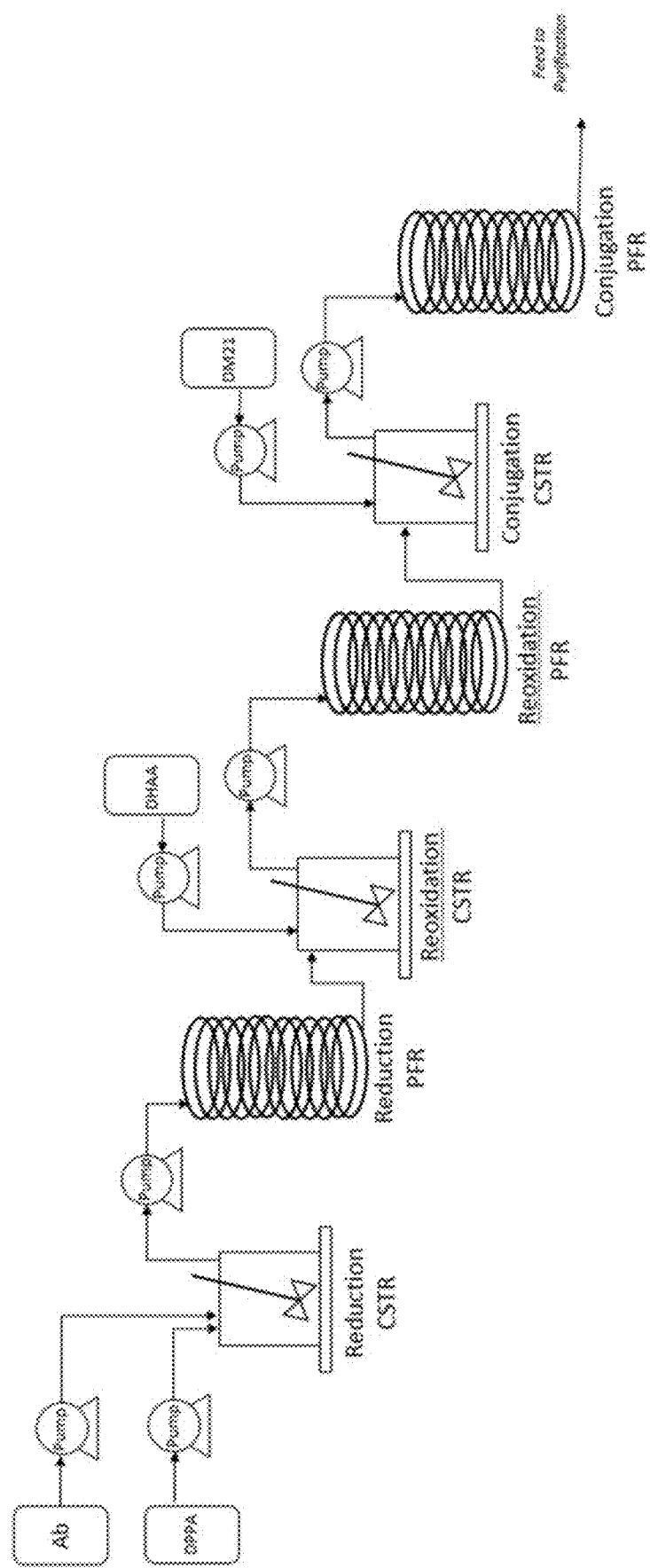
FIG. 5 shows integrated continuous manufacturing process for the CD123-targeting antibody drug conjugate (ADC) described in Example 5. Ab refers to the anti-CD123 monoclonal antibody G4723A.

The advantage of using CSTRs and PFRs in series was to reduce the overall volume requirements, improve mixing between reactant streams, and increase risk mitigation capabilities including broader residence time distributions. Reaction volumes were determined for the CSTR and PFR at each reaction step: reduction, reoxidation, and conjugation. Kinetic data for each reaction were generated and a desired target conversion for each reaction was specified. Based on these results the CSTR and PFR volumes for each reaction were specified based on the inner diameter of tubing used and volumetric flow rates required to achieve a desired residence time for each reaction step. The reaction schematic for the continuous one pot conjugation process is shown in FIG. 5.

First, the formulated G4723A antibody formulated at 50 mg/mL is diluted to the target reduction reaction concentration of 4 mg/mL with 30 mM potassium phosphate pH 6.5. This feed stream is fed into the reduction CSTR by peristaltic pump. In parallel, the DPPA stock solution prepared at 8.77 mM in DMA is fed into the reduction CSTR by syringe pump. The volumetric flow rates of these two feeds streams is set such that the reduction reaction achieves a 4.0 mg/mL concentration with a 16 fold molar excess of DPPA:Ab. Additionally, the volumetric concentration of DMA in the reduction reaction is 5% (v/v).

A peristaltic pump was used to withdraw material from the reduction reaction CSTR at the same volumetric flow rate as the combined flow rates into the reduction reaction CSTR (made up of the Ab and DPPA feed streams). The flow rates in and out of the CSTR were matched to keep the liquid level and residence time of the reduction reaction CSTR constant for steady-state operation. The material drawn from the reduction reaction CSTR was fed through the reduction PFR. The length of the tubing for the PFR was determined based on a target desired reaction conversion. The target conversion was used to set a residence time and the total volumetric flow rate through the PFR was determined to set a fixed length for the PFR reactor. The reduction PFR was submerged in a temperature-controlled water bath to ensure the temperature of the reaction was constant throughout.

The reduction PFR was fed directly into the reoxidation CSTR at the same volumetric flow rate as the material being withdrawn by peristaltic pump out of the reduction CSTR reactor. This feed stream mixed with the DHAA stock solution prepared in DMA that was also fed to the reoxidation CSTR by syringe pump. The DHAA stock solution was prepared at 55 mM in DMA and fed into the reactor such that the final reaction parameters for the reoxidation reaction were: 3.9 mg/mL antibody concentration, 24-fold molar excess of DHAA:Ab, and 6.5% DMA (v/v).

The combined flow rate of the two feeds streams into the reoxidation CSTR were determined and used to set the volumetric flow rate of an additional peristaltic pump used to remove material from the reoxidation CSTR at the same flow rate. Similar to the reduction CSTR, the matched flow rates in and out of the CSTR were chosen such that the liquid level and residence time were consistent during steady-state operation. The material being removed by pump from the reoxidation CSTR was directly fed into the reoxidation PFR. The reoxidation reaction PFR design approach was the same as the previously discussed reduction PFR. A desired reaction conversion based on kinetic data set the reaction residence time. This residence time combined with the volumetric flow rate through the reoxidation reaction was used to calculate the PFR design criteria. The reoxidation PFR was also submerged (similar to the reduction PFR) in a temperature-controlled water bath.

The output of the reoxidation reaction PFR was fed directly into the conjugation CSTR. The DM21-C stock solution was prepared at 3.20 mM in DMA and added to the conjugation CSTR by syringe pump. The two inlet streams were mixed in the CSTR bringing the final reaction conditions to 3.8 mg/mL antibody concentration, 4.6 molar excess of DM21:Ab, and 10% DMA (v/v). A peristaltic pump removed the conjugation reaction mixture at the combined volumetric flow rate of the reoxidation reaction and DM21-C stock solutions. This peristaltic pump matched the flow rate to maintain the liquid level in the vessel and was fed directly to the conjugation reaction PFR. The conjugation reaction PFR targeted a reaction conversion based on kinetic reaction data. This target conversion was used to define the residence time. The residence time and volumetric flow rate of the conjugation were used to define the conditions for the conjugation PFR. Similar to both the reduction and reoxidation PFRs, the conjugation reaction PFR was submerged in a temperature controlled water bath.

The conjugation reaction PFR eluted unpurified conjugation reaction mixture. This stream was fed to the counter-current TFF purification unit. The incoming crude reaction was at a concentration of approximately 3.8 mg/mL and 10% DMA (v/v). A stream of diafiltration buffer (10 mM sodium succinate, 9% (w/v) sucrose, pH 4.7) combined with the incoming unpurified conjugate reaction mixture to dilute the incoming feed stream. This feed stream was combined with the permeate stream from Module 2 as shown in FIG. 6, further diluting the feed concentration of conjugate to Module 1. For Module 1 and Module 2, Pall Cadence in-line concentrator (ILC) membranes were used.

The retentate from Module 1 was fed directly into Module 2. An additional feed of DF buffer was combined with the retentate from Module 1 ahead of the inlet to Module 2. The permeate from Module 1 was routed to waste for disposal. The purified conjugate was recovered from the retentate of Module 2. The permeate from Module 2 was recycled and combined with the feed to Module 1 as described above (see FIG. 6). This counter-current set up effectively removes impurities from the crude reaction mixture and buffer-exchanges the conjugate into the DF buffer. To ensure removal of the payload impurities during counter-current TFF purification, pre-TFF and purified samples were characterized by the free drug method. The results show a highly effective removal of impurities from the incoming, unpurified feed stream across the two units (>99%). The results for the final purified conjugate for the continuous run and a batch control are shown in Table S.

TABLE S

Product Quality Summary for Integrated DS Manufacturing Run

| Product Quality Attribute | Continuous Conjugation (Counter-Current TFF) | Batch Control (NAP Purified) |
|---|---|---|
| HMW (%, by SEC) | 0.3 | 0.3 |
| Monomer (%, by SEC) | 99.7 | 99.7 |
| Free Drug Removal (%) | 99.89 | N/A |
| Purified Free Drug (ug/mL) | <LOQ | N/A |
| DAR (by UV) | 1.95 | N/A |
| DAR (by SEC-MS) | 1.9 | N/A |
| Crude Reaction DAR (by SEC) | 2.0 | 2.1 |
| HL (%, by Gel Chip) | 3 | 4 |
| H2L2 (%, by Gel Chip) | 81 | 82 |

Example 7. One-Pot Conjugation Process Under Inert Atmosphere

To test the impact of performing the entire one-pot conjugation process in an $N_2$ purged system to better mimic the expected conditions during GMP manufacturing. The performance of the reduction and re-oxidation reactions is tested by comparing identical reactions under $N_2$ and under a normal air atmosphere. Reduction was performed at an antibody concentration of 4.5 mg/mL in pH 6.5, 30 mL potassium phosphate with 5% DMA. The reaction was set up with 16 equivalents of DPPA and was performed at 23° C. for 5 hours. Reoxidation was performed at an antibody concentration of 4.0 mg/mL in pH 6.5, 30 mM potassium phosphate with 7% DMA. The reaction was set up with 24 equivalents of DHAA and was performed at 23° C. for 6 hours. Conjugation was performed at an antibody concentration of 3.5 mg/mL in pH 6.5, 30 mM potassium phosphate with 10% DMA. The reaction was set up with 4.6 equivalents of DM21-C and was performed at 23° C. for 12 hours. Two reactions at 175 mg scale were set up in the EasyMax system with internal temperature control to 23.0° C. and overhead mixing at 70 rpm. The headspace of one reaction was continuously purged with $N_2$ for the duration of the experiment. Additionally, for this reaction, the water and 30 mM potassium phosphate buffer solutions were bubbled with $N_2$ for 15-30 minutes prior to their addition to the reaction.

As shown in Table T, there are no significant differences between running the reaction in a Nitrogen purged system versus leaving the conjugation reaction vessel open to the atmosphere. All analytical data (SEC Monomer, SEC DAR, HIC DAR, GelChip) for the reaction run under nitrogen are consistent with the control and previous scale up run that employed the same raw materials.

TABLE T

Summary of Product Quality

| | N2 Rxn (crude) | Air Rxn (crude) | previous scale up run* |
|---|---|---|---|
| SEC DAR | 2.04 | 2.01 | 2.04 |
| HIC DAR | 1.98 | 1.97 | 1.98 |
| % Monomer | 98.35 | 98.35 | 98.71 |
| % HMW | 1.47 | 1.54 | 1.22 |
| % LMW | 0.18 | 0.11 | 0.07 |
| % D0 | Not Found | Not Found | 0.02 |
| % D1 | 2.56 | 2.96 | 2.82 |
| % D2 | 97.32 | 97.04 | 96.90 |
| % D4 | 0.12 | Not Found | 0.26 |
| % HL | 6.18 | 5.14 | 5.84 |
| % H2L2 | 78.36 | 80.92 | 78.54 |
| % Overall Yield | NA | NA | 93.60 |

*the previous scale up run uses the same Ab lot, DPPA, and payload lot as the reactions described here

The invention claimed is:

1. A method of preparing a cell-binding agent-cytotoxic agent conjugate comprising a cell-binding agent (CysCBA) having one or more unpaired cysteine residues covalently linked to a cytotoxic agent, wherein the CysCBA is a cysteine-engineered antibody (CysAb) or antigen-binding fragment thereof and the method comprises the steps of:
(a) reacting a reducing agent with a capped cell-binding agent (cCysCBA) having one or more unpaired cysteine residues capped with a capping agent to form a reduced cell-binding agent, wherein the capping agent is removed to form a free thiol (—SH) group in the reduced cell-binding agent;
(b) reacting the reduced cell-binding agent with a selective oxidizing agent to form the CysCBA, wherein the free thiol group in the unpaired cysteine residue is not oxidized; and
(c) reacting the CysCBA with a compound of formula (I):

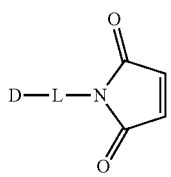
(I)

or a pharmaceutically acceptable salt thereof, thereby forming the conjugate, wherein the reduced cell-binding agent in step (a) is used in step (b) without purification; and the CysCBA in step (b) is used in step (c) without purification, wherein:
D is a cytotoxic agent represented by the following formula:

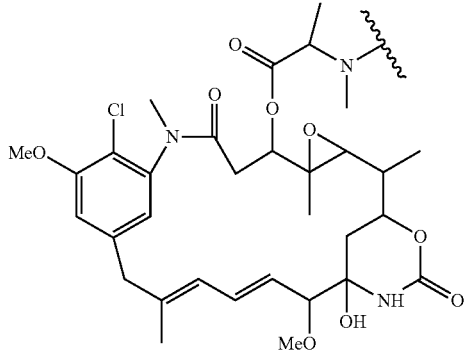 [SMILES: *N(C)C(C)C(=O)OC1CC(=O)N(C)c2cc(cc(OC)c2Cl)C/C(C)=C/C=C/C(OC)C2(O)CC(OC(=O)N2)C(C)C2OC12C]

or a pharmaceutically acceptable salt thereof;
the reducing agent is tris(2-carboxyethyl)phosphine hydrochloride (TCEP), trishydroxypropyl phosphine (THPP), tris (2-cyanoethyl)phosphine, dithiothreitol (DTT), (dicyclohexylphosphino)benzenesulfonic acid, bis(p-sulfonatophenyl)phenylphosphine, (diphenylphosphino)benzenesulfonic acid, (diphenylphosphino)benzoic acid, 2-(diphenylphosphino)-N,N,N-trimethylbenzylammonium triflate, (diphenylphosphino)ethylamine, 2-(diisopropylphosphino)ethylamine, or 3-(diphenylphosphino)propylamine (DPPA); and
L is a linker.

2. The method of claim 1, wherein the oxidizing agent is dehydroascorbic acid (DHAA), copper sulfate, oxygen or air.

3. The method of claim 1, wherein the reducing agent is TCEP and the reaction of step (a) is carried out at a pH between 6.0 and 8.0.

4. The method of claim 1, wherein the reducing agent is DPPA and the reaction of step (a) is carried out at a pH between 6.0 and 8.0.

5. The method of claim 1, wherein the molar ratio of the reducing agent in step (a) to the oxidizing agent in step (b) is between 2:1 and 1:2.

6. The method of claim 1, wherein the compound of formula (I) is represented by the following formula:

$$L_2'\text{-A-NH}—CR^{14}R^{24}—S-L_1\text{-D} \qquad (I\text{-a}),$$

or a pharmaceutically acceptable salt thereof, wherein:
$L_2'$ is represented by the following structural formula:

(L2a')

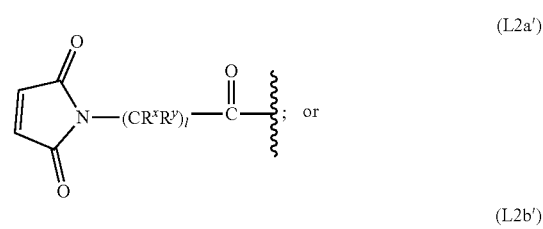
(L2b')

wherein:
$R^x$ and $R^y$, for each occurrence, are independently H, —OH, halogen, —O—($C_{1-4}$ alkyl), —SO$_3$H, or a $C_{1-4}$ alkyl optionally substituted with —OH, halogen, or —SO$_3$H;
l and ll are each independently an integer from 1 to 10;
k1 is an integer from 1 to 12;
A is an amino acid or a peptide comprising 2 to 20 amino acids;
$R^{14}$ and $R^{24}$ are each independently H or a $C_{1-3}$alkyl;
$L_1$ is -$L_1'$—C(=O)—; and $L_1'$ is $C_{1-10}$alkylene; and
D is represented by the following formula:

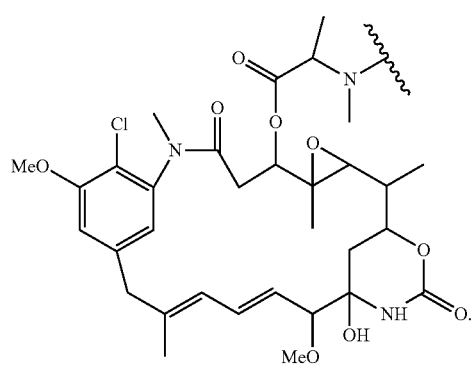 [SMILES: *N(C)C(C)C(=O)OC1CC(=O)N(C)c2cc(cc(OC)c2Cl)C/C(C)=C/C=C/C(OC)C2(O)CC(OC(=O)N2)C(C)C2OC12C]

7. The method of claim 1, wherein the compound of formula (I) is represented by the following formula:

(I-d)
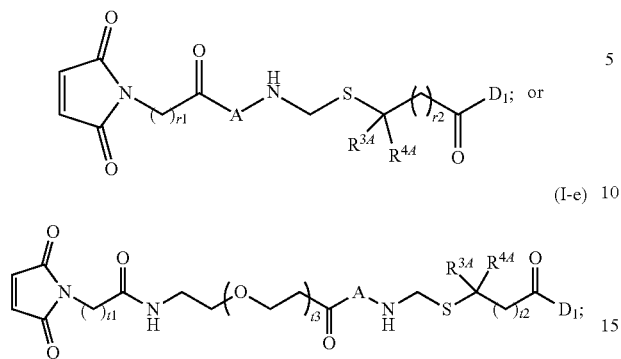
(I-e)
wherein:
r1 and t1 are each an integer from 2 to 6;
r2 and t2 are each an integer from 2 to 5; and
t3 is an integer from 2 to 12
A is an amino acid or a peptide comprising 2 to 20 amino acids;
$R^{3A}$ and $R^{4A}$ are each independently H or Me;
$D_1$ is represented by the following formula:
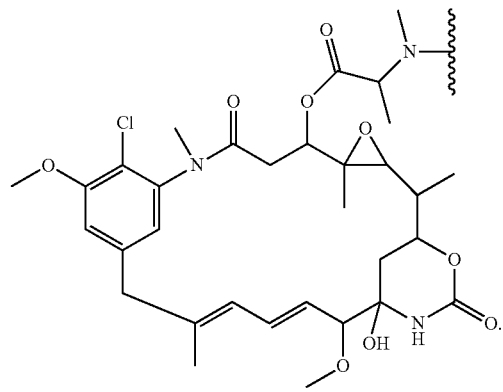 [SMILES: *N(C)C(C)C(=O)OC1CC(=O)N(C)c2cc(cc(OC)c2Cl)C/C(C)=C/C=C/C(OC)C2(O)CC(OC(=O)N2)C(C)C2OC12C]
8. The method of claim 7, wherein the compound is represented by the following formula:
(I10)
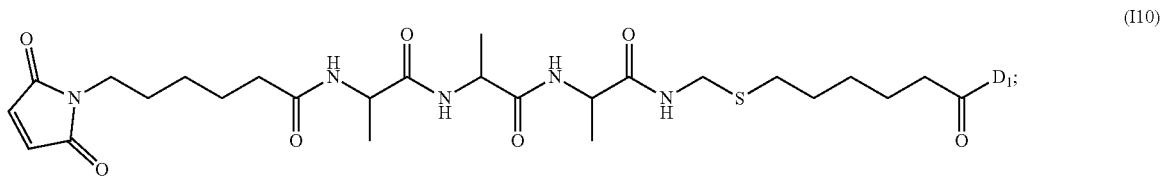
(I11)
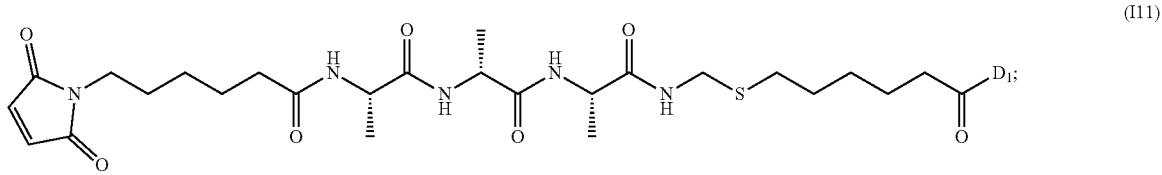
(I12)
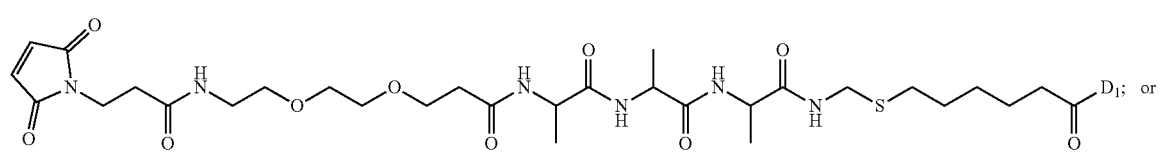
(I13)
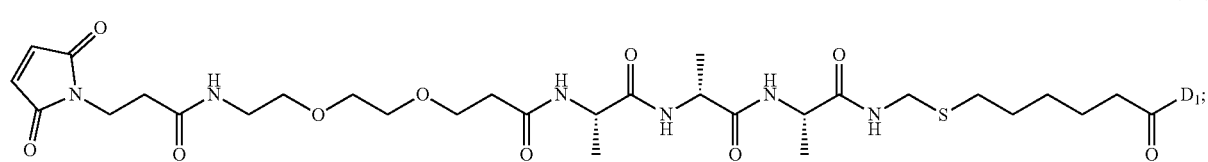

wherein D₁ is represented by the following formula:

$$D_1 \text{ structure}$$

9. The method of claim 1, wherein the method is for preparing an antibody-cytotoxic agent conjugate (ADC) represented by the following formula:

$$\text{ADC structure}$$

and the method comprises the steps of:
(a) reacting a reducing agent with a capped cysteine-engineered antibody (cCysAb) represented by the following formula:

$$\text{Ab-S-Cap}_{q_c},$$

to form a reduced antibody or antigen-binding fragment thereof, wherein a capping agent (Cap) is removed to form a free thiol (—SH) group in the reduced antibody or antigen-binding fragment thereof;
(b) reacting the reduced antibody or antigen-binding fragment thereof with a selective oxidizing agent to form the CysAb, wherein the free thiol group in the engineered cysteine residue is not oxidized; and
(c) reacting the CysAb with a compound represented by the following formula:

$$\text{Compound structure}$$

or a pharmaceutically acceptable salt thereof, thereby forming the ADC, wherein the reduced antibody or antigen-binding fragment thereof in step (a) is used in step (b) without purification, and the CysAb or antigen-binding fragment thereof of step (b) is used in step (c) without purification, wherein:

$$\text{Ab-S-}$$

is a cysteine-engineered antibody (CysAb) or antigen-binding fragment thereof covalently linked to the cytotoxic agent through the thiol group located on the engineered cysteine residue; and wherein the CysAb or antigen-binding fragment thereof is a humanized anti-ADAM9 antibody or ADAM9-binding fragment thereof comprising a $CDR_H1$ domain, a $CDR_H2$ domain, and a $CDR_H3$ domain and a $CDR_L1$ domain, a $CDR_L2$ domain, and a $CDR_L3$ domain having the sequences of SEQ ID NOs: 24, 25, and 26 and SEQ ID NOs: 21, 22, 23, respectively;

$q_c$ is 1 or 2;

D₁ is represented by the following formula:

$$D_1 \text{ structure (I11)}$$

and the capping agent is cysteine, glutathione, homocysteine, or a combination thereof.

* * * * *

SEQUENCE LISTING

<160> NUMBER OF SEQ ID NOS: 66

<210> SEQ ID NO 1
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Arg Ala Ser Gln Asp Ile Asn Ser Tyr Leu Ser
1               5                   10

<210> SEQ ID NO 2
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

-continued

```
Arg Val Asn Arg Leu Val Asp
1               5

<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Leu Gln Tyr Asp Ala Phe Pro Tyr Thr
1               5

<210> SEQ ID NO 4
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ser Ser Ile Met His
1               5

<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Tyr Ile Lys Pro Tyr Asn Asp Gly Thr Lys Tyr Asn Glu Lys Phe Lys
1               5                   10                  15

Gly

<210> SEQ ID NO 6
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Glu Gly Gly Asn Asp Tyr Tyr Asp Thr Met Asp Tyr
1               5                   10

<210> SEQ ID NO 7
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Val Gln Leu Val Gln Ser Gly Ala Glu Val Lys Lys Pro Gly Ala
```

```
                1               5                  10                 15
        Ser Val Lys Val Ser Cys Lys Ala Ser Gly Tyr Ile Phe Thr Ser Ser
                        20                 25                30

Ile Met His Trp Val Arg Gln Ala Pro Gly Gln Gly Leu Glu Trp Ile
                        35                 40                 45

Gly Tyr Ile Lys Pro Tyr Asn Asp Gly Thr Lys Tyr Asn Glu Lys Phe
                    50                 55                 60

Lys Gly Arg Ala Thr Leu Thr Ser Asp Arg Ser Thr Ser Thr Ala Tyr
        65                      70                 75                 80

Met Glu Leu Ser Ser Leu Arg Ser Glu Asp Thr Ala Val Tyr Tyr Cys
                            85                 90                 95

Ala Arg Glu Gly Gly Asn Asp Tyr Tyr Asp Thr Met Asp Tyr Trp Gly
                        100                105                110

Gln Gly Thr Leu Val Thr Val Ser Ser
                        115                120

<210> SEQ ID NO 8
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Gln Val Gln Leu Val Gln Ser Gly Ala Glu Val Lys Lys Pro Gly Ala
        1               5                  10                 15

Ser Val Lys Val Ser Cys Lys Ala Ser Gly Tyr Ile Phe Thr Ser Ser
                        20                 25                 30

Ile Met His Trp Val Arg Gln Ala Pro Gly Gln Gly Leu Glu Trp Ile
                        35                 40                 45

Gly Tyr Ile Lys Pro Tyr Asn Asp Gly Thr Lys Tyr Asn Glu Lys Phe
                    50                 55                 60

Lys Gly Arg Ala Thr Leu Thr Ser Asp Arg Ser Thr Ser Thr Ala Tyr
        65                      70                 75                 80

Met Glu Leu Ser Ser Leu Arg Ser Glu Asp Thr Ala Val Tyr Tyr Cys
                            85                 90                 95

Ala Arg Glu Gly Gly Asn Asp Tyr Tyr Asp Thr Met Asp Tyr Trp Gly
                        100                105                110

Gln Gly Thr Leu Val Thr Val Ser Ser Ala Ser Thr Lys Gly Pro Ser
                        115                120                125

Val Phe Pro Leu Ala Pro Ser Ser Lys Ser Thr Ser Gly Gly Thr Ala
        130                 135                140

Ala Leu Gly Cys Leu Val Lys Asp Tyr Phe Pro Glu Pro Val Thr Val
        145                 150                155                160

Ser Trp Asn Ser Gly Ala Leu Thr Ser Gly Val His Thr Phe Pro Ala
                        165                170                175

Val Leu Gln Ser Ser Gly Leu Tyr Ser Leu Ser Ser Val Val Thr Val
                        180                185                190

Pro Ser Ser Ser Leu Gly Thr Gln Thr Tyr Ile Cys Asn Val Asn His
                        195                200                205

Lys Pro Ser Asn Thr Lys Val Asp Lys Lys Val Glu Pro Lys Ser Cys
                    210                215                 220

Asp Lys Thr His Thr Cys Pro Pro Cys Pro Ala Pro Glu Leu Leu Gly
        225                 230                 235                240
```

```
Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450

<210> SEQ ID NO 9
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg
            100                 105

<210> SEQ ID NO 10
<211> LENGTH: 214
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Lys Ser Ser Gln Ser Val Phe Phe Ser Ser Gln Lys Asn Tyr Leu
1               5                   10                  15

Ala

<210> SEQ ID NO 12
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12
```

```
Trp Ala Ser Thr Arg Glu Ser
1               5

<210> SEQ ID NO 13
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

His Gln Tyr Leu Ser Ser Arg Thr
1               5

<210> SEQ ID NO 14
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ser Tyr Tyr Ile His
1               5

<210> SEQ ID NO 15
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Val Ile Tyr Pro Gly Asn Asp Asp Ile Ser Tyr Asn Gln Lys Phe Gln
1               5                   10                  15

Gly

<210> SEQ ID NO 16
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Glu Val Arg Leu Arg Tyr Phe Asp Val
1               5

<210> SEQ ID NO 17
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Gln Val Gln Leu Gln Gln Pro Gly Ala Glu Val Val Lys Pro Gly Ala
```

```
            1               5                  10                  15
Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
            35                  40                  45

Gly Val Ile Tyr Pro Gly Asn Asp Asp Ile Ser Tyr Asn Gln Lys Phe
            50                  55                  60

Gln Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
            85                  90                  95

Ala Arg Glu Val Arg Leu Arg Tyr Phe Asp Val Trp Gly Gln Gly Thr
            100                 105                 110

Thr Val Thr Val Ser Ser
            115
```

<210> SEQ ID NO 18
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (443)..(443)
<223> OTHER INFORMATION: /replace="Cys"
<220> FEATURE:
<221> NAME/KEY: SITE
<222> LOCATION: (1)..(447)
<223> OTHER INFORMATION: /note="Variant residues given in the sequence
      have no preference with respect to those in the annotations for
      variant positions"

<400> SEQUENCE: 18

```
Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
            35                  40                  45

Gly Val Ile Tyr Pro Gly Asn Asp Asp Ile Ser Tyr Asn Gln Lys Phe
            50                  55                  60

Gln Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
            85                  90                  95

Ala Arg Glu Val Arg Leu Arg Tyr Phe Asp Val Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
```

180                 185                 190
Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 19
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Ile Tyr Tyr Cys His Gln
                85                  90                  95

```
Tyr Leu Ser Ser Arg Thr Phe Gly Gln Gly Thr Lys Leu Glu Ile Lys
            100                 105                 110
Arg

<210> SEQ ID NO 20
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
            20                  25                  30

Ser Ser Gln Lys Asn Tyr Leu Ala Trp Tyr Gln Ile Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Ile Tyr Tyr Cys His Gln
                85                  90                  95

Tyr Leu Ser Ser Arg Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 21
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Lys Ala Ser Gln Ser Val Asp Tyr Ser Gly Asp Ser Tyr Met Asn
1               5                   10                  15

<210> SEQ ID NO 22
<211> LENGTH: 7
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Ala Ala Ser Asp Leu Glu Ser
1               5

<210> SEQ ID NO 23
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Gln Gln Ser His Glu Asp Pro Phe Thr
1               5

<210> SEQ ID NO 24
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Ser Tyr Trp Met His
1               5

<210> SEQ ID NO 25
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Glu Ile Ile Pro Ile Phe Gly His Thr Asn Tyr Asn Glu Lys Phe Lys
1               5                   10                  15

Ser

<210> SEQ ID NO 26
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Gly Gly Tyr Tyr Tyr Tyr Pro Arg Gln Gly Phe Leu Asp Tyr
1               5                   10

<210> SEQ ID NO 27
<211> LENGTH: 123
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic polypeptide"

<400> SEQUENCE: 27

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Gly Glu Ile Ile Pro Ile Phe Gly His Thr Asn Tyr Asn Glu Lys Phe
    50                  55                  60

Lys Ser Arg Phe Thr Ile Ser Leu Asp Asn Ser Lys Asn Thr Leu Tyr
65              70                  75                  80

Leu Gln Met Gly Ser Leu Arg Ala Glu Asp Thr Ala Val Tyr Tyr Cys
            85                  90                  95

Ala Arg Gly Gly Tyr Tyr Tyr Pro Arg Gln Gly Phe Leu Asp Tyr
            100                 105                 110

Trp Gly Gln Gly Thr Thr Val Thr Val Ser Ser
        115                 120
```

<210> SEQ ID NO 28
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

```
Asp Ile Val Met Thr Gln Ser Pro Asp Ser Leu Ala Val Ser Leu Gly
1               5                   10                  15

Glu Arg Ala Thr Ile Ser Cys Lys Ala Ser Gln Ser Val Asp Tyr Ser
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asp Leu Glu Ser Gly Ile Pro Ala
    50                  55                  60

Arg Phe Ser Gly Ser Gly Ser Gly Thr Asp Phe Thr Leu Thr Ile Ser
65              70                  75                  80

Ser Leu Glu Pro Glu Asp Phe Ala Thr Tyr Tyr Cys Gln Gln Ser His
            85                  90                  95

Glu Asp Pro Phe Thr Phe Gly Gln Gly Thr Lys Leu Glu Ile Lys
            100                 105                 110
```

<210> SEQ ID NO 29
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
```

-continued

```
                20                  25                  30
Trp Met His Trp Val Arg Gln Ala Pro Gly Lys Gly Leu Glu Trp Val
            35                  40                  45
Gly Glu Ile Ile Pro Ile Phe Gly His Thr Asn Tyr Asn Glu Lys Phe
50                  55                  60
Lys Ser Arg Phe Thr Ile Ser Leu Asp Asn Ser Lys Asn Thr Leu Tyr
65                  70                  75                  80
Leu Gln Met Gly Ser Leu Arg Ala Glu Asp Thr Ala Val Tyr Tyr Cys
                85                  90                  95
Ala Arg Gly Gly Tyr Tyr Tyr Pro Arg Gln Gly Phe Leu Asp Tyr
            100                 105                 110
Trp Gly Gln Gly Thr Thr Val Thr Val Ser Ser Ala Ser Thr Lys Gly
            115                 120                 125
Pro Ser Val Phe Pro Leu Ala Pro Ser Ser Lys Ser Thr Ser Gly Gly
        130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Arg Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Tyr Ile Thr Arg Glu Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Glu Glu Met Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Cys
        435                 440                 445
```

```
Leu Ser Pro Gly
    450

<210> SEQ ID NO 30
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Asp Ile Val Met Thr Gln Ser Pro Asp Ser Leu Ala Val Ser Leu Gly
1               5                   10                  15

Glu Arg Ala Thr Ile Ser Cys Lys Ala Ser Gln Ser Val Asp Tyr Ser
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asp Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Thr Tyr Tyr Cys Gln Gln Ser His
                85                  90                  95

Glu Asp Pro Phe Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 31
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Arg Ser Ser Arg Ser Leu Leu His Ser Asp Gly Phe Thr Tyr Leu Tyr
1               5                   10                  15

<210> SEQ ID NO 32
<211> LENGTH: 7
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 32

Gln Thr Ser Asn Leu Ala Ser
1               5

<210> SEQ ID NO 33
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Ala Gln Asn Leu Glu Leu Pro Asn Thr
1               5

<210> SEQ ID NO 34
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Asn Tyr Tyr Ile His
1               5

<210> SEQ ID NO 35
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Trp Ile Tyr Pro Gly Asn Val Tyr Ile Gln Tyr Asn Glu Lys Phe Lys
1               5                   10                  15

Gly

<210> SEQ ID NO 36
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Asp Gly Pro Trp Phe Ala Tyr
1               5

<210> SEQ ID NO 37
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Arg Leu Glu Tyr Ile
        35                  40                  45

Gly Trp Ile Tyr Pro Gly Asn Val Tyr Ile Gln Tyr Asn Glu Lys Phe
    50                  55                  60

Lys Gly Arg Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Pro Trp Phe Ala Tyr Trp Gly Gln Gly Thr Leu Val
            100                 105                 110

Thr Val Ser Ser
            115

<210> SEQ ID NO 38
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Asp Ile Val Leu Thr Gln Thr Pro Leu Ser Leu Ser Val Thr Pro Gly
1               5                   10                  15

Gln Pro Ala Ser Ile Ser Cys Arg Ser Ser Arg Ser Leu Leu His Ser
            20                  25                  30

Asp Gly Phe Thr Tyr Leu Tyr Trp Phe Leu Gln Lys Pro Gly Gln Ser
        35                  40                  45

Pro Gln Leu Leu Ile Tyr Gln Thr Ser Asn Leu Ala Ser Gly Val Pro
    50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Asn Thr Phe Gly Gln Gly Thr Lys Leu Glu Ile Lys
            100                 105                 110

<210> SEQ ID NO 39
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (441)..(441)
<223> OTHER INFORMATION: /replace="Cys"
<220> FEATURE:
<221> NAME/KEY: SITE
<222> LOCATION: (1)..(445)
<223> OTHER INFORMATION: /note="Variant residues given in the sequence
      have no preference with respect to those in the annotations for variant positions"

<400> SEQUENCE: 39

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Arg Leu Glu Tyr Ile
        35                  40                  45

Gly Trp Ile Tyr Pro Gly Asn Val Tyr Ile Gln Tyr Asn Glu Lys Phe
    50                  55                  60

Lys Gly Arg Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Pro Trp Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400
```

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 40
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Asp Ile Val Leu Thr Gln Thr Pro Leu Ser Leu Ser Val Thr Pro Gly
1               5                   10                  15

Gln Pro Ala Ser Ile Ser Cys Arg Ser Ser Arg Ser Leu Leu His Ser
            20                  25                  30

Asp Gly Phe Thr Tyr Leu Tyr Trp Phe Leu Gln Lys Pro Gly Gln Ser
        35                  40                  45

Pro Gln Leu Leu Ile Tyr Gln Thr Ser Asn Leu Ala Ser Gly Val Pro
    50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Asn Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 41
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Lys Ala Ser Gln Ser Val Ser Phe Ala Gly Thr Ser Leu Met His
1               5                   10                  15

```
<210> SEQ ID NO 42
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Arg Ala Ser Asn Leu Glu Ala
1               5

<210> SEQ ID NO 43
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Gln Gln Ser Arg Glu Tyr Pro Tyr Thr
1               5

<210> SEQ ID NO 44
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gly Tyr Phe Met Asn
1               5

<210> SEQ ID NO 45
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Arg Ile His Pro Tyr Asp Gly Asp Thr Phe Tyr Asn Gln Lys Phe Gln
1               5                   10                  15

Gly

<210> SEQ ID NO 46
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Tyr Asp Gly Ser Arg Ala Met Asp Tyr
1               5

<210> SEQ ID NO 47
<211> LENGTH: 10
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Gly Tyr Thr Phe Thr Gly Tyr Phe Met Asn
1               5                   10

<210> SEQ ID NO 48
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Arg Ile His Pro Tyr Asp Gly Asp Thr Phe
1               5                   10

<210> SEQ ID NO 49
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
        50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
                100                 105                 110

Thr Val Thr Val Ser Ser
            115

<210> SEQ ID NO 50
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
```

```
                    20                  25                  30

Gly Thr Ser Leu Met His Trp Tyr His Gln Lys Pro Gly Gln Gln Pro
            35                  40                  45

Arg Leu Leu Ile Tyr Arg Ala Ser Asn Leu Glu Ala Gly Val Pro Asp
        50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

<210> SEQ ID NO 51
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

<210> SEQ ID NO 52
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (443)..(443)
<223> OTHER INFORMATION: /replace="Ser"
<220> FEATURE:
<221> NAME/KEY: VARIANT
<222> LOCATION: (448)..(448)
<223> OTHER INFORMATION: /replace=" "
<220> FEATURE:
<221> NAME/KEY: SITE
<222> LOCATION: (1)..(448)
<223> OTHER INFORMATION: /note="Variant residues given in the sequence
      have no preference with respect to those in the annotations for
      variant positions"

<400> SEQUENCE: 52

Gln Val Gln Leu Val Gln Ser Gly Ala Glu Val Val Lys Pro Gly Ala
1               5                   10                  15
```

-continued

```
Ser Val Lys Ile Ser Cys Lys Ala Ser Gly Tyr Thr Phe Thr Gly Tyr
            20                  25                  30
Phe Met Asn Trp Val Lys Gln Ser Pro Gly Gln Ser Leu Glu Trp Ile
        35                  40                  45
Gly Arg Ile His Pro Tyr Asp Gly Asp Thr Phe Tyr Asn Gln Lys Phe
    50                  55                  60
Gln Gly Lys Ala Thr Leu Thr Val Asp Lys Ser Ser Asn Thr Ala His
65                  70                  75                  80
Met Glu Leu Leu Ser Leu Thr Ser Glu Asp Phe Ala Val Tyr Tyr Cys
                85                  90                  95
Thr Arg Tyr Asp Gly Ser Arg Ala Met Asp Tyr Trp Gly Gln Gly Thr
            100                 105                 110
Thr Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Cys Leu Ser Pro Gly Lys
```

-continued

```
                435                 440                 445
```

<210> SEQ ID NO 53
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 54
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60
```

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 55
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Ala Leu Ala Leu
1

<210> SEQ ID NO 56
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Ala

<400> SEQUENCE: 56

Xaa Leu Ala Leu
1

<210> SEQ ID NO 57
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Gly Phe Leu Gly
1

```
<210> SEQ ID NO 58
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Ala

<400> SEQUENCE: 58

Xaa Gly Gly Gly
1

<210> SEQ ID NO 59
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gly Ser Gly Gly Ser
1               5

<210> SEQ ID NO 60
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Gly Gly Gly Ser
1

<210> SEQ ID NO 61
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Gly Gly Ser Gly
1

<210> SEQ ID NO 62
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 62

Gly Gly Ser Gly Gly
1               5

<210> SEQ ID NO 63
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Gly Ser Gly Ser Gly
1               5

<210> SEQ ID NO 64
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Gly Ser Gly Gly Gly
1               5

<210> SEQ ID NO 65
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Gly Gly Gly Ser Gly
1               5

<210> SEQ ID NO 66
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Gly Ser Ser Ser Gly
1               5
```

UNITED STATES PATENT AND TRADEMARK OFFICE
CERTIFICATE OF CORRECTION

PATENT NO. : 11,833,214 B2
APPLICATION NO. : 16/825127
DATED : December 5, 2023
INVENTOR(S) : Scott A. Hilderbrand et al.

It is certified that error appears in the above-identified patent and that said Letters Patent is hereby corrected as shown below:

In the Claims

At Column 198, Line 14, Claim number 9, replace:
"ADAMS antibody or ADAMS-binding fragment"
With:
--"ADAM9 antibody or ADAM9-binding fragment"--

Signed and Sealed this
First Day of October, 2024

Katherine Kelly Vidal
*Director of the United States Patent and Trademark Office*